US008343996B2

(12) United States Patent
Duggan

(10) Patent No.: US 8,343,996 B2
(45) Date of Patent: Jan. 1, 2013

(54) AZAQUINOLINONE DERIVATIVES AND USES THEREOF

(75) Inventor: Mark E. Duggan, Wellesley, MA (US)

(73) Assignee: AstraZeneca AB, Sodertalje (SE)

( * ) Notice: Subject to any disclaimer, the term of this patent is extended or adjusted under 35 U.S.C. 154(b) by 439 days.

(21) Appl. No.: 12/618,336

(22) Filed: Nov. 13, 2009

(65) Prior Publication Data
US 2010/0130540 A1 May 27, 2010

Related U.S. Application Data

(60) Provisional application No. 61/114,303, filed on Nov. 13, 2008, provisional application No. 61/231,434, filed on Aug. 5, 2009.

(51) Int. Cl.
A61K 31/4375 (2006.01)
C07D 471/04 (2006.01)
A61P 25/00 (2006.01)
A61P 9/00 (2006.01)
A61P 29/00 (2006.01)

(52) U.S. Cl. .................................. 514/300; 546/122
(58) Field of Classification Search .................. 546/122; 514/300
See application file for complete search history.

(56) References Cited

U.S. PATENT DOCUMENTS

| 3,988,461 A | 10/1976 | Kosoczky et al. |
| 4,110,536 A | 8/1978 | Havera et al. |
| 4,576,957 A | 3/1986 | Marsico, Jr. et al. |
| 4,863,962 A | 9/1989 | Karoum et al. |
| 4,902,205 A | 2/1990 | DaCosta et al. |
| 4,902,505 A | 2/1990 | Pardridge et al. |
| 4,933,324 A | 6/1990 | Shashoua |
| 4,939,174 A | 7/1990 | Shashoua |
| 5,004,697 A | 4/1991 | Pardridge |
| 5,017,584 A | 5/1991 | Hlasta |
| 5,112,596 A | 5/1992 | Malfroy-Camine |
| 5,185,248 A | 2/1993 | Barbacid et al. |
| 5,268,164 A | 12/1993 | Kozarich et al. |
| 5,322,950 A | 6/1994 | Sircar et al. |
| 5,371,227 A | 12/1994 | Cremer et al. |
| 5,374,615 A | 12/1994 | Poss |
| 5,523,317 A | 6/1996 | Masaki et al. |
| 5,525,479 A | 6/1996 | Anthony et al. |
| 5,527,527 A | 6/1996 | Friden |
| 5,614,560 A | 3/1997 | Lipton |
| 5,616,601 A | 4/1997 | Khanna et al. |
| 5,633,376 A | 5/1997 | Thurkauf et al. |
| 5,656,644 A | 8/1997 | Adams et al. |
| 5,696,121 A | 12/1997 | Bishop et al. |
| 5,714,609 A | 2/1998 | Doll et al. |
| 5,716,966 A | 2/1998 | Cupps et al. |
| 5,719,148 A | 2/1998 | Bishop et al. |
| 5,726,197 A | 3/1998 | Clark et al. |
| 5,739,148 A | 4/1998 | Cupps et al. |
| 5,756,516 A | 5/1998 | Liu et al. |
| 5,792,783 A | 8/1998 | Tang et al. |
| 5,807,853 A | 9/1998 | Bishop et al. |
| 5,856,326 A | 1/1999 | Anthony et al. |
| 5,859,012 A | 1/1999 | Dinsmore et al. |
| 5,874,442 A | 2/1999 | Doll et al. |
| 5,919,785 A | 7/1999 | Dinsmore et al. |
| 5,925,757 A | 7/1999 | Mallams |
| 5,939,416 A | 8/1999 | Rane et al. |
| 5,939,439 A | 8/1999 | Anthony et al. |
| 5,968,952 A | 10/1999 | Venet et al. |
| 5,977,307 A | 11/1999 | Friden et al. |
| 5,994,932 A | 11/1999 | Ando |
| 6,011,029 A | 1/2000 | Ding et al. |
| 6,013,662 A | 1/2000 | Bourzat et al. |
| 6,037,350 A | 3/2000 | Venet et al. |
| 6,060,038 A | 5/2000 | Burns et al. |
| 6,103,487 A | 8/2000 | Barnett et al. |
| 6,107,499 A | 8/2000 | Shashoua |
| 6,143,758 A | 11/2000 | Doll et al. |
| 6,150,377 A | 11/2000 | Lyssikatos et al. |
| 6,156,746 A | 12/2000 | Leftheris et al. |
| 6,160,118 A | 12/2000 | Askin et al. |
| 6,169,096 B1 | 1/2001 | Venet et al. |
| 6,177,432 B1 | 1/2001 | Angibaud et al. |
| 6,187,786 B1 | 2/2001 | Venet et al. |
| 6,214,828 B1 | 4/2001 | Doll et al. |
| 6,242,458 B1 | 6/2001 | Bishop et al. |
| 6,258,824 B1 | 7/2001 | Yang |
| 6,258,836 B1 | 7/2001 | Shashoua |
| 6,284,755 B1 | 9/2001 | deSolms et al. |
| 6,294,552 B1 | 9/2001 | Lyssikatos et al. |

(Continued)

FOREIGN PATENT DOCUMENTS

AU 2003272539 A1 4/2004

(Continued)

OTHER PUBLICATIONS

Li et al., Bioorganic & Medicinal Chemistry Letters, (2005) vol. 15(8), pp. 2033-2039.*
Appels et al., "Development of Farnesyl Transferase Inhibitors: A Review", Oncologist, 10(8):565-578 (2005).
Ashar et al., "The Farnesyl Transferase Inhibitor SCH 66336 Induces a G(2) → M or G(1) Pause in Sensitive Human Tumor Cell Lines", Exp. Cell Res., 262(1):17-27 (2001).
Baldereschi et. al., "Parkinson's disease and parkinsonism in a longitudinal study: two-fold higher incidence in men ILSA Working Group. Italian Longitudinal Study on Aging", Neurology, 55(9):1358-1363 (2000).
Barrachina et al. "Reduced ubiquitin C-terminal hydrolase-1 expression levels in dementia with Lewy bodies", Neurobiology of Disease, Blackwell Scientific Publications, Oxford, GB, 22(2), pp. 265-273 (2006).
Caballero et al., "Interaction and colocalization of PGP9.5 with JAB1 and p27(Kip1)", Oncogene, 21(19):3003-3010 (2002).
Chen et al., "Neuroprotective therapy in Parkinson disease", Am. J. Ther., 13(5):445-457 (2006).
Cleary et al., "Antidepressive-like effects of rapamycin in animal models: implications for mTOR inhibition as a new target for treatment of affective disorders", Brain Res. Bulletin, 76:469-473 (2008).
Crul et al., "Phase I clinical and pharmacologic study of chronic oral administration of the farnesyl protein transferase inhibitor R115777 in advanced cancer", J. Clin. Oncol., 20(11):2726-2735 (2002).

(Continued)

Primary Examiner — Niloofar Rahmani
(74) Attorney, Agent, or Firm — Mintz Levin Cohn Ferris Glovsky and Popeo, P.C.; Ivor R. Elrifi; Jennifer L. Loebach

(57) ABSTRACT

The present invention provides compounds and methods for treating or preventing the development of a disease, disorder, or condition in a subject or patient.

13 Claims, No Drawings

U.S. PATENT DOCUMENTS

| | | |
|---|---|---|
| 6,329,376 B1 | 12/2001 | Bergman |
| 6,358,961 B1 | 3/2002 | Angibaud et al. |
| 6,358,968 B1 | 3/2002 | Remiszewski et al. |
| 6,365,588 B1 | 4/2002 | Bishop et al. |
| 6,365,600 B1 | 4/2002 | End et al. |
| 6,387,903 B1 | 5/2002 | Dinsmore et al. |
| 6,387,926 B1 | 5/2002 | Bhide et al. |
| 6,388,092 B2 | 5/2002 | Yang |
| 6,407,137 B2 | 6/2002 | Shashoua |
| 6,420,122 B1 | 7/2002 | Housman et al. |
| 6,420,387 B1 | 7/2002 | Venet et al. |
| 6,444,812 B1 | 9/2002 | Venet et al. |
| 6,451,812 B1 | 9/2002 | End et al. |
| 6,455,523 B1 | 9/2002 | Ding et al. |
| 6,458,783 B1 | 10/2002 | Ding et al. |
| 6,458,800 B1 | 10/2002 | Angibaud et al. |
| 6,479,513 B2 | 11/2002 | Yang |
| 6,511,800 B1 | 1/2003 | Singh |
| 6,537,988 B2 | 3/2003 | Lee |
| 6,541,491 B1 | 4/2003 | Davies et al. |
| 6,545,020 B1 | 4/2003 | Van Ginckel et al. |
| 6,562,823 B1 | 5/2003 | Dinsmore et al. |
| 6,576,639 B1 | 6/2003 | Doll et al. |
| 6,579,887 B2 | 6/2003 | Lyssikatos et al. |
| 6,602,883 B1 | 8/2003 | Bhide et al. |
| 6,624,157 B2 | 9/2003 | Ding |
| 6,632,626 B1 | 10/2003 | Brown et al. |
| 6,645,966 B2 | 11/2003 | Windsor et al. |
| 6,645,982 B2 | 11/2003 | Lyssikatos et al. |
| 6,710,209 B2 | 3/2004 | Yang |
| 6,734,194 B2 | 5/2004 | End et al. |
| 6,734,308 B2 | 5/2004 | Lyssikatos et al. |
| 6,740,757 B2 | 5/2004 | Guinn et al. |
| 6,743,805 B2 | 6/2004 | End et al. |
| 6,784,198 B1 | 8/2004 | Pevarello et al. |
| 6,838,467 B2 | 1/2005 | End |
| 6,844,357 B2 | 1/2005 | Yang |
| 6,914,066 B2 | 7/2005 | Angibaud et al. |
| 7,049,058 B2 | 5/2006 | Singh |
| 7,053,105 B2 | 5/2006 | Angibaud et al. |
| 7,101,897 B2 | 9/2006 | Wardleworth et al. |
| 7,129,356 B2 | 10/2006 | Angibaud et al. |
| 7,153,958 B2 | 12/2006 | Angibaud et al. |
| 7,173,040 B2 | 2/2007 | Angibaud et al. |
| 7,176,315 B2 | 2/2007 | Guinn et al. |
| 7,196,094 B2 | 3/2007 | Angibaud et al. |
| 7,241,777 B2 | 7/2007 | Angibaud et al. |
| 7,253,183 B2 | 8/2007 | End et al. |
| 7,572,916 B2 | 8/2009 | Filliers et al. |
| 2001/0051642 A1 | 12/2001 | Ahn et al. |
| 2002/0002162 A1 | 1/2002 | Lee |
| 2002/0010184 A1 | 1/2002 | Dinsmore et al. |
| 2002/0022099 A1 | 2/2002 | Schmidt et al. |
| 2002/0035128 A1 | 3/2002 | Pratt |
| 2002/0043733 A1 | 4/2002 | Brady et al. |
| 2002/0052380 A1 | 5/2002 | Dinsmore et al. |
| 2002/0064142 A1 | 5/2002 | Antonio et al. |
| 2002/0068742 A1 | 6/2002 | Bishop et al. |
| 2002/0077301 A1 | 6/2002 | Daley et al. |
| 2002/0085364 A1 | 7/2002 | Downes et al. |
| 2002/0091138 A1 | 7/2002 | End et al. |
| 2002/0119981 A1 | 8/2002 | Remiszewski et al. |
| 2002/0136744 A1 | 9/2002 | McGlynn et al. |
| 2002/0151563 A1 | 10/2002 | Kajiji |
| 2002/0169313 A1 | 11/2002 | Gao et al. |
| 2003/0022918 A1 | 1/2003 | Horak et al. |
| 2003/0027808 A1 | 2/2003 | Palmer et al. |
| 2003/0027839 A1 | 2/2003 | Palmer et al. |
| 2003/0050323 A1 | 3/2003 | Rybak |
| 2003/0055065 A1 | 3/2003 | Bishop et al. |
| 2003/0060450 A1 | 3/2003 | End |
| 2003/0060480 A1 | 3/2003 | Horak et al. |
| 2003/0073677 A1 | 4/2003 | Lee |
| 2003/0078281 A1 | 4/2003 | Rybak |
| 2003/0092705 A1 | 5/2003 | Windsor et al. |
| 2003/0100553 A1 | 5/2003 | Palmer et al. |
| 2003/0125268 A1 | 7/2003 | Rybak |
| 2003/0125326 A1 | 7/2003 | Rybak |
| 2003/0134846 A1 | 7/2003 | Windsor et al. |
| 2003/0162965 A1 | 8/2003 | Kronenthal et al. |
| 2003/0162966 A1 | 8/2003 | Kano et al. |
| 2003/0181473 A1 | 9/2003 | Palmer et al. |
| 2003/0186925 A1 | 10/2003 | Palmer et al. |
| 2003/0199547 A1 | 10/2003 | Angibaud et al. |
| 2003/0207887 A1 | 11/2003 | Angibaud et al. |
| 2003/0212008 A1 | 11/2003 | Palmer et al. |
| 2003/0220241 A1 | 11/2003 | Defeo-Jones et al. |
| 2003/0232795 A1 | 12/2003 | McDonnell et al. |
| 2004/0006087 A1 | 1/2004 | Cutler et al. |
| 2004/0006091 A1 | 1/2004 | Kyle et al. |
| 2004/0019121 A1 | 1/2004 | Adamson et al. |
| 2004/0044032 A1 | 3/2004 | End et al. |
| 2004/0063770 A1 | 4/2004 | Ahn et al. |
| 2004/0127471 A1 | 7/2004 | Reisberg |
| 2004/0157773 A1 | 8/2004 | End |
| 2004/0181068 A1 | 9/2004 | Bhide |
| 2004/0194821 A1 | 10/2004 | Chittibabu et al. |
| 2004/0225077 A1 | 11/2004 | Gravett et al. |
| 2005/0154451 A1 | 7/2005 | Hezi-Yamit et al. |
| 2005/0272068 A1 | 12/2005 | Lansbury et al. |
| 2005/0272722 A1 | 12/2005 | Lansbury et al. |
| 2005/0277629 A1 | 12/2005 | Lansbury et al. |
| 2005/0288298 A1 | 12/2005 | Lansbury et al. |
| 2006/0052416 A1 | 3/2006 | Dickson et al. |
| 2006/0106060 A1 | 5/2006 | Lansbury et al. |
| 2006/0111398 A1 | 5/2006 | Fourie |
| 2006/0194821 A1 | 8/2006 | Lansbury et al. |
| 2007/0054886 A1 | 3/2007 | Kloog et al. |
| 2007/0213366 A1 | 9/2007 | Justman et al. |
| 2007/0287706 A1 | 12/2007 | Dickson et al. |
| 2007/0293539 A1 | 12/2007 | Lansbury et al. |
| 2008/0131375 A1 | 6/2008 | Gordon et al. |
| 2008/0139517 A1 | 6/2008 | Reisberg |
| 2008/0153758 A1 | 6/2008 | Schweighoffer et al. |
| 2008/0255171 A1 | 10/2008 | Manley |
| 2009/0048313 A1 | 2/2009 | Dickson, Jr. et al. |
| 2009/0082346 A1 | 3/2009 | Brasca et al. |
| 2009/0270465 A1 | 10/2009 | Albright et al. |

FOREIGN PATENT DOCUMENTS

| | | |
|---|---|---|
| EP | 1656931 A1 | 5/2006 |
| WO | WO-9410138 A1 | 5/1994 |
| WO | WO-9630343 A1 | 10/1996 |
| WO | WO-9630363 A1 | 10/1996 |
| WO | WO-9716443 A1 | 5/1997 |
| WO | WO-9721701 A1 | 6/1997 |
| WO | WO-9723478 A1 | 7/1997 |
| WO | WO-9730992 A1 | 8/1997 |
| WO | WO-9736587 A1 | 10/1997 |
| WO | WO-9736888 A1 | 10/1997 |
| WO | WO-9736889 A1 | 10/1997 |
| WO | WO-9738664 A2 | 10/1997 |
| WO | WO-9745412 A1 | 12/1997 |
| WO | WO-9804549 A1 | 2/1998 |
| WO | WO-9811092 A1 | 3/1998 |
| WO | WO-98/40383 A1 | 9/1998 |
| WO | WO-9844797 A1 | 10/1998 |
| WO | WO-9854966 A1 | 12/1998 |
| WO | WO-9855124 A1 | 12/1998 |
| WO | WO-9857948 A1 | 12/1998 |
| WO | WO-9857959 A1 | 12/1998 |
| WO | WO-9857962 A1 | 12/1998 |
| WO | WO-9857970 A1 | 12/1998 |
| WO | WO-9900654 A2 | 1/1999 |
| WO | WO-9901431 A1 | 1/1999 |
| WO | WO-9901434 A1 | 1/1999 |
| WO | WO-9908682 A1 | 2/1999 |
| WO | WO-9909985 A1 | 3/1999 |
| WO | WO-9910523 A1 | 3/1999 |
| WO | WO-9910524 A1 | 3/1999 |
| WO | WO-9910525 A1 | 3/1999 |
| WO | WO-9918951 A1 | 4/1999 |
| WO | WO-9933834 A1 | 7/1999 |
| WO | WO-0001386 A1 | 1/2000 |

| | | |
|---|---|---|
| WO | WO-0001411 A1 | 1/2000 |
| WO | WO-0001678 A1 | 1/2000 |
| WO | WO-0001691 A1 | 1/2000 |
| WO | WO-0001702 A1 | 1/2000 |
| WO | WO-0012499 A1 | 3/2000 |
| WO | WO-0016626 A1 | 3/2000 |
| WO | WO-0016778 A1 | 3/2000 |
| WO | WO-0025788 A1 | 5/2000 |
| WO | WO-0025789 A1 | 5/2000 |
| WO | WO-0031548 A1 | 6/2000 |
| WO | WO-0042849 A1 | 7/2000 |
| WO | WO-0047574 A1 | 8/2000 |
| WO | WO-0059930 A1 | 10/2000 |
| WO | WO-0070083 A1 | 11/2000 |
| WO | WO-0105430 A1 | 1/2001 |
| WO | WO-0107437 A1 | 2/2001 |
| WO | WO-0132149 A1 | 5/2001 |
| WO | WO-0146137 A1 | 6/2001 |
| WO | WO-0153289 A1 | 7/2001 |
| WO | WO-0156552 A2 | 8/2001 |
| WO | WO-0160368 A1 | 8/2001 |
| WO | WO-0160815 A1 | 8/2001 |
| WO | WO-0162234 A2 | 8/2001 |
| WO | WO-0164194 A2 | 9/2001 |
| WO | WO-0164195 A2 | 9/2001 |
| WO | WO-0164196 A2 | 9/2001 |
| WO | WO-0164197 A2 | 9/2001 |
| WO | WO-0164198 A2 | 9/2001 |
| WO | WO-0164199 A2 | 9/2001 |
| WO | WO-0164217 A2 | 9/2001 |
| WO | WO-0164218 A2 | 9/2001 |
| WO | WO-0164226 A2 | 9/2001 |
| WO | WO-0164246 A2 | 9/2001 |
| WO | WO-0164252 A2 | 9/2001 |
| WO | WO-0172721 A2 | 10/2001 |
| WO | WO-0176693 A1 | 10/2001 |
| WO | WO-0224683 A1 | 3/2002 |
| WO | WO-0224686 A2 | 3/2002 |
| WO | WO-0224687 A1 | 3/2002 |
| WO | WO-0228409 A2 | 4/2002 |
| WO | WO-0240015 A1 | 5/2002 |
| WO | WO-0243733 A1 | 6/2002 |
| WO | WO-0250058 A1 | 6/2002 |
| WO | WO-02056884 A2 | 7/2002 |
| WO | WO-02064142 A1 | 8/2002 |
| WO | WO-02072085 A1 | 9/2002 |
| WO | WO-02072574 A1 | 9/2002 |
| WO | WO-02078706 A1 | 10/2002 |
| WO | WO-02080895 A2 | 10/2002 |
| WO | WO-02085364 A1 | 10/2002 |
| WO | WO-02085819 A2 | 10/2002 |
| WO | WO-03018538 A1 | 3/2003 |
| WO | WO-03021355 A1 | 3/2003 |
| WO | WO-03041658 A2 | 5/2003 |
| WO | WO-03047586 A1 | 6/2003 |
| WO | WO-03072549 A1 | 9/2003 |
| WO | WO-03076660 A1 | 9/2003 |
| WO | WO-03080058 A1 | 10/2003 |
| WO | WO-03092671 A1 | 11/2003 |
| WO | WO-2004026246 A2 | 4/2004 |
| WO | WO-2004028541 A2 | 4/2004 |
| WO | WO-2004103352 A1 | 12/2004 |
| WO | WO-2005089496 A2 | 9/2005 |
| WO | WO-2005089502 A2 | 9/2005 |
| WO | WO-2005089504 A2 | 9/2005 |
| WO | WO-2005089515 A2 | 9/2005 |
| WO | WO-2005089518 A2 | 9/2005 |
| WO | WO-2005117864 A1 | 12/2005 |
| WO | WO-2006020767 A2 | 2/2006 |
| WO | WO-2006051423 A1 | 5/2006 |
| WO | WO-2006116716 A2 | 11/2006 |
| WO | WO-2007109251 A2 | 9/2007 |
| WO | WO-2007110709 A2 | 10/2007 |
| WO | WO-2007136592 A2 | 11/2007 |
| WO | WO-2008002621 A2 | 1/2008 |
| WO | WO-2008012511 A1 | 1/2008 |
| WO | WO-2008112525 A2 | 9/2008 |
| WO | WO-2008137692 A1 | 11/2008 |
| WO | WO-2009036275 A1 | 3/2009 |
| WO | WO-2009151683 A2 | 12/2009 |

OTHER PUBLICATIONS

El-Agnaf et al., "A strategy for designing inhibitors of α-synuclein aggregation and toxicity as a novel treatment for Parkinson's disease and related disorders", *FASEB J.*, express article 10.1096/fj.03-1346fje. Published online Jun. 4, 2004.

El-Agnaf et al., "Detection of oligomeric forms of alpha-synuclein protein in human plasma as a potential biomarker for Parkinson's disease", *FASEB J*, 20(3):419-425 (2006).

Elbaz et al., "S18Y polymorphism in the UCH-L1 gene and Parkinson's disease: evidence for an age-dependent relationship", *Mov. Disord.*, 18(2):130-137 (2003).

Emborg, M. E., "Evaluation of animal models of Parkinson's disease for neuroprotective strategies", *J. Neurosci. Meth.*, 139:121-143 (2004).

End et al., "Characterization of the antitumor effects of the selective farnesyl protein transferase inhibitor R115777 in vivo and in vitro", *Cancer Res.*, 61(1):131-137 (2001).

Ferrer et al., "[Alpha-synucleinopathies]", *Neurologia*, 16(4):163-170. (2001) (Abstract Only).

Hara et al., "Identification of Ras farnesyltransferase inhibitors by microbial screening", *Proc. Natl. Acad. Sci. U.S.A.*, 90(6):2281-2285 (1993).

Hibi et al., "PGP9.5 as a candidate tumor marker for non-small-cell lung cancer", *Am. J. Pathol.*, 155(3):711-715 (1999).

Huber et al., "Anions modulate the potency of geranylgeranyl-protein transferase I inhibitors", *J. Biol. Chem.*, 276(27):24457-24465 (2001), Epub Mar. 26, 2001.

Iwai, A., "Properties of NACP/alpha-synuclein and its role in Alzheimer's disease", *Biochim. Biophys. Acta*, 1502(1):95-109 (2000).

Johnston et al., Database CAPLUS on STN Online, No. 2003:161471, BMS-214662 Bristol-Myers Squibb, 6(1):1369-7056 (2003) (Abstract Only).

Johnston, S.R.D., "BMS-214662 Bristol-Myers Squibb", *IDrugs*, 6(1), 72-78 (2003).

Kawakami et al., "The rationale for E2020 as a potent acetylcholinesterase inhibitor", *Bioorg. Med. Chem.*, 4(9):1429-1446 (1996).

Kelland et al., "Preclinical antitumor activity and pharmacodynamic studies with the farnesyl protein transferase inhibitor R115777 in human breast cancer", *Clin. Cancer Res.*, 7:3544-3550 (2001).

Kelland et al., Database CAPLUS on STN Online, No. 2003:149630, "Farnesyl transferase inhibitors in the treatment of breast cancer", *Exp. Opin. Invest. Drugs*, 12(3):413-421 (2003) (Abstract Only).

Krab et al., "Oncogenes on my mind: ERK and MTOR signaling in cognitive diseases", *Trends in Genetics*, 24(10):498-510 (2008).

Lamango et al., "Farnesyl-l-cysteine analogs block SAM-induced Parkinson's disease-like symptoms in rats", *Pharma. Biochem. Beh.*, 66(4):841-849 (2000).

Liu et al. "Membrane-associated farnesylated UCH-L1 promotes α-synuclein neurotoxicity and is a therapeutic target for Parkinson's disease" *PNAS*, 106(12), pp. 4635-4640 (2009).

Liu et al., "Antitumor activity of SCH 66336, an orally bioavailable tricyclic inhibitor of farnesyl protein transferase, in human tumor xenograft models and wap-ras transgenic mice", *Cancer Res.*, 58(21):4947-4956 (1998).

Liu et al., "Discovery of inhibitors that elucidate the role of UCH-L1 activity in the H1299 lung cancer cell line", *Chem. Biol.*, 10(9):837-846 (2003).

Liu et al., "The UCH-L1 gene encodes two opposing enzymatic activities that affect alpha-synuclein degradation and Parkinson's disease susceptibility", *Cell*, 111(2):209-218 (2002).

Maguire-Zeiss, K. A., "α-Synuclein: A therapeutic target for Parkinson's disease?", *Pharmacol. Res.*, 58:272-280 (2008).

Maraganore et al., "Case-control study of the ubiquitin carboxy-terminal hydrolase LI gene in Parkinson's disease", *Neurology*, 53(8):1858-1860 (1999).

Maraganore et al., "Complex interactions in Parkinson's disease: a two-phased approach", *Mov. Disord.*, 18(6):631-636 (2003).

Martin et al., "The farneslytransferase inhibitor R115777 (tipifarnib) in combination with tamoxifen acts synergistically to inhibit MCF-7 breast cancer cell proliferation and cell cycle progression in vitro and in vivo", *Mol. Cancer Ther.*, 6(9):2458-2467 (2007).

Masliah et al., "Dopaminergic loss and inclusion body formation in alpha-synuclein mice: implications for neurodegenerative disorders", *Science*, 287(5456):1265-1269 (2000).

Masliah et al., β-Amyloid peptides enhance α-synuclein accumulation and neuronal deficits in a transgenic mouse model linking Alzheimer's disease and Parkinson's disease, *Proc. Natl. Acad. Sci. U.S.A.*, 98(21)12245-12250 (2001).

McNaught et al., "Impairment of the ubiquitin-proteasome system causes dopaminergic cell death and inclusion body formation in ventral mesencephalic cultures" *J. Neurochem.*, 81(2):301-306 (2002).

McNaught et al., "Proteasome inhibition causes nigral degeneration with inclusion bodies in rats", *Neuroreport*, 13(11):1437-1441 (2002).

Meredith et al., "Animal models of Parkinson's disease progression", *Acta Neuropathol.*, 115:385-398 (2008).

Morgan et al., "Emerging drugs for Parkinson's disease", *Exp. Opin. Emerging Drugs*, 11:403-417 (2006).

Njoroge et al., "(+)-4-[2-[4-(8-Chloro-3,10-dibromo-6,11-dihydro-5H-benzo[5,6]cyclohepta[1,2-b)-pyridin-11(R)-yl)-1-piperidinyl]-2-oxo-ethyl]-1-piperidinecarboxamide (SCH-66336): A very potent farnesyl protein transferase inhibitor as a novel antitumor agent", *J. Med. Chem.*, 41:4890-4902 (1998).

Olanow et al., "Lewy-body formation is an aggresome-related process: a hypothesis", *Lancet—Neurol.*, 3:496-503 (2004).

Ovaa et al., "Activity-based ubiquitin-specific protease (USP) profiling of virus-infected and malignant human cells", *Proc. Natl. Acad. Sci. U.S.A.*, 101(8) (2003).

Palmer et al., "Neuroprotection by NMDA receptor antagonists in a variety of neuropathologies", *Curr. Drug Targets*, 2(3):241-271 (2001).

Periquet et al., "Aggregated α-Synuclein Mediates Dopaminergic Neurotoxicity In Vivo", *J. Neurosci.*, 27(12):3338-3346 (2007).

Pickart, C. M., "Targeting of substrates to the 26S proteasome", *FASEB J.*, 11(13):1055-1066 (1997).

Pope et al., "The carcinogenic and toxic effects of tobacco smoke: Are women particularly susceptible?", *J. Gend. Specif. Med.*, 2(6):45-51 (1991).

Qiu et al., "The farnesyltransferase inhibitor R115777 up-regulates the expression of death receptor 5 and enhances TRAIL-induced apoptosis in human lung cancer cells", *Cancer Res.*, 67(10):4973-4980 (2007).

Rose et al., "Preclinical antitumor activity of BMS-214662, a highly apoptotic and novel farnesyltransferase inhibitor", *Cancer Res.*, 61(20):7507-7517 (2001).

Schellens et al., "Phase 1 and pharmacologic study with the novel farnesyltransferase inhibitor (FTI) R115777", *Proc. Am. Soc. Clin. Oncol.*, 19:715 (2000) (Abstract Only).

Singleton et al., "Alpha-Synuclein locus triplication causes Parkinson's disease", *Science*, 302(5646):841 (2003).

Stoessl, A. J., "Potential therapeutic targets for Parkinson's disease", *Exp. Opin. Thera. Drugs*, 12(4):425-436 (2008).

Tezel et al., "PGP9.5 as a prognostic factor in pancreatic cancer", *Clin. Cancer Res.*, 6(12):4764-4767 (2000).

Vanacore et al., "Mortality cancer risk in parkinsonian patients: a population-based study", *Neurology*, 52(2):395-398 (1999).

Verslype et al., "Phase I trial of 5-FU/LV in combination with the farnesyltransferase inhibitor (FTI) R115777", *Proc. Am. Soc. Clin. Oncol.*, 20:681 (2001) (Abstract Only).

Wallace et al., "Selection of potent inhibitors of farnesyl-protein transferase from a synthetic tetrapeptide combinatorial library", *J. Biol. Chem.*, 271(49):31306-31311 (1996).

Warnberg et al., "Effect of a farnesyl transferase inhibitor (R115777) on ductal carcinoma in situ of the breast in a human xenograft model and on breast and ovarian cancer cell growth in vitro and in vivo", *Breast Cancer Res.*, 8(2):R21 (2006) Epub Apr. 12, 2006.

Yamazaki et al., "PGP9.5 as a marker for invasive colorectal cancer", *Clin. Cancer Res.*, 8(1):192-195 (2002).

Bishop et al., "Novel Tricyclic Inhibitors of Farnesyl Protein Transferase", *The Journal of Biological Chemistry*, 270(51), 30611-30618 (1995).

* cited by examiner

SEQUENCE LISTING

<160> NUMBER OF SEQ ID NOS: 23

<210> SEQ ID NO 1
<211> LENGTH: 20
<212> TYPE: DNA
<213> ORGANISM: Artificial sequence
<220> FEATURE:
<223> OTHER INFORMATION: Chemically synthesized primer

<400> SEQUENCE: 1
aacggatttg gtcgtattgg          20

<210> SEQ ID NO 2
<211> LENGTH: 20
<212> TYPE: DNA
<213> ORGANISM: Artificial sequence
<220> FEATURE:
<223> OTHER INFORMATION: Chemically synthesized primer

<400> SEQUENCE: 2
gctcctggaa gatggtgatg          20

<210> SEQ ID NO 3

```
<211> LENGTH: 20
<212> TYPE: DNA
<213> ORGANISM: Artificial sequence
<220> FEATURE:
<223> OTHER INFORMATION: Chemically synthesized primer

<400> SEQUENCE: 3
aagccatcaa ggtgatgagg                                                    20

<210> SEQ ID NO 4
<211> LENGTH: 20
<212> TYPE: DNA
<213> ORGANISM: Artificial sequence
<220> FEATURE:
<223> OTHER INFORMATION: Chemically synthesized primer

<400> SEQUENCE: 4
ggtcacacgc cacataacag                                                    20

<210> SEQ ID NO 5
<211> LENGTH: 22
<212> TYPE: DNA
<213> ORGANISM: Artificial sequence
<220> FEATURE:
<223> OTHER INFORMATION: Chemically synthesized primer

<400> SEQUENCE: 5
atcacctagt ccaccactgt cc                                                 22

<210> SEQ ID NO 6
<211> LENGTH: 19
<212> TYPE: DNA
<213> ORGANISM: Artificial sequence
<220> FEATURE:
<223> OTHER INFORMATION: Chemically synthesized primer

<400> SEQUENCE: 6
gtatctacca tccgccatc                                                     19

<210> SEQ ID NO 7
<211> LENGTH: 20
<212> TYPE: DNA
<213> ORGANISM: Artificial sequence
<220> FEATURE:
<223> OTHER INFORMATION: Chemically synthesized primer

<400> SEQUENCE: 7
ttatgtcatg tcgggtgtgg                                                    20

<210> SEQ ID NO 8
<211> LENGTH: 19
<212> TYPE: DNA
<213> ORGANISM: Artificial sequence
<220> FEATURE:
<223> OTHER INFORMATION: Chemically synthesized primer

<400> SEQUENCE: 8
acaggtgtag ggctctgtg                                                     19

<210> SEQ ID NO 9
<211> LENGTH: 20
<212> TYPE: DNA
<213> ORGANISM: Artificial sequence
<220> FEATURE:
<223> OTHER INFORMATION: Chemically synthesized primer

<400> SEQUENCE: 9
```

-continued

| | |
|---|---|
| gaggaaagca gaggtgatgc | 20 |

<210> SEQ ID NO 10
<211> LENGTH: 20
<212> TYPE: DNA
<213> ORGANISM: Artificial sequence
<220> FEATURE:
<223> OTHER INFORMATION: Chemically synthesized primer

<400> SEQUENCE: 10

| | |
|---|---|
| gaggcaacct gaccagaaac | 20 |

<210> SEQ ID NO 11
<211> LENGTH: 20
<212> TYPE: DNA
<213> ORGANISM: Artificial sequence
<220> FEATURE:
<223> OTHER INFORMATION: Chemically synthesized primer

<400> SEQUENCE: 11

| | |
|---|---|
| ggttgagaaa ggcgagacac | 20 |

<210> SEQ ID NO 12
<211> LENGTH: 20
<212> TYPE: DNA
<213> ORGANISM: Artificial sequence
<220> FEATURE:
<223> OTHER INFORMATION: Chemically synthesized primer

<400> SEQUENCE: 12

| | |
|---|---|
| tgaggacacc caagcaagac | 20 |

<210> SEQ ID NO 13
<211> LENGTH: 20
<212> TYPE: DNA
<213> ORGANISM: Artificial sequence
<220> FEATURE:
<223> OTHER INFORMATION: Chemically synthsized primer

<400> SEQUENCE: 13

| | |
|---|---|
| gaacatggtg ctggtttcct | 20 |

<210> SEQ ID NO 14
<211> LENGTH: 20
<212> TYPE: DNA
<213> ORGANISM: Artificial sequence
<220> FEATURE:
<223> OTHER INFORMATION: Chemically synthesized primer

<400> SEQUENCE: 14

| | |
|---|---|
| catccagggt actgggctaa | 20 |

<210> SEQ ID NO 15
<211> LENGTH: 20
<212> TYPE: DNA
<213> ORGANISM: Artificial sequence
<220> FEATURE:
<223> OTHER INFORMATION: Chemically synthesized primer

<400> SEQUENCE: 15

| | |
|---|---|
| agggacaacc ctaacacgac | 20 |

<210> SEQ ID NO 16
<211> LENGTH: 20
<212> TYPE: DNA
<213> ORGANISM: Artificial sequence
<220> FEATURE:

```
<223> OTHER INFORMATION: Chemically synthesized primer

<400> SEQUENCE: 16
agcaggagaa agacgaggac                                               20

<210> SEQ ID NO 17
<211> LENGTH: 20
<212> TYPE: DNA
<213> ORGANISM: Artificial sequence
<220> FEATURE:
<223> OTHER INFORMATION: Chemically synthesized primer

<400> SEQUENCE: 17
gaagctgcaa cacagactgc                                               20

<210> SEQ ID NO 18
<211> LENGTH: 20
<212> TYPE: DNA
<213> ORGANISM: Artificial sequence
<220> FEATURE:
<223> OTHER INFORMATION: Chemically synthesized primer

<400> SEQUENCE: 18
ttgaatgact agccgggaac                                               20

<210> SEQ ID NO 19
<211> LENGTH: 20
<212> TYPE: DNA
<213> ORGANISM: Artificial sequence
<220> FEATURE:
<223> OTHER INFORMATION: Chemically synthesized primer

<400> SEQUENCE: 19
gcatggccat cttctctttc                                               20

<210> SEQ ID NO 20
<211> LENGTH: 20
<212> TYPE: DNA
<213> ORGANISM: Artificial sequence
<220> FEATURE:
<223> OTHER INFORMATION: Chemically synthesized primer

<400> SEQUENCE: 20
tggatgggac tccatagctc                                               20

<210> SEQ ID NO 21
<211> LENGTH: 6
<212> TYPE: PRT
<213> ORGANISM: Artificial sequence
<220> FEATURE:
<223> OTHER INFORMATION: Synuclein repeat

<400> SEQUENCE: 21

Lys Thr Lys Glu Gly Val
1               5

<210> SEQ ID NO 22
<211> LENGTH: 5
<212> TYPE: PRT
<213> ORGANISM: Artificial sequence
<220> FEATURE:
<223> OTHER INFORMATION: Dansyl-pentapeptide
<220> FEATURE:
<221> NAME/KEY: MISC_FEATURE
<222> LOCATION: (1)..(5)
<223> OTHER INFORMATION: wherein said peptide is a dansyl-pentapeptide.

<400> SEQUENCE: 22
```

```
Gly Cys Val Leu Ser
1               5

<210> SEQ ID NO 23
<211> LENGTH: 4
<212> TYPE: PRT
<213> ORGANISM: Artificial sequence
<220> FEATURE:
<223> OTHER INFORMATION: farnesylation sequence

<400> SEQUENCE: 23

Cys Lys Ala Ala
1
```

AZAQUINOLINONE DERIVATIVES AND USES THEREOF

RELATED APPLICATIONS

This application claims priority to U.S. Application No. 61/114,303, filed Nov. 13, 2008 and U.S. Application No. 61/231,434, filed Aug. 5, 2009. The entire contents of the above-identified applications are hereby incorporated by reference.

BACKGROUND

A variety of disorders are associated with abnormal protein folding and/or aggregation. For example, several neurodegenerative diseases and/or conditions associated with congnitive impairment are often characterized by intracellular and/or extracellular accumulation of specific proteins. To give but a couple of examples, Alzheimer's disease (AD) and Parkinson's Disease both involve abnormal protein folding and/or aggregation of specific proteins.

Pharmacologic treatment of neurodegenerative diseases such as Parkinson's disease and AD specifically, and of cognitive impairment and dementia more generally may be divided into three main areas: pharmacologic interventions targeting the specific underlying pathophysiology; pharmacological agents that ameliorate specific symptoms; and behavioral interventions. There remains a need for improved pharmacologic approaches in the treatment and prevention of neurodegenerative diseases.

SUMMARY

The present invention encompasses the finding that certain aminopyrrolidinone derivatives are useful in therapeutic and other applications, including those described herein. In certain embodiments, provided compounds are of formula I:

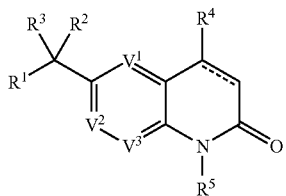

or a pharmaceutically acceptable salt thereof, wherein each of $R^1$, $R^2$, $R^3$, $R^4$, $R^5$, $V^1$, $V^2$, $V^3$ and ----- is as defined and described herein.

The present invention also provides methods of preparing such compounds and various compositions and uses of such compounds.

The present invention provides a compound or pharmaceutically acceptable salt thereof, wherein $V^3$ is N.

The present invention provides a compound or pharmaceutically acceptable salt thereof of any one of formulae I-a, I-b, or I-c:

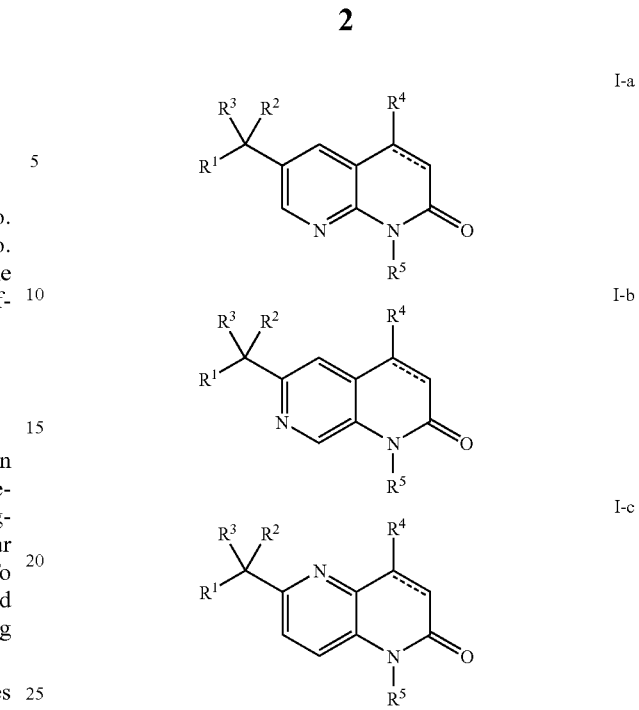

or a pharmaceutically acceptable salt thereof.

The present invention provides a compound or a pharmaceutically acceptable salt thereof, wherein ----- is a double bond.

The present invention provides a compound or a pharmaceutically acceptable salt thereof, wherein $R^1$ is phenyl, and wherein $R^1$ is optionally substituted with 0, 1, 2, 3, 4, or 5 —$R^w$.

The present invention provides a compound or a pharmaceutically acceptable salt thereof, wherein $R^3$ is a 5 membered monocyclic heteroaryl ring having 1, 2, or 3 heteroatoms independently selected from nitrogen, oxygen, and sulfur, and optionally substituted with 1 or 2 $R^x$ groups.

The present invention provides a compound or a pharmaceutically acceptable salt thereof, wherein $R^4$ is phenyl substituted with 0, 1, 2, or 3 $R^y$ groups.

The present invention provides a compound of formula I-q:

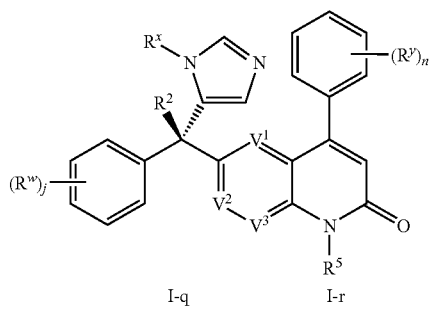

or a pharmaceutically acceptable salt thereof.

The present invention provides a compound or a pharmaceutically acceptable salt thereof, wherein at least one $R^w$ group is independently selected from the group consisting of R, halogen, —OR, —N(R')$_2$, and —C(R)$_3$.

The present invention provides a compound or a pharmaceutically acceptable salt thereof, wherein $R^2$ is selected from the group consisting of —OR, halogen, and —N(R')$_2$.

The present invention provides a compound or a pharmaceutically acceptable salt thereof, wherein at least one $R^x$ group is independently selected from methyl, ethyl, propyl, and butyl.

The present invention provides a compound or a pharmaceutically acceptable salt thereof, wherein at least one $R^y$ group is independently selected from halogen, acetylene, and —OR.

The present invention provides a compound or a pharmaceutically acceptable salt thereof, wherein $R^5$ is an acyclic $C_{1-12}$ aliphatic moiety.

The present invention provides a compound having any one of the following structures shown in Table 1 (shown below) or a pharmaceutically acceptable salt thereof.

The present invention provides a pharmaceutical composition comprising a compound of the invention or a pharmaceutically acceptable salt thereof, and a pharmaceutically acceptable excipient.

The present invention provides a compound of the invention or a pharmaceutically acceptable salt thereof for use in a method of treating or preventing a proteinopathy, the method comprising administering the compound or pharmaceutically acceptable salt thereof in a therapeutically effective amount to a subject in need thereof. The present invention provides a method of treating or preventing a proteinopathy, the method comprising administering a compound, pharmaceutically acceptable salt or composition of the invention in a therapeutically effective amount to a subject in need thereof.

The present invention provides the use of a compound of the invention or a pharmaceutically acceptable salt thereof in the manufacture of a medicament for treating or preventing a proteinopathy in a subject in need thereof.

The present invention provides a compound of the invention or pharmaceutically acceptable salt thereof (or the use of a compound of the invention or pharmaceutically acceptable salt thereof), wherein the proteinopathy is selected from neurodegenerative disease, proliferative disease, inflammatory disease, and cardiovascular disease. The present invention provides a method, wherein the proteinopathy is selected from neurodegenerative disease, proliferative disease, inflammatory disease, and cardiovascular disease.

The present invention provides a compound of the invention or a pharmaceutically acceptable salt (or the use of a compound of the invention or a pharmaceutically acceptable salt), wherein the proteinopathy is a synucleinopathy. The present invention provides a method, wherein the proteinopathy is a synucleinopathy.

The present invention provides a compound of the invention or pharmaceutically acceptable salt thereof (or use of a compound of the invention or pharmaceutically acceptable salt thereof), wherein the proteinopathy is a synucleinopathy selected from the group consisting of Parkinson's disease, diffuse Lewy body disease, and multiple system atrophy disorder. The present invention provides a method wherein the proteinopathy is selected from the group consisting of Parkinson's disease, diffuse Lewy body disease, and multiple system atrophy disorder.

The present invention provides a compound of the invention or a pharmaceutically acceptable salt thereof (or use of compound of the invention or a pharmaceutically acceptable salt thereof), wherein the proteinopathy is an amyloidopathy. The present invention provides a method wherein the proteinopathy is an amyloidopathy.

The present invention provides a compound of the invention or pharmaceutically acceptable salt thereof (or use of a compound of the invention or pharmaceutically acceptable salt thereof), wherein the proteinopathy is an amyloidopathy selected from the group consisting of atherosclerosis, stroke, cerebrovascular disease, vascular dementia, multi-infarct dementia, Parkinson's disease and Parkinson's disease dementia, Lewy body disease, Pick's disease, Alzheimer's disease, mild cognitive impairment, Huntington's disease, AIDS and AIDS-related dementia, brain neoplasms, brain lesions, epilepsy, multiple sclerosis, Down's syndrome, Rett's syndrome, progressive supranuclear palsy, frontal lobe syndrome, schizophrenia, traumatic brain injury, post coronary artery by-pass graft surgery, cognitive impairment due to electroconvulsive shock therapy, cognitive impairment due to chemotherapy, cognitive impairment due to a history of drug abuse, attention deficit disorder (ADD), attention deficit hyperactivity disorder (ADHD), autism, dyslexia, depression, bipolar disorder, post-traumatic stress disorder, apathy, myasthenia gravis, cognitive impairment during waking hours due to sleep apnea, Tourette's syndrome, autoimmune vasculitis, systemic lupus erythematosus, polymyalgia rheumatica, hepatic conditions, metabolic diseases, Kufs' disease, adrenoleukodystrophy, metachromatic leukodystrophy, storage diseases, infectious vasculitis, syphillis, neurosyphillis, Lyme disease, complications from intracerebral hemorrhage, hypothyroidism, B12 deficiency, folic acid deficiency, niacin deficiency, thiamine deficiency, hydrocephalus, complications post anoxia, prion disease (Creutzfeldt-Jakob disease), Fragile X syndrome, phenylketonuria, malnutrition, neurofibromatosis, maple syrup urine disease, hypercalcemia, hypothyroidism, hypercalcemia, and hypoglycemia. The present invention provides a method, wherein the proteinopathy is an amyloidopathy selected from one of the amyloidopathies listed above.

The present invention provides a compound of the invention or a pharmaceutically acceptable salt thereof (or use of a compound of the invention or a pharmaceutically acceptable salt thereof), wherein the proteinopathy is a taupathy. The present invention provides a method, wherein the proteinopathy is a taupathy.

The present invention provides a compound of the invention or a pharmaceutically acceptable salt thereof (or use of a compound of the invention or a pharmaceutically acceptable salt thereof), wherein the proteinopathy is a taupathy comprises a taupathy selected from the group consisting of atherosclerosis, stroke, cerebrovascular disease, vascular dementia, multi-infarct dementia, Parkinson's disease and Parkinson's disease dementia, Lewy body disease, Pick's disease, Alzheimer's disease, mild cognitive impairment, Huntington's disease, AIDS and AIDS-related dementia, brain neoplasms, brain lesions, epilepsy, multiple sclerosis, Down's syndrome, Rett's syndrome, progressive supranuclear palsy, frontal lobe syndrome, schizophrenia, traumatic brain injury, post coronary artery by-pass graft surgery, cognitive impairment due to electroconvulsive shock therapy, cognitive impairment due to chemotherapy, cognitive impairment due to a history of drug abuse, attention deficit disorder (ADD), attention deficit hyperactivity disorder (ADHD), autism, dyslexia, depression, bipolar disorder, post-traumatic stress disorder, apathy, myasthenia gravis, cognitive impairment during waking hours due to sleep apnea, Tourette's syndrome, autoimmune vasculitis, systemic lupus erythematosus, polymyalgia rheumatica, hepatic conditions, metabolic diseases, Kufs' disease, adrenoleukodystrophy, metachromatic leukodystrophy, storage diseases, infectious vasculitis, syphillis, neurosyphillis, Lyme disease, complications from intracerebral hemorrhage, hypothyroidism, B12 deficiency, folic acid deficiency, niacin deficiency, thiamine deficiency, hydrocephalus, complications post anoxia, prion disease (Creutzfeldt-Jakob disease), Fragile X syndrome, phenylketonuria, malnutrition, neurofibromatosis, maple syrup urine disease, hypercalcemia, hypothyroidism, hypercalcemia, and hypoglycemia. The present invention provides a method, wherein the proteinopathy is an taupathy selected from one of the taupathies listed above.

The present invention provides a compound of the invention or pharmaceutically acceptable salt thereof (or use of a compound of the invention or pharmaceutically acceptable salt thereof), wherein the treating or preventing comprises administering to the subject in need thereof a compound of the invention or a pharmaceutically acceptable salt thereof and one or more non-farnesyl transferase inhibitor compounds. The present invention provides a method further comprising administering to the subject a compound of the invention or a pharmaceutically acceptable salt thereof and an amount of one or more non-farnesyl transferase inhibitor compounds effective to treat or prevent the proteinopathy.

The present invention provides the use of a compound of the invention or a pharmaceutically acceptable salt thereof in the manufacture of a medicament for treating or preventing a proteinopathy in a subject in need thereof, further wherein the medicament comprises the compound of the invention or a pharmaceutically acceptable salt thereof and a non-farnesyl transferase inhibitor as two separate separate pharmaceutical formulations.

The present invention provides the use of a compound of the invention or a pharmaceutically acceptable salt thereof in the manufacture of a medicament for treating or preventing a proteinopathy in a subject in need thereof, further wherein the medicament comprises the compound of the invention or a pharmaceutically acceptable salt thereof and a non-farnesyl transferase inhibitor as a single pharmaceutical formulation comprising both moieties.

The present invention provides a compound of the invention or pharmaceutically acceptable salt thereof, wherein the method of treating or preventing a proteinopathy, further comprises each non-farnesyl transferase inhibitor compound to be selected from the group consisting of dopamine agonist, DOPA decarboxylase inhibitor, dopamine precursor, monoamine oxidase blocker, cathechol O-methyl transferase inhibitor, anticholinergic, and NMDA antagonist. The present invention provides a method, wherein each non-farnesyl transferase inhibitor is selected from the list above.

The present invention provides a compound of the invention or pharmaceutically acceptable salt thereof (or use of a compound of the invention or pharmaceutically acceptable salt thereof), wherein the treating or preventing comprises administering to the subject in need thereof a compound of the invention or a pharmaceutically acceptable salt thereof and one or more agents selected from the group consisting of one or more treatments for Parkinson's Disease such as L-DOPA/carbidopa, entacapone, ropinrole, pramipexole, bromocriptine, pergolide, trihexephendyl, amantadine, levodopa, carbodopa, levodopa (Sinemet and Sinemet CR), Stalevo (carbodopa, levodopa, and entacapone), anticholinergics (trihexyphenidyl, benztropine mesylate, procyclidine, artane, cogentin), bromocriptidine (Parlodel), pergolide (Permax), ropinirol (Requip), pramipexole (Mirapex), cabergoline (Dostinex), apomorphine (Apokyn), rotigotine (Neupro), Ergolide, Mirapex and Requip. The present invention provides a method, wherein the agent is selected from the list above.

The present invention provides the use of a compound of the invention or a pharmaceutically acceptable salt thereof in the manufacture of a medicament for treating or preventing a proteinopathy in a subject in need thereof, further wherein the medicament comprises the compound of the invention or a pharmaceutically acceptable salt thereof and one or more agents selected from the group consisting of one or more treatments for Parkinson's Disease such as L-DOPA/carbidopa, entacapone, ropinrole, pramipexole, bromocriptine, pergolide, trihexephendyl, amantadine, levodopa, carbodopa, levodopa (Sinemet and Sinemet CR), Stalevo (carbodopa, levodopa, and entacapone), anticholinergics (trihexyphenidyl, benztropine mesylate, procyclidine, artane, cogentin), bromocriptidine (Parlodel), pergolide (Permax), ropinirol (Requip), pramipexole (Mirapex), cabergoline (Dostinex), apomorphine (Apokyn), rotigotine (Neupro), Ergolide, Mirapex and Requip as two separate separate pharmaceutical formulations.

The present invention provides the use of a compound of the invention or a pharmaceutically acceptable salt thereof in the manufacture of a medicament for treating or preventing a proteinopathy in a subject in need thereof, further wherein the medicament comprises the compound of the invention or a pharmaceutically acceptable salt thereof and one or more agents selected from the group consisting of one or more treatments for Parkinson's Disease such as L-DOPA/carbidopa, entacapone, ropinrole, pramipexole, bromocriptine, pergolide, trihexephendyl, amantadine, levodopa, carbodopa, levodopa (Sinemet and Sinemet CR), Stalevo (carbodopa, levodopa, and entacapone), anticholinergics (trihexyphenidyl, benztropine mesylate, procyclidine, artane, cogentin), bromocriptidine (Parlodel), pergolide (Permax), ropinirol (Requip), pramipexole (Mirapex), cabergoline (Dostinex), apomorphine (Apokyn), rotigotine (Neupro), Ergolide, Mirapex and Requip as a single pharmaceutical formulation comprising both moieties.

DETAILED DESCRIPTION OF CERTAIN EMBODIMENTS OF THE INVENTION

1. General Description of Compounds of the Invention

In certain embodiments, the present invention provides a compound of formula I:

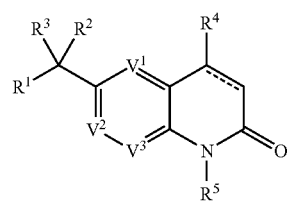

or a pharmaceutically acceptable salt thereof, wherein:
----- is a single or double bond;
each of $V^1$, $V^2$, and $V^3$ is independently CH or N, wherein at least one of $V^1$, $V^2$, or $V^3$ is N;
$R^1$ is phenyl, a 5-6 membered monocyclic heteroaryl ring having 1-4 heteroatoms independently selected from nitrogen, oxygen, or sulfur, or an 8-10 membered bicyclic ring having 0-4 heteroatoms independently selected from nitrogen, oxygen, or sulfur, and wherein $R^1$ is optionally substituted with $-(R^w)_j$, wherein j is 0-5;
each $R^w$ is independently selected from —R, halogen, —OR, —CN, —NO$_2$, —SR, —S(O)R, —SO$_2$R', —SO$_2$N(R')$_2$, —C(O)R, —CO$_2$R, —OC(O)R, —OC(O)N(R')$_2$, —C(O)N(R')$_2$, —NR'C(O)R, —NR'C(O)N(R')$_2$, —NR'SO$_2$R, —N(R')$_2$, —C(R)$_3$, or —Si(R)$_3$;

each R is independently hydrogen, deuterium, or an optionally substituted group selected from $C_{1-12}$ aliphatic, phenyl, a 5-6 membered monocyclic heteroaryl ring having 1-4 heteroatoms independently selected from nitrogen, oxygen, or sulfur, or an 8-10 membered bicyclic aryl ring having 0-4 heteroatoms independently selected from nitrogen, oxygen, or sulfur, or wherein:
  two R on the same nitrogen are taken together to form a 5-6 membered saturated, partially saturated, or aromatic ring having 1-3 heteroatoms independently selected from nitrogen, oxygen, and sulfur;
each R' is independently selected from R, —C(O)R, —CO$_2$R—, —S(O)R, and —SO$_2$R;
$R^2$ is —R, halogen, —OR, —CN, —NO$_2$, —SR, —S(O)R, —SO$_2$R, —SO$_2$N(R')$_2$, —C(O)R, —CO$_2$R, —C(R)$_2$CO$_2$R, —OC(O)R, —OC(O)N(R')$_2$, —C(O)N(R')$_2$, —NR'C(O)R, —NR'C(O)N(R')$_2$, —NR'SO$_2$R, —N(R')$_2$, —C(R)$_3$, —Si(R)$_3$, —OPO$_3$H$_2$, —OCH$_2$OPO$_3$H$_2$, or —OCH$_2$OC(O)(CH$_2$)$_k$CH$_3$, wherein k is 0-12;
$R^3$ is phenyl, a 5-6 membered monocyclic heteroaryl ring having 1-4 heteroatoms independently selected from nitrogen, oxygen, or sulfur, or an 8-10 membered bicyclic ring having 0-4 heteroatoms independently selected from nitrogen, oxygen, or sulfur, wherein $R^3$ is optionally substituted with —(R$^x$)$_m$, wherein m is 0-5, or:
$R^3$ is —(CH$_2$)$_p$R$^z$— wherein R$^z$ is selected from N-hydroxyurea, —CO$_2$R, —C(O)C(O)NHMe, —NHCHO, —NHC(O)CH$_2$SH, —NHC(O)NHNH$_2$, NHC(O)CH$_2$Br, —NHC(O)CH$_2$SAc, or —NHC(O)CH$_2$OH,

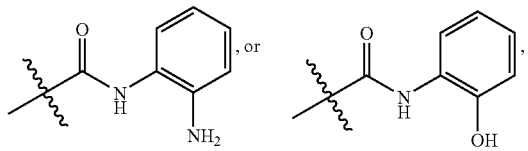 [SMILES: *C(=O)Nc1ccccc1N ; *C(=O)Nc1ccccc1O]

and wherein p is 0-5;
each R$^x$ is independently selected from —R, halogen, —OR, —CN, —NO$_2$, —SR, —S(O)R, —SO$_2$R, —SO$_2$N(R')$_2$, —C(O)R, —CO$_2$R, —OC(O)R, —OC(O)N(R')$_2$, —C(O)N(R')$_2$, —NR'C(O)R, —NR'C(O)N(R')$_2$, —NR'SO$_2$R, —N(R')$_2$, —C(R)$_3$, —Si(R)$_3$, or an optionally substituted benzyl group;
$R^4$ is phenyl, a 5-6 membered monocyclic heteroaryl ring having 1-4 heteroatoms independently selected from nitrogen, oxygen, or sulfur, or an 8-10 membered bicyclic ring having 0-4 heteroatoms independently selected from nitrogen, oxygen, or sulfur, and wherein $R^4$ is optionally substituted with —(R$^y$)$_n$, wherein n is 0-4;
each R$^y$ is independently selected from —R, halogen, —OR, —CN, —NO$_2$, —SR, —S(O)R, —SO$_2$R, —SO$_2$N(R')$_2$, —C(O)R, —CO$_2$R, —OC(O)R, —OC(O)N(R')$_2$, —C(O)N(R')$_2$, —NR'C(O)R, —NR'C(O)N(R')$_2$, —NR'SO$_2$R, —N(R')$_2$, —C(R)$_3$, or —Si(R)$_3$; and
$R^5$ is R'.

2. Definitions

As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, genetically-engineered animal, and/or a clone.

As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value).

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

As used herein, the term "in vitro" refers to events that occur in an artificial environment, e.g., in a test tube or reaction vessel, in cell culture, etc., rather than within an organism (e.g., animal, plant, and/or microbe).

As used herein, the term "in vivo" refers to events that occur within an organism (e.g., animal, plant, and/or microbe).

As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, at least 4, at least 5, at least 6, at least 7, at least 8, at least 9, at least 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

As used herein, the term "patient" or "subject" refers to any organism to which a composition of this invention may be administered, e.g., for experimental, diagnostic, prophylactic, and/or therapeutic purposes. Typical subjects include animals (e.g., mammals such as mice, rats, rabbits, non-human primates, and humans; insects; worms; etc.). In some embodiments, a subject may be infected with, suffering from, and/or susceptible to a disease, disorder, and/or condition, and/or may be of normal genotype, or have one or more engineered transgenes inserted in their genome.

As used herein, the term "synucleinopathic subject" or "subject with a synucleinopathy" refers to a subject that is diagnosed with, affected by, or at risk of developing a synucleinopathy (e.g., predisposed or susceptible, for example genetically predisposed, to developing a synucleinopathy) and/or any neurodegenerative disorder characterized by pathological synuclein aggregations. In one aspect, a synucleinopathic subject is diagnosed with a synucleinopathy. In one aspect, a synucleinopathic subject is affected by a synucleinopathy. In one aspect, a synucleinopathic subject is at risk of developing a synucleinopathy. Several neurodegenerative disorders including Parkinson's disease, diffuse Lewy body disease (DLBD), and multiple system atrophy (MSA) are collectively grouped as synucleinopathies. Subjects suffering from or susceptible to synucleinopathies can be readily identified by persons of ordinary skill in the art by symptomatic diagnosis and neurologic examination and/or in some instances in conjunction with genetic screening, brain scans, SPEC, PET imaging, etc.

The term "synucleionopathy" is used herein to refer to diseases, disorders, or conditions that are associated with or characterized by pathological accumulation of α-synuclein. According to the present invention, disorders such as (but not limited to) PD, DLBD, and MSA are considered to be synucleinopathies.

As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence) or can be a portion, e.g., a characteristic portion, thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

As used herein, the term "proteinopathy" refers to diseases, disorders, and/or conditions associated with the pathogenic accumulation and/or aggregation of one or more types of proteins (for example, but not invited to e.g., α-synuclein, amyloid beta proteins, and/or tau proteins). In some embodiments, a proteinopathy may involve alterations in one or more of protein folding, depredation (e.g., autophagy) transportation, etc. Some proteinopathies may be neurodegenerative diseases, some may be inflammatory diseases, some may be cardiovascular diseases, some may be proliferative diseases, etc. Included under the umbrella definition of proteinopathies are such specific pathologies as synucleinopathies, tauopathies, amyloidopathies, TDP-43 proteinopathies and others. Exemplary proteins involved in proteinopathies include: α-synuclein in the case of PD, Lewy body disease, and other synucleinopathies; Tau and Aβ in the case of AD and certain other neurodegenerative diseases; SOD1 and TDP-43 in the case of ALS; huntingtin in the case of Huntington's disease, rhodopsin in the case of retinitis pigmentosa, and a number of proteins in the case of the diseases collectively known as lysosomal storage disease. Indeed, in lysosomal storage diseases, there is often an accumulation of certain lipids eg glucosylceramide or cholesterol, or of certain proteins (e.g., subunit c of ATP synthase), or of certain damaged organelles or organelle fragments eg fragmented mitochondria.

In general, a "small molecule" is understood in the art to be an organic molecule that is less than about 2000 g/mol in size. In some embodiments, the small molecule is less than about 1500 g/mol or less than about 1000 g/mol. In some embodiments, the small molecule is less than about 800 g/mol or less than about 500 g/mol. In some embodiments, small molecules are non-polymeric and/or non-oligomeric. In some embodiments, small molecules are not proteins, peptides, or amino acids. In some embodiments, small molecules are not nucleic acids or nucleotides. In some embodiments, small molecules are not saccharides or polysaccharides.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

An individual who is "suffering from" a disease, disorder, and/or condition has been diagnosed with and/or displays one or more symptoms of a disease, disorder, and/or condition.

An individual who is "susceptible to" a disease, disorder, and/or condition typically has not been diagnosed with a disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

In some embodiments, an individual is considered to be susceptible to a particular disease, disorder, and/or condition because that individual is determined to have an increased risk of developing the disease, disorder, or condition than is observed in the general population.

As used herein, the phrase "therapeutic agent" refers to any agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of reduce severity of, and/or reduce incidence of one or more symptoms or features of a disease, disorder, and/or condition.

As used herein, the term "therapeutically effective amount" means an amount of a substance (e.g., a therapeutic agent, composition, and/or formulation) that elicits a desired biological response. In some embodiments, a therapeutically effective amount of a substance is an amount that is sufficient, when administered to a subject suffering from or susceptible to a disease, disorder, and/or condition, to treat, diagnose, prevent, and/or delay and/or alleviate one or more symptoms of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of a formulation to treat a disease, disorder, and/or condition is the amount that alleviates, ameliorates, relieves, inhibits, prevents, delays onset of reduces severity of and/or reduces incidence of one or more symptoms or features of the disease, disorder, and/or condition. Furthermore, an effective amount may be administered via a single dose or via multiple doses within a treatment regimen. In some embodiments, individual doses or compositions are considered to contain a "therapeutically effective amount" when they contain an amount effective as a dose in the context of a treatment regimen. Those of ordinary skill in the art will appreciate that a dose or amount may be considered to be effective if it is or has been demonstrated to show statistically significant effectiveness when administered to a population of patients; a particular result need not be achieved in a particular individual patient in order for an amount to be considered to be therapeutically effective as described herein.

As used herein, the term "treat," "treatment," or "treating" refers to any method used to partially or completely alleviate, ameliorate, relieve, inhibit, reduce severity of and/or reduce incidence of one or more symptoms or features of a disease, disorder, and/or condition. In some embodiments, treatment may be administered to a subject who exhibits only early signs of the disease, disorder, and/or condition for the purpose of decreasing the risk of developing pathology associated with the disease, disorder, and/or condition.

As used herein, the term "prevent," "prevention," or "preventing" means causing the clinical symptoms of a disease, disorder, and/or condition not to develop i.e., delaying or inhibiting the onset of a disease, disorder, and/or condition, in a subject that may be exposed to or predisposed to a disease, disorder, and/or condition, but does not yet experience or display symptoms of the disease, disorder, and/or condition. Prevention includes administration to a subject who does not exhibit signs of a disease, disorder, and/or condition.

The term "stereochemically isomeric forms" of compounds, as used herein, include all possible compounds made up of the same atoms bonded by the same sequence of bonds but having different three-dimensional structures which are not interchangeable, which the compounds may possess. The present invention encompasses each and every stereochemically isomeric form of a designated compound. Furthermore, the present invention encompasses all such stereochemically isomeric forms (e.g., all diastereomers and/or enantiomers) in pure form and/or in any combination with one another, including in racemic mixtures.

Some of the compounds provided herein may exist in tautomeric forms. Such forms are encompassed by the present invention, whether or not explicitly depicted in displayed chemical formulas.

Compounds of the present invention may be provided in the form of "prodrugs", as is known in the art. For examples of common known prodrug derivatives, see:

a) *Design of Prodrugs*, edited by H. Bundgaard, (Elsevier, 1985) and *Methods in Enzymology*, 42:309-396, edited by K. Widder, et al. (Academic Press, 1985);

b) A Textbook of Drug Design and Development, edited by Krogsgaard-Larsen;

c) Bundgaard, Chapter 5 "Design and Application of Prodrugs", by H. Bundgaard, p. 113-191 (1991);

d) H. Bundgaard, *Advanced Drug Delivery Reviews*, 8:1-38 (1992);

e) H. Bundgaard, et al., *Journal of Pharmaceutical Sciences*, 77:285 (1988); and f) N. Kakeya, et al., *Chem. Pharm. Bull.*, 32:692 (1984).

The methods and structures described herein relating to compounds of the invention may be applied to, for example, pharmaceutically acceptable acid or base addition salts, prodrugs, tautomeric forms, and/or stereoisomerric forms of described compounds.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-12 aliphatic carbon atoms. In some embodiments, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl) alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR⁺ (as in N-substituted pyrrolidinyl)).

The term "unsaturated", as used herein, means that a moiety has one or more units of unsaturation.

The term "alkylene" refers to a saturated bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, chromanyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or ⁺NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As used herein, the term "valence" is defined as the maximum number of univalent atoms (originally hydrogen or chlorine atoms) that may combine with an atom of the element under consideration, or with a fragment, or for which an atom of this element can be substituted. Thus, the term "monovalent" as used herein refers to an atom or fragment that may combine with one other atom or fragment. The term "bivalent" as used herein refers to an atom or fragment that may combine with two other atoms or fragments.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium (herein denoted as 'D'), halogen; —(CH$_2$)$_{0-4}$R°;

—$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with R°; —$(CH_2)_{0-4}O(CH_2)_{0-1}Ph$ which may be substituted with R°; —CH=CHPh, which may be substituted with R°; —$(CH_2)_{0-4}O(CH_2)_{0-1}$-pyridyl which may be substituted with R°; —$NO_2$; —CN; —$N_3$; —$(CH_2)_{0-4}N(R°)_2$; —$(CH_2)_{0-4}N(R°)C(O)R°$; —N(R°)C(S)R°; —$(CH_2)_{0-4}N(R°)C(O)NR°_2$; —N(R°)C(S)NR°$_2$; —$(CH_2)_{0-4}N(R°)C(O)OR°$; —N(R°)N(R°)C(O)R°; —N(R°)N(R°)C(O)NR°$_2$; —N(R°)N(R°)C(O)OR°; —$(CH_2)_{0-4}C(O)R°$; —C(S)R°; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR$—, SC(S)SR°; —$(CH_2)_{0-4}SC(O)R°$; —$(CH_2)_{0-4}C(O)NR°_2$; —C(S)NR°$_2$; —C(S)SR°; —SC(S)SR°, —$(CH_2)_{0-4}OC(O)NR°_2$; —C(O)N(OR°)R°; —C(O)C(O)R°; —C(O)CH$_2$C(O)R°; —C(NOR°)R°; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_{2l\ R}°$; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched)alkylene)C(O)O—N(R°)$_2$, wherein each R° may be substituted as defined below and is independently hydrogen, deuterium, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently hydrogen, deuterium, halogen, —(CH$_2$)$_{0-2}$R$^•$, -(haloR$^•$), —(CH$_2$)$_{0-2}$OH, —(CH$_2$)$_{0-2}$OR$^•$, —(CH$_2$)$_{0-2}$CH(OR$^•$)$_2$; —O(haloR$^•$), —CN, —N$_3$, —(CH$_2$)$_{0-2}$C(O)R$^•$, —(CH$_2$)$_{0-2}$C(O)OH, —(CH$_2$)$_{0-2}$C(O)OR$^•$, —(CH$_2$)$_{0-2}$SR$^•$, —(CH$_2$)$_{0-2}$SH, —(CH$_2$)$_{0-2}$NH$_2$, —(CH$_2$)$_{0-2}$NHR$^•$, —(CH$_2$)$_{0-2}$NR$^•_2$, —NO$_2$, —SiR$^•_3$, —OSiR$^•_3$, —C(O)SR$^•$, —(C$_{1-4}$ straight or branched alkylene)C(O)OR$^•$, or —SSR$^•$ wherein each R$^•$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "protecting group," as used herein, is well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Trot), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Allot), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenyl methyl carbamate, 2-methylthioethyl carbamate, 2-methylsulfonylethyl carbamate, 2-(p-toluenesulfonyl)ethyl carbamate, [2-(1,3-dithianyl)]

methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl) methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylsdenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'- pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate(levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate(mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate(mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

Certain provided compounds may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention. In certain embodiments, the present invention relates to a compound represented by any of the structures outlined herein, wherein the compound is a single stereoisomer.

Contemplated equivalents of compounds described herein include compounds which otherwise correspond thereto, and which have the same general properties thereof, wherein one or more simple variations of substituents are made which do not adversely affect the efficacy of the compound. In general, provided compounds may be prepared by the methods illustrated in the general reaction schemes as, for example, described below, or by modifications thereof, using readily available starting materials, reagents and conventional synthesis procedures. In these reactions, it is also possible to make use of variants, which are in themselves known, but are not mentioned here.

For purposes of this invention, the chemical elements are identified in accordance with the Periodic Table of the Elements, CAS version, *Handbook of Chemistry and Physics*, 67th Ed., 1986-87, inside cover.

In another aspect, the present invention provides pharmaceutical compositions, which comprise a therapeutically effective amount of one or more compounds described herein, formulated together with one or more pharmaceutically acceptable carriers (additives) and/or diluents. As described in detail herein, pharmaceutical compositions of the present invention may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

As set out herein, certain embodiments of the present compounds may contain a basic functional group, such as amino or alkylamino, and are, thus, capable of forming pharmaceutically acceptable salts with pharmaceutically acceptable acids. The term "pharmaceutically acceptable salts" in this respect refers to the relatively non-toxic, inorganic and organic acid addition salts of provided compounds. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. See, for example, Berge et al. (1977) "Pharmaceutical Salts", *J. Pharm. Sal.* 66:1-19; incorporated herein by reference.

Pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the provided compounds may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of provided compounds. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically acceptable metal cation, with ammonia, or with a pharmaceutically-acceptable organic primary, secondary or tertiary amine. Appropriate base salt forms include, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. See, for example, Berge et al., supra. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

The phrases "systemic administration," "administered systemically," "peripheral administration," and "administered peripherally" as used herein mean the administration of a compound, drug or other material other than directly into the central nervous system, such that it enters the patient's system and, thus, is subject to metabolism and other like processes, for example, subcutaneous administration.

As used herein, the term "subject with cognitive impairment" refers to a subject that is diagnosed with, affected by, or at risk of developing cognitive impairment. The cognitive impairment may stem from any etiology. Exemplary causes of cognitive impairment include neurodegenerative diseases, neurological diseases, psychiatric disorders, genetic diseases, infectious diseases, metabolic diseases, cardiovascular diseases, vascular diseases, aging, trauma, malnutrition, childhood diseases, chemotherapy, autoimmune diseases, and inflammatory diseases. Particular disease that are associated with cognitive impairment include, but are not limited to, atherosclerosis, stroke, cerebrovascular disease, vascular dementia, multi-infarct dementia, Parkinson's disease and Parkinson's disease dementia, Lewy body disease, Pick's disease, Alzheimer's disease, mild cognitive impairment, Huntington's disease, AIDS and AIDS-related dementia, brain neoplasms, brain lesions, epilepsy, multiple sclerosis, Down's syndrome, Rett's syndrome, progressive supranuclear palsy, frontal lobe syndrome, schizophrenia, traumatic brain injury, post coronary artery by-pass graft surgery, cognitive impairment due to electroconvulsive shock therapy, cognitive impairment due to chemotherapy, cognitive impairment due to a history of drug abuse, attention deficit disorder (ADD), attention deficit hyperactivity disorder (ADHD), autism, dyslexia, depression, bipolar disorder, post-traumatic stress disorder, apathy, myasthenia gravis, cognitive impairment during waking hours due to sleep apnea, Tourette's syndrome, autoimmune vasculitis, systemic lupus erythematosus, polymyalgia rheumatica, hepatic conditions, metabolic diseases, Kufs' disease, adrenoleukodystrophy, metachromatic leukodystrophy, storage diseases, infectious vasculitis, syphillis, neurosyphillis, Lyme disease, complications from intracerebral hemorrhage, hypothyroidism, B12 deficiency, folic acid deficiency, niacin deficiency, thiamine deficiency, hydrocephalus, complications post anoxia, prion disease (Creutzfeldt-Jakob disease), Fragile X syndrome, phenylketonuria, malnutrition, neurofibromatosis, maple syrup urine disease, hypercalcemia, hypothyroidism, hypercalcemia, and hypoglycemia. The degree of cognitive impairment may be assessed by a health care professional. A variety of standardized test are available for assessing cognition, including, but not limited to, the Mini-Mental Status Examination, the Dementia Symptom Assessmant Scale, and the ADAS. Such tests typically provide a measurable score of congnitive impairment.

As used herein, the term "subject with depression" refers to a subject that is diagnosed with, affected by, or at risk of developing depression.

As used herein, the term "subject with anxiety" refers to a subject that is diagnosed with, affected by, or at risk of developing anxiety. The anxiety may stem from a variety of causes. Based on mouse studies, farnesyl transferase inhibitors may be used as anxiolytics.

3. Description of Exemplary Compounds

As defined above and herein, ----- is a single or double bond. In some embodiments, ----- is a single bond. In some embodiments, ----- is a double bond.

As defined above and herein, each of $V^1$, $V^2$, and $V^3$ is independently CH or N, wherein at least one of $V^1$, $V^2$, or $V^3$ is N. In some embodiments, $V^1$ is CH. In some embodiments, $V^1$ is N. In some embodiments, $V^2$ is CH. In some embodiments, $V^2$ is N. In some embodiments, $V^3$ is CH. In some embodiments, $V^3$ is N. In some embodiments, at least two of $V^1$, $V^2$, or $V^3$ are N. In some embodiments, each of $V^1$, $V^2$, and $V^3$ are N. In certain embodiments, $V^1$ is CH, $V^2$ is CH and $V^3$ is N.

As defined above and herein, $R^1$ is phenyl, a 5 or 6 membered monocyclic heteroaryl ring having 1, 2, 3, or 4 heteroatoms independently selected from nitrogen, oxygen, or sulfur, or an 8, 9 or 10 membered bicyclic ring having 0, 1, 2, 3, or 4 heteroatoms independently selected from nitrogen, oxygen, or sulfur, wherein $R^1$ is optionally substituted with $-(R^2)_j$, wherein j is 0, 1, 2, 3, 4, or 5.

In some embodiments, $R^1$ is unsubstituted phenyl. In some embodiments, $R^1$ is phenyl substituted with 1, 2, 3, 4, or 5 $R^w$ groups. In some embodiments, $R^1$ is phenyl substituted with 1, 2, or 3 $R^w$ groups. In some embodiments, $R^1$ is phenyl substituted with one $R^w$ group. In certain embodiments, $R^1$ is phenyl and at least one $R^w$ is halogen. In certain embodiments, $R^1$ is phenyl and at least one $R^w$ is chlorine.

In some embodiments, $R^1$ is of the formula:

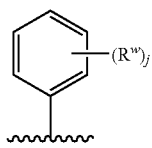

wherein $R^w$ and j are as defined above and herein.

In some embodiments, $R^1$ is of one of the following formulae:

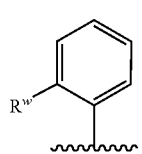 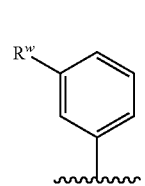 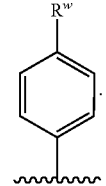

In some embodiments, $R^1$ is of one of the following formulae:

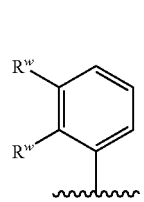 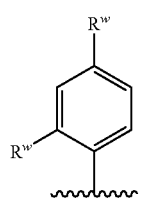 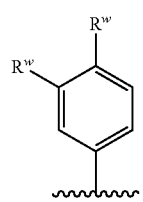

In some embodiments, $R^1$ is of one of the following formulae:

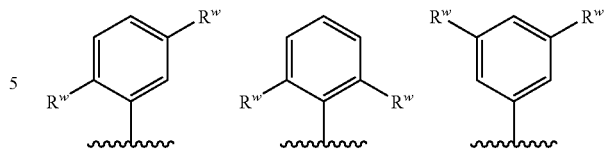

In some embodiments, $R^1$ is of one of the following formulae:

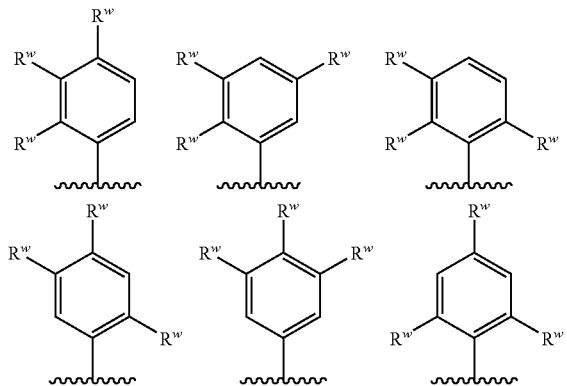

In some embodiments, $R^1$ is of one of the following formulae:

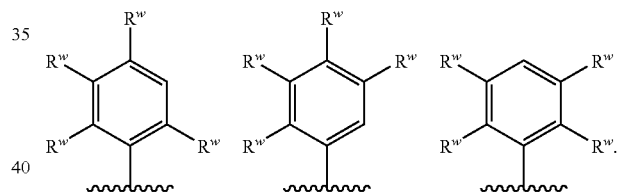

In some embodiments, $R^1$ is of the formula:

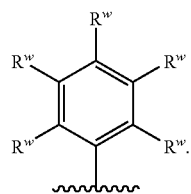

In some embodiments, $R^1$ is of the formula:

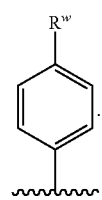

In certain embodiments, $R^1$ is of the formula:

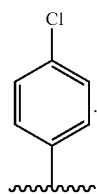 [SMILES: *c1ccc(Cl)cc1]

In some embodiments, $R^1$ is unsubstituted naphthyl. In some embodiments, $R^1$ is naphthyl substituted with 1, 2, 3, 4, or 5 $R^w$ groups. In some embodiments, $R^1$ is naphthyl substituted with 1, 2, or 3 $R^w$ groups. In some embodiments, $R^1$ is naphthyl substituted with 1 $R^w$ group.

In some embodiments, $R^1$ is a 5 or 6 membered monocyclic heteroaryl ring having 1-4 heteroatoms independently selected from nitrogen, oxygen, or sulfur, and optionally substituted with 1, 2, 3, 4, or 5 $R^w$ groups. In some embodiments, $R^1$ is a 5 membered monocyclic heteroaryl ring having 1, 2, or 3 heteroatoms independently selected from nitrogen, oxygen, or sulfur, and optionally substituted with 1 or 2 $R^w$ groups. In other embodiments, $R^1$ is a 6 membered monocyclic heteroaryl ring having 1 or 2 heteroatoms independently selected from nitrogen, oxygen, or sulfur, and optionally substituted with 1 or 2 $R^w$ groups.

In certain embodiments, $R^1$ is an 8, 9, or 10 membered bicyclic ring having 0, 1, 2, 3, or 4 heteroatoms independently selected from nitrogen, oxygen, or sulfur, and optionally substituted with 1, 2, 3, 4, or 5 $R^w$ groups. In some embodiments, $R^1$ is an 8 membered bicyclic ring having 1, 2, or 3 heteroatoms independently selected from nitrogen, oxygen, or sulfur, and optionally substituted with 1, 2, or 3 $R^w$ groups. In some embodiments, $R^1$ is a 9 membered bicyclic ring having 1, 2, or 3 heteroatoms independently selected from nitrogen, oxygen, or sulfur, and optionally substituted with 1, 2, or 3 $R^w$ groups. In some embodiments, $R^1$ is a 10 membered bicyclic ring having 1, 2, or 3 heteroatoms independently selected from nitrogen, oxygen, or sulfur, and optionally substituted with 1, 2, or 3 $R^w$ groups. In some embodiments, $R^1$ is an 8, 9 or 10 membered bicyclic ring comprised of 0, 1, or 2 aromatic rings, and optionally substituted with 1, 2, or 3 $R^w$ groups.

Exemplary $R^1$ heteroaryl groups include thienyl, (uranyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, pyrido[2,3-b]-1,4-oxazin-3(4H)-one, or chromanyl, wherein each ring is optionally substituted with 1, 2, or 3 $R^w$ groups.

In certain embodiments, $R^1$ is a pyridinyl group optionally substituted with 1, 2, 3, or 4 $R^w$ groups.

In certain embodiments, $R^1$ is naphthyl optionally substituted with 1, 2, 3, 4, or 5 $R^w$ groups.

In some embodiments, $R^1$ is of any one of the following formulae:

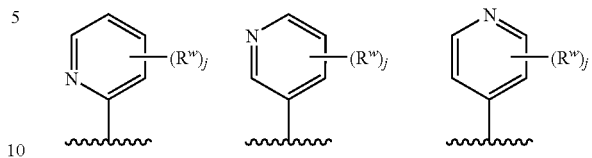

wherein $R^w$ and j are as defined above and herein.

As defined generally above and herein, each $R^w$ is independently selected from —R, halogen, —OR, —CN, —NO$_2$, —SR, —S(O)R, —SO$_2$R, —SO$_2$N(R')$_2$, —C(O)R, —CO$_2$R, —OC(O)R, —OC(O)N(R')$_2$, —C(O)N(R')$_2$, —NR'C(O)R, —NR'C(O)N(R')$_2$, —NR'SO$_2$R, —N(R')$_2$, —C(R)$_3$, or —Si(R)$_3$.

In some embodiments, at least one $R^w$ group is independently R, halogen, OR, —N(R')$_2$, or C(R)$_3$. In certain embodiments, $R^w$ is halogen.

In certain embodiments, at least one $R^w$ group is independently methyl, ethyl, propyl, butyl, pentyl, or hexyl.

In some embodiments, at least one $R^w$ group is halogen. In certain embodiments, at least one $R^w$ group is fluorine or chlorine. In some embodiments, $R^w$ is chlorine.

R is independently hydrogen, deuterium, or an optionally substituted group selected from $C_{1-12}$ aliphatic, phenyl, a 5 or 6 membered monocyclic heteroaryl ring having 1, 2, 3, or 4 heteroatoms independently selected from nitrogen, oxygen, or sulfur, or an 8, 9, or 10 membered bicyclic aryl ring having 0, 1, 2, 3, or 4 heteroatoms independently selected from nitrogen, oxygen, or sulfur, or wherein:

two R on the same nitrogen are taken together to form a 5 or 6 membered saturated, partially saturated, or aromatic ring having 1, 2, or 3 heteroatoms independently selected from nitrogen, oxygen, and sulfur;

each R' is independently selected from R, —C(O)R, —CO$_2$R—, —S(O)R, and —SO$_2$R;

As defined generally above and herein, $R^2$ is —R, halogen, —OR, —CN, —NO$_2$, —SR, —S(O)R, —SO$_2$R, —SO$_2$N(R')$_2$, —C(O)R, —CO$_2$R, —C(R)$_2$CO$_2$R, —OC(O)R, —OC(O)N(R')$_2$, —C(O)M(R')$_2$, —NR'C(O)R, —NR'C(O)N(R')$_2$, —NR'SO$_2$R, —N(R')$_2$, —C(R)$_3$, —Si(R)$_3$, —OPO$_3$H$_2$, —OCH$_2$OPO$_3$H$_2$, or —OCH$_2$OC(O)(CH$_2$)$_k$CH$_3$, wherein k is 0, 1, 2, 3, 4, 5, 6, 7, 8, 9, 10, 11, or 12;

In some embodiments, $R^2$ is R, halogen, —OR, or —N(R')$_2$. In some embodiments, $R^2$ is R, —OR, or —N(R')$_2$. In some embodiments, $R^2$ is not halogen.

In some embodiments, $R^2$ is selected from hydrogen, deuterium, methyl, ethyl, propyl, butyl, —CF$_3$, —CF$_2$H, —CFH$_2$, —CF$_2$CF$_3$, —CFHCF$_3$, —CH$_2$CF$_3$, —CF$_2$CF$_2$H, —CF$_2$CFH$_2$, —CF$_2$CH$_3$, —CFHCF$_2$H, —CFHCFH$_2$, or —CFHCH$_3$.

In some embodiments, $R^2$ is —OR, wherein R is independently selected from hydrogen, methyl, ethyl, propyl, —CF$_3$, —CF$_2$H, —CFH$_2$, —CF$_2$CF$_3$, —CFHCF$_3$, —CH$_2$ CF$_3$, —CF$_2$CF$_2$H, —CF$_2$CFH$_2$, —CF$_2$CH$_3$, —CFHCF$_2$H, —CFHCFH$_2$, or —CFHCH$_3$.

In some embodiments, $R^2$ is selected from the group consisting of —R, —OR, —OC(O)R, —OC(O)N(R')$_2$, —OPO$_3$H$_2$, —OCH$_2$OPO$_3$H$_2$, and —OCH$_2$OC(O)(CH$_2$)$_k$CH$_3$.

In some embodiments, $R^2$ is selected from the group consisting of —OH, —OMe, —OPO$_3$H$_2$, —OCH$_2$OPO$_3$H$_2$, —OCH$_2$OC(O)(C$_{1-12}$ alkyl), or —OC(O)(C$_{1-12}$ alkyl). In certain embodiments, R² is —OH. In certain embodiments, R² is —OMe. In certain embodiments, R² is halogen.

In some embodiments, R² is selected from the group consisting of —CN, —C(O)R, —CO₂R, —C(R)₂CO₂R, and —C(O)N(R')₂.

In some embodiments, R² is selected from the group consisting of —N(R')₂, —NR'C(O)R, —NR'C(O)N(R')₂, or —NR'SO₂R. In some embodiments, R² is —N(R')₂. In certain embodiments, R² is —N(R')₂, wherein each R' is independently hydrogen, methyl, ethyl, propyl, butyl, pentyl, or hexyl. In certain embodiments, R² is —NH₂, —NH(CH₃), or —N(CH₃)₂. In certain embodiments, R² is —NHPO₃H₂. In some embodiments, two R' on the same nitrogen are both R taken together to form a 5 or 6 membered saturated, partially saturated, or aromatic ring having 1, 2, or 3 heteroatoms independently selected from nitrogen, oxygen, and sulfur. In some embodiments, two R' on the same nitrogen are both R taken together to form a 5 membered saturated, partially saturated, or aromatic ring having 1, 2, or 3 heteroatoms independently selected from nitrogen, oxygen, and sulfur. In some embodiments, two R' on the same nitrogen are both R taken together to form a 6 membered saturated, partially saturated, or aromatic ring having 1, 2, or 3 heteroatoms independently selected from nitrogen, oxygen, and sulfur.

In some embodiments, R² is —SR, —S(O)R, —SO₂R, or —SO₂N(R')₂ wherein each R is independently hydrogen, methyl, ethyl, or propyl.

In some embodiments, R² is —SR, —S(O)R, or —SO₂R wherein each R is independently hydrogen, methyl, ethyl, or propyl.

In some embodiments, R² is —C(O)R—CO₂R, or —C(R)₂CO₂R wherein each R is independently hydrogen, methyl, ethyl, or propyl. In certain embodiments, R² is —CH₂CO₂H.

In some embodiments, R² is —C(O)N(R')₂, —NR'C(O)R, —NR'C(O)N(R')₂, or —NR'SO₂R, wherein each R is independently hydrogen, methyl, ethyl, or propyl.

In certain embodiments, R² is —CH₂OC(O)(CH₂)ₖCH₃ wherein k is 0, 1, 2, 3, 4, 5, 6, 7, 8, 9, 10, 11, or 12. In certain embodiments, R² is —CH₂OC(O)(CH₂)ₖCH₃ wherein k is 0 to 6. In certain embodiments, R² is —CH₂OC(O)(CH₂)ₖCH₃ wherein k is 6, 7, 8, 9, 10, 11, or 12. In certain embodiments, R² is —CH₂OC(O)(CH₂)ₖCH₃ wherein k is 1, 2, or 3.

In certain embodiments, R² is either —C(R)₃ or —Si(R)₃.

As defined generally above and herein, R³ is phenyl, a 5 or 6 membered monocyclic heteroaryl ring having 1, 2, 3, or 4 heteroatoms independently selected from nitrogen, oxygen, or sulfur, or an 8, 9 or 10 membered bicyclic ring having 0-4 heteroatoms independently selected from nitrogen, oxygen, or sulfur, wherein R³ is optionally substituted with —(Rˣ)ₘ, wherein m is 0, 1, 2, 3, 4, or 5, or R³ is —(CH₂)ₚRᶻ— wherein Rᶻ is selected from N-hydroxyurea, —CO₂Me, —C(O)C(O)NHMe, —NOHCHO, —NHC(O)CH₂SH, —NHC(O)NHNH₂, NHC(O)CH₂Br, —NHC(O)CH₂SAc, —NHC(O)CH₂OH,

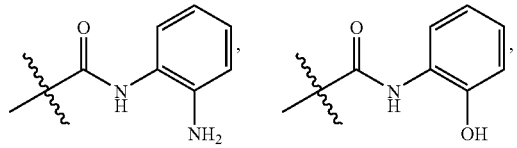 [SMILES: *C(=O)Nc1ccccc1N ; *C(=O)Nc1ccccc1O]

and wherein p is 0, 1, 2, 3, 4, or 5. In certain embodiments, R³ is phenyl substituted with 1, 2, 3, 4, or 5 Rˣ groups. In certain embodiments, R³ is phenyl substituted with 0, 1, 2, or 3 Rˣ groups. In certain embodiments, R³ is unsubstituted phenyl.

In certain embodiments, R³ is naphthyl substituted with 1-5 Rˣ groups. In certain embodiments, R³ is naphthyl substituted with 0, 1, 2, or 3 Rˣ groups. In certain embodiments, R³ is unsubstituted naphthyl.

In some embodiments, R³ is a 5 or 6 membered monocyclic saturated, partially unsaturated or aromatic heterocyclic ring having 1, 2, 3, or 4 heteroatoms independently selected from nitrogen, oxygen, or sulfur, and optionally substituted with 1, 2, 3, 4, or 5 Rˣ groups. In some embodiments, R³ is a 5 membered monocyclic heteroaryl ring having 1-3 heteroatoms independently selected from nitrogen, oxygen, or sulfur, and optionally substituted with 1 or 2 Rˣ groups. In other embodiments, R³ is a 6 membered monocyclic heteroaryl ring having 1 or 2 nitrogens independently selected from nitrogen, oxygen, or sulfur, and optionally substituted with 1 or 2 Rˣ groups.

In certain embodiments, R³ is an 8, 9, or 10 membered bicyclic ring having 0, 1, 2, 3, or 4 heteroatoms independently selected from nitrogen, oxygen, or sulfur, and optionally substituted with 1, 2, 3, 4, or 5 Rˣ groups. In some embodiments, R³ is an 8 membered bicyclic ring having 1, 2, or 3 heteroatoms independently selected from nitrogen, oxygen, or sulfur, and optionally substituted with 1, 2, or 3 Rˣ groups. In some embodiments, R³ is a 9 membered bicyclic ring having 1, 2, or 3 heteroatoms independently selected from nitrogen, oxygen, or sulfur, and optionally substituted with 1, 2, or 3 Rˣ groups. In some embodiments, R³ is a 10 membered bicyclic ring having 1, 2, or 3 heteroatoms independently selected from nitrogen, oxygen, or sulfur, and optionally substituted with 1, 2, or 3 Rˣ groups. In some embodiments, R³ is an 8, 9, or 10 membered bicyclic ring comprised of 0, 1, or 2 aromatic rings and optionally substituted with 1, 2, 3, 4, or 5 Rˣ groups.

Exemplary R³ heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, pyrido[2,3-b]-1,4-oxazin-3(4H)-one, or chromanyl, wherein each ring is optionally substituted with 1, 2, or 3 Rˣ groups.

In certain embodiments, R³ is imidazolyl, pyrrolyl, triazolyl, pyrimidinyl, pyridazinyl, or pyrazinyl, wherein each ring is optionally substituted with 1, 2, or 3 Rˣ groups.

In some embodiments, R³ is imidazolyl.

In some embodiments, R³ is of the formula:

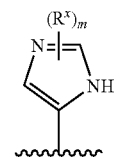

wherein Rˣ and m are as defined above and herein.

In some embodiments, R³ is of any of the following formulae:

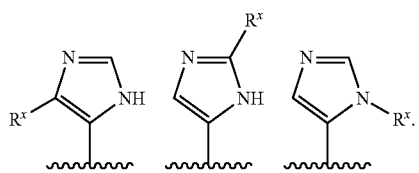

In some embodiments, R³ is of any of the following formulae:

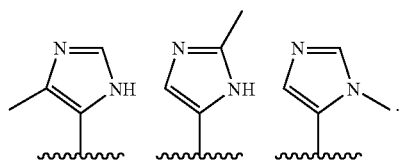

In some embodiments, R³ is of the formula:

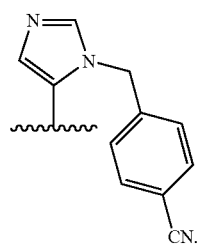 [SMILES: *c1cncn1Cc1ccc(C#N)cc1]

In some embodiments, R³ is of the formula:

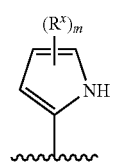

wherein R$^x$ and m are as defined above and herein.
In some embodiments, R³ is of the formula:

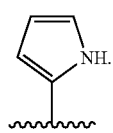

In some embodiments, R³ is of any of the following formulae:

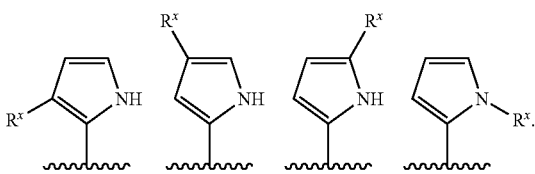

In some embodiments, R³ is of any of the following formulae:

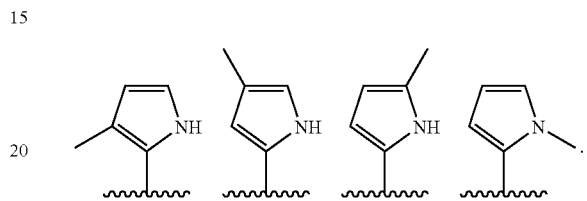

In some embodiments, R³ is of any of the following formulae:

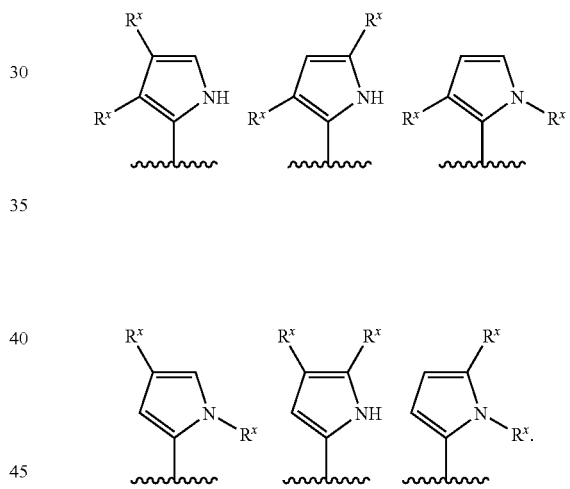

In some embodiments, R³ is of the formula:

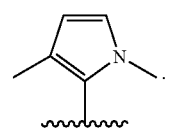

In some embodiments, R³ is of one of the following formulae:

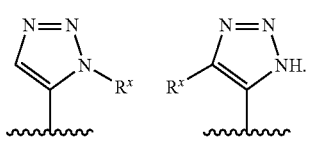

In some embodiments, R³ is of the formula:

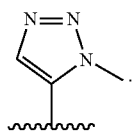

In some embodiments, R³ is of any of the following formulae:

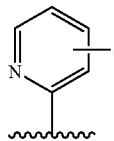 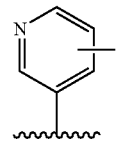 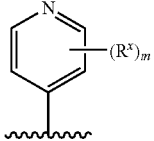

wherein R$^x$ and m are as defined above and herein.

In some embodiments, R³ is of the formula:

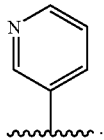

In some embodiments, R³ is of the formula:

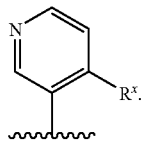

In some embodiments, R³ is of the formula:

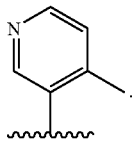 [SMILES: *c1cnccc1C]

In some embodiments, R³ is of any of the following formulae:

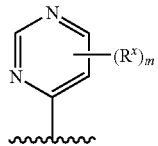 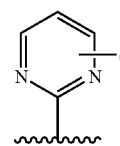 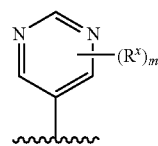

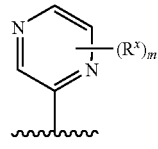

In some embodiments, R³ is of one of the following formulae:

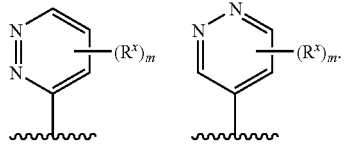 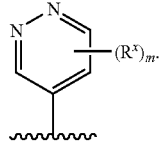

In some embodiments, R³ is —(CH$_2$)$_p$R$^z$, wherein R$^z$ is selected from N-hydroxyurea, —CO$_2$Me, —C(O)C(O)NHMe, —NOHCHO, —NHC(O)CH$_2$SH, —NHC(O)NHNH$_2$, NHC(O)CH$_2$Br, —NHC(O)CH$_2$SAc, —NHC(O)CH$_2$OH,

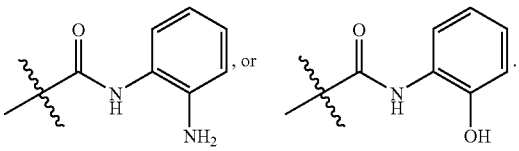 [SMILES: *C(=O)Nc1ccccc1N ; *C(=O)Nc1ccccc1O] 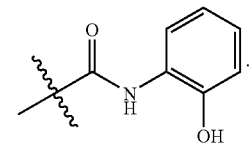

As defined generally above and herein, each R$^x$ is independently selected from —R, halogen, —OR, —CN, —NO$_2$, —SR, —S(O)R, —SO$_2$R, —SO$_2$N(R')$_2$, —C(O)R, —CO$_2$R, —OC(O)R, —OC(O)N(R')$_2$, —C(O)N(R')$_2$, —NR'C(O)R, —NR'C(O)N(R')$_2$, —NR'SO$_2$R, —N(R')$_2$, —C(OR)$_3$, —Si(R)$_3$, or an optionally substituted benzyl group.

In some embodiments, each R$^x$ group is independently R. In certain embodiments, each R$^x$ group is independently methyl, ethyl, propyl, or butyl. In certain embodiments, at least one R$^x$ group is methyl.

In some embodiments, at least one R$^x$ group is optionally substituted benzyl. In certain embodiments, at least one R$^x$ group is of the formula:

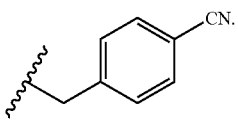 [SMILES: *Cc1ccc(C#N)cc1]

As defined generally above and herein, R⁴ is phenyl, a 5 or 6 membered monocyclic heteroaryl ring having 1, 2, 3, or 4 heteroatoms independently selected from nitrogen, oxygen, or sulfur, or an 8, 9 or 10 membered bicyclic ring having 0, 1, 2, 3, or 4 heteroatoms independently selected from nitrogen, oxygen, or sulfur, and wherein R⁴ is optionally substituted with —(R$^y$)$_n$.

In certain embodiments, R⁴ is phenyl substituted with 1, 2, 3, 4, or 5 R$^y$ groups. In certain embodiments, R⁴ is phenyl substituted with 0, 1, 2, or 3 R$^y$ groups. In certain embodiments, R⁴ is unsubstituted phenyl.

In certain embodiments, R⁴ is naphthyl substituted with 1, 2, 3, 4, or 5 R$^y$ groups. In certain embodiments, R⁴ is naphthyl substituted with 0, 1, 2, or 3 R$^y$ groups. In certain embodiments, R⁴ is unsubstituted naphthyl.

In some embodiments, R⁴ is a 5 or 6 membered monocyclic saturated, partially unsaturated or aromatic heterocyclic ring having 1, 2, 3, or 4 heteroatoms independently selected from nitrogen, oxygen, or sulfur, and optionally substituted with 1, 2, 3, 4 or 5 R$^y$ groups. In some embodiments, R⁴ is a 5 membered monocyclic heteroaryl ring having 1, 2, or 3 heteroatoms independently selected from nitrogen, oxygen, or sulfur, and optionally substituted with 1 or 2 $R^y$ groups. In other embodiments, $R^4$ is a 6 membered monocyclic heteroaryl ring having 1 or 2 nitrogens independently selected from nitrogen, oxygen, or sulfur, and optionally substituted with 1 or 2 $R^y$ groups.

In certain embodiments, $R^4$ is an 8, 9 or 10 membered bicyclic ring having 0, 1, 2, 3, or 4 heteroatoms independently selected from nitrogen, oxygen, or sulfur, and optionally substituted with 1, 2, 3, 4, or 5 $R^y$ groups. In some embodiments, $R^4$ is an 8 membered bicyclic ring having 1, 2, or 3 heteroatoms independently selected from nitrogen, oxygen, or sulfur, and optionally substituted with 1, 2, or 3 $R^y$ groups. In some embodiments, $R^4$ is a 9 membered bicyclic ring having 1, 2, or 3 heteroatoms independently selected from nitrogen, oxygen, or sulfur, and optionally substituted with 1, 2, or 3 $R^y$ groups. In some embodiments, $R^4$ is a 10 membered bicyclic ring having 1, 2, or 3 heteroatoms independently selected from nitrogen, oxygen, or sulfur, and optionally substituted with 1, 2, or 3 $R^y$ groups. In some embodiments, $R^4$ is an 8, 9, or 10 membered bicyclic ring comprised of 0, 1, or 2 aromatic rings and optionally substituted with 1, 2, 3, 4, or 5 $R^y$ groups.

Exemplary $R^4$ heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, pyrido[2,3-b]-1,4-oxazin-3(4H)-one, or chromanyl, wherein each ring is optionally substituted with 1, 2, 3, or 4 $R^y$ groups.

As defined generally above and herein, each $R^y$ group is independently selected from —R, halogen, —OR, —CN, —NO₂, —SR, —S(O)R, —SO₂R, —SO₂N(R')₂, —C(O)R, —CO₂R, —OC(O)R, —OC(O)N(R')₂, —C(O)N(R')₂, NR'C(O)R, —NR'C(O)N(R')₂, —NR'SO₂R, —N(R')₂, —C(R)₃, or —Si(R)₃.

In certain embodiments, at least one $R^y$ group is independently halogen or optionally substituted $C_{1-6}$ aliphatic. In certain embodiments, at least one $R^y$ group is independently fluorine, chlorine, bromine, methyl, ethyl, propyl, —CF₃, —CF₂H, or CFH₂. In certain embodiments at least one $R^y$ group is independently acetylene.

In certain embodiments, at least one $R^y$ group is independently —OR.

In certain embodiments, at least one $R^y$ group is independently —N(R')₂.

In certain embodiments, at least one $R^y$ group is independently —C(O)R.

In some embodiments, $R^4$ is of the formula:

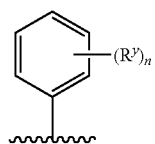

wherein $R^y$ and n are as defined above and herein.

In some embodiments, $R^4$ is of any of the following formulae:

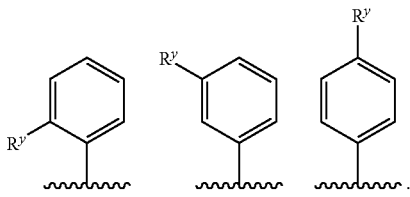

In some embodiments, $R^4$ is of any of the following formulae:

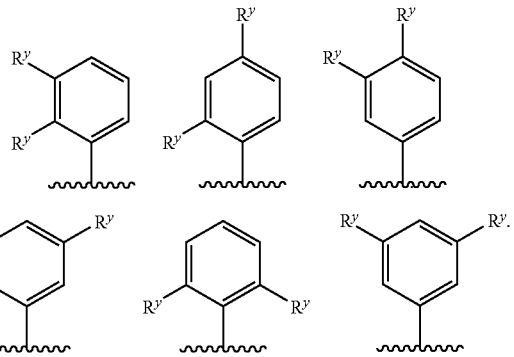

In some embodiments, $R^4$ is of any of the following formulae:

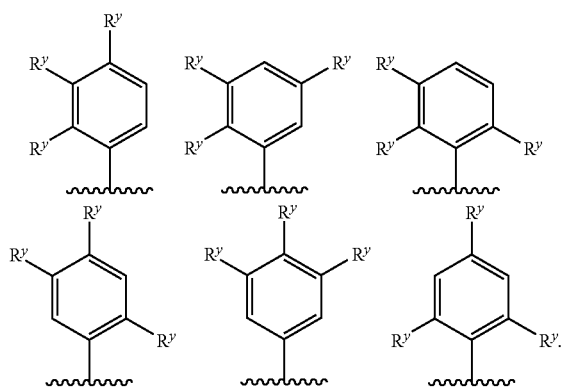

In some embodiments, $R^4$ is of any of the following formulae:

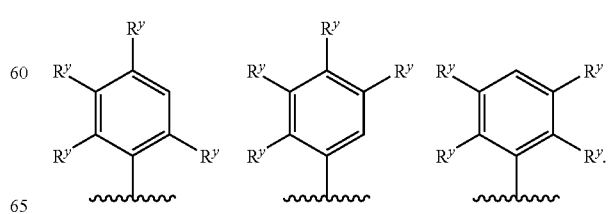

In some embodiments, $R^4$ is of the following formula:

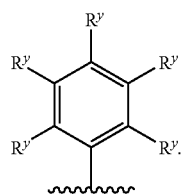

In certain embodiments, $R^4$ is of any of the following formulae:

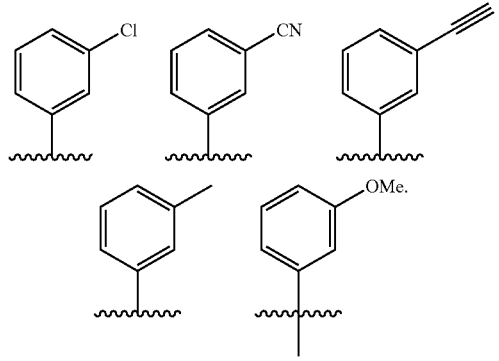

In certain embodiments, $R^4$ is of any of the following formulae:

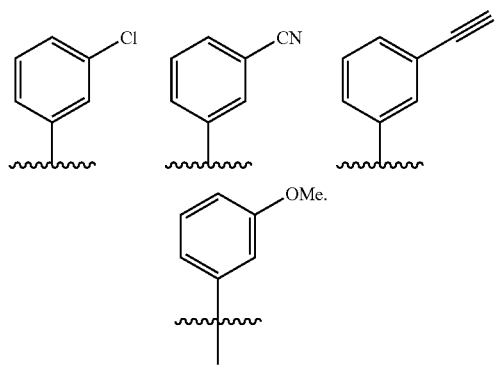

In certain embodiments, $R^4$ is of any of the following formulae:

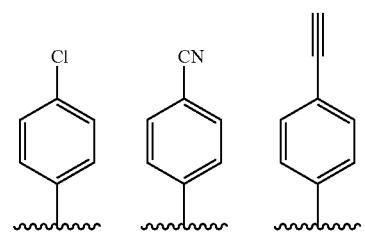

-continued

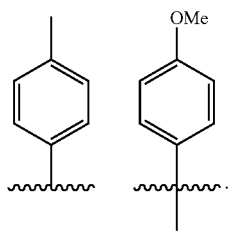

In some embodiments, $R^4$ is of any of the following formulae:

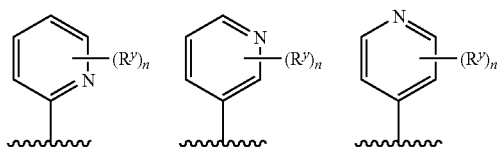

wherein $R^y$ and n are as defined above and herein.

In some embodiments, $R^4$ is of any of the following formulae:

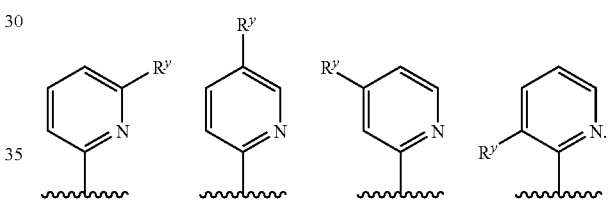

In some embodiments, $R^4$ is of any of the following formulae:

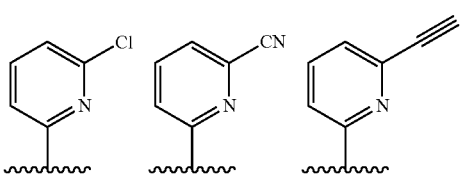

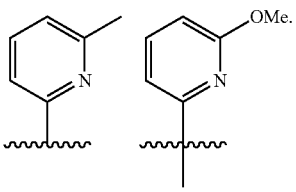

In some embodiments, $R^4$ is of any of the following formulae:

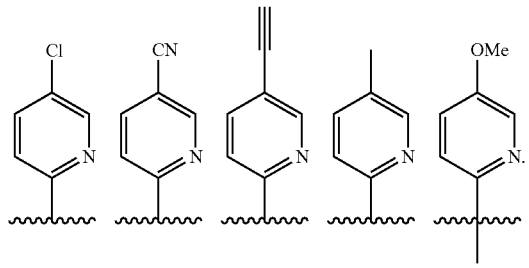

In some embodiments, $R^4$ is of any of the following formulae:

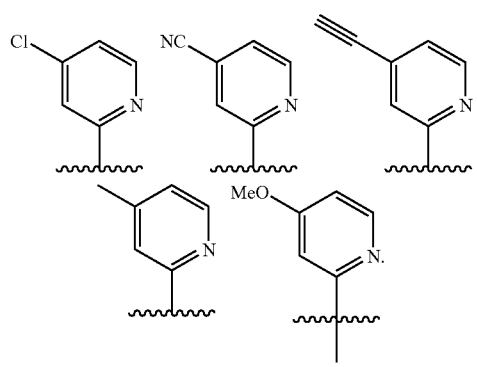

In some embodiments, $R^4$ is of any of the following formulae:

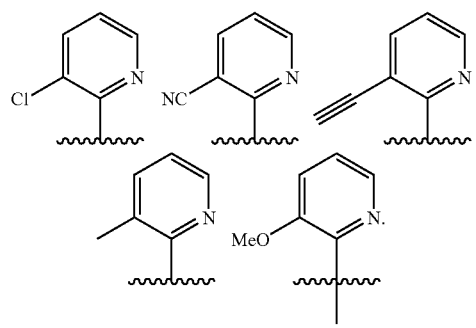

In some embodiments, $R^4$ is of any of the following formulae:

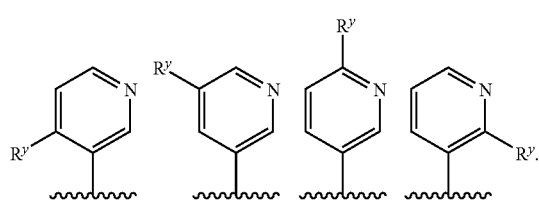

In some embodiments, $R^4$ is of any of the following formulae:

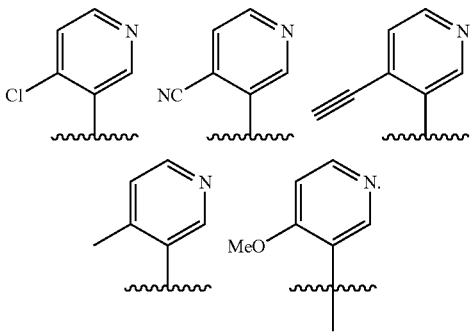

In some embodiments, $R^4$ is of any of the following formulae:

In some embodiments, $R^4$ is of any of the following formulae:

In some embodiments, $R^4$ is of any of the following formulae:

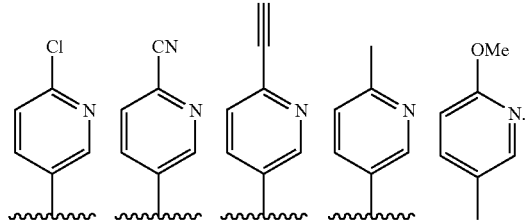

In some embodiments, $R^4$ is of any of the following formulae:

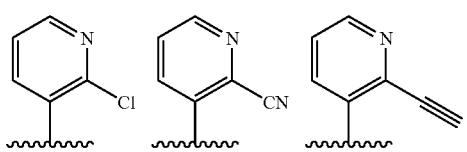

-continued

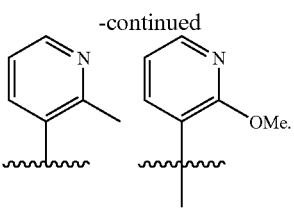

In some embodiments, R⁴ is of any of the following formulae:

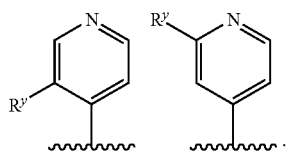

In some embodiments, R⁴ is of any of the following formulae:

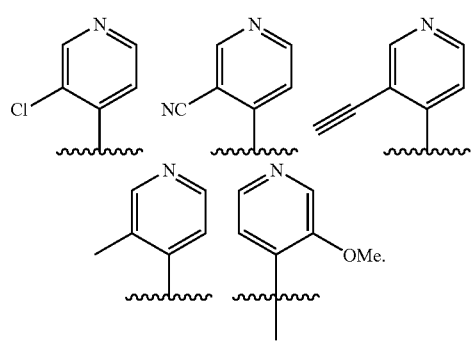

In some embodiments, R⁴ is of any of the following formulae:

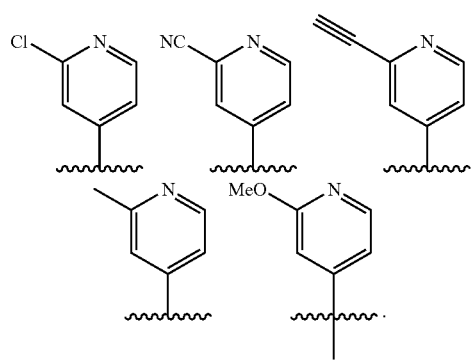

In some embodiments, R⁴ is of the formula:

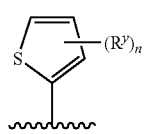

wherein $R^y$ and n are as defined above and herein.

In some embodiments, R⁴ is of any of the following formulae:

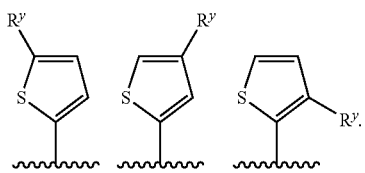

In some embodiments, R⁴ is of any of the following formulae:

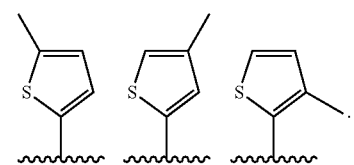

In some embodiments, R⁴ is of the formula:

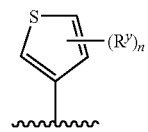

wherein $R^y$ and n are as defined above and herein.

In some embodiments, R⁴ is of any of the following formulae:

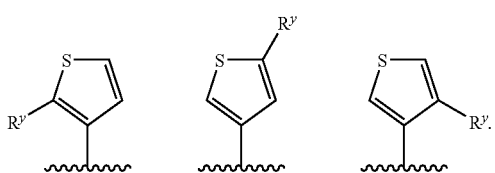

In some embodiments, R⁴ is of any of the following formulae:

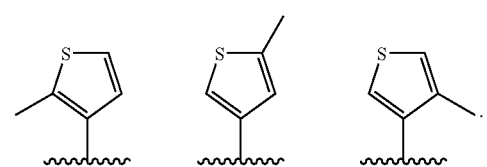

In some embodiments, at least one $R^y$ group is independently halogen or optionally substituted $C_{1-6}$ aliphatic.

In some embodiments, at least one $R^y$ group is independently selected from the group consisting of fluorine, chlorine, bromine, methyl, ethyl, propyl, —CF₃, —CF₂H, and CFH₂.

In some embodiments, at least one $R^y$ group is independently acetylene. In some embodiments, one $R^y$ group is acetylene. In some embodiments, at least of $R^y$ group is halogen, alkenyl or methoxy.

As defined generally above and herein, $R^5$ is R'. In some embodiments, $R^5$ is an optionally substituted cyclic or acyclic $C_{1-12}$ aliphatic moiety. In some embodiments, $R^5$ is selected from the group consisting of hydrogen, methyl, ethyl, propyl, butyl, pentyl and hexyl. In some embodiments, $R^5$ is hydrogen. In some embodiments, $R^5$ is methyl.

In certain embodiments, R' of $R^5$ is independently —C(O)R. Exemplary such —C(O)R groups include those wherein R is an optionally substituted group selected from $C_{1-12}$ aliphatic, phenyl, a 5 or 6 membered monocyclic heteroaryl ring having 1, 2, 3, or 4 heteroatoms independently selected from nitrogen, oxygen, or sulfur, or an 8, 9, or 10 membered bicyclic aryl ring having 0, 1, 2, 3, or 4 heteroatoms independently selected from nitrogen, oxygen, or sulfur.

In some embodiments, $R^5$ is a substituted cyclic aliphatic moiety. In some embodiments, $R^5$ is an unsubstituted cyclic aliphatic moiety. In certain embodiments, $R^5$ is of the following formula:

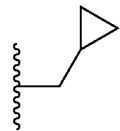

In some embodiments, $R^5$ is a substituted acyclic aliphatic moiety. In certain embodiments, $R^5$ is $CF_3$, $CF_2H$, or —$CFH_2$.

In some embodiments, $R^5$ is an unsubstituted acyclic aliphatic moiety. In certain embodiments, $R^5$ is methyl, ethyl, propyl, butyl, pentyl, or hexyl.

In some embodiments, the present invention provides a compound of formula I-a:

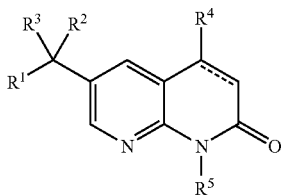

I-a or a pharmaceutically acceptable salt thereof, wherein each of $R^1$, $R^2$, $R^3$, $R^4$, $R^5$, and ----- is as defined and described herein.

In some embodiments, the present invention provides a compound of formula I-b:

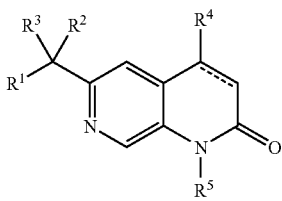

I-b or a pharmaceutically acceptable salt thereof, wherein each of $R^1$, $R^2$, $R^3$, $R^4$, $R^5$, and ----- is as defined and described herein.

In some embodiments, the present invention provides a compound of formula I-c:

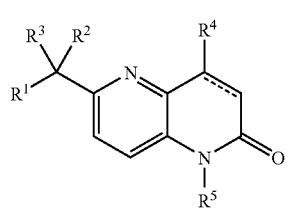

I-c or a pharmaceutically acceptable salt thereof, wherein each of $R^1$, $R^2$, $R^3$, $R^4$, $R^5$, and ----- is as defined and described herein.

In some embodiments, the present invention provides a compound of formula I-d:

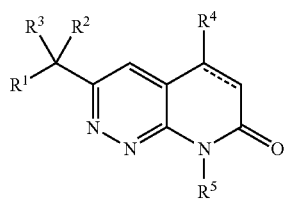

I-d or a pharmaceutically acceptable salt thereof, wherein each of $R^1$, $R^2$, $R^3$, $R^4$, $R^5$, and ----- is as defined and described herein.

In some embodiments, the present invention provides a compound of formula I-e:

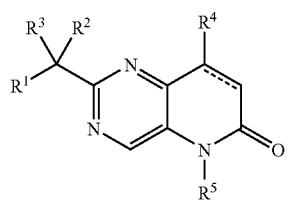

I-e or a pharmaceutically acceptable salt thereof, wherein each of $R^1$, $R^2$, $R^3$, $R^4$, $R^5$, and ----- is as defined and described herein.

In some embodiments, the present invention provides a compound of formula I-f:

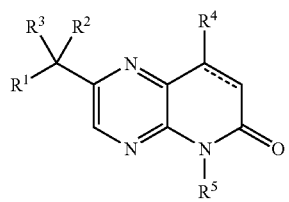

I-f or a pharmaceutically acceptable salt thereof, wherein each of $R^1$, $R^2$, $R^3$, $R^4$, $R^5$, and ----- is as defined and described herein.

In some embodiments, the present invention provides a compound of formula I-g:

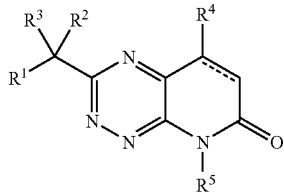

I-g or a pharmaceutically acceptable salt thereof, wherein each of $R^1$, $R^2$, $R^3$, $R^4$, $R^5$, and ----- is as defined and described herein.

In some embodiments, the present invention provides a compound of formula I-h:

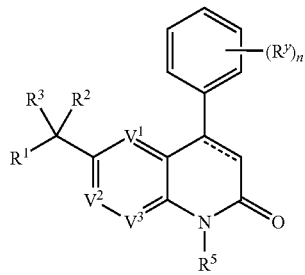

I-h or a pharmaceutically acceptable salt thereof, wherein each of $R^1$, $R^2$, $R^3$, $R^5$, $V^1$, $V^2$, $V^3$, $R^y$, n, and ----- is as defined and described herein.

In some embodiments, the present invention provides a compound of formula I-i:

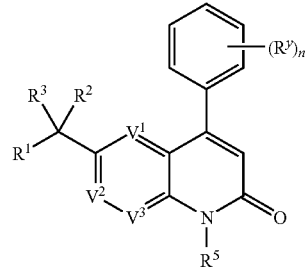

I-i or a pharmaceutically acceptable salt thereof, wherein each of $R^1$, $R^2$, $R^3$, $R^5$, $V^1$, $V^2$, $V^3$, $R^y$, and $n$ is as defined and described herein.

In some embodiments, the present invention provides a compound of formula I-j:

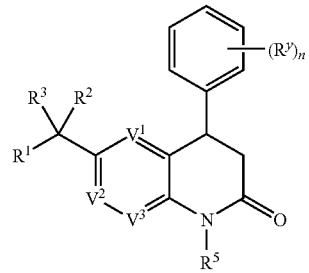

I-j or a pharmaceutically acceptable salt thereof, wherein each of $R^1$, $R^2$, $R^3$, $R^5$, $V^1$, $V^2$, $V^3$, $R^y$, and $n$ is as defined and described herein.

In some embodiments, the present invention provides a compound of formula I-k:

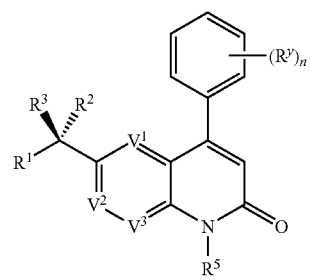

I-k or a pharmaceutically acceptable salt thereof, wherein each of $R^1$, $R^2$, $R^3$, $R^5$, $V^1$, $V^2$, $V^3$, $R^y$, and n is as defined and described herein.

In some embodiments, the present invention provides a compound of formula I-l:

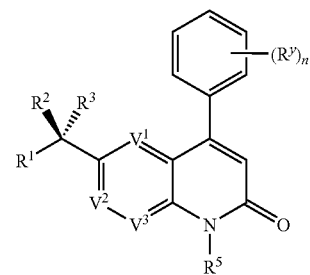

I-l or a pharmaceutically acceptable salt thereof, wherein each of $R^1$, $R^2$, $R^3$, $R^5$, $V^1$, $V^2$, $V^3$, $R^y$, and n is as defined and described herein.

In some embodiments, the present invention provides a compound of formula I-m:

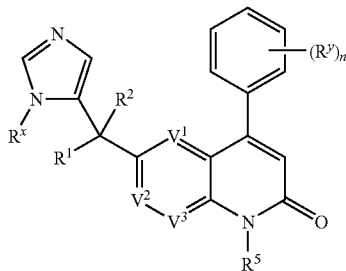

I-m or a pharmaceutically acceptable salt thereof, wherein each of $R^1$, $R^2$, $R^5$, $V^1$, $V^2$, $V^3$, $R^x$, $R^y$, and n is as defined and described herein.

In some embodiments, the present invention provides a compound of formula I-n:

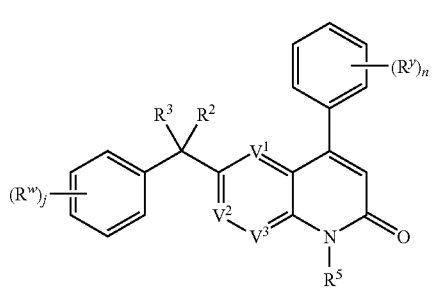

I-n or a pharmaceutically acceptable salt thereof, wherein each of $R^2$, $R^3$, $R^5$, $V^1$, $V^2$, $V^3$, $R^w$, $R^y$, j, and n is as defined and described herein.

In some embodiments, the present invention provides a compound of formula I-o:

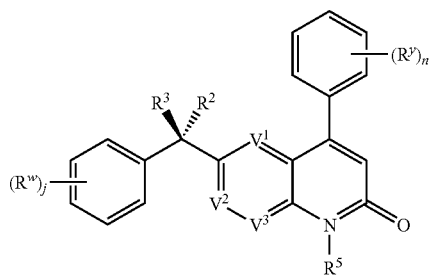

I-o or a pharmaceutically acceptable salt thereof, wherein each of $R^2$, $R^3$, $R^5$, $V^1$, $V^2$, $V^3$, $R^w$, $R^y$, j, and n is as defined and described herein.

In some embodiments, the present invention provides a compound of formula I-p:

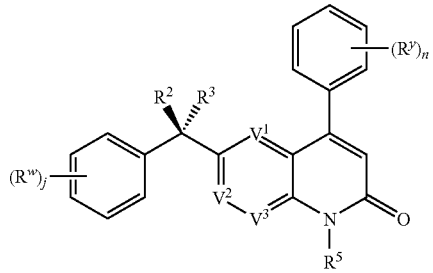

I-p or a pharmaceutically acceptable salt thereof, wherein each of $R^2$, $R^3$, $R^5$, $V^1$, $V^2$, $V^3$, $R^w$, $R^y$, j, and n is as defined and described herein.

In some embodiments, the present invention provides a compound of formula I-q:

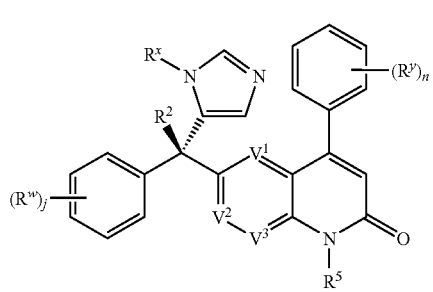

I-q or a pharmaceutically acceptable salt thereof, wherein each of $R^2$, $R^5$, $V^1$, $V^2$, $V^3$, $R^w$, $R^x$, $R^y$, j, and n is as defined and described herein.

In some embodiments, the present invention provides a compound of formula I-r:

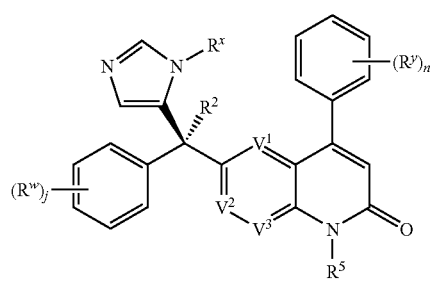

I-r or a pharmaceutically acceptable salt thereof, wherein each of $R^2$, $R^5$, $V^2$, $V^3$, $R^w$, $R^x$, $R^y$, j, and n is as defined and described herein.

In some embodiments, the present invention provides a compound of any of formulae II-a, II-b, or II-c:

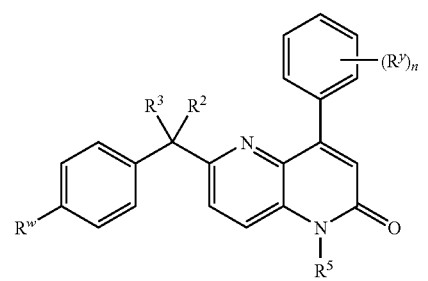

II-a

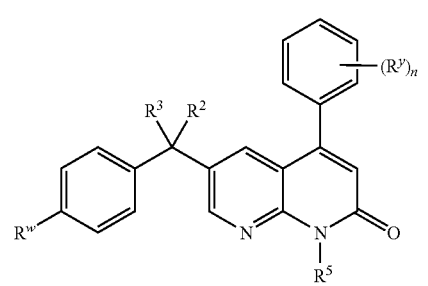

II-b

-continued

II-c

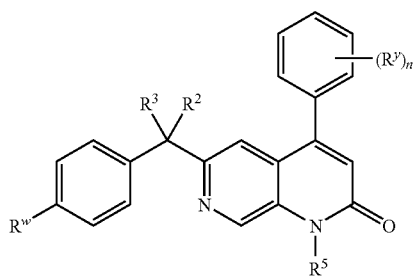

or a pharmaceutically acceptable salt thereof, wherein each of $R^2$, $R^3$, $R^5$, $R^w$, $R^y$, and $n$ is as defined and described herein.

In some embodiments, the present invention provides a compound of any of formulae II-d, II-e, or II-f:

II-d

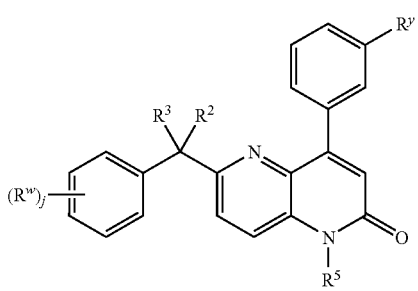

II-e

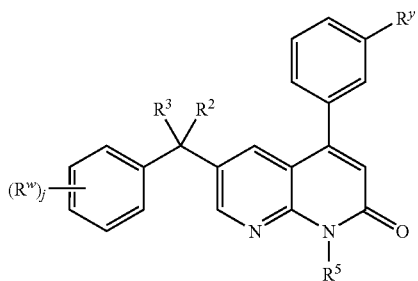

II-f

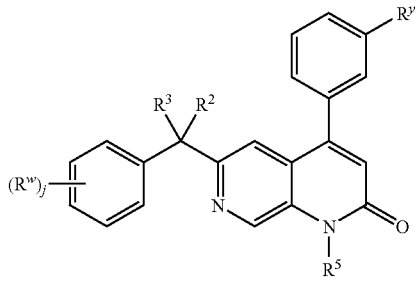

or a pharmaceutically acceptable salt thereof, wherein each of $R^2$, $R^3$, $R^5$, $R^w$, $R^y$, and $j$ is as defined and described herein.

In some embodiments, the present invention provides a compound of any of formulae II-g, II-h, or II-i:

II-g

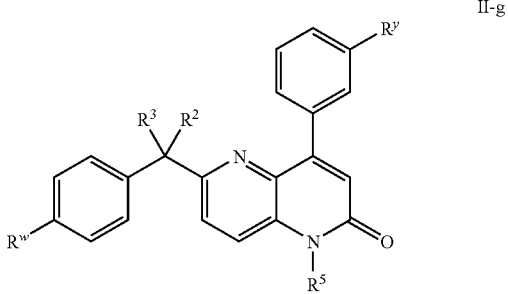

II-h

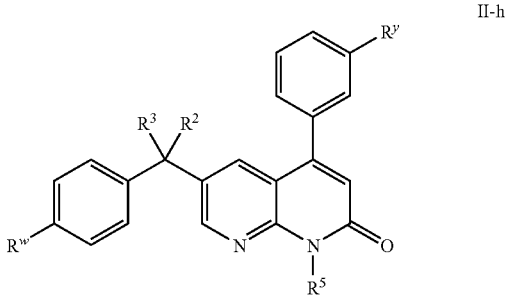

II-i

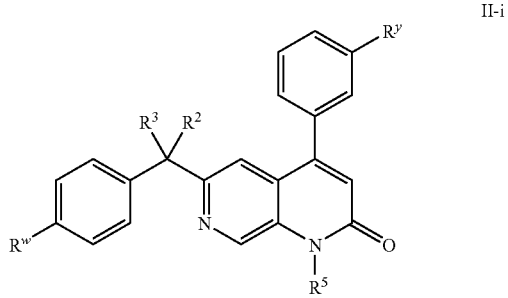

or a pharmaceutically acceptable salt thereof, wherein each of $R^2$, $R^3$, $R^5$, $R^w$, and $R^y$ is as defined and described herein.

In some embodiments, the present invention provides a compound of any of formulae II-j, II-k, or II-l:

II-j

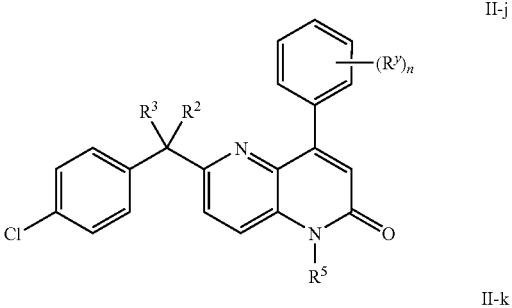

II-k

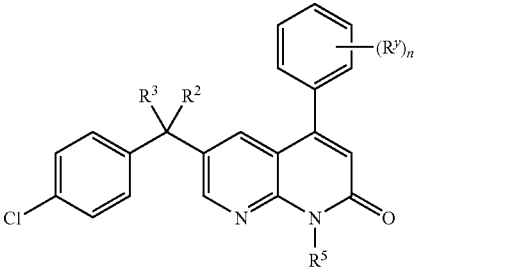

-continued

II-l or a pharmaceutically acceptable salt thereof, wherein each of R², R³, R⁵, Rʸ, and n is as defined and described herein.

In some embodiments, the present invention provides a compound of any of formulae II-m, II-n, or II-o:

II-m

II-n

II-o or a pharmaceutically acceptable salt thereof, wherein each of R², R³, and R⁵ is as defined and described herein.

In some embodiments, the present invention provides a compound of any of formulae III-a, III-b, or III-c:

III-a

III-b

III-c or a pharmaceutically acceptable salt thereof, wherein R³ is as defined and described herein.

In some embodiments, the present invention provides a compound of any of formulae III-d, III-e, or III-f:

III-d

-continued

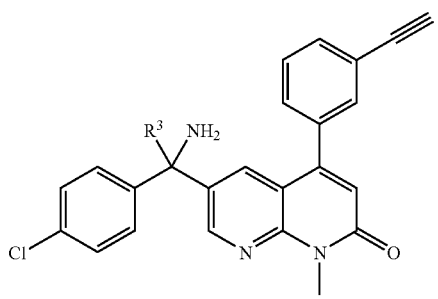
III-e

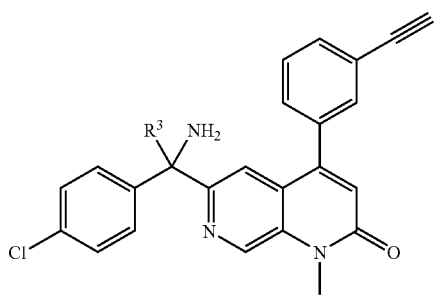
III-f or a pharmaceutically acceptable salt thereof, wherein R³ is as defined and described herein.

In some embodiments, the present invention provides a compound of any of formulae III-g, III-h, or III-i:

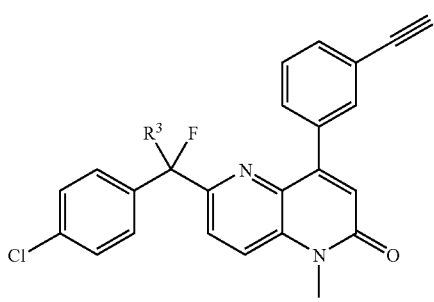
III-g

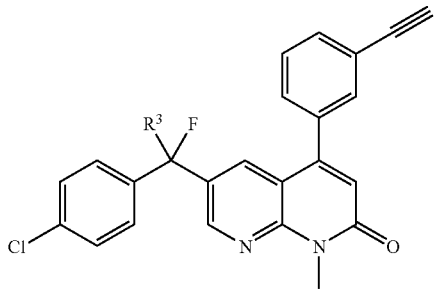
III-h

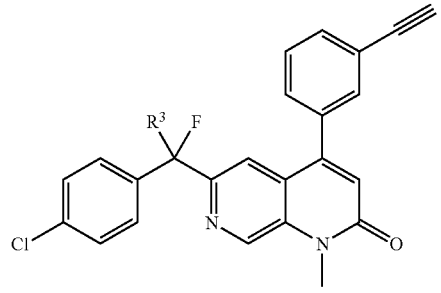
III-i or a pharmaceutically acceptable salt thereof, wherein R³ is as defined and described herein.

In some embodiments, the present invention provides a compound of any of formulae III-j, III-k, or III-l:

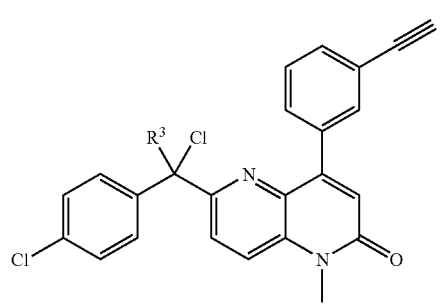
III-j

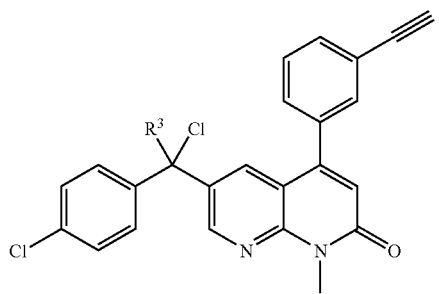
III-k

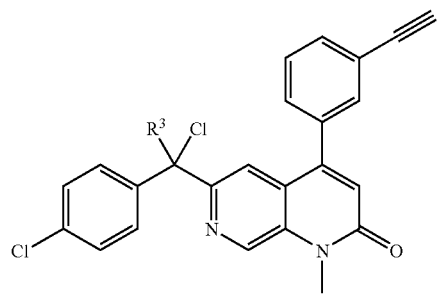
III-l or a pharmaceutically acceptable salt thereof, wherein R³ is as defined and described herein.

In some embodiments, the present invention provides a compound of any of formulae IV-a, IV-b, or IV-c:
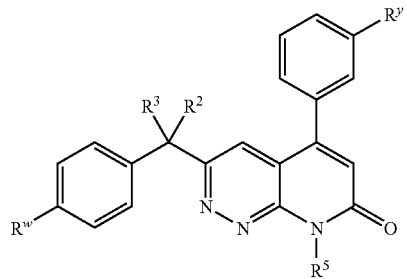
IV-a
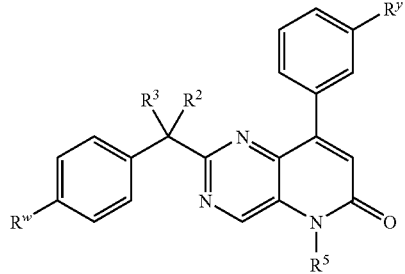
IV-b
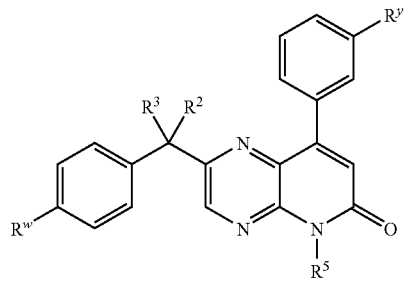
IV-c
or a pharmaceutically acceptable salt thereof, wherein $R^2$, $R^3$, $R^5$, $R^w$, and $R^y$ are as defined and described herein.
In certain embodiments, the compound of Formula I is of any of the following formulae shown in Table 1:
TABLE 1
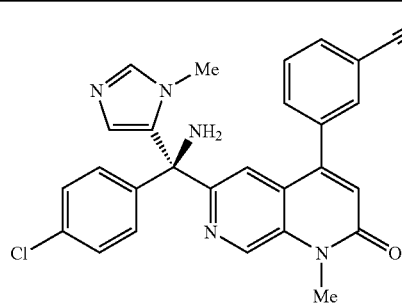
TABLE 1-continued
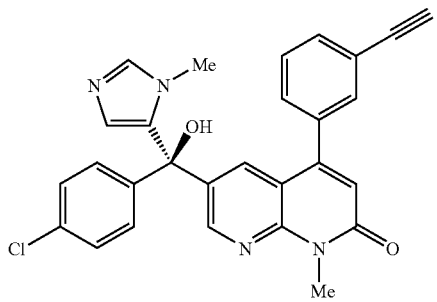 [SMILES: C#Cc1cccc(-c2cc(=O)n(C)c3ncc([C@](O)(c4ccc(Cl)cc4)c4cncn4C)cc23)c1]
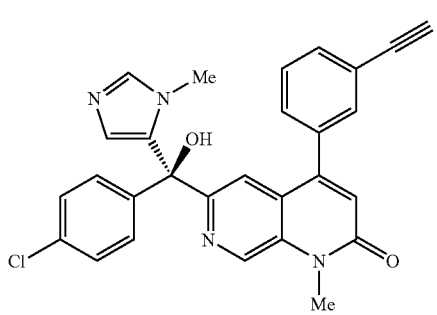 [SMILES: C#Cc1cccc(-c2cc(=O)n(C)c3cnc([C@](O)(c4ccc(Cl)cc4)c4cncn4C)cc23)c1]
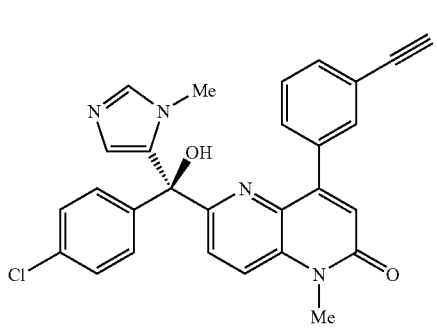 [SMILES: C#Cc1cccc(-c2cc(=O)n(C)c3ccc([C@](O)(c4ccc(Cl)cc4)c4cncn4C)nc23)c1]
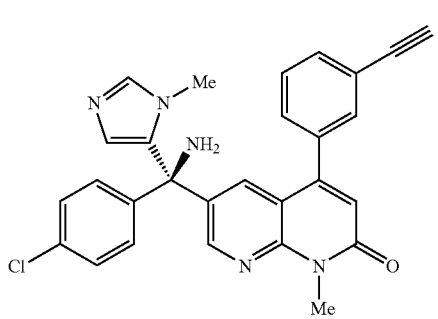
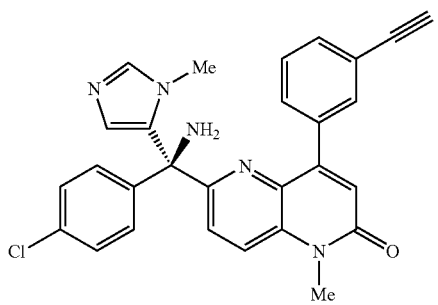

TABLE 1-continued
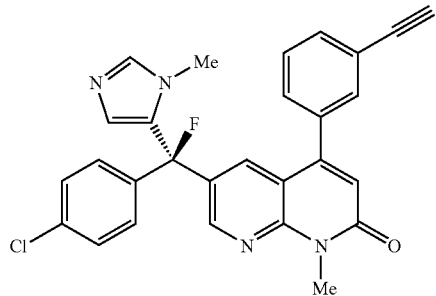 [SMILES: C#Cc1cccc(-c2cc(=O)n(C)c3ncc([C@](F)(c4ccc(Cl)cc4)c4cncn4C)cc23)c1]
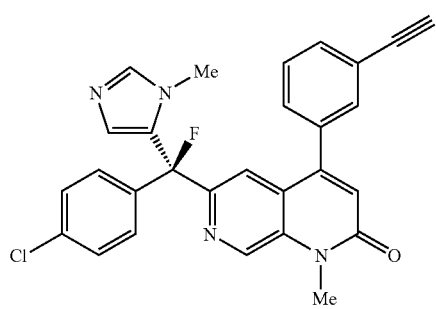 [SMILES: C#Cc1cccc(-c2cc(=O)n(C)c3cnc([C@](F)(c4ccc(Cl)cc4)c4cncn4C)cc23)c1]
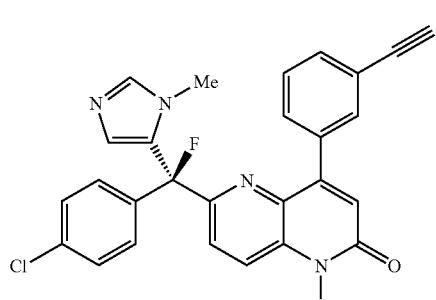
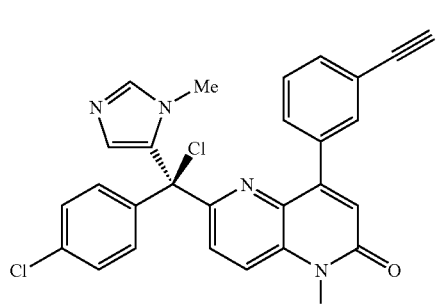
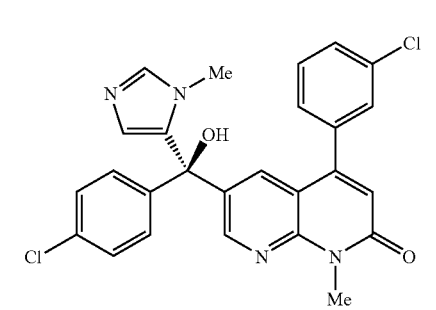 [SMILES: Cn1cncc1[C@@](O)(c1ccc(Cl)cc1)c1cnc2c(c1)c(-c1cccc(Cl)c1)cc(=O)n2C]
TABLE 1-continued
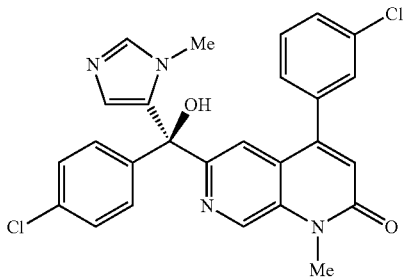 [SMILES: Cn1cncc1[C@@](O)(c1ccc(Cl)cc1)c1cc2c(-c3cccc(Cl)c3)cc(=O)n(C)c2cn1]
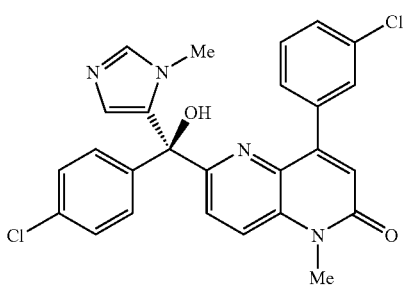
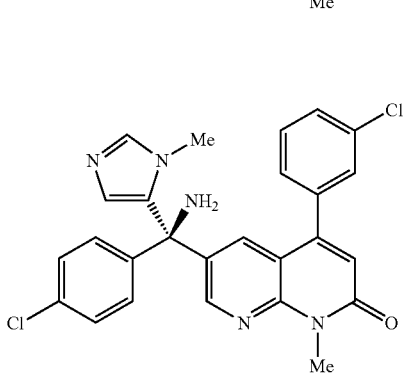
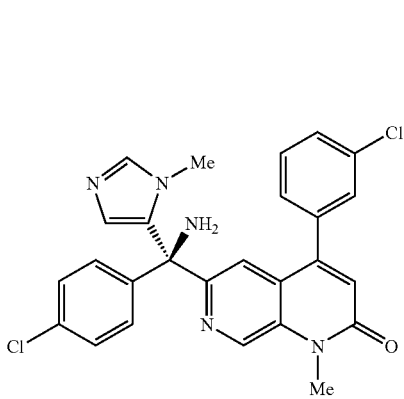
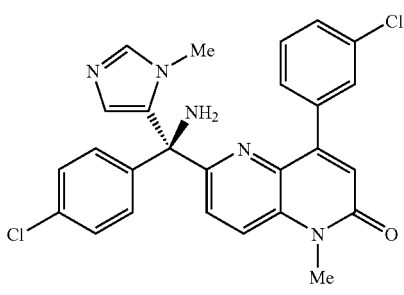

TABLE 1-continued
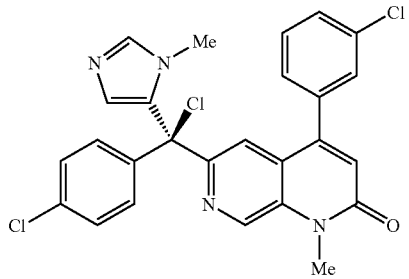
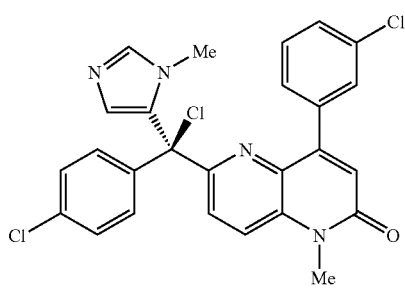 [SMILES: Cn1cncc1[C@@](Cl)(c1ccc(Cl)cc1)c1ccc2c(n1)c(-c1cccc(Cl)c1)cc(=O)n2C]
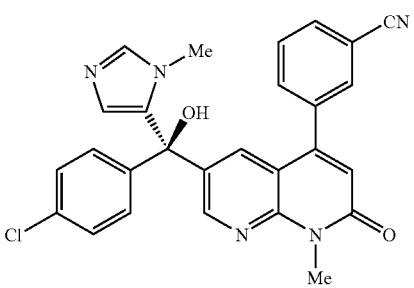 [SMILES: Cn1cncc1[C@@](O)(c1ccc(Cl)cc1)c1cnc2c(c1)c(-c1cccc(C#N)c1)cc(=O)n2C]
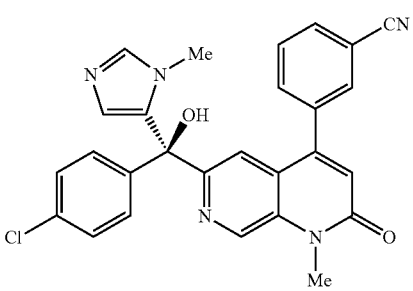
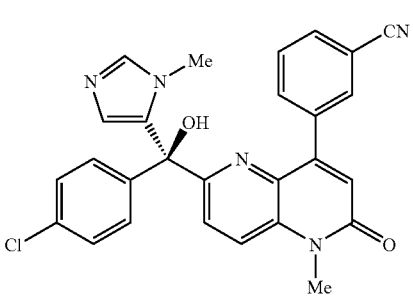 [SMILES: Cn1cncc1[C@@](O)(c1ccc(Cl)cc1)c1ccc2c(n1)c(-c1cccc(C#N)c1)cc(=O)n2C]
TABLE 1-continued
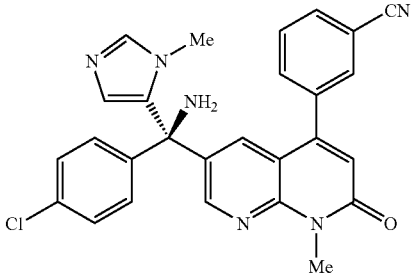 [SMILES: Cn1cncc1[C@@](N)(c1ccc(Cl)cc1)c1cnc2c(c1)c(-c1cccc(C#N)c1)cc(=O)n2C]
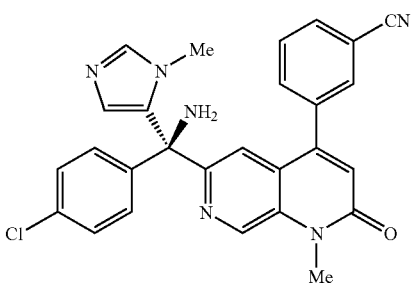
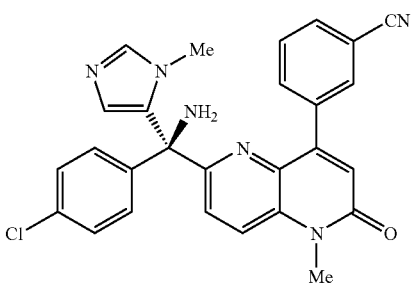
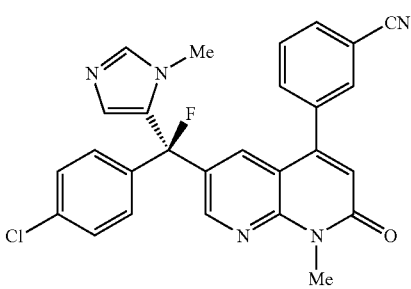 [SMILES: Cn1cncc1[C@@](F)(c1ccc(Cl)cc1)c1cnc2c(c1)c(-c1cccc(C#N)c1)cc(=O)n2C]
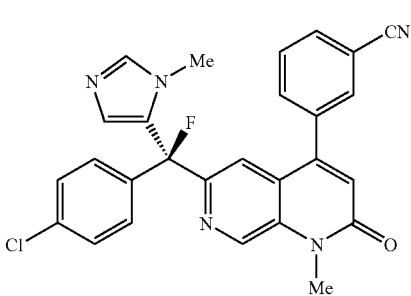 [SMILES: Cn1cncc1[C@@](F)(c1ccc(Cl)cc1)c1cc2c(-c3cccc(C#N)c3)cc(=O)n(C)c2cn1]

TABLE 1-continued
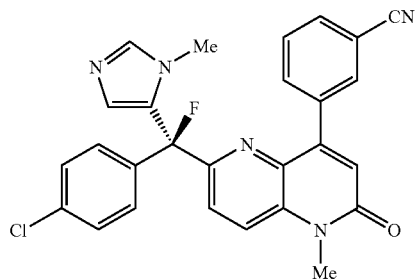 [SMILES: Cn1cncc1[C@@](F)(c1ccc(Cl)cc1)c1ccc2c(n1)c(-c1cccc(C#N)c1)cc(=O)n2C]
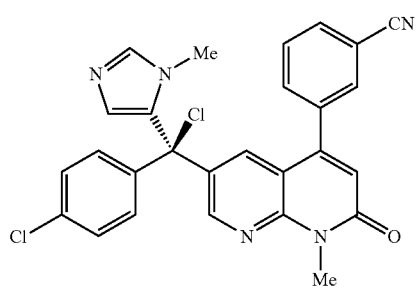
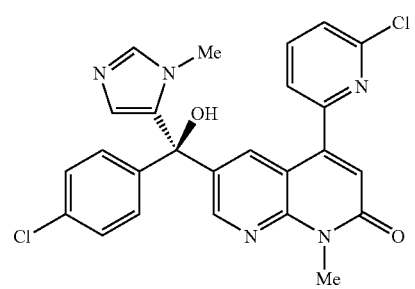
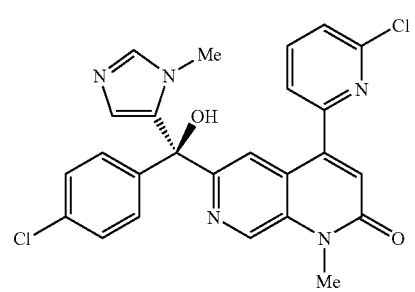
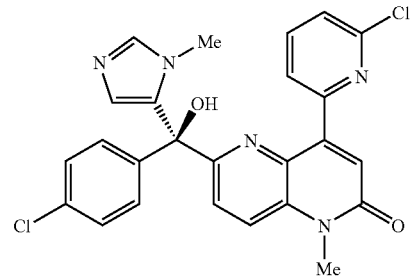 [SMILES: Cn1cncc1[C@@](O)(c1ccc(Cl)cc1)c1ccc2c(n1)c(-c1cccc(Cl)n1)cc(=O)n2C]
TABLE 1-continued
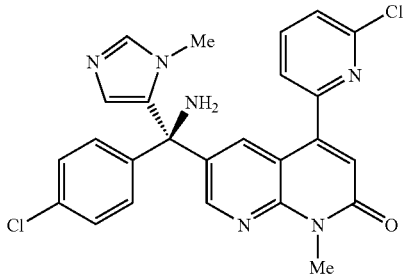 [SMILES: Cn1cncc1[C@@](N)(c1ccc(Cl)cc1)c1cnc2c(c1)c(-c1cccc(Cl)n1)cc(=O)n2C]
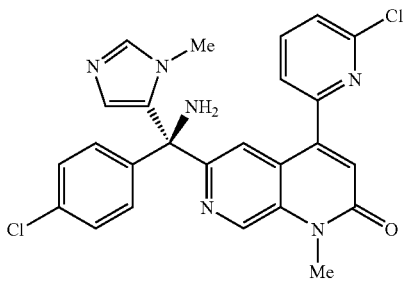
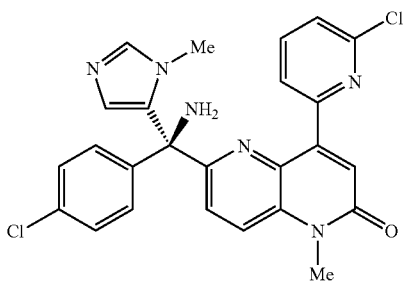 [SMILES: Cn1cncc1[C@@](N)(c1ccc(Cl)cc1)c1ccc2c(n1)c(-c1cccc(Cl)n1)cc(=O)n2C]
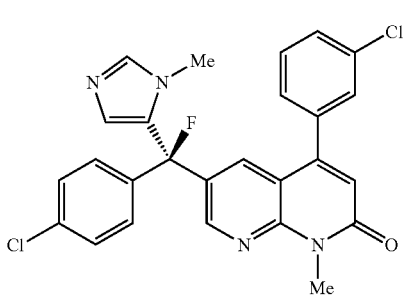 [SMILES: Cn1cncc1[C@@](F)(c1ccc(Cl)cc1)c1cnc2c(c1)c(-c1cccc(Cl)c1)cc(=O)n2C]
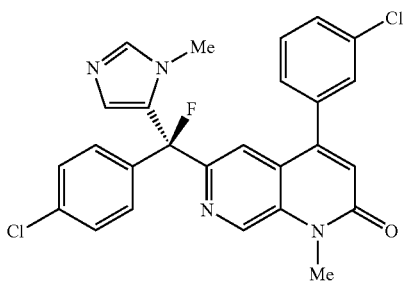 [SMILES: Cn1cncc1[C@@](F)(c1ccc(Cl)cc1)c1cc2c(-c3cccc(Cl)c3)cc(=O)n(C)c2cn1]

TABLE 1-continued
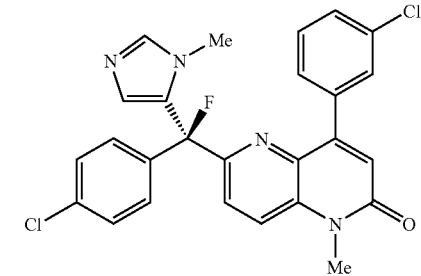
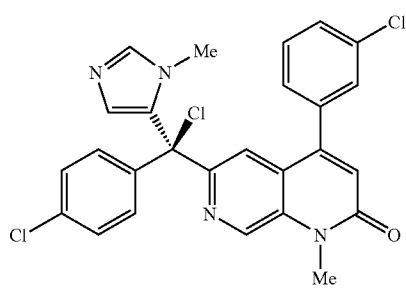
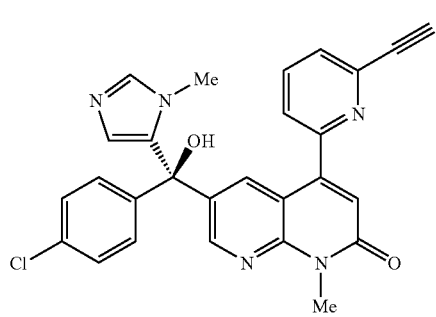
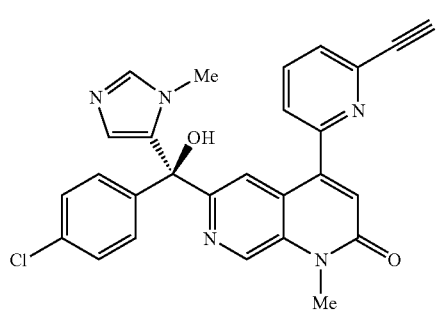
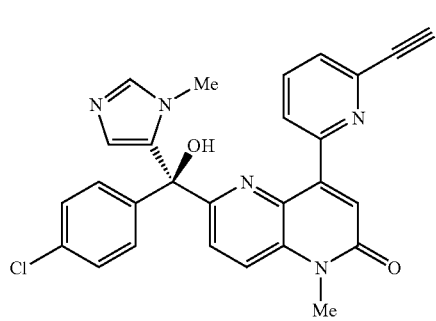 [SMILES: C#Cc1cccc(-c2cc(=O)n(C)c3ccc([C@](O)(c4ccc(Cl)cc4)c4cncn4C)nc23)n1]
TABLE 1-continued
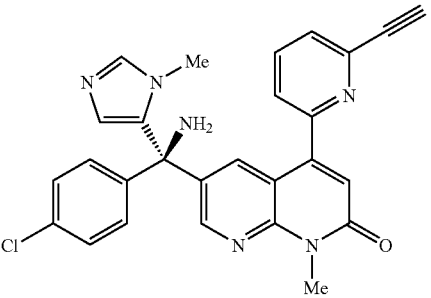 [SMILES: C#Cc1cccc(-c2cc(=O)n(C)c3ncc([C@](N)(c4ccc(Cl)cc4)c4cncn4C)cc23)n1]
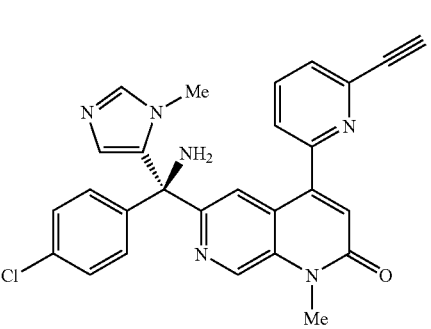
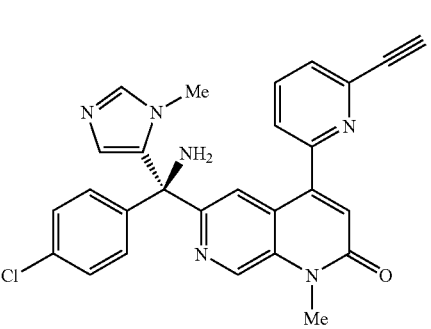
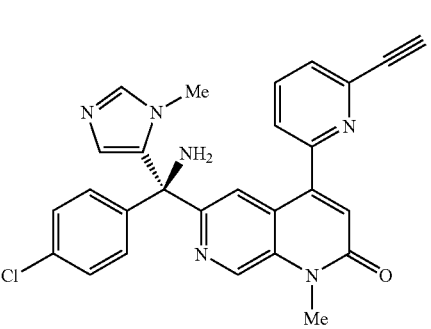
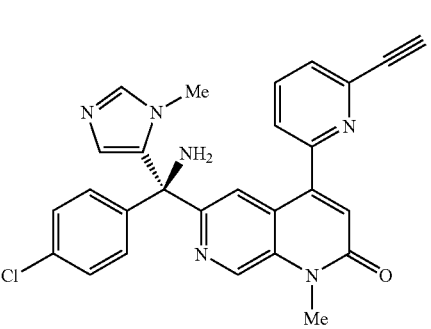

TABLE 1-continued
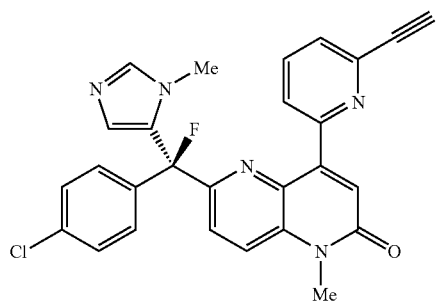 [SMILES: C#Cc1cccc(-c2cc(=O)n(C)c3ccc([C@](F)(c4ccc(Cl)cc4)c4cncn4C)nc23)n1]
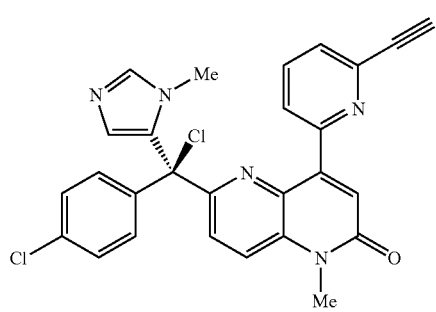 [SMILES: C#Cc1cccc(-c2cc(=O)n(C)c3ccc([C@](Cl)(c4ccc(Cl)cc4)c4cncn4C)nc23)n1]
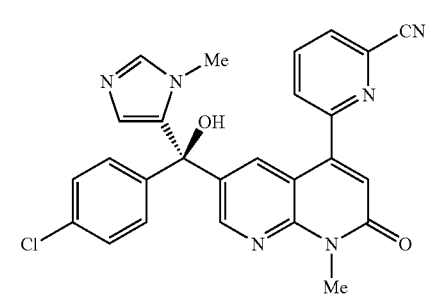 [SMILES: Cn1cncc1[C@@](O)(c1ccc(Cl)cc1)c1cnc2c(c1)c(-c1cccc(C#N)n1)cc(=O)n2C]
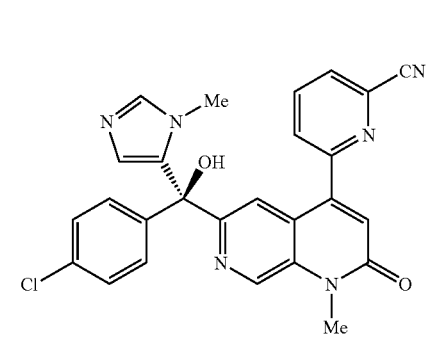 [SMILES: Cn1cncc1[C@@](O)(c1ccc(Cl)cc1)c1cc2c(-c3cccc(C#N)n3)cc(=O)n(C)c2cn1]
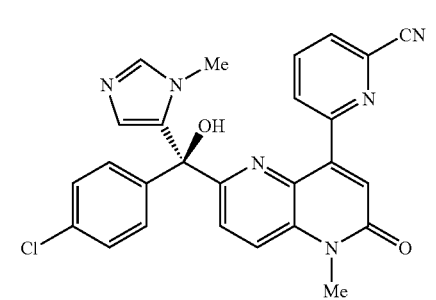
TABLE 1-continued
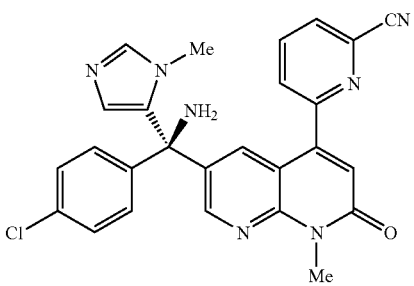
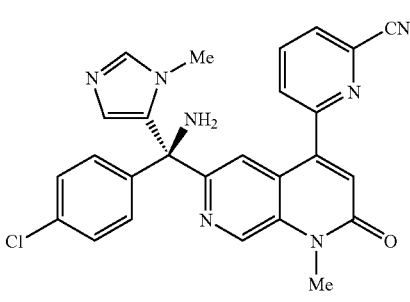
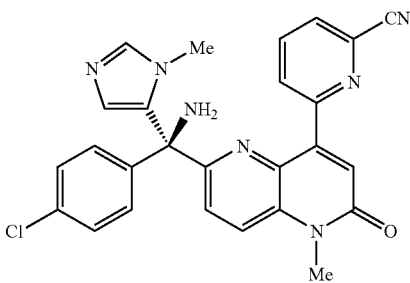 [SMILES: Cn1cncc1[C@@](N)(c1ccc(Cl)cc1)c1cc2c(-c3cccc(C#N)n3)cc(=O)n(C)c2cn1]
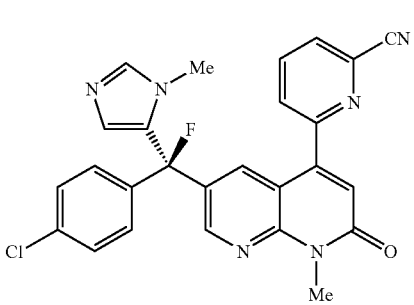
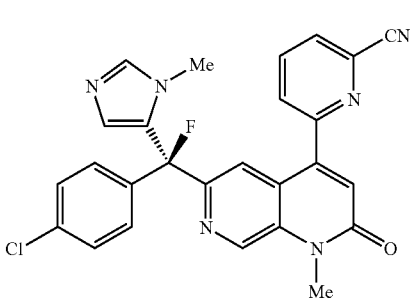

TABLE 1-continued
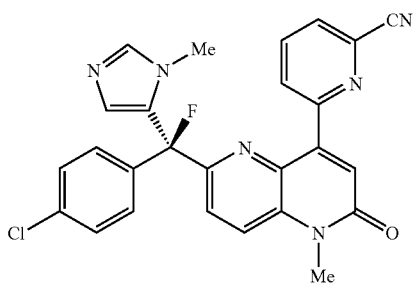
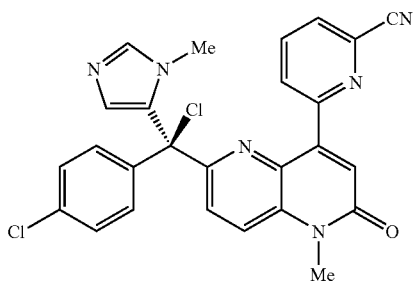 [SMILES: Cn1cncc1[C@@](Cl)(c1ccc(Cl)cc1)c1ccc2c(n1)c(-c1cccc(C#N)n1)cc(=O)n2C]
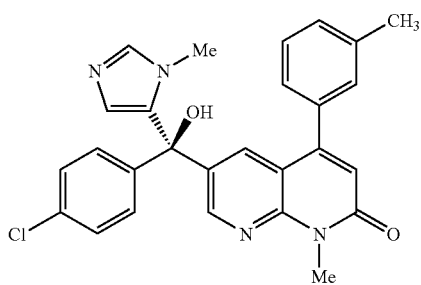 [SMILES: Cc1cccc(-c2cc(=O)n(C)c3cnc([C@](O)(c4ccc(Cl)cc4)c4cncn4C)cc23)c1]
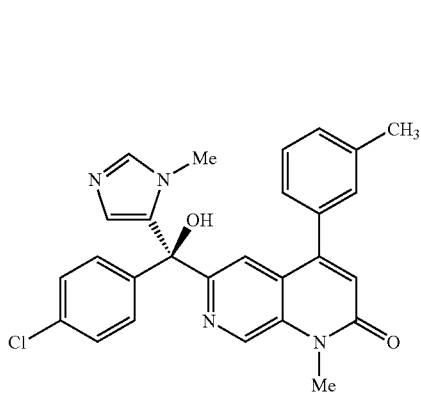
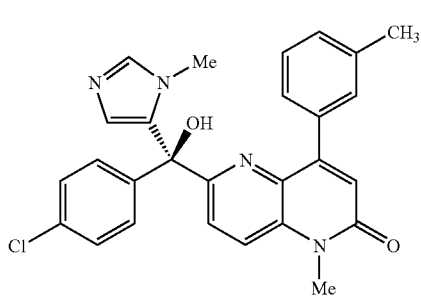
TABLE 1-continued
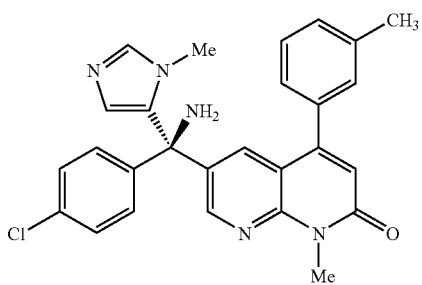 [SMILES: Cc1cccc(-c2cc(=O)n(C)c3ncc([C@](F)(c4ccc(Cl)cc4)c4cncn4C)cc23)c1]
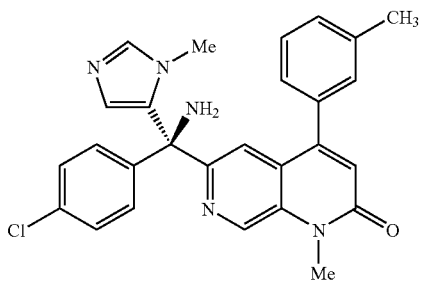
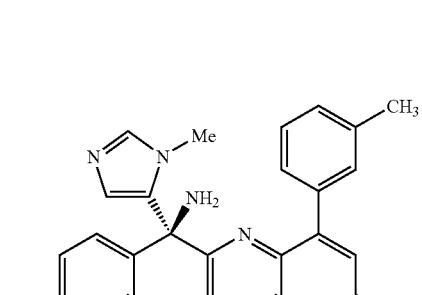
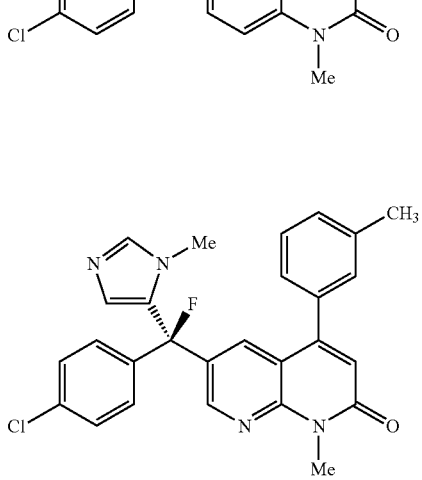
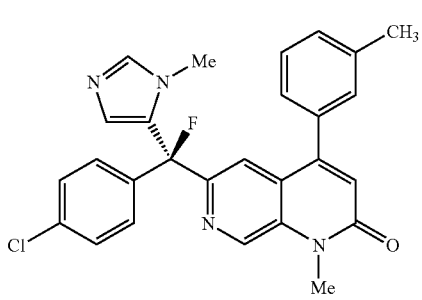 [SMILES: Cc1cccc(-c2cc(=O)n(C)c3cnc([C@](F)(c4ccc(Cl)cc4)c4cncn4C)cc23)c1]

TABLE 1-continued
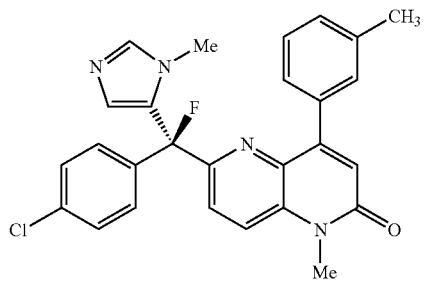
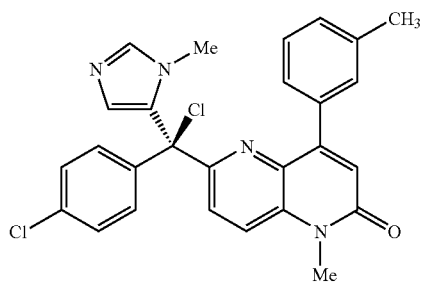 [SMILES: Cc1cccc(-c2cc(=O)n(C)c3ccc([C@](Cl)(c4ccc(Cl)cc4)c4cncn4C)nc23)c1]
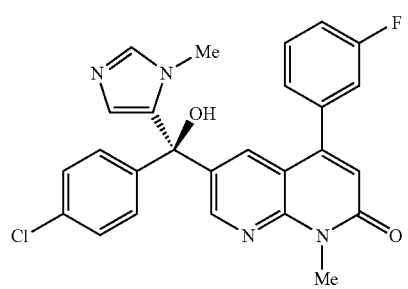
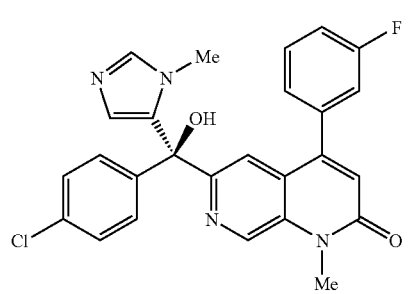
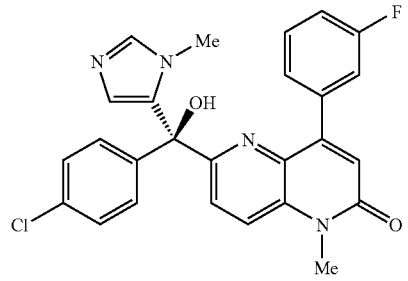
TABLE 1-continued
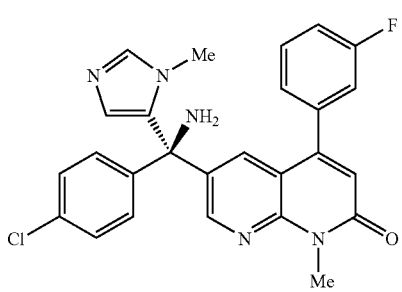 [SMILES: Cn1cncc1[C@@](O)(c1ccc(Cl)cc1)c1cnc2c(c1)c(-c1cccc(F)c1)cc(=O)n2C]
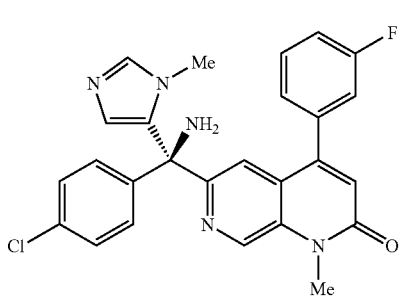
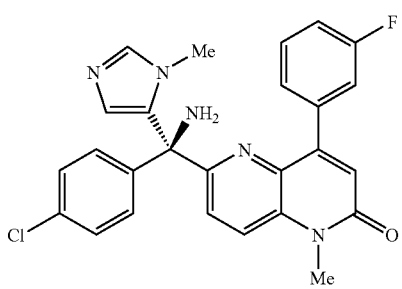 [SMILES: Cn1cncc1[C@@](O)(c1ccc(Cl)cc1)c1ccc2c(n1)c(-c1cccc(F)c1)cc(=O)n2C]
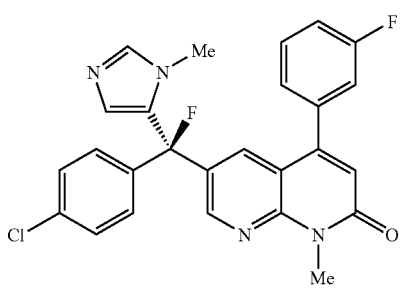 [SMILES: Cn1cncc1[C@@](F)(c1ccc(Cl)cc1)c1cc2c(-c3cccc(F)c3)cc(=O)n(C)c2cn1]
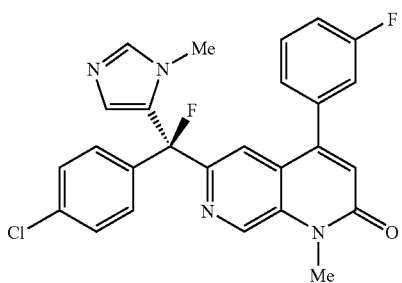

TABLE 1-continued
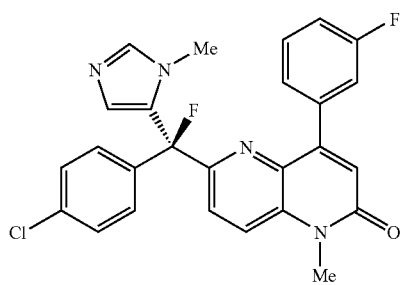 [SMILES: Cn1cncc1[C@@](F)(c1ccc(Cl)cc1)c1ccc2c(n1)c(-c1cccc(F)c1)cc(=O)n2C]
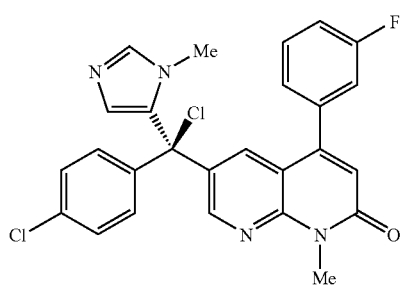
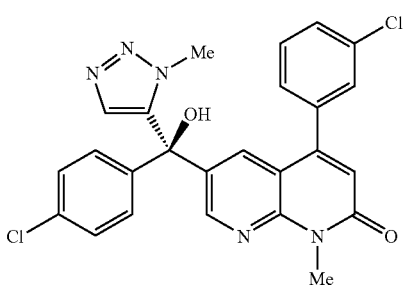
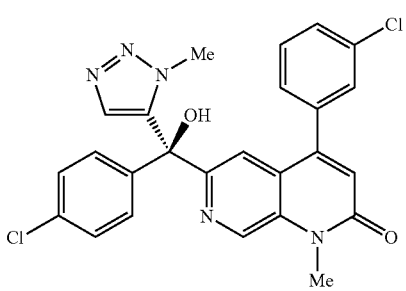
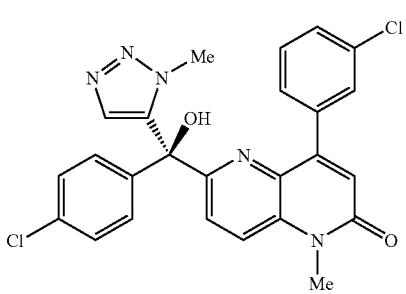 [SMILES: Cn1nncc1[C@@](O)(c1ccc(Cl)cc1)c1ccc2c(n1)c(-c1cccc(Cl)c1)cc(=O)n2C]
TABLE 1-continued
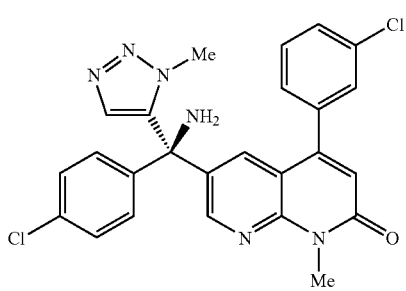 [SMILES: Cn1nncc1[C@@](N)(c1ccc(Cl)cc1)c1cnc2c(c1)c(-c1cccc(Cl)c1)cc(=O)n2C]
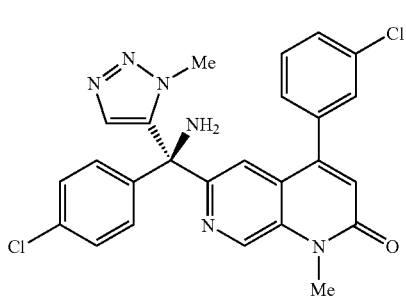 [SMILES: Cn1nncc1[C@@](N)(c1ccc(Cl)cc1)c1cc2c(-c3cccc(Cl)c3)cc(=O)n(C)c2cn1]
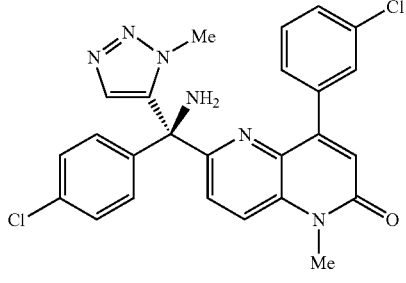
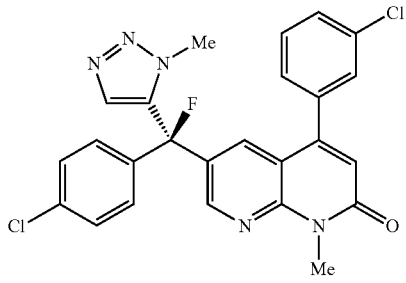
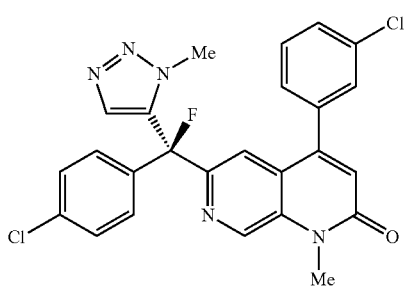

TABLE 1-continued
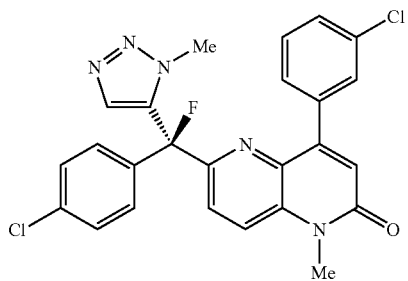 [SMILES: Cn1nncc1[C@@](F)(c1ccc(Cl)cc1)c1ccc2c(n1)c(-c1cccc(Cl)c1)cc(=O)n2C]
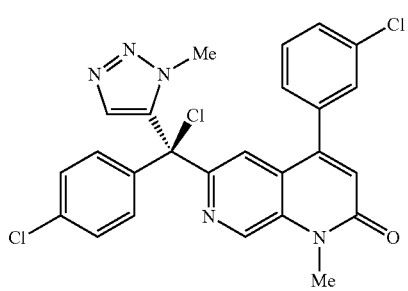
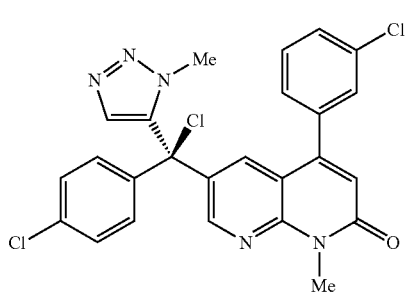
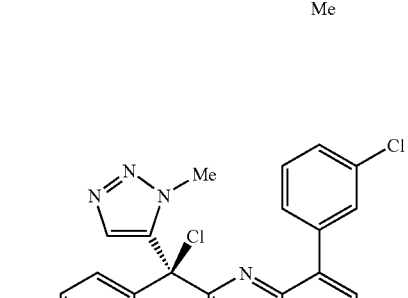
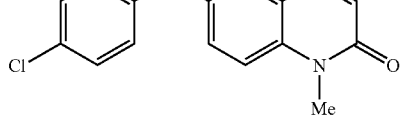
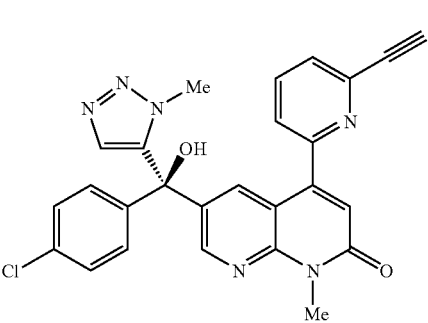 [SMILES: C#Cc1cccc(-c2cc(=O)n(C)c3ncc([C@](O)(c4ccc(Cl)cc4)c4cnnn4C)cc23)n1]
TABLE 1-continued
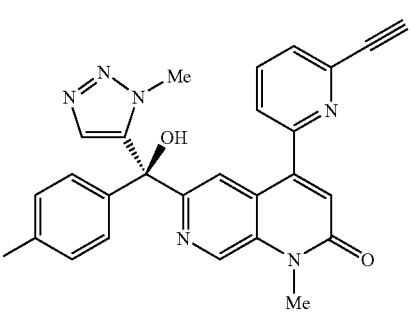
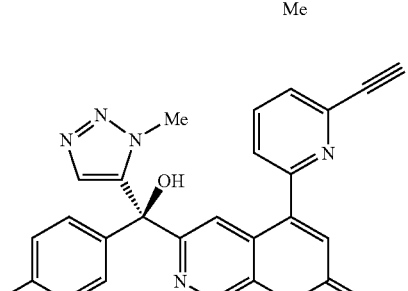
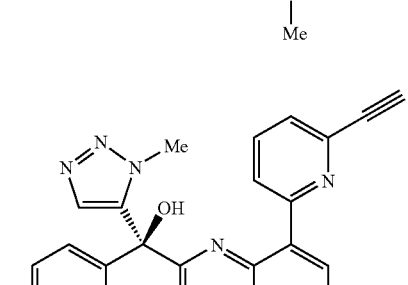
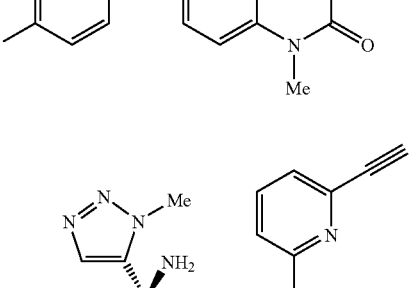
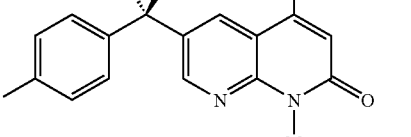
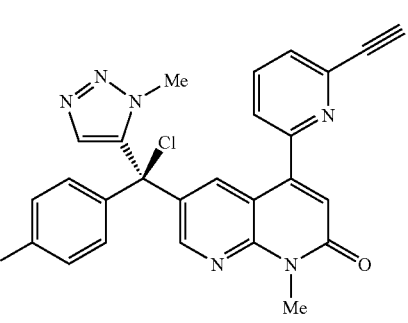

TABLE 1-continued
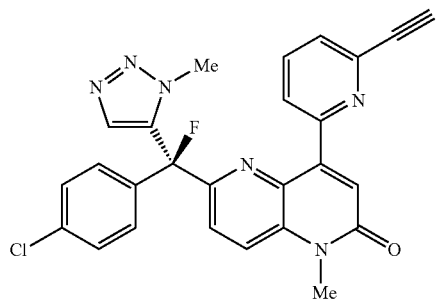
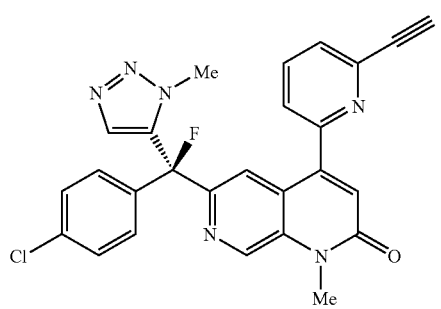
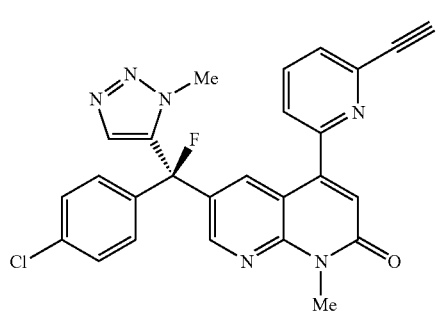
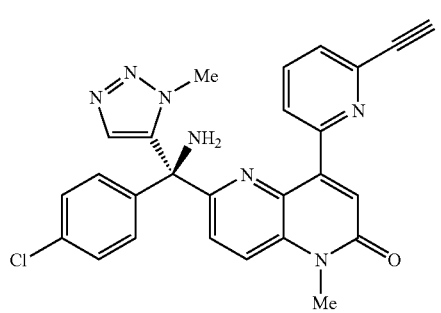
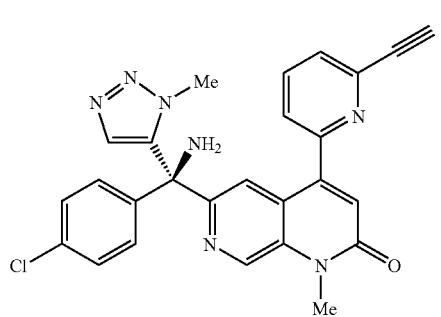 [SMILES: C#Cc1cccc(-c2cc(=O)n(C)c3cnc([C@](N)(c4ccc(Cl)cc4)c4cnnn4C)cc23)n1]
TABLE 1-continued
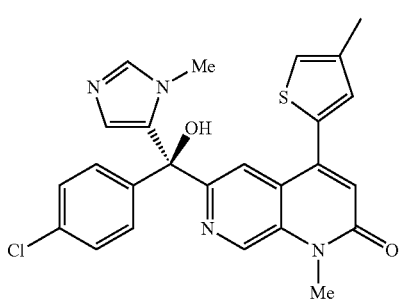 [SMILES: Cc1csc(-c2cc(=O)n(C)c3cnc([C@](O)(c4ccc(Cl)cc4)c4cncn4C)cc23)c1]
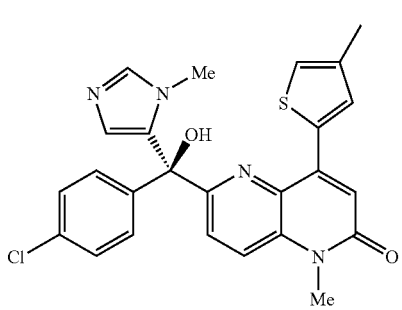 [SMILES: Cc1csc(-c2cc(=O)n(C)c3ccc([C@](O)(c4ccc(Cl)cc4)c4cncn4C)nc23)c1]
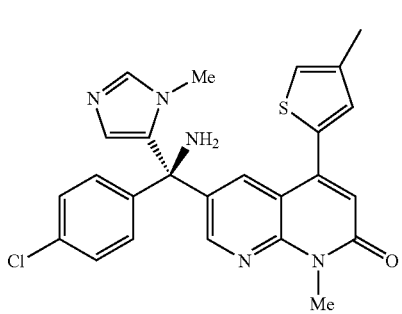 [SMILES: Cc1csc(-c2cc(=O)n(C)c3ncc([C@](N)(c4ccc(Cl)cc4)c4cncn4C)cc23)c1]
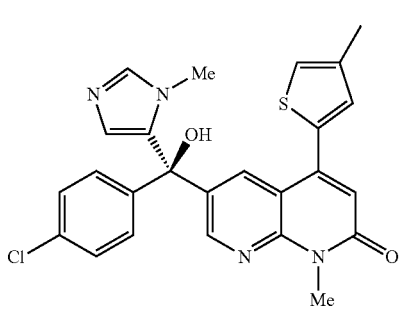
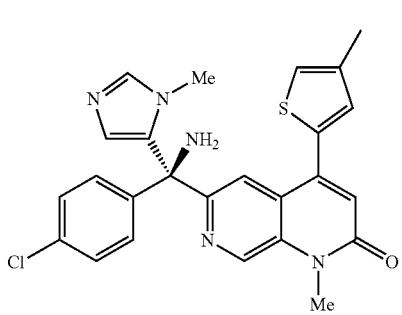

| | |
|---|---|
| 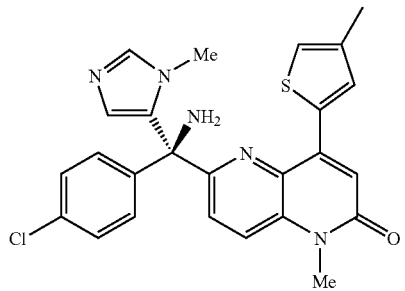 [SMILES: Cc1csc(-c2cc(=O)n(C)c3ccc([C@](N)(c4ccc(Cl)cc4)c4cncn4C)nc23)c1] | 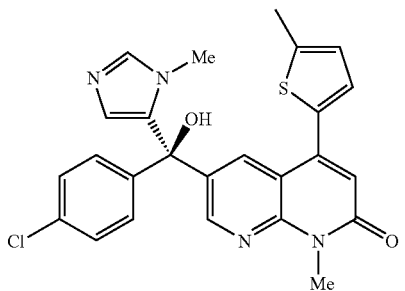 |
| 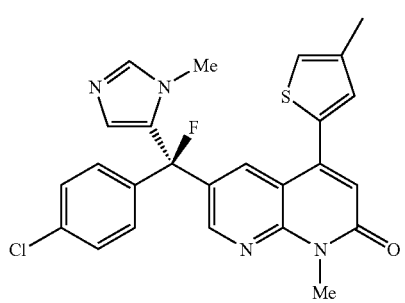 | 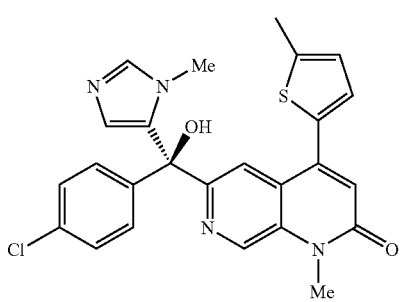 |
| 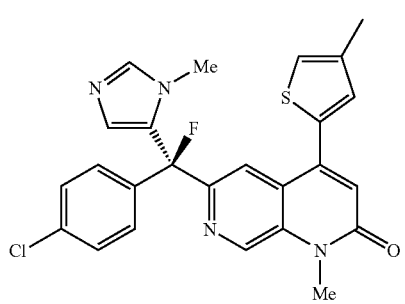 [SMILES: Cc1csc(-c2cc(=O)n(C)c3cnc([C@](F)(c4ccc(Cl)cc4)c4cncn4C)cc23)c1] | 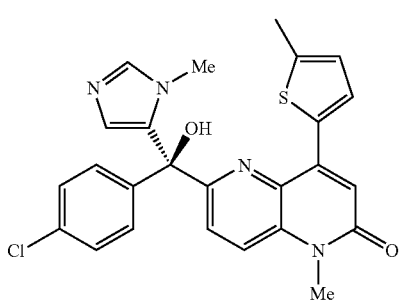 |
| 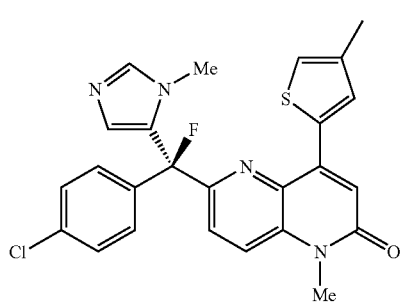 [SMILES: Cc1csc(-c2cc(=O)n(C)c3ccc([C@](F)(c4ccc(Cl)cc4)c4cncn4C)nc23)c1] | 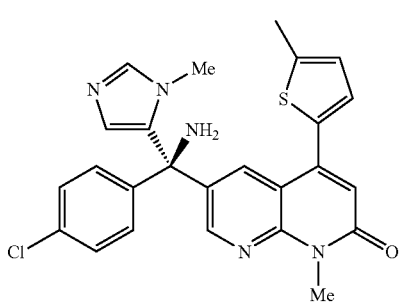 |
| 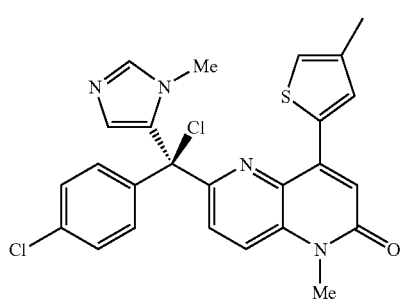 [SMILES: Cc1csc(-c2cc(=O)n(C)c3ccc([C@](Cl)(c4ccc(Cl)cc4)c4cncn4C)nc23)c1] | 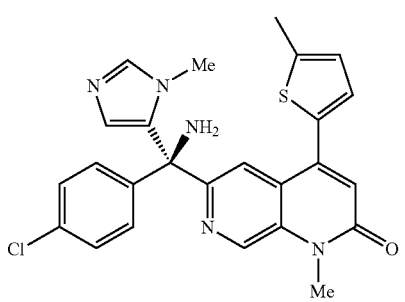 [SMILES: Cc1ccc(-c2cc(=O)n(C)c3cnc([C@](N)(c4ccc(Cl)cc4)c4cncn4C)cc23)s1] |

TABLE 1-continued
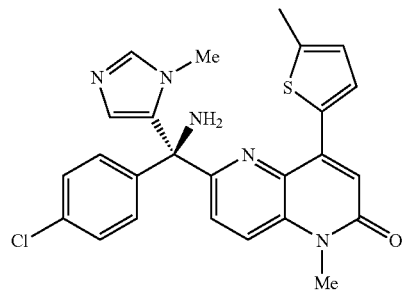
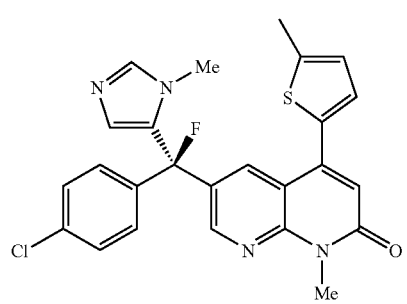
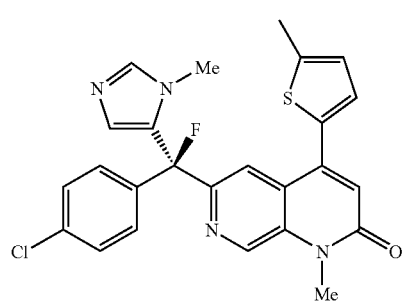 [SMILES: Cc1ccc(-c2cc(=O)n(C)c3ccc([C@](F)(c4ccc(Cl)cc4)c4cncn4C)nc23)s1]
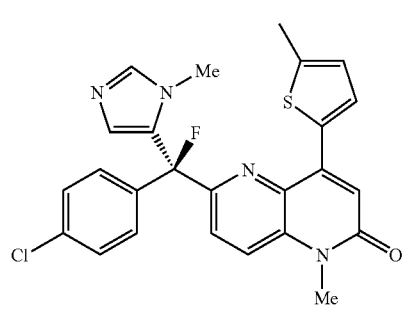
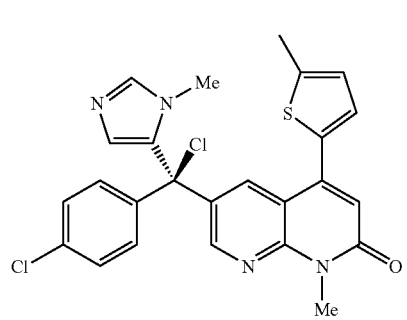 [SMILES: Cc1ccc(-c2cc(=O)n(C)c3ncc([C@](Cl)(c4ccc(Cl)cc4)c4cncn4C)cc23)s1]
TABLE 1-continued
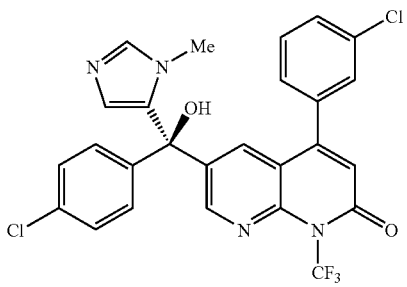 [SMILES: Cn1cncc1[C@@](O)(c1ccc(Cl)cc1)c1cnc2c(c1)c(-c1cccc(Cl)c1)cc(=O)n2C(F)(F)F]
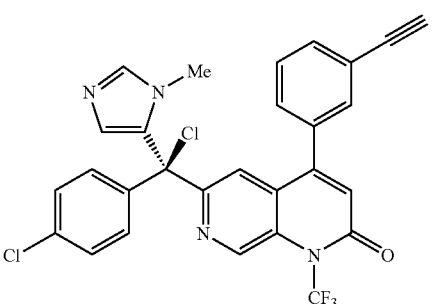
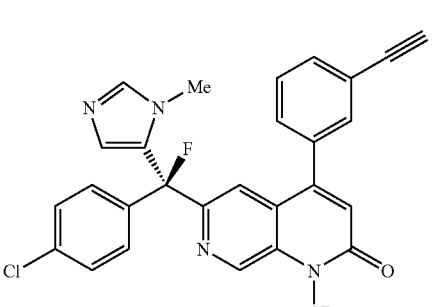
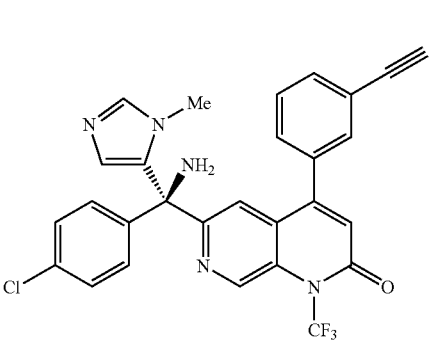
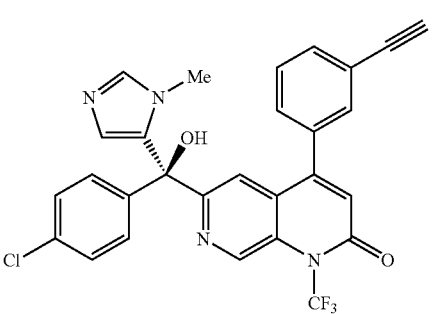 [SMILES: C#Cc1cccc(-c2cc(=O)n(C(F)(F)F)c3cnc([C@](N)(c4ccc(Cl)cc4)c4cncn4C)cc23)c1]

TABLE 1-continued

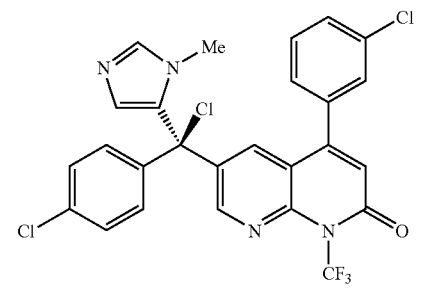 [SMILES: Cn1cncc1[C@@](Cl)(c1ccc(Cl)cc1)c1cnc2c(c1)c(-c1cccc(Cl)c1)cc(=O)n2C(F)(F)F]

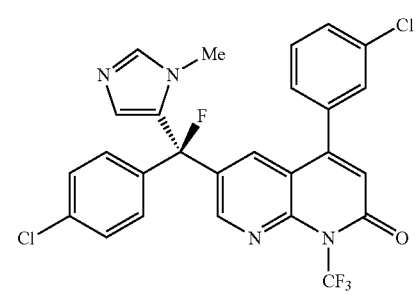

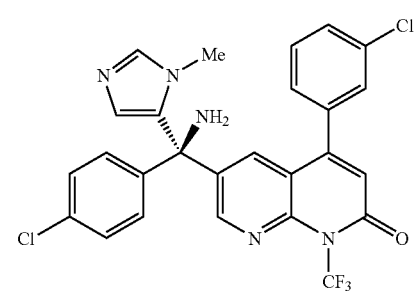 [SMILES: Cn1cncc1[C@@](N)(c1ccc(Cl)cc1)c1cnc2c(c1)c(-c1cccc(Cl)c1)cc(=O)n2C(F)(F)F]

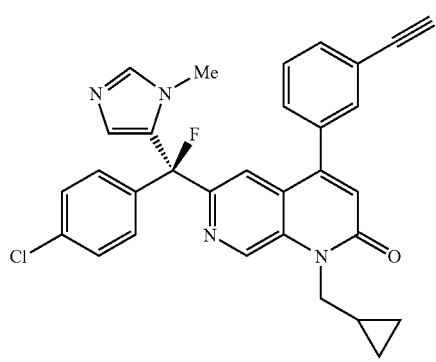 [SMILES: C#Cc1cccc(-c2cc(=O)n(CC3CC3)c3cnc([C@](F)(c4ccc(Cl)cc4)c4cncn4C)cc23)c1]

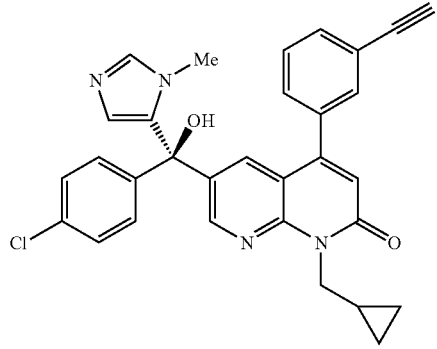 [SMILES: C#Cc1cccc(-c2cc(=O)n(CC3CC3)c3ncc([C@](O)(c4ccc(Cl)cc4)c4cncn4C)cc23)c1]

TABLE 1-continued

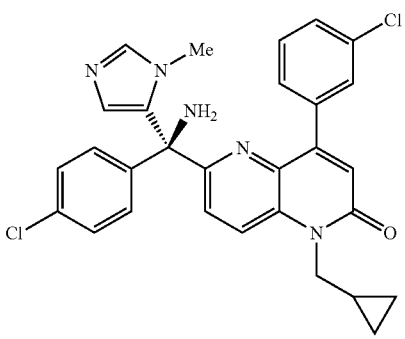 [SMILES: Cn1cncc1[C@@](N)(c1ccc(Cl)cc1)c1ccc2c(n1)c(-c1cccc(Cl)c1)cc(=O)n2CC1CC1]

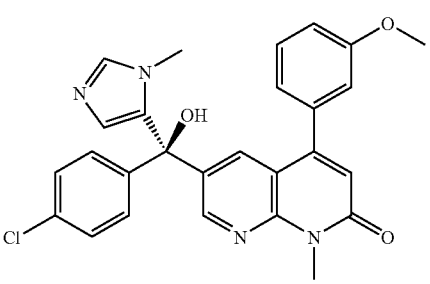

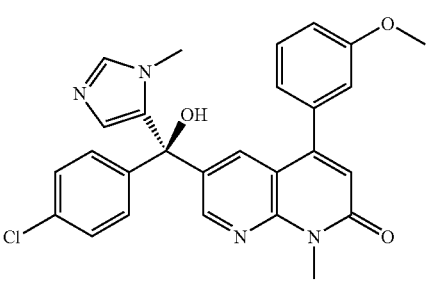 [SMILES: COc1cccc(-c2cc(=O)n(C)c3ncc([C@](O)(c4ccc(Cl)cc4)c4cncn4C)cc23)c1]

In addition to compounds of Formula I contemplated above, the present invention also provides compounds of formula V shown below.

In some embodiments, the present invention provides a compound of formula V:

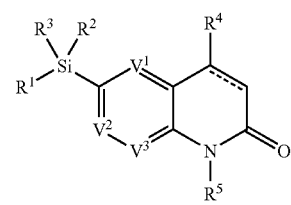

or a pharmaceutically acceptable salt thereof, wherein each of $R^1$, $R^2$, $R^3$, $R^4$, $R^5$, $V^1$, $V^2$, $V^3$ and ----- is as defined and described above and herein for Formula I.

In some embodiments, the present invention provides a compound of formula V-a:

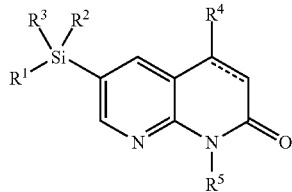

V-a or a pharmaceutically acceptable salt thereof, wherein each of $R^1$, $R^2$, $R^3$, $R^4$, $R^5$, and ----- is as defined and described herein for Formula I.

In some embodiments, the present invention provides a compound of formula V-b:

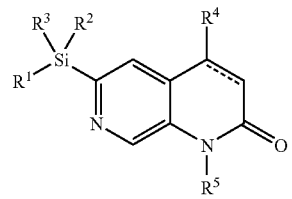

V-b or a pharmaceutically acceptable salt thereof, wherein each of $R^1$, $R^2$, $R^3$, $R^4$, $R^5$, and ----- is as defined and described herein for Formula I.

In some embodiments, the present invention provides a compound of formula V-c:

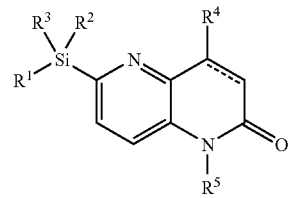

V-c or a pharmaceutically acceptable salt thereof, wherein each of $R^1$, $R^2$, $R^3$, $R^4$, $R^5$, and ----- is as defined and described herein.

In some embodiments, the present invention provides a compound of formula V-d:

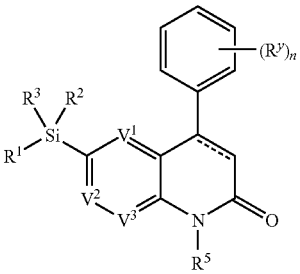

V-d or a pharmaceutically acceptable salt thereof, wherein each of $R^1$, $R^2$, $R^3$, $R^5$, $V^1$, $V^2$, $V^3$, $R^y$, n, and ----- is as defined and described herein for Formula I.

In some embodiments, the present invention provides a compound of formula V-e:

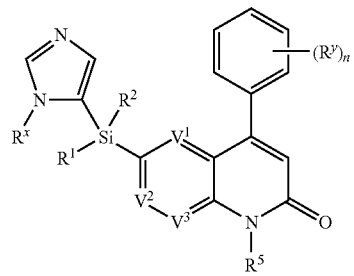

V-e or a pharmaceutically acceptable salt thereof, wherein each of $R^1$, $R^2$, $R^5$, $V^1$, $V^2$, $V^3$, $R^x$, $R^y$, and n is as defined and described herein for Formula I.

In some embodiments, the present invention provides a compound of formula V-f:

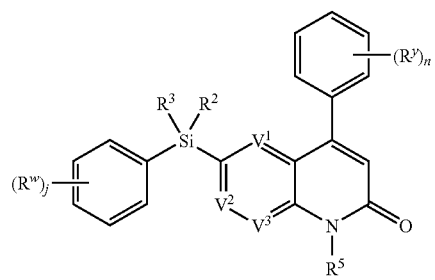

V-f or a pharmaceutically acceptable salt thereof, wherein each of $R^2$, $R^3$, $R^5$, $V^1$, $V^2$, $V^3$, $R^w$, $R^y$, j, and n is as defined and described herein for Formula I.

In some embodiments, the present invention provides a compound of formula V-g;

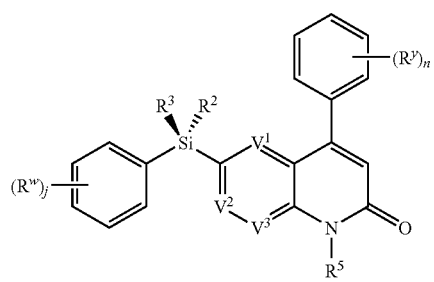

V-g or a pharmaceutically acceptable salt thereof, wherein each of $R^2$, $R^3$, $R^5$, $V^1$, $V^2$, $V^3$, $R^w$, $R^y$, j, and n is as defined and described herein for Formula I.

In some embodiments, the present invention provides a compound of formula V-h:

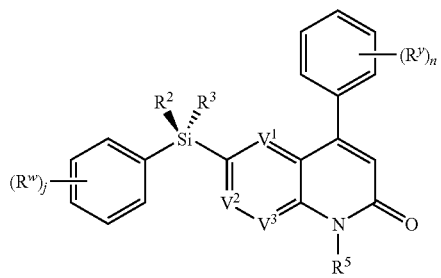

V-h or a pharmaceutically acceptable salt thereof, wherein each of $R^2$, $R^3$, $R^5$, $V^1$, $V^2$, $V^3$, $R^w$, $R^y$, j, and n is as defined and described herein for Formula I.

In some embodiments, the present invention provides a compound of formula V-i:

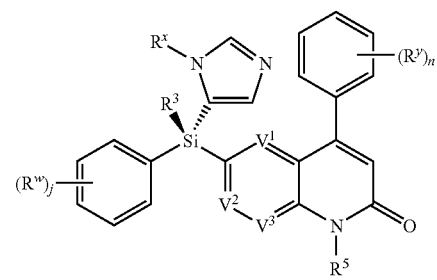

V-i or a pharmaceutically acceptable salt thereof, wherein each of $R^2$, $R^5$, $V^1$, $V^2$, $V^3$, $R^w$, $R^x$, $R^y$, j, and n is as defined and described herein for Formula I.

In some embodiments, the present invention provides a compound of formula V-j:

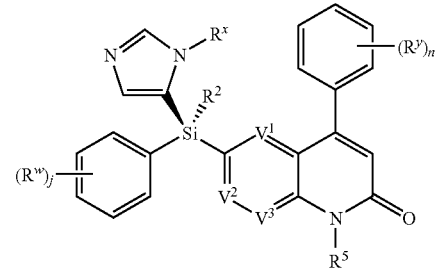

V-j or a pharmaceutically acceptable salt thereof, wherein each of $R^2$, $R^5$, $V^1$, $V^2$, $V^3$, $R^w$, $R^x$, $R^y$, j, and n is as defined and described herein for Formula I.

In certain embodiments, the compound of Formula V is of any of the following formulae shown in Table 2:

TABLE 2

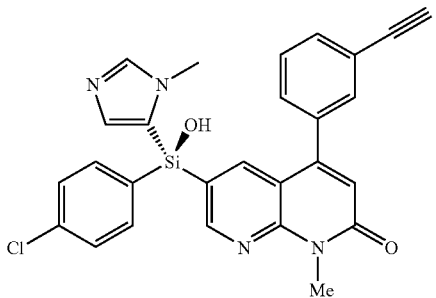 [SMILES: C#Cc1cccc(-c2cc(=O)n(C)c3ncc([Si@](O)(c4ccc(Cl)cc4)c4cncn4C)cc23)c1]

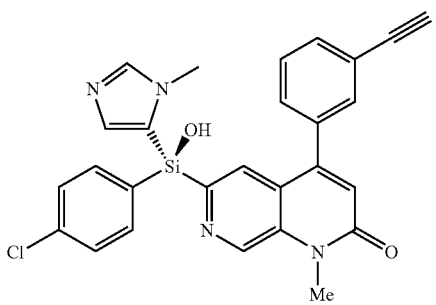 [SMILES: C#Cc1cccc(-c2cc(=O)n(C)c3cnc([Si@](O)(c4ccc(Cl)cc4)c4cncn4C)cc23)c1]

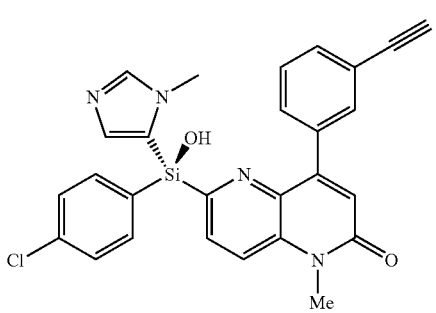 [SMILES: C#Cc1cccc(-c2cc(=O)n(C)c3ccc([Si@](O)(c4ccc(Cl)cc4)c4cncn4C)nc23)c1]

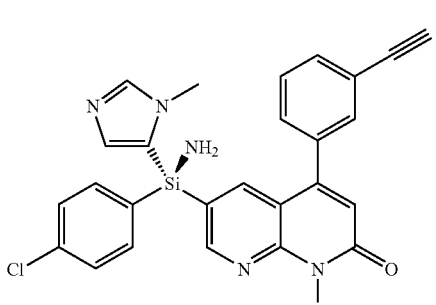

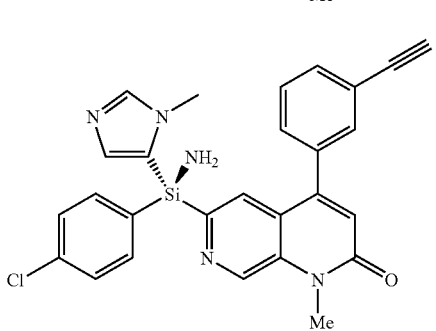

TABLE 2-continued
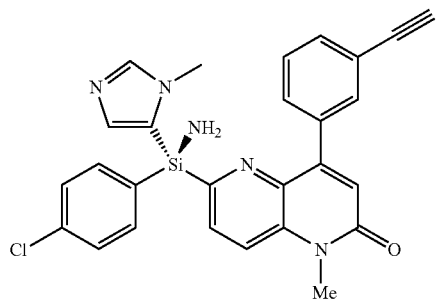 [SMILES: C#Cc1cccc(-c2cc(=O)n(C)c3ccc([Si@](N)(c4ccc(Cl)cc4)c4cncn4C)nc23)c1]
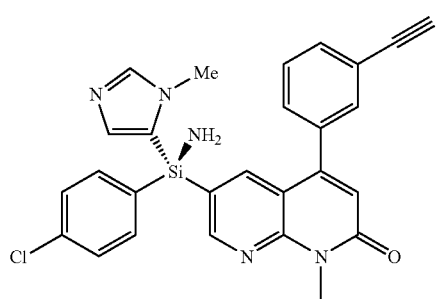 [SMILES: C#Cc1cccc(-c2cc(=O)n(C)c3ncc([Si@](N)(c4ccc(Cl)cc4)c4cncn4C)cc23)c1]
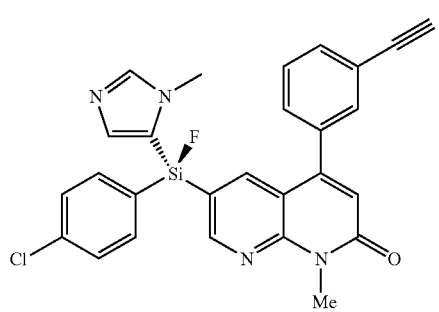 [SMILES: C#Cc1cccc(-c2cc(=O)n(C)c3ncc([Si@](F)(c4ccc(Cl)cc4)c4cncn4C)cc23)c1]
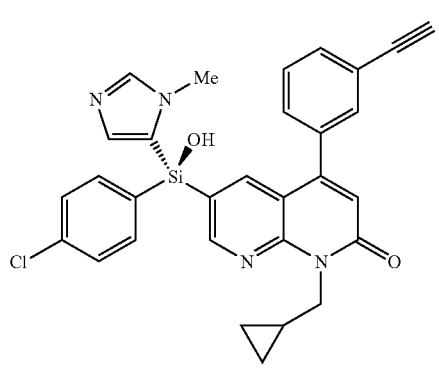 [SMILES: C#Cc1cccc(-c2cc(=O)n(CC3CC3)c3ncc([Si@](O)(c4ccc(Cl)cc4)c4cncn4C)cc23)c1]
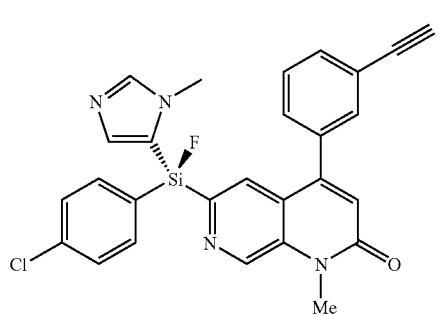
TABLE 2-continued
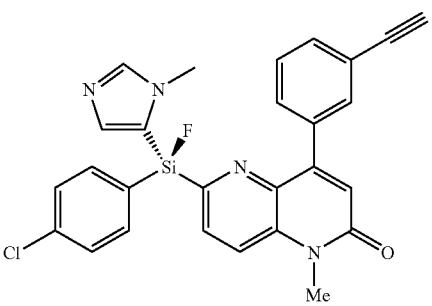 [SMILES: C#Cc1cccc(-c2cc(=O)n(C)c3ccc([Si@](F)(c4ccc(Cl)cc4)c4cncn4C)nc23)c1]
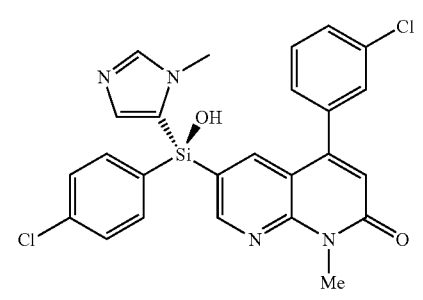
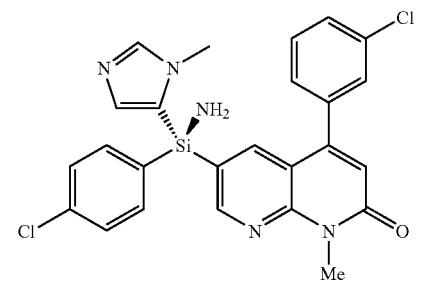
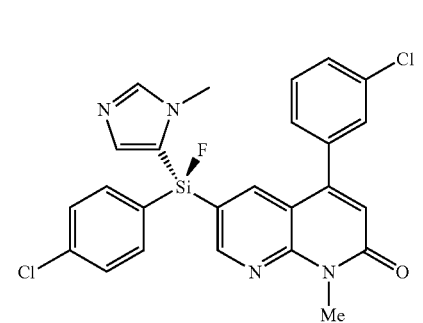 [SMILES: Cn1cncc1[Si@@](F)(c1ccc(Cl)cc1)c1cnc2c(c1)c(-c1cccc(Cl)c1)cc(=O)n2C]
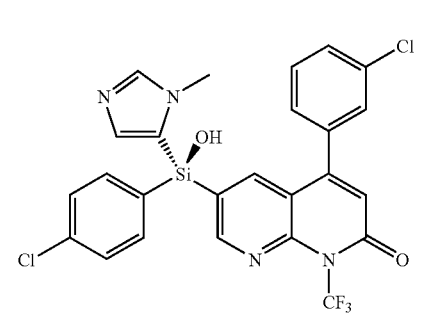 [SMILES: Cn1cncc1[Si@@](O)(c1ccc(Cl)cc1)c1cnc2c(c1)c(-c1cccc(Cl)n1)cc(=O)n2C(F)(F)F]

TABLE 2-continued

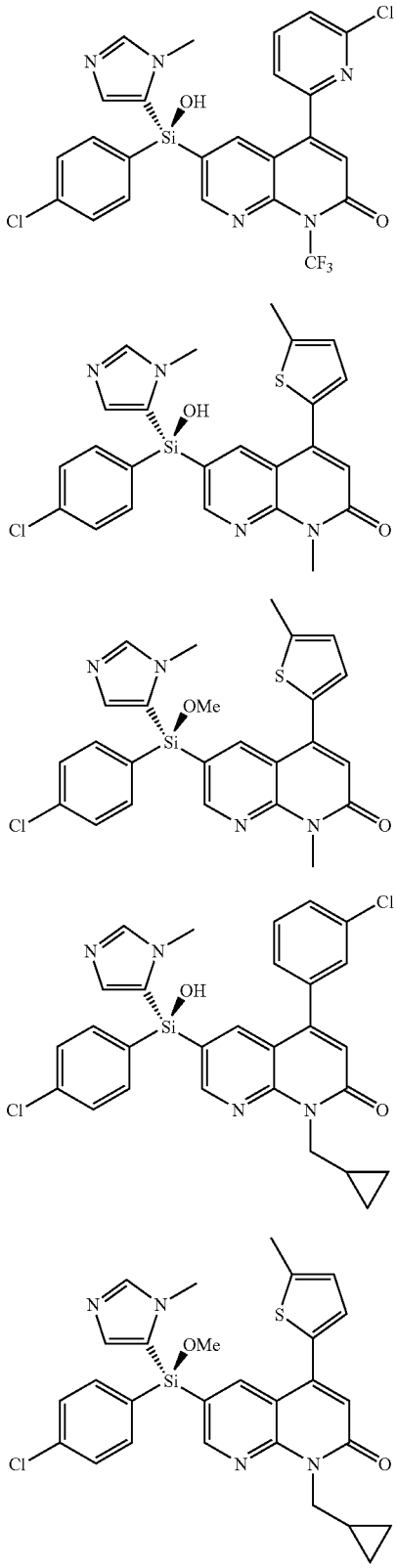

In some embodiments of the present invention, compounds provided herein are characterized by an ability to inhibit farnesylation of one or more farnesylated target proteins. Such provided compounds and/or compositions are considered to be "farnesyl transferase inhibitors".

It should be appreciated that the term "farnesyl transferase inhibitor" has commonly been used in the art to describe compounds that inhibit farnesylation of a particular target protein. Most commonly, the term "farnesyl transferase inhibitor" has been used to apply to agents that inhibit farnesylation of Ras and/or of proteins that contain "CaaX-box" sequence element, in which a is an amino acid with an aliphatic side chain, at their C-terminus (farnesylation occurs on the cysteine residue). More recently, the term "farnesyl transferase inhibitor" has been used to apply to agents that inhibit farnesylation of other targets (e.g., UCH-L1) (see, for example, 60/555,092 Filed Mar. 18, 2004; Ser. No. 11/084,715 Filed: Mar. 18, 2005; 60/555,071 Filed: Mar. 18, 2004; Ser. No. 11/084,739 Filed: Mar. 18, 2005; 60/555,020 Filed: Mar. 18, 2004; 60/555,019; Filed: Mar. 19, 2004; Ser. No. 11/084,740; Filed: Mar. 18, 2005; 60/555,070; Filed: Mar. 18, 2004; Ser. No. 11/084,695; Filed: Mar. 18, 2005 60/753,809; Filed: Dec. 23, 2005; Ser. No. 11/615,088; Filed: Dec. 22, 2006; 60/764,678; Filed: Feb. 2, 2006; U.S. Ser. No. 12/161,650; Filed: Feb. 2, 2007; 60/813,181; Filed: Jun. 13, 2006; 60/554,634; Filed: Mar. 18, 2004; Ser. No. 11/084,716; Filed: Mar. 18, 2005; 60/653,983; Filed: Feb. 18, 2005; Ser. No. 11/354,896; Filed: Feb. 16, 2006; 60/894,086 Filed: Mar. 9, 2007; PCT/US08/56162; Filed: Mar. 7, 2008; 60/915,828; Filed: May 3, 2007; PCT/US08/62437 Filed: May 2, 2008; 61/121,373; Filed: Dec. 10, 2008). Typically, a compound is considered to be a "farnesyl transferase inhibitor" whether it directly targets (e.g., binds to) the farnesyl transferase enzyme, or whether it otherwise achieves a reduction in farnesylation of one or more targets of interest.

The modification of a protein by a farnesyl group can have an important effect on function for a number of proteins. Farnesylated proteins typically undergo further C-terminal modification events that include a proteolytic removal of three C-terminal amino acids and carboxymethylation of C-terminal cystines. These C-terminal modifications facilitate protein-membrane association as well as protein-protein interactions. Farnesylation is catalyzed by a protein farnesyltransferase (FTase), a heterodimeric enzyme that recognizes the a cysteine-containing motif present at the C-terminus of the substrate protein. FTase transfers a farnesyl group from farnesyl pyrophosphate and forms a thioether linkage between the farnesyl and the relevant cystine residue.

In certain embodiments, inhibitory activity of a provided compound with respect to farnesylation of a particular target may be assayed by in vivo and/or in vitro assays. In certain embodiments, the $IC_{50}$ as measured in an in vitro assay using recombinant farnesyl transferase is less than about 100 nM. In certain embodiments, the $IC_{50}$ is less than about 50 nM. In certain embodiments, the $IC_{50}$ is less than about 10 nM. In certain embodiments, the $IC_{50}$ is less than about 5 nM. In certain embodiments, the $IC_{50}$ is less than about 1 nM.

In some embodiments of the present invention, provided compounds that act as farnesyl transferase inhibitors characterized by and/or are administered under conditions and/or according to a regimen that achieves differential effects on farnesylation of different target proteins (i.e., at least one favored target and at least one disfavored target). In many embodiments, the disfavored target is Ras. In some embodiments, the disfavored target contains a CaaX sequence element; in some such embodiments, X is any amino acid; in some such embodiments, X is serine, methionine, gutamine, alanin, or threonine. In some embodiments, the favored target is a non-Ras target. In some embodiments, the favored target does not contain a CaaX-COOH sequence element (as described herein). In some embodiments, the favored target contains a CKaa-COOH sequence element (where K is lysine). In some embodiments, the favored target contains a CKAA-COOH (SEQ ID NO: 23) sequence element (where A is alanine). In some embodiments, the favored target may be UCH-L1. It has recently been discovered that UCH-L1 is farnesylated in vivo. UCH-L 1 is associated with the membrane and this membrane association is mediated by farnesylation. Farnesylated UCH-L1 also stabilizes the accumulation of α-synuclein. The invention relates to the prevention or inhibition of UCH-L1 farnesylation which would result in UCH-L1 membrane disassociation and acceleration of the degradation of α-synuclein. Since α-synuclein accumulation is pathogenic in PD, DLBD, and MSA, an increased degradation of α-synuclein and/or inhibition of α-synuclein accumulation ameliorates the toxicity associated with a pathogenic accumulation of α-synuclein.

The effect of the compounds of the invention may be brought about through a mechanism not involving the inhibition of protein farnesylation. For example, an FTI along, or an FTI/FTase/farnesyl pyrophosphate or FTI/FTase complex, may interact with one or more intracellular protein/s, including microtubules and HDAC, to affect a biochemical/physiological pathway involved in a proteinopathy. Further, at lower concentrations or doses of an FTI, the interaction of the FTI with other intracellular proteins, with or without FTase involvement, for example acetylation mechanisms of microtubules, may result in a non-farnesylated substrate mechanism of therapeutic treatment of a proteinopathy.

In some embodiments, where compounds provided herein are characterized by and/or are administered under conditions and/or according to a regimen that achieves differential effects on farnesylation of different target proteins (i.e., at least one favored target and at least one disfavored target), the effect on the favored target is at least 2, 3, 4, 5, 6, 7, 8, 9, 10, 15, 20, 25, 30, 35, 40, 45, 50, 100, 500, or 1000 times, or more greater than the effect on the disfavored target.

In some embodiments, farnesyl transferase inhibitors utilized in accordance with the present invention are characterized by and/or are administered under conditions and/or according to a regimen that achieves a less than 50% reduction in Ras farnesylation. In some embodiments, Ras farnesylation is reduced less than 45%, 40%, 35%, 30%, 25%, 20%, 15%, 10%, 5% or less. It will be appreciated by those of ordinary skill in the art that studies have illustrated that Ras farnesylation must be reduced by more than 50%, and often much more than 50%, in order to achieve beneficial effects in the treatment of cancer. In some embodiments of the present invention, farnesyl transferase inhibitors are utilized at doses that are at least 2, 3, 4, 5, 6, 7, 8, 9, 10, 15, 20, 25, 30, 35, 40, 45, 50, 100, 500, 1000 fold or more lower than doses required for effects in the treatment of cancer.

In some embodiments, compounds utilized in accordance with the present invention are characterized by and/or are administered under conditions and/or according to a regimen that achieves a reduction in levels of aggregates of one or more proteins of interest. In some embodiments, rates of aggregation and/or of disaggregation and/or protein destruction are altered. In some such embodiments, administration of a compound provided herein to an organism reduces levels of aggregates in one or more particular tissues of interest. In some embodiments, the aggregates are aggregates of a protein selected from the group consisting of α-synuclein (synucleinopathies), tau (tauopathies), amyloid (amyloidopathies), SOD1 (SOD1 proteinopathies), TDP-43 (TDP-43 proteinopathies), huntingtin, and combinations thereof. In some embodiments, the target tissues are or include brain. In some embodiments, aggregate levels are reduced at least 90%, 85%, 80%, 75%, 70%, 65%, 60%, 55%, 50%, 45%, 40%, 35%, 30%, 25%, 20%, 15%, 10%, 5% or more.

In some embodiments of the present invention, compounds provided herein are characterized by and/or are administered under conditions and/or according to a regimen that achieves no significant inhibition of cell cycle progression. For example, in some embodiments, compounds provided herein are characterized by and/or are administered under conditions and/or according to a regimen that achieves less than 100%, 95%, 90%, 85%, 80%, 75%, 70%, 65%, 60%, 55%, 50%, 45%, 40%, 35%, 30%, 25%, 20%, 15%, 10% inhibition of cell cycle progression. In some embodiments, compounds provided herein show a Ki within the range of 0.001-0.010 nM, 0.01-0.10 nM, 0.10-1 nM, or 1-10 nM, when tested for effects on proliferation of cancer cells in vitro.

In some embodiments, compounds provided herein are characterized by and/or are administered under conditions and/or according to a regimen that achieves stimulation of a protein clearance pathway (e.g., through inhibition of farnesylation). In some embodiments, compounds provided herein are characterized by and/or are administered under conditions and/or according to a regimen that achieves stimulation of autophagy. In some embodiments, compounds provided herein are characterized by and/or are administered under conditions and/or according to a regimen that achieves stimulation of neural autophagy, macroautophagy, and/or microautophagy.

In some embodiments, compounds provided herein are characterized by and/or are administered under conditions and/or according to a regimen that achieves one or more of alteration of protein folding pathways, reduction of protein aggregation, alteration of protein degradation pathways, etc. In some embodiments, such alterations stimulate the relevant pathways. In some embodiments, such alterations inhibit the relevant pathways.

In some embodiments, compounds provided herein are characterized by and/or are administered under conditions and/or according to a regimen that achieves no significant inhibition of geranylgeranyltransferase "GGTase" activity. In some embodiments, GGTase activity is inhibited no more than 1%, 2%, 3%, 4%, 5%, 6%, 7%, 8%, 9%, 10%, 12%, 15%, 20%, 25%, 30%, 35%, 40%, 45%, 50%, 55%, 60%, 65%, 70%, or 75%.

In some embodiments, compounds provided herein are characterized by and/or are administered under conditions and/or according to a regimen that achieves differential inhibition of farnesyl transferase activity (with respect to a favored target) as compared with GGTase activity. In some embodiments, compounds provided herein are characterized by and/or are administered under conditions and/or according to a regimen that achieve a level of farnesyl transferase inhibition (with respect to a favored target) that is at least 2, 3, 4, 5, 6, 7, 8, 9, 10, 15, 20, 25, 30, 35, 40, 45, 50, 100, 500, or 1000 times greater, or more, than the achieved level of GGTase inhibition.

4. General Methods of Providing the Present Compounds

Provided compounds are prepared by methods known to one of ordinary skill in the art and including methods illustrated in Schemes 1-4, below. Unless otherwise noted, all variables are as defined above and in classes and subclasses herein.

In the Schemes below, where a particular protecting group, leaving group, or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, 5th Edition, John Wiley & Sons, 2001, *Comprehensive Organic Transformations*, R. C. Larock, 2nd Edition, John Wiley & Sons, 1999, and *Protecting Groups in Organic Synthesis*, T. W. Greene and P. G. M. Wuts, 3rd edition, John Wiley & Sons, 1999, the entirety of each of which is hereby incorporated herein by reference.

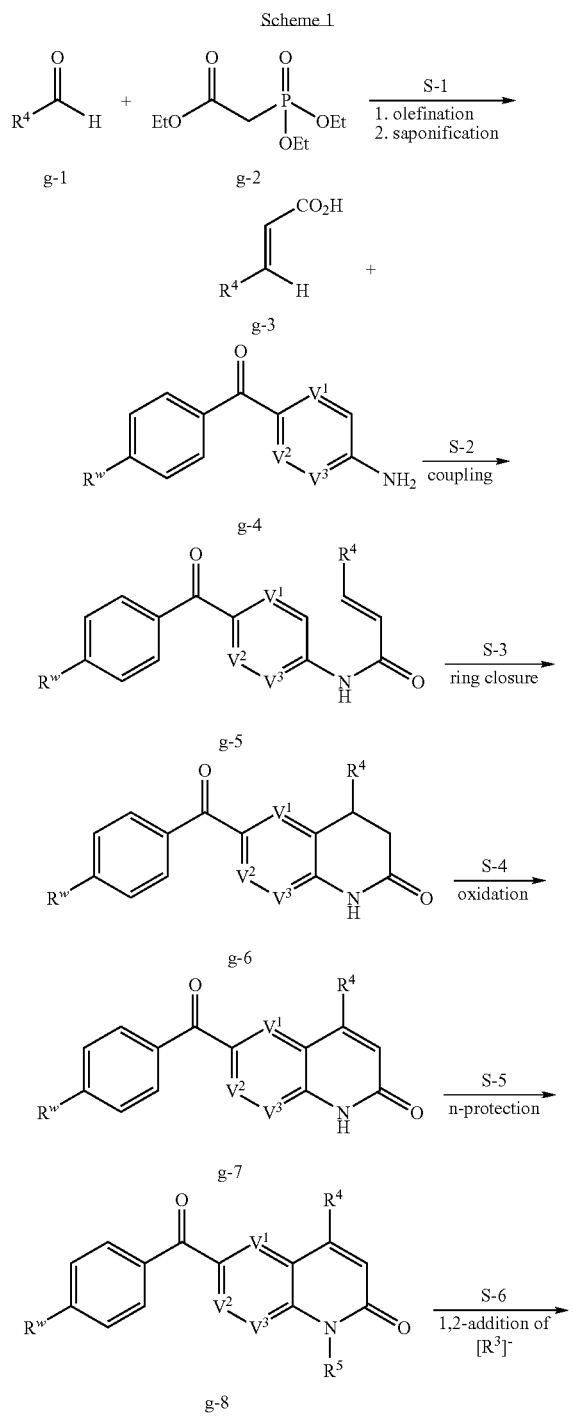

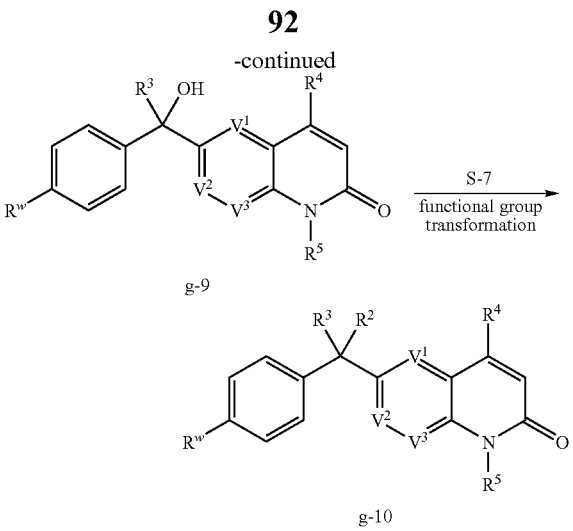

As depicted in step S-1 of Scheme 1 above, olefination of aldehyde g-1 with diethylphosphonate g-2 affords an α,β-unsaturated ethyl ester which, upon subsequent saponification, furnishes the corresponding α,β-unsaturated acid g-3. In some embodiments, olefination proceeds under basic conditions (e.g., sodium hydride) in an aprotic medium such as, for instance, an ethereal solvent (e.g., tetrahydrofuran (THF)). In some embodiments, saponification occurs under basic, aqueous conditions (e.g., aqueous hydroxide) at elevated temperatures (e.g., reflux).

In step S-2 above, α,β-unsaturated acid 3 is coupled to amine g-4 to provide α,β-unsaturated amide g-5. In some embodiments, coupling proceeds under basic conditions (diisopropylethylamine (DIPEA)) in a suitable solvent (e.g., dimethylformamide (DMF)) using one or more of any coupling reagents (e.g., 1-ethyl-3-(3-dimethylaminopropyl)-carbodiimide (EDC)) known to effect the desired transformation to the α,β-unsaturated amide g-5.

As illustrated in step S-3 above, α,β-unsaturated amide g-5 undergoes a ring closure to afford cyclized lactam g-6. In certain embodiments, cyclization occurs upon exposure to an appropriate catalyst. In some embodiments, the catalyst is an acid (e.g., polyphosphoric acid (PAA)) and cyclization occurs at elevated temperatures (ca. 100° C.).

As depicted in step S-4 above, oxidation of compound g-6 furnishes unsaturated compound g-7. Oxidation may be achieved using any oxidant known in the art to effect the desired transformation. In sonic embodiments, oxidation occurs via exposure of compound g-6 to a halogen in a suitable solvent (e.g., bromine in bromobenzene) at elevated temperatures (ca 160° C.) for approximately 12 h.

Step S-5 illustrates protection and/or substitution of the nitrogen of the amide moiety of compound g-7 to furnish compound g-8. In some embodiments, nitrogen is acylated using a suitable acylating reagent (e.g., a suitable anhydride or acid chloride). In some embodiments, nitrogen is alkylated using a suitable alkylating reagent (e.g., methyl iodide) under basic conditions (e.g., sodium hydroxide). In certain embodiments, alkylation occurs in the presence of an ammonium chloride salt (e.g., benzyltriethylammonium chloride (Bn(Et)³NCl).

As depicted in step S-6 above, installation of R³ occurs via addition of an appropriate nucleophile to ketone g-8, furnishing carbinol g-9. In some embodiments, the nucleophile is an organolithium or organometallic compound preformed by, for instance, either deprotonation or lithium-halogen exchange using a suitable base or lithiating reagent (e.g., butyllithium) under anhydrous conditions in dry, ethereal solvent (e.g., THF) at reduced temperatures (e.g., −78° C.).

As described in step S-7 above, carbinol g-9 can undergo a variety of functional group transformations and/or substitution reactions with a suitable nucleophile to install $R^2$ and afford compound g-10. In certain embodiments, substitution occurs via exposure to an activating agent (e.g., sulfonyl chloride) in the presence of a nucleophile (e.g., ammonium hydroxide). It will be readily apparent to those of skill in the art that any number of activating agents and nucleophiles can be used to install $R^2$. Additionally, although S-7 is described herein as a functional group transformation it would be apparent to one of ordinary skill in the art that any number of reactions may take place at this site and such methods are also contemplated.

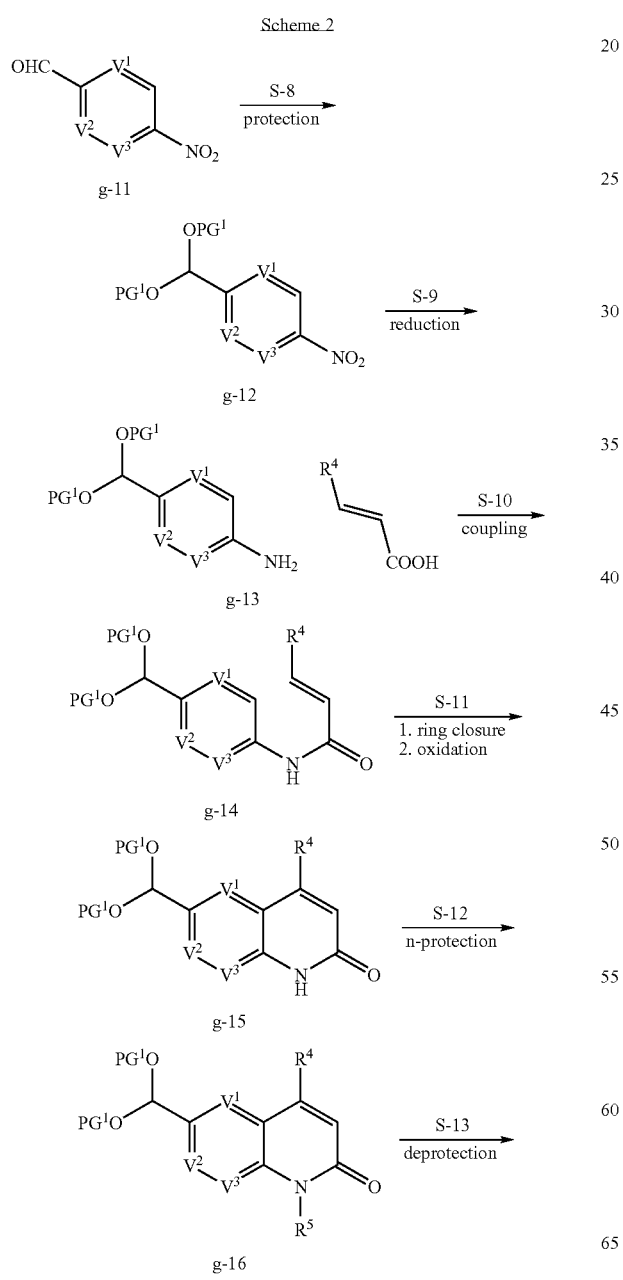

Scheme 2 depicts an alternative synthesis of the provided compounds.

As depicted in step S-8 above, aldehyde g-11 is protected using a suitable protecting group to provide acetal g-12. In some embodiments, the acetal is a cyclic acetal formed using a an appropriate diol (e.g., ethylene glycol) in the presence of an acid catalyst. In certain embodiments, the acid catalyst is an organic acid (e.g., para-toluenesulfonic acid (PTSA)).

As depicted in step S-9 above, reduction of the nitro moiety of g-12 affords the corresponding amine g-13. In certain embodiments, reduction occurs using a hydride reducing agent (e.g., lithium aluminum hydride (LAH)).

As shown in step S-10 above, amine g-13 is coupled to an α,β-unsaturated acid (e.g., compound g-3 in Scheme 1, above) under basic conditions (diisopropylethylamine (DIPEA)) in a suitable solvent (e.g., dimethylformamide (DMF)) using one or more coupling reagent(s) (e.g., 1-ethyl-3-(3-dimethylaminopropyl)-carbodiimide (EDC) and n-hydroxybenzotriazole (HOBt)) in order to form α,β-unsaturated amide g-14.

As illustrated in step S-11 above, ring closure of α,β-unsaturated amide g-14 furnishes the cyclized compound, which is subsequently oxidized to afford compound g-15. In some embodiments, cyclization requires a catalyst. In certain embodiments, cyclization occurs under acidic conditions at elevated temperatures (e.g., polyphosphoric acid at 100° C.).

As depicted in step S-12 above, N-protection of the nitrogen of the α,β-unsaturated lactam moiety of g-15 affords compound g-16. Although this reaction is described herein as a protection reaction it would be apparent to one of ordinary skill in the art that any number of reactions may take place at this site and such methods are also contemplated. By way of non-limiting example, depending on the reagent used, the above-described reaction may be an alkylation or an acylation reaction.

As shown in step S-13 above, deprotection of the acetal protecting group of compound g-16 affords aldehyde g-17. In some embodiments, deprotection occurs upon exposure to acid. In certain embodiments, the acid is an organic acid (e.g., pTSA).

As depicted in step S-14 above, addition of a suitable nucleophile to aldehyde g-17 installs the $R^1$ group and produces the corresponding carbinol intermediate. In some embodiments, the nucleophile is preformed using an appropriate base and/or metallating reagent prior to exposure to the aldehyde. In certain embodiments, the nucleophile is generated by forming the corresponding Grignard reagent in an aprotic solvent such as, for instance, an ethereal solvent (e.g., THF). The alcohol intermediate resulting from 1,2-addition to the carbonyl group of aldehyde 17 is then oxidized to the corresponding ketone g-18. In some embodiments, oxidation is effected using an appropriate metal oxide (e.g., $MnO_2$).

As depicted in step S-15 above, addition of a nucleophile to ketone g-18 installs $R^3$ and provides the corresponding carbinol g-19. In some embodiments, the nucleophile is preformed using an appropriate base and/or metallating reagent prior to exposure to the ketone. In certain embodiments, the nucleophile is preformed using a lithiating reagent (e.g., n-butyllithium) in an aprotic solvent such as, for instance, an ethereal solvent (e.g., THF). In some embodiments, a Lewis acid catyst is used to activate the carbonyl towards addition. In certain embodiments, the Lewis acid catalyst is a trialkylsilylhalide (e.g., triethylsilylchloride (TESCl) or trimethylsilyl chloride (TMSCl)).

As depicted in S-16 above, carbinol intermediate g-19 can then undergo a variety of reactions to transform the hydroxyl moiety into $R^2$ of compound g-20. Exemplary such methods are as described in step S-7 of Scheme 1 above.

As shown in step S-17, compound g-20 can be resolved using any methods known in the chemical arts. In certain embodiments, resolution via chiral HPLC affords g-21a and g-21b. For each of the aforementioned Schemes, it will be readily apparent to one of ordinary skill in the art that a variety of suitable reagents and reaction conditions may be employed to carry out the described syntheses.

5. Compositions and Formulations

According to certain embodiments, the present invention provides a composition comprising a provided compound, or a pharmaceutically acceptable salt thereof, and a pharmaceutically acceptable carrier, adjuvant, or vehicle. In certain embodiments, the present invention provides a pharmaceutical composition comprising a compound of Table 1 or Table 2, or a pharmaceutically acceptable salt thereof, and a pharmaceutically acceptable carrier, adjuvant, or vehicle. The amount of compound in provided compositions typically is such that is effective to measurably inhibit farnesylation of a target, in a biological sample or in a patient, for example when administered as part of a dosing regimen. In certain embodiments, a composition of this invention is formulated for administration to a patient in need of such composition. In some embodiments, a composition of this invention is formulated for oral administration to a patient.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment or prevention includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a provided compound. In certain embodiments, an aforementioned formulation renders orally bioavailable a provided compound.

Methods of preparing a provided formulation or composition can include a step of bringing into association a provided compound with the carrier and, optionally, one or more accessory ingredients. In general, the formulations are prepared by uniformly and intimately bringing into association a provided compound with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a provided compound, or composition thereat as an active ingredient. A provided compound may also be administered as a bolus, electuary or paste.

In solid dosage forms of the invention for oral administration (capsules, tablets, pills, dragees, powders, granules and the like), a provided compound, or composition thereof, is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lathyl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

Tablets, and other solid dosage forms of pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of a provided compound, or composition thereof, include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, oral formulations can also include adjuvants such as wetting agents, emulsifying and suspending agents, sweetening, flavoring, coloring, perfuming and preservative agents.

Suspensions, in addition to a provided compound, or composition thereof, may contain one or more suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound, or composition thereof, of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a provided compound, or composition thereof, to the body. Dissolving or dispersing a compound, or composition thereof, in the proper medium can make such dosage forms. Absorption enhancers can also be used to increase the flux of compound, or composition thereof, across the skin. Either providing a rate controlling membrane or dispersing compound, or composition thereof, in a polymer matrix or gel can control the rate of such flux.

Ophthalmic formulations, eye ointments, powders, solutions and the like, are also contemplated as being within the scope of this invention.

Pharmaceutical formulations of this invention suitable for parenteral administration comprise one or more compounds, or composition thereof, of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These formulations may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions, which are compatible with body tissue.

In certain embodiments, a compound or pharmaceutical preparation is administered orally. In other embodiments, the compound or pharmaceutical preparation is administered intravenously. Alternative routs of administration include sublingual, intramuscular, and transdermal administrations.

When the provided compounds are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, provided compounds, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular provided compound employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In some embodiments, a compound or pharmaceutical composition of the invention is provided to a subject chronically. Chronic treatments include any form of repeated administration for an extended period of time, such as repeated administrations for one or more months, between a month and a year, one or more years, or longer. In many embodiments, a chronic treatment involves administering a compound or pharmaceutical composition of the invention repeatedly over the life of the subject. Preferred chronic treatments involve regular administrations, for example one or more times a day, one or more times a week, or one or more times a month. In general, a suitable dose such as a daily dose of a compound of the invention will be that amount of the compound that is the lowest dose effective to produce a therapeutic effect. Such an effective dose will generally depend upon the factors described above.

Generally, doses of the compounds of this invention for a patient, when used for the indicated effects, will range from about 0.0001 to about 100 mg per kg of body weight per day. Preferably the daily dosage will range from 0.001 to 50 mg of compound per kg of body weight, and even more preferably from 0.01 to 10 mg of compound per kg of body weight. However, lower or higher doses can be used. In some embodiments, an effective amount comprises about 10 ng/kg of body weight to about 1000 mg/kg of body weight. In some embodiments, the dose administered to a subject may be modified as the physiology of the subject changes due to age, disease progression, weight, or other factors.

If desired, the effective daily dose of the active compound may be administered as two, three, four, five, six or more sub-doses administered separately at appropriate intervals throughout the day, optionally, in unit dosage forms.

While it is possible for a provided compound to be administered alone, it is preferable to administer the compound as a pharmaceutical formulation (composition) as described above.

The compounds according to the invention may be formulated for administration in any convenient way for use in human or veterinary medicine, by analogy with other pharmaceuticals.

According to the invention, compounds for treating or preventing neurodegenerative diseases, disorders, and/or conditions can be formulated or administered using methods that help the compounds cross the blood brain barrier (BBB). The vertebrate brain (and CNS) has a unique capillary system unlike that in any other organ in the body. The unique capillary system has morphologic characteristics which make up the blood-brain barrier (BBB). The blood-brain barrier acts as a system-wide cellular membrane that separates the brain interstitial space from the blood.

The unique morphologic characteristics of the brain capillaries that make up the BBB are: (a) epithelial-like high resistance tight junctions which literally cement all endothelia of brain capillaries together, and (b) scanty pinocytosis or transendothelial channels, which are abundant in endothelia of peripheral organs. Due to the unique characteristics of the blood-brain barrier, hydrophilic drugs and peptides that readily gain access to other tissues in the body are barred from entry into the brain or their rates of entry and/or accumulation in the brain are very low.

Various strategies have been developed for introducing those drugs into the brain which otherwise would not cross the blood-brain barrier. Widely used strategies involve invasive procedures where the drug is delivered directly into the brain. One such procedure is the implantation of a catheter into the ventricular system to bypass the blood-brain barrier and deliver the drug directly to the brain. These procedures have been used in the treatment of brain diseases which have a predilection for the meninges, e.g., leukemic involvement of the brain (U.S. Pat. No. 4,902,505, incorporated herein in its entirety by reference).

Although invasive procedures for the direct delivery of drugs to the brain ventricles have experienced some success, they are limited in that they may only distribute the drug to superficial areas of the brain tissues, and not to the structures deep within the brain. Further, the invasive procedures are potentially harmful to the patient.

Other approaches to circumventing the blood-brain barrier utilize pharmacologic-based procedures involving drug latentiation or the conversion of hydrophilic drugs into lipid-soluble drugs. The majority of the latentiation approaches involve blocking the hydroxyl, carboxyl and primary amine groups on the drug to make it more lipid-soluble and therefore more easily able to cross the blood-brain barrier.

Another approach to increasing the permeability of the BBB to drugs involves the intra-arterial infusion of hypertonic substances which transiently open the blood-brain barrier to allow passage of hydrophilic drugs. However, hypertonic substances are potentially toxic and may damage the blood-brain barrier.

Peptide compositions of the invention may be administered using chimeric peptides wherein the hydrophilic peptide drug is conjugated to a transportable peptide, capable of crossing the blood-brain barrier by transcytosis at a much higher rate than the hydrophilic peptides alone. Suitable transportable peptides include, but are not limited to, histone, insulin, transferrin, insulin-like growth factor I (IGF-I), insulin-like growth factor II (IGF-II), basic albumin and prolactin.

Antibodies are another method for delivery of compositions of the invention. For example, an antibody that is reactive with a transferrin receptor present on a brain capillary endothelial cell, can be conjugated to a neuropharmaceutical agent to produce an antibody-neuropharmaceutical agent conjugate (U.S. Pat. No. 5,004,697, incorporated herein in its entirety by reference). The method is conducted under conditions whereby the antibody binds to the transferrin receptor on the brain capillary endothelial cell and the neuropharmaceutical agent is transferred across the blood brain barrier in a pharmaceutically active form. The uptake or transport of antibodies into the brain can also be greatly increased by cationizing the antibodies to form cationized antibodies having an isoelectric point of between about 8.0 to 11.0 (U.S. Pat. No. 5,527,527, incorporated herein in its entirety by reference).

A ligand-neuropharmaceutical agent fusion protein is another method useful for delivery of compositions to a host (U.S. Pat. No. 5,977,307, incorporated herein in its entirety by reference). The ligand is reactive with a brain capillary endothelial cell receptor. The method is conducted under conditions whereby the ligand binds to the receptor on a brain capillary endothelial cell and the neuropharmaceutical agent is transferred across the blood brain barrier in a pharmaceutically active form. In some embodiments, a ligand-neuropharmaceutical agent fusion protein, which has both ligand binding and neuropharmaceutical characteristics, can be produced as a contiguous protein by using genetic engineering techniques. Gene constructs can be prepared comprising DNA encoding the ligand fused to DNA encoding the protein, polypeptide or peptide to be delivered across the blood brain barrier. The ligand coding sequence and the agent coding sequence are inserted in the expression vectors in a suitable manner for proper expression of the desired fusion protein. The gene fusion is expressed as a contiguous protein molecule containing both a ligand portion and a neuropharmaceutical agent portion.

Permeability of the blood brain barrier can often be increased by administering a blood brain barrier agonist, for example bradykinin (U.S. Pat. No. 5,112,596, incorporated herein in its entirety by reference), or polypeptides called receptor mediated permeabilizers (RMP) (U.S. Pat. No. 5,268,164, incorporated herein in its entirety by reference). Exogenous molecules can be administered to the host's bloodstream parenterally by subcutaneous, intravenous or intramuscular injection or by absorption through a bodily tissue, such as the digestive tract, the respiratory system or the skin. The form in which the molecule is administered (e.g., capsule, tablet, solution, emulsion) depends, at least in part, on the route by which it is administered. Administration of the exogenous molecule to the host's bloodstream and the intravenous injection of the agonist of blood-brain barrier permeability can occur simultaneously or sequentially in time.

For example, a therapeutic drug can be administered orally in tablet form while the intravenous administration of an agonist of blood-brain barrier permeability is given later (e.g., between 30 minutes later and several hours later). This allows time for the drug to be absorbed in the gastrointestinal tract and taken up by the bloodstream before the agonist is given to increase the permeability of the blood-brain barrier to the drug. On the other hand, an agonist of blood-brain barrier permeability (e.g., bradykinin) can be administered before or at the same time as an intravenous injection of a drug. Thus, the term "co-administration" is used herein to mean that the agonist of blood-brain barrier and the exogenous molecule will be administered at times that will achieve significant concentrations in the blood for producing the simultaneous effects of increasing the permeability of the blood-brain barrier and allowing the maximum passage of the exogenous molecule from the blood to the cells of the central nervous system.

In other embodiments, compounds of the invention can be formulated as a prodrug with a fatty acid carrier (and optionally with another neuroactive drug). The prodrug is stable in the environment of both the stomach and the bloodstream and may be delivered by ingestion. The prodrug passes readily through the blood brain barrier. The prodrug preferably has a brain penetration index of at least two times the brain penetration index of the drug alone. Once in the central nervous system, the prodrug, which preferably is inactive, is hydrolyzed into the fatty acid carrier and the farnesyl transferase inhibitor (and optionally another drug). The carrier preferably is a normal component of the central nervous system and is inactive and harmless. The compound and/or drug, once released from the fatty acid carrier, is active. Preferably, the fatty acid carrier is a partially-saturated straight chain molecule having between about 16 and 26 carbon atoms, and more preferably 20 and 24 carbon atoms. Examples of fatty acid carriers are provided in U.S. Pat. Nos. 4,939,174; 4,933,324; 5,994,932; 6,107,499; 6,258,836; and 6,407,137.

6. Combination Therapy

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated or prevented."

In certain embodiments of the present invention, compounds provided herein may be administered in combination with one or more additional therapeutic agents. Such additional therapeutic agents may be administered separately from an inventive compound-containing composition, as part of a multiple dosage regimen. Alternatively or additionally, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a provided compound, an additional therapeutic agent, and a pharmaceutically acceptable carrier, adjuvant, or vehicle. Two or more agents are typically considered to be administered "in combination" when a patient or individual is simultaneously exposed to both agents. In many embodiments, two or more agents are considered to be administered "in combination" when a patient or individual simultaneously shows therapeutically relevant levels of the agents in a particular target tissue or sample (e.g., in brain, in serum, etc).

The amount of both a provided compound and additional therapeutic agent (in those compositions which comprise an additional therapeutic agent as described above)) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In some embodiments of the invention, agents that are utilized in combination may act synergistically. Therefore, the amount of either agent utilized in such situations may be less than that typically utilized or required in a monotherapy involving only that therapeutic agent. Commonly, a dosage of between 0.01-1,000 µg/kg body weight/day of the additional therapeutic agent can be administered.

In some embodiments, the invention provides a method of treating a proteinopathy by administering a compound of the invention or pharmaceutically acceptable salt thereof and an amount of one or more non-farnesyl transferase inhibitor compounds effective to treat or prevent a proteinopathy. In some embodiments, the invention further comprises administering to the subject an amount of one or more non-farnesyl transferase inhibitor compounds effective to treat or prevent the neurodegenerative disease. In some embodiments, the invention further comprises administering to the subject an amount of one or more non-farnesyl transferase inhibitor compounds effective to treat or prevent the synucleinopathy.

In some embodiments, each non-farnesyl transferase inhibitor compound is selected from the group consisting of dopamine agonist, DOPA decarboxylase inhibitor, dopamine precursor, monoamine oxidase blocker, cathechol O-methyl transferase inhibitor, anticholinergic, and NMDA antagonist.

In some embodiments, each dopamine agonist is selected from the group consisting of apomorphine hydrochloride (APO-go®), bromocriptine mesylate (Parlodel®), cabergoline (Cabaser®, Dostinex®), pergolide mesilate (Celance®), pramipexole dihydrochloride (Mirapexin®), ropinirole hydrochloride (Requip®), rotigotine (Neupro®), and combinations thereof.

In some embodiments, the invention further comprises administering to the subject an amount of one or more agents selected from the group consisting of one or more treatments for Parkinson's Disease such as L-DOPA/carbidopa, entacapone, ropinrole, pramipexole, bromocriptine, pergolide, trihexephendyl, and amantadine; For example, methods of the present invention can be used in combination with medications for treating PD. Such therapeutic agents include levodopa, carbodopa, levodopa (Sinemet and Sinemet CR), Stalevo (carbodopa, levodopa, and entacapone), anticholinergics (trihyxyphenidyl, benztropine mesylate, procyclidine, artane, cogentin), bromocriptidine (Parlodel), pergolide (Permax), ropinirol (Requip), pramipexole (Mirapex), cabergoline (Dostinex), apomorphine (Apokyn), rotigotine (Neupro), Ergolide, Mirapex or Requip.

In some embodiments, the invention comprises administering to the subject an amount of one or more non-farnesyl transferase compounds effective to treat or prevent the amyloidopathy.

In some embodiments, the invention further comprises administering to the subject an amount of one or more non-farnesyl transferase inhibitor compounds effective to treat or prevent the taupathy. In some embodiments, the non-farnesyl transferase inhibitor is Memantine. In some embodiments, each non-farnesyl transferase inhibitor compound is selected from the group consisting of Aricept and other acetylcholinesterase inhibitors.

The amount of additional therapeutic agent present utilized in combination therapy according to the present invention typically will be no more than the amount that would normally be administered in a composition comprising that therapeutic agent as the only active agent. Preferably the amount of additional therapeutic agent utilized will range from about 50% to 100% of the amount normally utilized in therapies involving that agent as the only therapeutically active agent. Established dosing regimens for known therapeutic agents are known in the art and incorporated herein by reference.

For example, compounds of the present invention, or pharmaceutically acceptable compositions thereof, can be administered in combination with treatments for Alzheimer's disease such as Aricept® and Excelon®. In some embodiments, provided compositions and formulations may be administered in combination with one or more treatments for Parkinson's Disease such as ABT-126 (Abbott Laboratories), pozanicline (Abbott Laboratories), MABT-5102A (AC Immune), Affitope AD-01 (AFFiRiS GmbH), Affitope AD-02 (AFFiRiS GmbH), davunetide (Allon Therapeutics Inc), nilvadipine derivative (Archer Pharmaceuticals), Anapsos (ASAC Pharmaceutical International AIE), ASP-2535 (Astellas Pharma Inc), ASP-2905 (Astellas Pharma Inc), 11C-AZD-2184 (AstraZeneca plc), 11C-AZD-2995 (AstraZeneca plc), 18F-AZD-4694 (AstraZeneca plc), AV-965 (Avera Pharmaceuticals Inc), AVN-101 (Avineuro Pharmaceuticals Inc), immune globulin intravenous (Baxter International Inc), EVP-6124 (Bayer AG), nimodipine (Bayer AG), BMS-708163 (Bristol-Myers Squibb Co), CERE-110 (Ceregene Inc), CLL-502 (CLL Pharma), CAD-106 (Cytos Biotechnology AG), mimopezil ((Debiopharm SA), DCB-AD1 (Development Centre for Biotechnology), EGb-761 ((Dr Willmar Schwabe GmbH & Co), E-2012 (Eisai Co Ltd), ACC-001 (Elan Corp plc), bapineuzumab (Elan Corp plc), ELND-006 (Elan Pharmaceuticals Inc), atomoxetine (Eli Lilly & Co), LY-2811376 (Eli Lilly & Co), LY-451395 (Eli Lilly & Co), m266 (Eli Lilly & Co), semagacestat (Eli Lilly & Co), solanezumab (Eli Lilly & Co), AZD-103 (Ellipsis Neurotherapeutics Inc), FGLL (ENKAM Pharmaceuticals A/S), EHT-0202 (ExonHit Therapeutics SA), celecoxib (GD Searle & Co), GSK-933776A (GlaxoSmithKline plc), rosiglitazone XR (GlaxoSmithKline plc), SB-742457 (GlaxoSmithKline plc), R-1578 (Hoffmann-La Roche AG), HF-0220 (Hunter-Fleming Ltd), oxiracetam (ISF Societa Per Azioni), KD-501 (Kwang Dong Pharmaceutical Co Ltd), NGX-267 (Life Science Research Israel), huperzine A (Mayo Foundation), Dimebon (Medivation Inc), MEM-1414 (Memory Pharmaceuticals Corp), MEM-3454 (Memory Pharmaceuticals Corp), MEM-63908 (Memory Pharmaceuticals Corp), MK-0249 (Merck & Co Inc), MK-0752 (Merck & Co Inc), simvastatin (Merck & Co Inc), V-950 (Merck & Co Inc), memantine (Merz & Co GmbH), neramexane (Merz & Co GmbH), Epadel (Mochida Pharmaceutical Co Ltd), 123I-MNI-330 (Molecular Neuroimaging Llc), gantenerumab (MorphoSys AG), NIC5-15 (Mount Sinai School of Medicine), huperzine A (Neuro-Hitech Inc), OXIGON (New York University), NP-12 (Noscira SA), NP-61 (Noscira SA), rivastigmine (Novartis AG), ECT-AD (NsGene A/S), arundic acid (Ono Pharmaceutical Co Ltd), PF-3084014 (Pfizer Inc), PF-3654746 (Pfizer Inc), RQ-00000009 (Pfizer Inc), PYM-50028 (Phytopharm plc), Gero-46 (PN Gerolymatos SA), PBT-2 (Prana Biotechnology Ltd), PRX-03140 (Predix Pharmaceuticals Inc), Exebryl-1 (ProteoTech Inc), PF-4360365 (Rinat Neuroscience Corp), HuCAL anti-beta amyloid monoclonal antibodies (Roche AG), EVT-302 (Roche Holding AG), nilvadipine (Roskamp Institute), galantamine (Sanochemia Pharmazeutika AG), SAR-110894 (sanofi-aventis), INM-176 (Scigenic & Scigen Harvest), mimopezil (Shanghai Institute of Materia Medica of the Chinese Academy of Sciences), NEBO-178 (Stegram Pharmaceuticals), SUVN-502 (Suven Life Sciences), TAK-065 (Takeda Pharmaceutical), ispronicline (Targacept Inc), rasagiline (Teva Pharmaceutical Industries), T-817MA (Toyama Chemical), PF-4494700 (TransTech Pharma Inc), CX-717 (University of California), 18F-FDDNP (University of California Los Angeles), GTS-21 (University of Florida), 18F-AV-133 (University of Michigan), 18F-AV-45 (University of Michigan), tetrathiomolybdate (University of Michigan), 123I-IMPY (University of Pennsylvania), 18F-AV-1/ZK (University of Pennsylvania), 11C-6-Me-BTA-1 (University of Pittsburgh), 18F-6-OH-BTA-1 (University of Pittsburgh), MCD-386 (University of Toledo), leuprolide acetate implant (Voyager Pharmaceutical Corp), aleplasinin (Wyeth), begacestat (Wyeth), GSI-136 (Wyeth), NSA-789 (Wyeth), SAM-531 (Wyeth), CTS-21166 (Zapaq), and ZSET-1446 (Zenyaku Kogyo).

Alternatively or additionally, in some embodiments, provided compositions and formulations may be administered in combination with one or more treatments for Parkinson's Disease such as L-DOPA/carbidopa, entacapone, ropinrole, pramipexole, bromocriptine, pergolide, trihexephendyl, and amantadine; For example, methods of the present invention can be used in combination with medications for treating or preventing PD. Such therapeutic agents include levodopa, carbodopa, levodopa (Sinemet and Sinemet CR), Stalevo (carbodopa, levodopa, and entacapone), anticholinergics (trihexyphenidyl, benztropine mesylate, procyclidine, artane, cogentin), bromocriptidine (Parlodel), pergolide (Permax), ropinirol (Requip), pramipexole (Mirapex), cabergoline (Dostinex), apomorphine (Apokyn), rotigotine (Neupro), Ergolide, Mirapex or Requip.

In some embodiments, provided compositions and formulations may be administered in combination with one or more treatments for Parkinson's Disease such as ACR-343, rotigotine (Schwarz), rotigotine patch (UCB), apomorphine (Amarin), apomorphine (Archimedes), AZD-3241 (Astra Zeneca), creatine (Avicena), AV-201 (Avigen), lisuride (Axxonis/Biovail), nebicapone (BIAL Group), apomorphine (Mylan), CERE-120 (Ceregene), melevodopa+carbidopa (Cita Neuropharmaceuticals), piclozotan (Daiichi), GM1 Ganglioside (Fidia Farmaceutici), Altropane (Harvard University), Fluoratec (Harvard University), fipamezole (Juvantia Pharma), istradefylline (Kyowa Hakko Kogyo), GPI-1485 (MGI GP), Neu-120 (Neurim Pharmaceuticals), NGN-9076 (NeuroGeneration Inc), NLX-P101 (Neurologix), AFQ-056 (Novartis), arundic acid (Ono/Merck & Co), COMT inhibitor (Orion), ProSavin (Oxford Biomedica), safinamide (Pharmacia & Upjohn), PYM-50028 (Phytopharm), PTX-200 (Phytix), 123I-iometopane (Research Triangle Institute), SYN-115 (Roche Holding), preladenant (Schering Plough), ST-1535 (Sigma-Tau Ind. Farm), ropinirole (SmithKline Beecham), pardoprunox (Solvay), SPN-803 (Supernus Pharmaceuticals), nitisinone (Syngenta), TAK-065 (Takeda), cell therapy (Titan Pharmaceuticals), PD gene therapy (University of Auckland/Weill Medical College), 18F-AV-133 (University of Michigan), mitoquinone/mitoquinol redox mixture (Antipodean Pharmaceuticals), 99m-Tc-tropantiol (University of Pennsylvania), apomorphine (Vectura), BIIB-014 (Vernalis Group), aplindore (Wyeth), and XP-21279 (XenoPort Inc).

Alternatively or additionally, in some embodiments, provided compositions and formulations may be administered in combination with one or more treatments for Huntington's disease such as ACR-16 (A Carlsson Research AB), creatine (Avicena Group, Inc.), dimebon (Medivation, Inc.), AMR-101 (Scotia Holdings, Inc.), or glatiramer acetate (Teva Pharmaceuticals).

Alternatively or additionally, in some embodiments, provided compositions and formulations may be administered in combination with one or more treatments for motor neuronal disorders, such as AEOL-10150 (Aeolus Pharmaceuticals Inc), riluzole (Aventis Pharma AG), ALS-08 (Avicena Group Inc), creatine (Avicena Group Inc), arimoclomol (Biorex Research and Development Co), mecobalamin (Eisai Co Ltd), talampanel (Eli Lilly & Co), R-7010 (F Hoffmann-La Roche Ltd), edaravone (Mitsubishi-Tokyo Pharmaceuticals Inc), arundic acid (Ono Pharmaceutical Co Ltd), PYM-50018 (Phytopharm plc), RPI-MN (ReceptoPharm Inc), SB-509 (Sangamo BioSciences Inc), olesoxime (Trophos SA), sodium phenylbutyrate (Ucyclyd Pharma Inc), and R-pramipexole (University of Virginia).

Alternatively or additionally, in some embodiments, provided and formulations may be administered in combination with one or more treatments for Multiple Sclerosis such as laquinimod (Active Biotech AB), Alfaferone (Alfa Wassermann SpA), ATX-MS-1467 (Apitope Technology (Bristol) Ltd), Anapsos (ASAC Pharmaceutical International AIE), AZD-5904 (AstraZeneca), teriflunomide (Aventis Pharma AG), BaroFeron (BaroFold Inc), BHT-3009 (Bayhill Therapeutics Inc), Tovaxin (Baylor College of Medicine), PEGylated IFN beta 1-a (Biogen Idec Inc), abatacept (Bristol-Myers Squibb Co), BGC-20-0134 (BTG plc), alemtuzumab (Cambridge University), CCX-140 (ChemoCentryx Inc), Betaseron (Chiron Corp), DWP-419 (Daewoong Pharmaceutical), Biferonex (Dr Rentschler Biotechnologie GmbH), Oral E3 (Effective Pharmaceuticals Inc), perampanel (Eisai Co Ltd), ELND-002 (Elan Corp), fampridine (Elan Corp), natalizumab (Elan Corp plc anti IL-23 (Eli Lilly & Co), LY-2127399 (Eli Lilly & Co), FAR-404 (Farmacija doo), BG-12 (Fumapharm AG), GEM-SP (Gemac Bio), ocrelizumab (Genentech Inc), ofatumumab (Genmab A/S), GRC-4039 (Glenmark Pharmaceuticals Ltd), nabiximols (GW Pharmaceuticals), nerispirdine (Hoechst AG), rituximab (IDEC Pharmaceuticals Corp mitoxantrone (Immunex Corp), INCB-5696 (Incyte Corp), TV-1102 (Isis Pharmaceuticals Inc), BOW-304 (Kingston Scientific Partnership), ibudilast (Kyorin Pharmaceutical), KRP-203 (Kyorin Pharmaceutical), erythropoietin (Max-Planck Institute for Experimental Medicine), Rebif (Merck Serono SA), MLN-1202 (Millennium Pharmaceuticals Inc), BAF-312 (Novartis AG), ONO-4641 (Ono Pharmaceutical), VG-1000 (Oregon Health & Science University), daclizumab (PDL BioPharma Inc), Tauferon (Pepgen Corp), PI-2301 (Peptimmune), RPI-78M (ReceptoPharm Inc), CTLA4-Ig, (RepliGen Corp), CS-0777 (Sankyo), cladribine (Scripps Research Institute), firategrast (Tanabe Seiyaku), GBR-500 (Targeted Molecules Corp), glatiramer acetate (Teva Pharmaceutical Industries), CDP-323 (UCB Celltech), dirucotide (University of Alberta), recombinant chaperonin 10 (University of Queensland), fingolimod (Welfide Corp), atacicept (ZymoGenetics Inc), etc. In some embodiments, agents for treating Multiple Sclerosis (MS) include but are not limited to beta interferon (e.g., Avonex® and Rebif®), Copaxone®, and/or mitoxantrone, and combinations thereof.

Alternatively or additionally, provided compositions and formulations may be administered in combination with one or more treatments for lysosomal storage diseases, such as bone marrow transplant, stem cell replacement therapy, enzyme replacement therapy (e.g., with enzyme replacement with α-1-iduronidase for MPS Type I/Hurler's disease; glucocerebrosidase for Gaucher's type I or III; α-galactosidase A for Fabry's; etc), splenectomy, and/or treatment with certain therapeutic agents (e.g., a glucosylceramide synthase inhibitor such as miglustat for Gaucher's; statins and/or cholestyramine for Fabry's; etc). Particular known therapies for lysosomal storage diseases are included in the Table below:

| Lysosomal Storage Disease Therapy Table | | | |
|---|---|---|---|
| Name | Company | Action | Indication(s) |
| AGT-181 | ArmaGen Technologies Inc | Alpha-L-iduronidase stimulator | Mucopolysaccharidosis type I |
| | | Insulin receptor modulator | Lysosome storage disease |
| BMN-110 | BioMarin Pharmaceutical Inc | Sulfatase stimulator | Morquio syndrome |
| laronidase | BioMarin Pharmaceutical Inc | Alpha-L-iduronidase stimulator | Mucopolysaccharidosis type I; Lysosome storage disease |
| NZ-1002 | Novazyme Pharmaceuticals Inc | Unspecified enzyme modulator | Lysosome storage disease |
| recombinant human N-acetylgalactosamine-6-sulfatase (mucopolysaccharidosis IVA), Vivendy | Vivendy Therapeutics Ltd | Sulfatase stimulator | Morquio syndrome |
| glycan inhibitor (mucopolysaccharidosis), Zacharon | Zacharon Pharmaceuticals Inc | Glycosaminoglycan antagonist | Mucopolysaccharidosis |
| lysosomal acid lipase, LSBC | Childrens Hospital Medical Center (Cincinnati) | Lipase modulator Lipid metabolism modulator | Hypercholesterolemia Atherosclerosis |
| gene therapy (lysosomal storage disorders), Genzyme/Targeted Genetics | Genovo Inc | Unspecified virus based gene therapy | Lysosome storage disease |
| Genz-112638 | Genzyme General | Glycolipid inhibitor Glucosylceramide synthase inhibitor | Gaucher disease Lysosome storage disease |
| HTI-501 | Halozyme Therapeutics Inc | Protease stimulator Dermatological agent | Dermatological disease |
| lysosomal arylsulfatase A replacement therapy (FGE, metachromatic leukodystrophy), Shire | Shire Human Genetic Therapies Inc | Arylsulfatase A stimulator | Metachromatic leukodystrophy |
| HGT-1111 | Zymenex A/S | Arylsulfatase A stimulator | Metachromatic leukodystrophy |
| arylsulfatase B gene therapy (MPS-VI), | Freiburg University | Albert-Ludwigs-Universitaet Freibure | Arylsulfatase B stimulator |
| AAV-GUS | Avigen Inc | Gene therapy | Storage disease |
| BMN-110 | BioMarin Pharmaceutical Inc | Sulfatase stimulator | Morquio syndrome |
| galsulfase | BioMarin Pharmaceutical Inc | Arylsulfatase B stimulator | Maroteaux-Lamy syndrome |
| | | Glycosaminoglycan antagonist | Lysosome storage disease |
| migalastat | Amicus Therapeutics Inc | Alpha-galactosidase stimulator | Fabry disease |

-continued

Lysosomal Storage Disease Therapy Table

| Name | Company | Action | Indication(s) |
| --- | --- | --- | --- |
| AAV-alpha galactosidase A gene therapy (Fabry disease), Genzyme | Genzyme Corp | Adenovirus based gene therapy | Fabry disease |
| alpha-galactosidase A, LSBC | Large Scale Biology Corp | Alpha-galactosidase modulator | Fabry disease |
| PRX-102 | Protalix BioTherapeutics Inc | Alpha-galactosidase stimulator | Fabry disease |
| alpha-galactosidase A, Orphan | Research Corporation Technologies | Alpha-galactosidase stimulator | Fabry disease |
| agalsidase alfa | Shire Human Genetic Therapies Inc | Alpha-galactosidase stimulator | Fabry disease |
| afegostat tartrate | Amicus Therapeutics Inc | Glucosylceramidase stimulator | Gaucher disease |
| AAV gene therapy (Gaucher), Avigen | Avigen Inc | Adeno-associated virus based gene therapy | Gaucher disease |
| Gaucher's disease therapy, Neuraltus | Neuraltus Pharmaceuticals Inc | Glucosylceramidase stimulator | Gaucher disease |

Other examples of agents the inhibitors of this invention may also be combined with include, without limitation: chemotherapeutic agents to treat proliferative diseases and cancer. Examples of known chemotherapeutic agents include, but are not limited to, Adriamycin, dexamethasone, vincristine, cyclophosphamide, fluorouracil, topotecan, taxol, interferons, platinum derivatives, taxane (e.g., paclitaxel), vinca alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, emetine, trimetrexate, metoprine, cyclosporine, daunorubicin, teniposide, amphotericin, alkylating agents (e.g., chlorambucil), 5-fluorouracil, campthothecin, cisplatin, metronidazole, and Gleevec™, among others. In other embodiments, a compound of the present invention is administered in combination with a biologic agent, such as Avastin or Vectibix.

In certain embodiments, compounds of the present invention, or a pharmaceutically acceptable composition thereof, are administered in combination with an antiproliferative or chemotherapeutic agent selected from any one or more of Abarelix, aldesleukin, Aldesleukin, Alemtuzumab, Alitretinoin, Allopurinol, Altretamine, Amifostine, Anastrozole, Arsenic trioxide, Asparaginase, Azacitidine, BCG Live, Bevacuzimab, Fluorouracil, Bexarotene, Bleomycin, Bortezomib, Busulfan, Calusterone, Capecitabine, Camptothecin, Carboplatin, Carmustine, Celecoxib, Cetuximab, Chlorambucil, Cladribine, Clofarabine, Cyclophosphamide, Cytarabine, Dactinomycin, Darbepoetin alfa, Daunorubicin, Denileukin, Dexrazoxane, Docetaxel, Doxorubicin (neutral), Doxorubicin hydrochloride, Dromostanolone Propionate, Epirubicin, Epoetin alfa, Erlotinib, Estramustine, Etoposide Phosphate, Etoposide, Exemestane, Filgrastim, floxuridine fludarabine, Fulvestrant, Gefitinib, Gemcitabine, Gemtuzumab, Goserelin Acetate, Histrelin Acetate, Hydroxyurea, Ibritumomab, Idarubicin, Ifosfamide, Imatinib Mesylate, Interferon Alfa-2a, Interferon Alfa-2b, Irinotecan, Lenalidomide, Letrozole, Leucovorin, Leuprolide Acetate, Levamisole, Lomustine, Megestrol Acetate, Melphalan, Mercaptopurine, 6-MP, Mesna, Methotrexate, Methoxsalen, Mitomycin C, Mitotane, Mitoxantrone, Nandrolone, Nelarabine, Nofetumomab, Oprelvekin, Oxaliplatin, Paclitaxel, Palifermin, Pamidronate, Pegademase, Pegaspargase, Pegfilgrastim, Pemetrexed Disodium, Pentostatin, Pipobroman, Plicamycin, Porfimer Sodium, Procarbazine, Quinacrine, Rasburicase, Rituximab, Sargramostim, Sorafenib, Streptozocin, Sunitinib Maleate, Talc, Tamoxifen, Temozolomide, Teniposide, VM-26, Testolactone, Thioguanine, 6-TG, Thiotepa, Topotecan, Toremifene, Tositumomab, Trastuzumab, Tretinoin, ATRA, Uracil Mustard, Valrubicin, Vinblastine, Vincristine, Vinorelbine, Zoledronate, and/or Zoledronic acid.

In certain embodiments, compounds of the present invention, or a pharmaceutically acceptable composition thereof, are administered in combination with anti-inflammatory agents such as corticosteroids, TNF blockers, IL-1 RA, azathioprine, cyclophosphamide, sulfasalazine, methotrexate hydroxychlorogine, gold, penicillamine, azathioprine, sulfasalazine, and/or biologic drugs.

In certain embodiments, compounds of the present invention, or a pharmaceutically acceptable composition thereof, are administered in combination within aspirin and/or other nonsteroidal anti-inflammatory drugs (NSAIDs), such as ibuprofen (Motrin, and others), naproxen (Naprosyn, and others) and/or dicolfenac (Voltaren). Nonacetylated salicylates, such as sodium salicylate, salsalate (Disalcid, and others), and/or choline magnesium salicylate (Trilisate, and others), do not interfere with platelet function and may be safer than acetylated salicylates for aspirin-sensitive patients.

In certain embodiments, compounds of the present invention, or a pharmaceutically acceptable composition thereof, are administered in combination with agents for treating cardiovascular disease such as beta-blockers, ACE inhibitors, diuretics, nitrates, calcium channel blockers, and/or statins;

Additional therapeutic agents for administration in combination with a provided composition of formulation thereof, include: treatments for asthma such as albuterol and Singulair®; agents for treating schizophrenia such as zyprexa, risperdal, seroquel, and haloperidol; immunomodulatory and immunosuppressive agents such as cyclosporin, tacrolimus, rapamycin, mycophenolate mofetil, interferons, corticosteroids, cyclophosphamide, azathioprine, and sulfasalazine; agents for treating liver disease such as corticosteroids, cholestyramine, interferons, and anti-viral agents; agents for treating blood disorders such as corticosteroids, anti-leukemic agents, and growth factors; and/or agents for treating immunodeficiency disorders such as gamma globulin.

Compounds or compositions of the present invention can also be used in combination with surgical therapies for the treatment of PD. Surgical treatment is presently recommended for those who have failed medical management of PD. Unilateral thallamotomy can be used to reduce tremor. It is occasionally considered for patients with unilateral tremor not responding to medication. Bilateral procedures are not advised. Unilateral deep brain stimulation of the thalamus for tremor may also be a benefit for tremor. Unilateral pallidotomy is an effective technique for reducing contralateral drug-induced dyskinesias. Gamma knife surgery—thalamotomy or pallidotomy—can be performed as a radiological alternative to conventional surgery. The currently preferred neurosurgical intervention is, however, bilateral subthalamic nucleus stimulation. Neurotransplantation strategies remain experimental. In addition to surgery and medication, physical therapy in Parkinsonism maintains muscle tone, flexibility, and improves posture and gait.

7. Uses of Provided Compounds and Pharmaceutical Compositions Thereof

Provided compounds and/or compositions may be utilized in any of a variety of therapeutic or other contexts. In some embodiments, for example, provided compounds and/or compositions are utilized in the treatment or prevention of one or more neurodegenerative disorders. In some embodiments, provided compounds and/or compositions are utilized in the treatment or prevention of one or more inflammatory disorders. In certain embodiments, provided compounds and/or compositions are utilized in the treatment or prevention of one or more cardiovascular disorders. In certain embodiments, provided compounds and/or compositions are utilized in the treatment or prevention of one or more proliferative disorders. In some embodiments, provided compounds and/or compositions are utilized in the treatment or prevention of one or more proteinopathies (e.g., synucleinopathies, tauopathies, amyloidopathies, TDP-42 proteinopathies, etc.). In some embodiments, provided compounds and/or compositions are utilized in the treatment or prevention of one or more diseases, disorders, or conditions resulting from disruptions of cellular autophagy.

Compounds and/or compositions provided herein may be administered prophylactically or therapeutically. When provided prophylactically, compounds and/or compositions are provided in advance of symptoms. Prophylactic administration may, for example, delay onset of and/or reduce rate of onset of one or more symptoms the agent serves to prevent or reduce the rate of onset of symptoms of a neurodegenerative disease. When provided therapeutically, compounds and/or compositions are provided at (or after) the onset of the appearance of one or more symptoms. In some embodiments, the therapeutic administration may, for example, reduce severity, incidence, and/or duration of one or more symptoms.

Without wishing to be bound by any particular theory, it is proposed that beneficial (e.g., therapeutic) effects of compounds described herein may be at least partly attributable to activity of the compounds as inhibitors of farnesylation. As discussed herein, in some embodiments, provided compounds are characterized by (and/or administered under conditions and/or according to a regimen that achieves) inhibition of farnesylation of at least one favored target protein.

Alternatively or additionally, and also without wishing to be bound by any particular theory, it is proposed that beneficial (e.g., therapeutic) effects of compounds provided herein may be at least partly attributable to activity of the compounds as stimulators of protein degradation, particularly with respect to misfolded and/or aggregated proteins.

It is specifically proposed that compounds provided herein are useful in the treatment or prevention of disorders, diseases, or conditions associated with abnormal protein folding and/or accumulation of protein aggregates. It will be appreciated that in some embodiments, misfolded proteins, and/or protein aggregates may be considered to cause one or more symptoms or attributes of a particular disease, disorder or condition. So long as presence of misfolded proteins and/or protein aggregates correlates with presence of symptoms, the disease, disorder, or condition is considered to be associated with misfolded proteins and/or protein aggregates. Diseases, disorders or conditions associated with misfolded and/or aggregated proteins are referred to as "proteinopathies" herein. Proteinopathies of particular relevance include those associated with protein aggregates, and particularly with aggregates of one or more proteins selected from the group consisting of α-synuclein (synucleinopathies), tau (tauopathies), amyloid (amyloidopathies), SOD1 (SOD1 proteinopathies), TDP-43 (TDP-43 proteinopathies), huntingtin, subunit c of ATP synthase, etc. It will be appreciated by those of ordinary skill in the art that certain diseases, disorders and conditions may be associated with misfolding and/or aggregation of more than one different protein and therefore may fall into more than one disease category as described herein.

In one aspect of the invention, the proteinopathy is selected from the group consisting of atherosclerosis, stroke, cerebrovascular disease, vascular dementia, multi-infarct dementia, Parkinson's disease and Parkinson's disease dementia, Lewy body disease, Pick's disease, Alzheimer's disease, mild cognitive impairment, Huntington's disease, AIDS and AIDS-related dementia, brain neoplasms, brain lesions, epilepsy, multiple sclerosis, Down's syndrome, Rett's syndrome, progressive supranuclear palsy, frontal lobe syndrome, schizophrenia, traumatic brain injury, post coronary artery by-pass graft surgery, cognitive impairment due to electroconvulsive shock therapy, cognitive impairment due to chemotherapy, cognitive impairment due to a history of drug abuse, attention deficit disorder (ADD), attention deficit hyperactivity disorder (ADHD), autism, dyslexia, depression, bipolar disorder, post-traumatic stress disorder, apathy, myasthenia gravis, cognitive impairment during waking hours due to sleep apnea, Tourette's syndrome, autoimmune vasculitis, systemic lupus erythematosus, polymyalgia rheumatica, hepatic conditions, metabolic diseases, Kufs' disease, adrenoleukodystrophy, metachromatic leukodystrophy, storage diseases, infectious vasculitis, syphillis, neurosyphillis, Lyme disease, complications from intracerebral hemorrhage, hypothyroidism, B12 deficiency, folic acid deficiency, niacin deficiency, thiamine deficiency, hydrocephalus, complications post anoxia, prion disease (Creutzfeldt-Jakob disease), Fragile X syndrome, phenylketonuria, malnutrition, neurofibromatosis, maple syrup urine disease, hypercalcemia, hypothyroidism, hypercalcemia, and hypoglycemia.

Synucleins are small proteins (123 to 143 amino acids) characterized by repetitive imperfect repeats KTKEGV (SEQ ID NO: 21) distributed throughout most of the amino terminal half of the polypeptide in the acidic carboxy-terminal region. There are three human synuclein proteins termed α, β, and γ, and they are encoded by separate genes mapped to chromosomes 4221.3-q22, 5q23, and 10q23.2-q23.3, respectively. The most recently cloned synuclein protein synoretin, has a close homology to γ-synuclein and is predominantly expressed within the retina. α-Synuclein, also referred to as non-amyloid component of senile plaques precursor protein (NACP), SYN1 or synelfin, is a heat-stable, "natively unfolded" protein of poorly defined function. It is predominantly expressed in the central nervous system (CNS) neurons where it is localized to presynaptic terminals. Electron microscopy studies have localized α-synuclein in close proximity to synaptic vesicles at axonal termini, suggesting a role for α-synuclein in neurotransmission or synaptic organization, and biochemical analysis has revealed that a small fraction of α-synuclein may be associated with vesicular membranes but most α-synuclein is cytosolic.

Genetic and histopathological evidence supports the idea that α-synuclein is the major component of several proteinaceous inclusions characteristic of specific neurodegenerative diseases. Pathological synuclein aggregations are restricted to the α-synuclein isoforms, as β- and γ-synucleins have not been detected in these inclusions. The presence of α-synuclein positive aggregates is disease specific. Lewy bodies, neuronal fibrous cytoplasmic inclusions that are histopathological hallmarks of Parkinson's disease (PD) and diffuse Lewy body disease (DLBD) are strongly labeled with antibodies to α-synuclein. Dystrophic ubiquitin-positive neurites associated with PD pathology, termed Lewy neurites (LN) and CA2/CA3 ubiquitin neurites are also α-synuclein positive. Furthermore, pale bodies, putative precursors of LBs, thread-like structures in the perikarya of slightly swollen neurons and glial silver positive inclusions in the midbrains of patients with LB diseases are also immunoreactive for α-synuclein. α-Synuclein is likely the major component of glial cell inclusions (GCIs) and neuronal cytoplasmic inclusions in MSA and brain iron accumulation type I (PANK1). α-Synuclein immunoreactivity is present in some dystrophic neurites in senile plaques in Alzheimer's Disease (AD) and in the cord and cortex in amyotrophic lateral sclerosis (ALS). α-Synuclein immunoreactivity is prominent in transgenic and toxin-induced mouse models of PD, AD, ALS, and HD.

Further evidence supports the notion that α-synuclein is the actual building block of the fibrillary components of LBs, LNs, and GCIs. Immunoelectron microscopic studies have demonstrated that these fibrils are intensely labeled with α-synuclein antibodies in situ. Sarcosyl-insoluble α-synuclein filaments with straight and twisted morphologies can also be observed in extracts of DLBD and MSA brains. Moreover, α-synuclein can assemble in vitro into elongated homopolymers with similar widths as sarcosyl-insoluble fibrils or filaments visualized in situ. Polymerization is associated with a concomitant change in secondary structure from random coil to anti-parallel β-sheet structure consistent with the Thioflavine-S reactivity of these filaments. Furthermore, the PD-association with α-synuclein mutation, A53T, may accelerate this process, as recombinant A53T α-synuclein has a greater propensity to polymerize than wild-type α-synuclein. This mutation also affects the ultrastructure of the polymers; the filaments are slightly wider and are more twisted in appearance, as if assembled from two protofilaments. The A30P mutation may also modestly increase the propensity of α-synuclein to polymerize, but the pathological effects of this mutation also may be related to its reduced binding to vesicles. Interestingly, carboxyl-terminally truncated α-synuclein may be more prone to form filaments than the full-length protein.

Synucleinopathies are a diverse set of disorders that share a common association with lesions containing abnormal aggregates of insolution α-synuclein protein. Typically such lesions are found in selectively vulnerable populations of neurons and glia. Certain evidence links the formation of abnormal filamentous aggregates to the onset and progression of clinical symptoms and the degeneration of affected brain regions in neurodegenerative disorders including Parkinson's disease (PD), diffuse Lewy body disease (DLBD), multiple system atrophy (MSA), and disorders of brain iron concentration including pantothenate kinase-associated neurodegeneration (e.g., PANK1). In one aspect of the invention, the synucleinopathy is selected from Parkinson's disease, diffuse Lewy body disease and multiple system atrophy. The current treatment options for these diseases include symptomatic medications such as carbidopa-levodopa, anticholinergics, and monoamine oxidase inhibitors, with widely variable benefit. Even for the best responders, i.e., patients with idiopathic Parkinson's disease, an initial good response to levodopa is typically overshadowed by drug-induced complications such as motor fluctuations and debilitating dyskinesia, following the first five to seven years of therapy. For the rest of the disorders, the current medications offer marginal symptomatic benefit. Given the severe debilitating nature of these disorders and their prevalence, there is a clear need in the art for novel approaches towards preventing, treating and managing synucleinopathies.

The present invention provides methods relevant to synucleinopathies. For example, in some embodiments, the present invention provides a method of reducing α-synuclein toxicity in a cell, the method comprising administering to a cell a therapeutically effective amount of a provided compound. In some embodiments, the present invention provides a method of reducing the accumulation of α-synuclein in a cell, the method comprising administering to a cell a therapeutically effective amount of a provided compound. In some embodiments, the cell is a neuronal cell. In some embodiments, the cell expresses α-synuclein. In certain embodiments, the synucleinopathy is Parkinson's disease, diffuse Lewy body disease, and/or multiple system atrophy disorder.

The present invention provides methods relevant to amyloidopathies. For example, in some embodiments, the present invention provides a method of reducing amyloid beta toxicity in a cell, the method comprising administering to a cell a therapeutically effective amount of a provided compound. In some embodiments, the present invention provides a method of reducing the accumulation of amyloid beta proteins in a cell, the method comprising administering to a cell a therapeutically effective amount of a provided compound. In some embodiments, the cell is a neuronal cell. In some embodiments, the cell expresses amyloid beta proteins. In certain embodiments, the amyloidopathy is Alzheimer's disease, vascular dementia, and/or cognitive impairment.

In one aspect of the present invention, the amyloidopathy is selected from the group consisting of atherosclerosis, stroke, cerebrovascular disease, vascular dementia, multi-infarct dementia, Parkinson's disease and Parkinson's disease dementia, Lewy body disease, Pick's disease, Alzheimer's disease, mild cognitive impairment, Huntington's disease, AIDS and AIDS-related dementia, brain neoplasms, brain lesions, epilepsy, multiple sclerosis, Down's syndrome, Rett's syndrome, progressive supranuclear palsy, frontal lobe syndrome, schizophrenia, traumatic brain injury, post coronary artery by-pass graft surgery, cognitive impairment due to electroconvulsive shock therapy, cognitive impairment due to chemotherapy, cognitive impairment due to a history of drug abuse, attention deficit disorder (ADD), attention deficit hyperactivity disorder (ADHD), autism, dyslexia, depression, bipolar disorder, post-traumatic stress disorder, apathy, myasthenia gravis, cognitive impairment during waking hours due to sleep apnea, Tourette's syndrome, autoimmune vasculitis, systemic lupus erythematosus, polymyalgia rheumatica, hepatic conditions, metabolic diseases, Kufs' disease, adrenoleukodystrophy, metachromatic leukodystrophy, storage diseases, infectious vasculitis, syphillis, neurosyphillis, Lyme disease, complications from intracerebral hemorrhage, hypothyroidism, B12 deficiency, folic acid deficiency, niacin deficiency, thiamine deficiency, hydrocephalus, complications post anoxia, prion disease (Creutzfeldt-Jakob disease), Fragile X syndrome, phenylketonuria, malnutrition, neurofibromatosis, maple syrup urine disease, hypercalcemia, hypothyroidism, hypercalcemia, and hypoglycemia.

Taupathies are neurodegenerative disorders characterized by the presence of filamentous deposits, consisting of hyperphosphorylated tau protein, in neurons and glia. Abnormal tau phosphorylation and deposition in neurons and glial cells is one of the major features in taupathies. The term taupathy, was first used to describe a family with frontotemporal dementia (FTD) and abundant tau deposits. This term is now used to identify a group of diseases with widespread tau pathology in which tau accumulation appears to be directly associated with pathogenesis. Major neurodegenerative taupathies includes sporadic and hereditary diseases characterized by filamentous tau deposits in brain and spinal cord.

In the majority of taupathies, glial and neuronal tau inclusions are the sole or predominant CNS lesions. Exemplary such taupathies include amytrophic lateral sclerosis (ALS), parkinsonism, argyrophilic grain dementia, diffuse neurofibrillary tangles with calcification, frontotemporal dementia linked to chromosome 17, corticobasal degeneration, Pick's disease, progressive supranuclear palsy, progressive subcortical gliosis, and tangle only dementia.

Additionally, taupathies characterize a large group of diseases, disorders and conditions in which significant filaments and aggregates of tau protein are found. Exemplary such diseases, disorders, and conditions include sporadic and/or familial Alzheimer's Disease (AD), amyotrophic lateral sclerosis/parkinsonism-dementia complex (ALS-FTDP), argyrophilic grain dementia, dementia pugilistica, diffuse neurofibrillary tangles with calcification, Down syndrome, frontotemporal dementia, parkinsonism linked to chromosome 17 (FTDP-17), Gerstmann-Straussler-Scheinker disease, Hallervorden-Spatz disease, inclusion body myositis, Creutzfeld-Jakob disease (CJD), multiple system atrophy, Niemann-Pick disease (NPC), Pick's disease, prion protein cerebral amyloid angiopathy, progressive supranuclear palsy (PSP), subacute sclerosing panencephalitis, tangle-predominant Alzheimer's disease, corticobasal degeneration, (CBD), myotonic dystrophy, non-guanamian motor neuron disease with neurofibrillary tangles, postencephalitic parkinsonism, prion protein cerebral amyloid angiopathy, progressive subcortical gliosis, subacute sclerosing panencephalitis, and tangle-only dementia.

In one aspect of the invention, the taupathy is selected from the group consisting of atherosclerosis, stroke, cerebrovascular disease, vascular dementia, multi-infarct dementia, Parkinson's disease and Parkinson's disease dementia, Lewy body disease, Pick's disease, Alzheimer's disease, mild cognitive impairment, Huntington's disease, AIDS and AIDS-related dementia, brain neoplasms, brain lesions, epilepsy, multiple sclerosis, Down's syndrome, Rett's syndrome, progressive supranuclear palsy, frontal lobe syndrome, schizophrenia, traumatic brain injury, post coronary artery by-pass graft surgery, cognitive impairment due to electroconvulsive shock therapy, cognitive impairment due to chemotherapy, cognitive impairment due to a history of drug abuse, attention deficit disorder (ADD), attention deficit hyperactivity disorder (ADHD), autism, dyslexia, depression, bipolar disorder, post-traumatic stress disorder, apathy, myasthenia gravis, cognitive impairment during waking hours due to sleep apnea, Tourette's syndrome, autoimmune vasculitis, systemic lupus erythematosus, polymyalgia rheumatica, hepatic conditions, metabolic diseases, Kufs' disease, adrenoleukodystrophy, metachromatic leukodystrophy, storage diseases, infectious vasculitis, syphillis, neurosyphillis, Lyme disease, complications from intracerebral hemorrhage, hypothyroidism, B12 deficiency, folic acid deficiency, niacin deficiency, thiamine deficiency, hydrocephalus, complications post anoxia, prion disease (Creutzfeldt-Jakob disease), Fragile X syndrome, phenylketonuria, malnutrition, neurofibromatosis, maple syrup urine disease, hypercalcemia, hypothyroidism, hypercalcemia, and hypoglycemia.

Neurodegenerative diseases where tau pathology is found in conjunction with other abnormal protein lesions may be considered secondary taupathies. Examples include Alzheimer's Disease (AD) and certain diseases where prion protein, Bri, or α-synuclein are aggregated. Although tau is probably not the initial pathological factor, tau aggregates contribute to the final degeneration.

Tau deposits can also be found in several other neurodegenerative diseases in which tau pathology is evident in conjunction with other abnormal protein lesions protein. Abundant cytoplasmic inclusions consisting of aggregated hyperphosphorylated protein tau are a characteristic pathological observation in several neurodegenerative disorders such as Alzheimer's disease, Pick's disease, frontotemporal dementia, cortico-basal degeneration, and progressive supranuclear palsy.

The present invention provides methods relevant to tauopathies. For example, in some embodiments, the present invention provides a method of reducing tau toxicity in a cell, the method comprising administering to a cell a therapeutically effective amount of a provided compound. In some embodiments, the present invention provides a method of reducing the accumulation of tau proteins in a cell, the method comprising administering to a cell a therapeutically effective amount of a provided compound. In some embodiments, the cell is a neuronal cell. In some embodiments, the cell expresses tau proteins. In certain embodiments, the taupathy is Alzheimer's disease.

Certain particular diseases, disorders and conditions of interest are highlighted below.

7A. Neurodegenerative Diseases, Disorders and Conditions, Cognitive Impairment, and Dementia Many neurodegenerative diseases are linked to intracellular and/or extracellular accumulation of specific protein aggregates. In many cases, it is thought that these aggregates exert toxic effects on the brain, and contribute to disease pathology.

In one aspect, the present invention provides methods for treating a subject with a neurodegenerative diseases or preventing the development of a neurodegenerative diseases by administering a therapeutically effective amount of a provided compound or a composition thereof. In certain embodiments, the subject has a synucleinopathy, amyloidopathy, taupathy or other proteinopathy. In some embodiments the neurodegenerative disease is selected from the group consisting of Parkinson's disease, diffuse Lewy body disease, and multiple system atrophy disorder. In some embodiments, the subject suffers from one or more disorders of brain iron concentration including pantothenate kinase-associated neurodegeneration (e.g., PANK1). In some embodiments, other neurodegenerative diseases such as amyotrophic lateral sclerosis (ALS), Huntington's Disease (HD), Mild Cognitive Impairment, and Alzheimer's Disease (AD) may be treated with provided compounds. In some embodiments, other neurodegenerative diseases such as amyotrophic lateral sclerosis (ALS), Huntington's Disease (HD), Mild Cognitive Impairment, and Alzheimer's Disease (AD) may be prevented with the provided compounds.

Inclusion body myopathy with early-onset Paget disease and frontotemporal dementia (IBMPFD) is a condition that can affect the muscles, bones, and brain. The first symptom of IBMPFD is often muscle weakness (myopathy), which typically appears in mid-adulthood. Weakness first occurs in muscles of the hips and shoulders, making it difficult to climb stairs and raise the arms above the shoulders. As the disorder progresses, weakness develops in other muscles in the arms and legs. Muscle weakness can also affect respiratory and heart (cardiac) muscles, leading to life-threatening breathing difficulties and heart failure.

Alzheimer's Disease

Alzheimers is the leading cause of dementia and cognitive impairment in the elderly and a leading cause of death in developing nations after cardiovascular disease, cancer, and stroke. Up to 70% of cases of dementia are due to Alzheimer's disease, with vasucular disease being the second most common cause. The frequency of AD among 60-year-olds is approximately 1%. The incidence of AD doubles approximately every 5 years. Forsyth, *Phys. Ther.* 78:1325-1331, 1998; Evans et al., *JAMA* 262:2551-2556, 1989. AD afflicts an estimated four million people in the U.S. alone at a cost of $100 billion per year. Schumock, *J. Health Syst. Pharm.* 55(52):17-21, 1998; Hay & Ernst, *Am. J. Public Health* 77:1169-1175, 1987.

Alzheimers Disease is characterized by the deterioration of mental faculties (e.g., memory loss, confusion, loss of visual/spatial comprehension) and associated with both amyloidopathies and taupathies. The central role of the long form of amyloid beta-peptide, in particular $A\beta(1\text{-}42)$, in Alzheimer's disease has been established through a variety of histopathological, genetic and biochemical studies. Specifically, it has been found that deposition in the brain of $A\beta(1\text{-}42)$ is an early and invariant feature of all forms of Alzheimer's disease. This occurs before a diagnosis of Alzheimer's disease is possible and before the deposition of the shorter primary form of A-beta, $A\beta(1\text{-}40)$. Further implication of $A\beta(1\text{-}42)$ in disease etiology comes from the observation that mutations in presenilin (gamma secretase) genes associated with early onset familial forms of Alzheimer's disease uniformly result in increased levels of $A\beta(1\text{-}42)$. Additional mutations in the amyloid precursor protein APP raise total $A\beta$ and in some cases raise $A\beta(1\text{-}42)$ alone. Although the various APP mutations may influence the type, quantity, and location of $A\beta$ deposited, it has been found that the predominant and initial species deposited in the brain parenchyma is long $A\beta$. In early deposits of $A\beta$, when most deposited protein is in the form of amorphous or diffuse plaques, virtually all of the $A\beta$ is of the long form. These initial deposits of $A\beta(1\text{-}42)$ then are able to seed the further deposition of both long and short forms of A. In transgenic animals expressing $A\beta$, deposits were associated with elevated levels of $A\beta(1\text{-}42)$, and the pattern of deposition is similar to that seen in human disease with $A\beta(1\text{-}42)$ being deposited early followed by deposition of $A\beta(1\text{-}40)$. Similar patterns and timing of deposition are seen in Down's Syndrome patients in which $A\beta$ expression is elevated and deposition is accelerated. The association of Alzheimer's Diseases with amyloid plaques means that Alzheimer's Diseases is considered to be an amyloidopathy. Alzheimer's Disease is also associated with accumulation of tau aggregates and therefore is a taupathy.

Parkinson's Disease

Parkinson's disease (PD) is a neurodegenerative disorder characterized by bradykinesia, rigidity, tremor, and postural instability. The pathologic hallmark of PD is loss of neurons in the substantia nigra pars compacta (SNpc) and the appearance of Lewy bodies in remaining neurons. It appears that more than about 50% of the cells in the SNpc need to be lost before motor symptoms appear. Associated symptoms often include small handwriting (micrographia), seborrhea, orthostatic hypotension, urinary difficulties, constipation and other gastrointestinal dysfunction, sleep disorders, depression and other neuropsychiatric phenomena, dementia, and smelling disturbances (occurs early). Patients with Parkinsonism have greater mortality, about two times compared to general population without PD. This is attributed to greater frailty or reduced mobility.

Diagnosis of PD is mainly clinical and is based on the clinical findings listed above. Parkinsonism, refers to any combination of two of bradykinesia, rigidity, and/or tremor. PD is the most common cause of parkinsonism. Other causes of parkinsonism are side effects of drugs, mainly the major tranquilizers, such as Haldol, strokes involving the basal ganglia, and other neurodegenerative disorders, such as Diffuse Lewy Body Disease (DLBD), progressive supranuclear palsy (PSP), frontotemporal dementia (FTD), MSA, and Huntington's disease. The pathological hallmark of PD is the Lewy body, an intracytoplasmatic inclusion body typically seen in affected neurons of the substantia nigra and to a variable extent, in the cortex. Recently, α-synuclein has been identified as the main component of Lewy bodies in sporadic Parkinsonism.

Although parkinsonism can be clearly traced to viruses, stroke, or toxins in a few individuals, for the most part, the etiology of Parkinson's disease in any particular case is unknown. Environmental influences which may contribute to PD may include drinking well water, farming and industrial exposure to heavy metals (e.g., iron, zinc, copper, mercury, magnesium and manganese), alkylated phosphates, and orthonal chlorines. Paraquat (a herbicide) has also been associated with increased prevalence of Parkinsonism including PD. Cigarette smoking is associated with a decreased incidence of PD. The current consensus is that PD may either be caused by an uncommon toxin combined with high genetic susceptibility or a common toxin combined with relatively low genetic susceptibility.

A small percentage of subjects that are at risk of developing PD can be identified for example by genetic analysis. There is good evidence for certain genetic factors being associated with PD. Large pedigrees of autosomal dominantly inherited PDs have been reported. For example, a mutation in α-synuclein is responsible for one pedigree and triplication of the SNCA gene (the gene coding for α-synuclein) is associated with PD in others.

MSA

MSA is a neurodegenerative disease marked by a combination of symptoms; affecting movement, cognition, autonomic and other body functions, hence the label "multiple system atrophy". The cause of MSA is unknown. Symptoms of MSA vary in distribution of onset and severity from person to person. Because of this, the nomenclature initially included three distinct terms: Shy-Drager syndrome, striatonigral degeneration (SD), and olivopontocerebellar atrophy (OPCA).

In Shy-Drager syndrome, the most prominent symptoms are those involving the autonomic system; blood pressure, urinary function, and other functions not involving conscious control. Striatonigral degeneration causes Parkinsonism symptoms, such as slowed movements and rigidity, while OPCA principally affects balance, coordination and speech. The symptoms for MSA can also include orthostatic hypertension, male impotence, urinary difficulties, constipation, speech and swallowing difficulties, and blurred vision.

The initial diagnosis of MSA is usually made by carefully interviewing the patient and performing a physical examination. Several types of brain imaging, including computer tomography, scans, magnetic resonance imaging (MRI), and positron emission tomography (PET), can be used as corroborative studies. An incomplete and relatively poor response to dopamine replacement therapy, such as Sinemet, may be a clue that the presentation of bradykinesia and rigidity (parkinsonism) is not due to PD. A characteristic involvement of multiple brain systems with prominent autonomic dysfunction is a defining feature of MSA and one that at autopsy confirms the diagnosis. Patients with MSA can have the presence of glial cytoplasmic inclusions in certain types of brain cells, as well. Prototypic Lewy bodies are not present in MSA. However, α-synuclein staining by immunohistochemistry is prominent. In comparison to Parkinson's, in addition to the poor response to Sinemet, there are a few other observations that are strongly suggested for MSA, such as postural instability, low blood pressure on standing (orthostatic hypotension) and high blood pressure when lying down, urinary difficulties, impotence, constipation, speech and swallowing difficulties out of proportion to slowness and rigidity.

Methods of the present invention can be used in combination with one or more alternative medications for treating or preventing MSA. Typically, the drugs that can be used to treat various symptoms of MSA become less effective as the disease progresses. Levodopa and dopamine agonists used to treat PD are sometimes effective for the slowness and rigidity of MSA. Orthostatic hypertension can be improved with cortisone, midodrine, or other drugs that raise blood pressure. Male impotence may be treated with penile implants or drugs. Incontinence may be treated with medication or catheterization. Constipation may improve with increased dietary fiber or laxatives.

Cognitive Impairment, Dementia, Etc

Cognitive impairment and dementia are highly prevalent neurological conditions associated with any of a variety of diseases, disorders, and conditions. Dementia is commonly defined as a progressive decline in cognitive function due to damage or disease in the body beyond what is expected from normal aging. Dementia is described as a loss of mental function, involving problems with memory, reasoning, attention, language, and problem solving. Higher level functions are typically affected first. Dementia interferes with a person's ability to function in normal daily life.

Without wishing to be bound by any particular theory, it is proposed that one toxic effect of accumulated protein aggregates in the brain may be the development of cognitive impairment and/or dementia.

Cognitive impairment refers to a subject that is diagnosed with, affected by, or at risk of developing cognitive impairment or dementia. The cognitive impairment or dementia may stem from any etiology. Exemplary causes of cognitive impairment and dementia include neurodegenerative diseases, neurological diseases, psychiatric disorders, genetic diseases, infectious diseases, metabolic diseases, cardiovascular diseases, vascular diseases, aging, trauma, malnutrition, childhood diseases, chemotherapy, autoimmune diseases, and inflammatory diseases. In one aspect, the present invention provides a method of treating or preventing a cognitive impairment in a subject suffering therefrom, the method comprising administering to a subject a provided compound in a therapeutically effective amount. The cognitive impairment may be due to any of a variety of etiologies, including, but not limited to, atherosclerosis, stroke, cerebrovascular disease, vascular dementia, multi-infarct dementia, Parkinson's disease and Parkinson's disease dementia, Lewy body disease, Pick's disease, Alzheimer's disease, mild cognitive impairment, Huntington's disease, AIDS and AIDS-related dementia, brain neoplasms, brain lesions, epilepsy, multiple sclerosis, Down's syndrome, Rett's syndrome, progressive supranuclear palsy, frontal lobe syndrome, schizophrenia, traumatic brain injury, post coronary artery by-pass graft surgery, cognitive impairment due to electroconvulsive shock therapy, cognitive impairment due to chemotherapy, cognitive impairment due to a history of drug abuse, attention deficit disorder (ADD), attention deficit hyperactivity disorder (ADHD), autism, dyslexia, depression, bipolar disorder, post-traumatic stress disorder, apathy, myasthenia gravis, cognitive impairment during waking hours due to sleep apnea, Tourette's syndrome, autoimmune vasculitis, systemic lupus erythematosus, polymyalgia rheumatica, hepatic conditions, metabolic diseases, Kufs' disease, adrenoleukodystrophy, metachromatic leukodystrophy, storage diseases, infectious vasculitis, syphillis, neurosyphillis, Lyme disease, complications from intracerebral hemorrhage, hypothyroidism, B12 deficiency, folic acid deficiency, niacin deficiency, thiamine deficiency, hydrocephalus, complications post anoxia, prion disease (Creutzfeldt-Jakob disease), Fragile X syndrome, phenylketonuria, malnutrition, neurofibromatosis, maple syrup urine disease, hypercalcemia, hypothyroidism, hypercalcemia, and hypoglycemia.

In certain embodiments, the cognitive impairment being treated or prevented is associated with DLBD. DLBD is the second most common cause of neurodegenerative dementia in older people, it effects 7% of the general population older than 65 years and 30% of those aged over 80 years. It is part of a range of clinical presentations that share a neurotic pathology based on normal aggregation of the synaptic protein α-synuclein. DLBD has many of the clinical and pathological characteristics of the dementia that occurs during the course of Parkinson's disease. A "one year rule" can been used to separate DLBD from PD. According to this rule, onset of dementia within 12 months of Parkinsonism qualifies as DLBD, whereas more than 12 months of Parkinsonism before onset of dementia qualifies as PD. The central features of DLBD include progressive cognitive decline of sufficient magnitude to interfere with normal social and occupational function. Prominent or persistent memory impairment does not necessarily occur in the early stages, but it is evident with progression in most cases. Deficits on tests of attention and of frontal cortical skills and visual spatial ability can be especially prominent. According to the present invention, the term "synucleinopathic subject" also encompasses a subject that is affected by, or is at risk of developing DLBD. These subjects can be readily identified by persons of ordinary skill in the art by symptomatic diagnosis or by genetic screening, brain scans, SPECT, PET imaging etc.

In certain embodiments, the cognitive impairment being treated or prevented is associated with Alzheimer's disease.

In certain embodiments, the cognitive impairment is associated with a psychiatric disorder (e.g., schizophrenia).

In certain embodiments, the cognitive impairment being treated or prevented is associated with a genetic disease.

In certain embodiments, the cognitive impairment being treated or prevented is associated with an infectious disease (e.g., HIV, syphillis). In certain embodiments, the cognitive impairment is due to a proteinopathy. In certain embodiments, the proteinopathy is a neurodegenerative, proliferative, inflammatory, or cardiovascular disease, condition, or disorder. Exemplary proteinopathies include, for instance, α-synucleinopathy, amyloidopathy, and/or taupathies.

The present invention provides methods for treating or preventing a subject with cognitive impairment, including a step of administering to the subject a therapeutically effective amount of a provided compound or composition thereof. In certain embodiments, the subject is a mammal. In certain specific embodiments, the subject is a human. The human may be male or female, and the human may be at any stage of development.

The present invention further provides methods for treating or preventing a cognitive impairment in a subject suffering therefrom, the method comprising administering to a subject a provided compound in a therapeutically effective amount.

The present invention further provides methods for treating or preventing depression in a subject suffering therefrom, the method comprising administering to a subject a provided compound in a therapeutically effective amount.

The present invention further provides methods for treating or preventing anxiety in a subject suffering therefrom, the method comprising administering to a subject a provided compound in a therapeutically effective amount.

The present invention provides methods for treating or preventing cognitive impairment, depression, and anxiety using a provided compound. In some embodiments, said compound is an inhibitor of farnesyl transferase.

7B. Inflammatory Diseases, Disorders and Conditions

The mammalian immune system provides a means for the recognition and elimination of foreign pathogens. While the immune system normally provides a line of defense against foreign pathogens, there are many instances where the immune response itself is involved in the progression of disease. Exemplary of diseases caused or worsened by the host's own immune response are autoimmune diseases such as multiple sclerosis, lupus erythematosus, psoriasis, pulmonary fibrosis, and rheumatoid arthritis and diseases in which the immune response contributes to pathogenesis such as atherosclerosis, inflammatory diseases, osteomyelitis, ulcerative colitis, Crohn's disease, and graft versus host disease (GVHD) often resulting in organ transplant rejection. Additional exemplary inflammatory disease states include fibromyalgia, osteoarthritis, sarcoidosis, systemic sclerosis, Sjogren's syndrome, inflammations of the skin (e.g., psoriasis), glomerulonephritis, proliferative retinopathy, restenosis, and chronic inflammations.

In certain embodiments, inflammatory diseases, disorders, and conditions may include one or more of inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendictitis, pancreatitis, cholocystitus, irritable bowel syndrome, ulcerative colitis, glomerulonephritis, dermatomyositis, scleroderma, vasculitis, allergic disorders including asthma such as bronchial, allergic, intrinsic, extrinsic and dust asthma, particularly chronic or inveterate asthma (e.g. late asthma airways hyper-responsiveness) and bronchitis, chronic obstructive pulmonary disease (COPD), multiple sclerosis, rheumatoid arthritis, disorders of the gastrointestinal tract, including, without limitation, Coeliac disease, proctitis, eosinophilic gastro-enteritis, mastocytosis, pancreatitis, Crohn's disease, ulcerative colitis, food-related allergies which have effects remote from the gut, e.g. migraine, rhinitis and eczema. Conditions characterised by inflammation of the nasal mucus membrane, including acute rhinitis, allergic, atrophic thinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis, seasonal rhinitis including rhinitis nervosa (hay fever) and vasomotor rhinitis, sarcoidosis, farmer's lung and related diseases, fibroid lung and idiopathic interstitial pneumonia, acute pancreatitis, chronic pancreatitis, and adult respiratory distress syndrome, and/or acute inflammatory responses (such as acute respiratory distress syndrome and ischemia/reperfusion injury).

7C. Cardiovascular Diseases, Disorders and Conditions

Cardiovascular disease is the leading killer in America today. Over 50 million Americans have heart and cardiovascular related problems. By the time that cardiovascular heart problems are usually detected, the disease is usually quite advanced, having progressed for decades, and often too advanced to allow successful prevention of major permanent disability.

In some embodiments, cardiovascular disease may be a disease which involves the heart and/or blood vessels, arteries, and occasionally veins. In some embodiments, the disease is a vascular disease. These problems are most commonly due to consequences of arterial disease, atherosclerosis, atheroma, but also can be related to infection, valvular and clotting problems.

Exemplary particular cardiovascular diseases, disorders and conditions may include one or more of myocardial ischemia, myocardial infarction, vascular hyperplasia, cardiac hypertrophy, congestive heart failure, cardiomegaly, restenosis, atherosclerosis, hypertension, and/or angina pectoris.

In certain embodiments, the cardiovascular disease, disorder or condition is atherosclerosis, a coronary heart disease, an acute coronary symptom, unstable angina pectoris or acute myocardial infarction, stable angina pectoris, stroke, ischemic stroke, inflammation or autoimmune disease associated artheriosclerosis or restenosis.

In some embodiments, the invention related to the treatment or prevention of circulatory diseases, such as arteriosclerosis, atherosclerosis, vasculitis, polyarterities nodosa and/or myocarditis.

7D. Proliferative Diseases, Disorders and Conditions

In some embodiments, the invention provides methods for treating or preventing cell proliferative disorders, diseases or conditions. In general, cell proliferative disorders, diseases or conditions encompass a variety of conditions characterized by aberrant cell growth, preferably abnormally increased cellular proliferation. For example, cell proliferative disorders, diseases, or conditions include, but are not limited to, cancer, immune-mediated responses and diseases (e.g., transplant rejection, graft vs host disease, immune reaction to gene therapy, autoimmune diseases, pathogen-induced immune dysregulation, etc.), certain circulatory diseases, and certain neurodegenerative diseases.

In certain embodiments, the invention relates to methods of treating or preventing cancer. In general, cancer is a group of diseases which are characterized by uncontrolled growth and spread of abnormal cells. Examples of such diseases are carcinomas, sarcomas, leukemias, lymphomas and the like.

For example, cancers include, but are not limited to leukemias and lymphomas such as cutaneous T-cell lymphomas (CTCL), peripheral T-cell lymphomas, lymphomas associated with human T-cell lymphotropic virus (HTLV) such as adult T-cell leukemia/lymphoma (ATLL), B-cell lymphoma, acute lymphocytic leukemia, acute nonlymphocytic leukemias, chronic lymphocytic leukemia, chronic myelogenous leukemia, acute myelogenous leukemia, Hodgkin's disease, non-Hodgkin's lymphomas, multiple myeloma, myelodysplastic syndrome, mesothelioma, common solid tumors of adults such as head and neck cancers (e.g., oral, laryngeal and esophageal), genitourinary cancers (e.g., prostate, bladder, renal, uterine, ovarian, testicular, rectal and colon), lung cancer, breast cancer, pancreatic cancer, melanoma and other skin cancers, stomach cancer, brain tumors, liver cancer and thyroid cancer, and/or childhood solid tumors such as brain tumors, neuroblastoma, retinoblastoma, Wilms' tumor, bone tumors, and soft-tissue sarcomas.

In some embodiments, the invention relates to treatment or prevention of leukemias. For example, in some embodiments, the invention relates to treatment or prevention of chronic lymphocytic leukemia, chronic myelogenous leukemia, acute lymphocytic leukemia, acute myelogenous leukemia, and/or adult T cell leukemia/lymphoma. In certain embodiments, the invention relates to the treatment or prevention of AML. In certain embodiments, the invention relates to the treatment or prevention of ALL. In certain embodiments, the invention relates to the treatment or prevention of CML. In certain embodiments, the invention relates to the treatment or preventing of CLL.

In some embodiments, the invention relates to treatment or preventing of lymphomas. For example, in some embodiments, the invention relates to treatment or prevention of Hodgkin's or non-Hodgkin's (e.g., T-cell lymphomas such as peripheral T-cell lymphomas, cutaneous T-cell lymphomas, etc.) lymphoma.

In some embodiments, the invention relates to the treatment or prevention of myelomas and/or myelodysplastic syndromes. In some embodiments, the invention relates to treatment or prevention of solid tumors. In some such embodiments the invention relates to treatment or prevention of solid tumors such as lung, breast, colon, liver, pancreas, renal, prostate, ovarian, and/or brain. In some embodiments, the invention relates to treatment or prevention of pancreatic cancer. In some embodiments, the invention relates to treatment or prevention of renal cancer. In some embodiments, the invention relates to treatment or prevention of prostate cancer. In some embodiments, the invention relates to treatment or prevention of sarcomas. In some embodiments, the invention relates to treatment or prevention of soft tissue sarcomas. In some embodiments, the invention relates to methods of treating or preventing one or more immune-mediated responses and diseases.

For example, in some embodiments, the invention relates to treatment or prevention of rejection following transplantation of synthetic or organic grafting materials, cells, organs or tissue to replace all or part of the function of tissues, such as heart, kidney, liver, bone marrow, skin, cornea, vessels, lung, pancreas, intestine, limb, muscle, nerve tissue, duodenum, small-bowel, pancreatic-islet-cell, including xeno-transplants, etc.; treatment or preventing of graft-versus-host disease, autoimmune diseases, such as rheumatoid arthritis, systemic lupus erythematosus, thyroiditis, Hashimoto's thyroiditis, multiple sclerosis, myasthenia gravis, type I diabetes uveitis, juvenile-onset or recent-onset diabetes mellitus, uveitis, Graves' disease, psoriasis, atopic dermatitis, Crohn's disease, ulcerative colitis, vasculitis, auto-antibody mediated diseases, aplastic anemia, Evan's syndrome, autoimmune hemolytic anemia, and the like; and further to treatment or prevention of infectious diseases causing aberrant immune response and/or activation, such as traumatic or pathogen induced immune dysregulation, including for example, that which are caused by hepatitis B and C infections, HIV, *Staphylococcus aureus* infection, viral encephalitis, sepsis, parasitic diseases wherein damage is induced by an inflammatory response (e.g., leprosy). In some embodiments, the invention relates to treatment or prevention of graft vs host disease (especially with allogenic cells), rheumatoid arthritis, systemic lupus erythematosus, psoriasis, atopic dermatitis, Crohn's disease, ulcerative colitis and/or multiple sclerosis.

Alternatively or additionally, in some embodiments, the invention relates to treatment or prevention of an immune response associated with a gene therapy treatment, such as the introduction of foreign genes into autologous cells and expression of the encoded product. In some embodiments, the invention relates to treatment or prevention of circulatory diseases, such as arteriosclerosis, atherosclerosis, vasculitis, polyarteritis nodosa and/or myocarditis.

7E. Lysosomal Storage Diseases

Lysosomal Storage diseases are a group of disorders which are characterized by a defect in any aspect of lysosomal biology, which in turn prevents the degradation of lipids, proteins or organelles by the lysosome, or which prevents the proper trafficking of molecules into or out of the lysosome, or which prevents lysosome-mediated signaling. These diseases typically include neurological involvement which can be (though not always) progressive and degenerative; symptoms may include developmental delay, ataxia, visual problems, seizures etc. The lysosome, when healthy, processes unwanted material into substances that can be utilized by cells. Lysosomal storage diseases typically result when one or more of the enzymes involved in this processing is or becomes defective or absent. Defect or absence of such an enzyme results in accumulation of unwanted material in cells, eventually damaging the cells. Most lysosomal storage diseases are genetic diseases that show autosomal recessive inheritance; some (e.g., Fabry disease and Hunter syndrome) are X-linked.

Representative lysosomal storage diseases include, for example, Activator Deficiency/GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease (e.g., Type I, Type II, Type III), GM1 gangliosidosis (e.g., Infantile, Late infantile/Juvenile, Adult/Chronic), I-Cell disease/Mucolipidosis II, Infantile Free Sialic Acid Storage Disease/ISSD, Juvenile Hexosaminidase A Deficiency, Krabbe disease (e.g., Infantile Onset, Late Onset), Metachromatic Leukodystrophy, Mucopolysaccharidoses disorders, Pseudo-Hurler polydystrophy/Mucolipidosis IIIA (e.g., MPSI Hurler Syndrome, MPSI Scheie Syndrome, MPS I Hurler-Scheie Syndrome, MPS II Hunter syndrome, Sanfilippo syndrome Type A/MPS III A, Sanfilippo syndrome Type B/MPS III B, Sanfilippo syndrome Type C/MPS III C, Sanfilippo syndrome Type D/MPS III D, Morquio Type A/MPS IVA, Morquio Type B/MPS IVB, MPS IX Hyaluronidase Deficiency, MPS VI Maroteaux-Lamy, MPS VII Sly Syndrome, Mucolipidosis I/Sialidosis, Mucolipidosis IIIC, Mucolipidosis type IV), Multiple sulfatase deficiency, Niemann-Pick Disease (e.g., Type A, Type B, Type C), Neuronal Ceroid Lipofuscinoses (e.g., CLN6 disease—Atypical Late Infantile, Late Onset variant, Early Juvenile, Batten-Spielmeyer-Vogt/Juvenile NCL/CLN3 disease, Finnish Variant Late Infantile CLN5, Jansky-Bielschowsky disease/Late infantile CLN2/TPP1 Disease, Kufs/Adult-onset NCL/CLN4 disease, Northern Epilepsy/variant late infantile CLN8, Santavuori-Haltia/Infantile CLN1/PPT disease, Beta-mannosidosis), Pompe disease/Glycogen storage disease type II, Pycnodysostosis, Sandhoff disease/GM2 Gangliosidosis (e.g., Adult Onset, Infantile, Juvenile), Schindler disease, Salla disease/Sialic Acid Storage Disease, Tay-Sachs/GM2 gangliosidosis, Wolman disease, etc.

Lysosomal Storage diseases can result from a number of defects, including a primary defect in a lysosomal enzyme's activity, eg as in Gaucher disease or Fabry disease, or a defect the post-translational processing of a lysosomal enzyme eg as in Mucosuphatidosis, or a defect in the trafficking of a lysosomal enzyme eg as in Mucolipidosis type IIIA, or a defect in a lysosomal protein that is not an enzyme eg as in Danon disease, or a defect in a non-lysosomal protein eg as in a variant of Late Infantile Neuronal Ceroid Lipofuscinosis. In Lysosomal Storage disorders, there is often an accumulation of certain lipids eg glucosylceramide or cholesterol, or of certain proteins eg subunit c of ATP synthase, or of certain damaged organelles or organelle fragments eg fragmented mitochondria. Drug-induced stimulation of a cellular phagic response may be of therapeutic benefit in Lysosomal Storage disorders; such phagic responses may include microautophagy, macroautophagy, chaperone-mediated autophagy, mitophagy, pexophagy.

7F. Mitochondrial Diseases

Mitochondrial diseases may be caused by mutations, acquired or inherited, in mitochondrial DNA or in nuclear genes that code for mitochondrial components. They may also be the result of acquired mitochondrial dysfunction due to adverse effects of drugs, infections, or other environmental causes.

Mitochondrial DNA inheritance behaves differently from autosomal and sex-linked inheritance. Mitochondrial DNA, unlike nuclear DNA, is strictly inherited from the mother and each mitochondrial organelle typically contains multiple mtDNA copies. During cell division, the mitochondrial DNA copies segregate randomly between the two new mitochondria, and then those new mitochondria make more copies. As a result, if only a few of the mtDNA copies inherited from the mother are defective, mitochondrial division may cause most of the defective copies to end up in just one of the new mitochondria. Mitochondrial disease may become clinically apparent once the number of affected mitochondria reaches a certain level; this phenomenon is called 'threshold expression'. Mitochondrial DNA mutations occur frequently, due to the lack of the error checking capability that nuclear DNA has. This means that mitochondrial DNA disorders may occur spontaneously and relatively often. In addition, defects in enzymes that control mitochondrial DNA replication may cause mitochondrial DNA mutations.

Mitochondrial diseases include any clinically heterogeneous multisystem disease characterized by mutations of the brain-mitochondrial encephalopathies and/or muscle-mitochondrial myopathies due to alterations in the protein complexes of the electron transport chain of oxidative phosphorylation. In some embodiment, the invention relates to the treatment or prevention of a mitochondrial diseases. For example, the invention provides methods for the treatment or prevention of Leber's hereditary optic atrophy, MERRF (Myoclonus Epilepsy with Ragged Red Fibers), MELAS (Mitochondrial Encephalopathy, Lactic Acidosis and Stroke-like episodes); Alper syndrome, Lowe syndrome, Luft syndrome, Menke's kinky hair syndrome, Zellweger syndrome, mitochondrial myopathy, and rhizomelic chondrodysplasia punctata.

While not intending to be bound to any particular theory, compounds of the invention protect against neuronal dysfunction and death that causes the neurologic symptoms (e.g., cognitive losses, muscle weakness, cardiac dysfunction) diseases that are characterized by mitochondrial dysfunction. In these diseases, dysfunctional mitochondria accumulate. The normal mechanism of mitochondria recycling is unable to keep up with the increased demand. Compounds of the invention stimulate the so-called mitophagy pathway, leading to regeneration of fully functional mitochondria.

MELAS, MERFF, LHON (leber hereditary optic neuropathy), CPEO (chronic progressive external ophthalmoplegia), KSS (Kearns-Sayre syndrome), MNGIE (mitochondrial neurogastrointestinal encephalopathy), NARP (neuropathy, ataxia, retinitis pigmentosa and ptosis), Leigh syndrome, Alpers-Huttenlocher disease, Kearns-Sayre syndrome, Pearson syndrome, and Luft disease are examples of mitochondrial diseases treatable by this mechanism.

7G. Ocular Indications

In some embodiments, compounds of the invention are useful for the treatment of ocular indications that benefit from a compound that simulates cellular autophagy. Ocular indications include but are not limited to retinitis pigmentosa, wet and dry forms of age related macular degeneration, ocular hypertension, glaucoma, corneal dystrophies, retinoschises, Stargardt's disease, autosomal dominant druzen, Best's macular dystrophy, myocilin glaucoma, or Malattia Leventineses.

7H. Immunologic Disease

In some embodiments the invention relates to treatment or prevention of an immune disease or disorder. For example, rejection following transplantation of synthetic or organic grafting materials, cells, organs or tissue to replace all or part of the function of tissues, such as heart, kidney, liver, bone marrow, skin, cornea, vessels, lung, pancreas, intestine, limb, muscle, nerve tissue, duodenum, small-bowel, pancreatic-islet-cell, including xenotransplants, etc. the invention further may be related to treatment of immune disease including treatment or preventing of graft-versus-host disease, autoimmune diseases, such as rheumatoid arthritis, systemic lupus erythematosus, thyroiditis, Hashimoto's thyroiditis, multiple sclerosis, myasthenia gravis, type I diabetes uveitis, juvenile-onset or recent-onset diabetes mellitus, uveitis, Graves' disease, psoriasis, atopic dermatitis, Crohn's disease, ulcerative colitis, vasculitis, auto-antibody mediated diseases, aplastic anemia, Evan's syndrome, autoimmune hemolytic anemia, and the like. The invention further relates to treatment or prevention of infectious diseases causing aberrant immune response and/or activation, such as traumatic or pathogen induced immune dysregulation, including for example, that which are caused by hepatitis B and C infections, HIV, *Staphylococcus aureus* infection, viral encephalitis, sepsis, parasitic diseases wherein damage is induced by an inflammatory response (e.g., leprosy).

In some embodiments, the invention relates to treatment or prevention of graft vs host disease (especially with allogenic cells), rheumatoid arthritis, systemic lupus erythematosus, psoriasis, atopic dermatitis, Crohn's disease, ulcerative colitis, other forms of inflammatory bowel disease (collagenous colitis, lymphocytic colitis, ischemic colitis, diversion colitis, Behcet's syndrome, infective colitis, indeterminate colitis) and/or multiple sclerosis.

Alternatively or additionally, in some embodiments, the invention relates to treatment or prevention of an immune response associated with a gene therapy treatment, such as the introduction of foreign genes into autologous cells and expression of the encoded product.

Exemplary of diseases caused or worsened by the host's own immune response are autoimmune diseases such as multiple sclerosis, lupus erythematosus, psoriasis, pulmonary fibrosis, and rheumatoid arthritis and diseases in which the immune response contributes to pathogenesis such as atherosclerosis, inflammatory diseases, osteomyelitis, ulcerative colitis, Crohn's disease, and graft versus host disease (GVHD) often resulting in organ transplant rejection. Additional exemplary inflammatory disease states include fibromyalgia, osteoarthritis, sarcoidosis, systemic sclerosis, Sjogren's syndrome, inflammations of the skin (e.g., psoriasis), glomerulonephritis, proliferative retinopathy, restenosis, and chronic inflammations.

7I. Dosing

Compounds and/or compositions described herein may be administered according to any of a variety of dosing regimens.

In some embodiments, compounds are administered at a dose within the range from about 7 to 10,500 mg per kg of body weight per day, from about 7 to 3500 mg per kg of body weight per day, from 35 to 2100 mg per kg of body weight per day, and from about 280 to 1400 mg of compound per kg of body weight.

In some embodiment, compounds are administered at a dose within the range from about 0.0001-100 mg/kg. In some embodiments, doses within the range of 0.001-10 mg/kg are administered. In some embodiments, doses within the range of 0.001-1.0 mg/kg are administered. In some embodiments, doses within the range of 0.001-0.5 mg/kg are administered. In some embodiments, doses within the rage of 0.01-1.0, or 0.01-0.5, or 0.001-0.2, or 0.01-0.2 mg/kg are administered. In some embodiments, such doses are utilized as average daily doses.

In certain embodiments, an average daily dose for an adult human may be in the range of approximately 0.1 to approximately 150 mg. In certain embodiments, an average daily dose for an adult human may be in the range of approximately 0.1-approximately 100 mg. In some embodiments, an average daily dose for an adult human, may be in the range of approximately 0.1 to approximately 50 mg, approximately 0.1 approximately 10 mg, approximately 1 mg to approximately 50 mg, approximately 0.5 mg to approximately 30 mg, approximately 10 mg to approximately 50 mg, approximately 10 mg to approximately 30 mg, approximately 10 mg to approximately 25 mg, approximately 4 mg to approximately 20 mg.

In some embodiments, individual doses (e.g., average daily doses) of provided compounds are approximately 1, 5, 10, 15, 20, 25, 30, 35, 40, 45, or 50 mg.

In some embodiments, compounds and/or composition of the present invention are administered according to a regimen that achieves an area under the curve (AUC) that is less than approximately 2500 ng·hr/ml. In some embodiments, compounds and/or composition of the present invention are administered according to a regimen that achieves an area under the curve (AUC) that is less than approximately 2000, 1500, 1000, 500, 100, or 50 ng·hr/ml.

In some embodiments, compounds and/or compositions are administered using a chronic administration regimen. In some such embodiments, dosing is continued for one or more weeks, months, or years. In some embodiments, compounds and/or compositions are administered for the life of the individual. In some embodiments, chronic administration regimens administer compound and/or composition one or more times per day, week, month, year, etc.

In some embodiments, compounds and/or compositions provided herein are administered via an intermittent dosing regimen. In some embodiments, intermittent dosing involves administration of one or more doses, followed by a cessation of doses for a period of time. In some embodiments, doses are administered again after the period of cessation. To give but a couple of examples of intermittent dosing schedules, in some embodiments, compounds and/or compositions are administered over a period of 3-7 days (e.g., 3, 4, 5, 6, or 7 days), followed by a period of 3-7 days off. In some embodiments, compounds and/or compositions are administered periodically over several months, followed by several months off, etc. In some embodiments, compounds and/or compositions are administered every day for one week, followed by several weeks off and then repeated administration every day for one week, etc.

In some embodiments, compounds and/or compositions provided herein are administered every other day, every third day, every fourth day, once a week, every other week, twice a month, every third week, every fourth week, once a month, every other month, etc.

Various functions and advantages of these and other embodiments of the present invention will be more fully understood from the examples described below. The following examples are intended to illustrate the benefits of the present invention, but do not exemplify the full scope of the invention.

EXEMPLIFICATION

Example 1

Synthesis of Exemplary azaquinolin-2-ones

Compound B. N-Boc-protection of commercially available 6-aminonicotinic acid 1 affords amide 2. Formation of the Weinreb amide 3 from 2, followed by Grignard addition of aryl chloride 4 affords ketone 5, which is subsequently deprotected to yield coupling partner B (shown in Scheme 5).

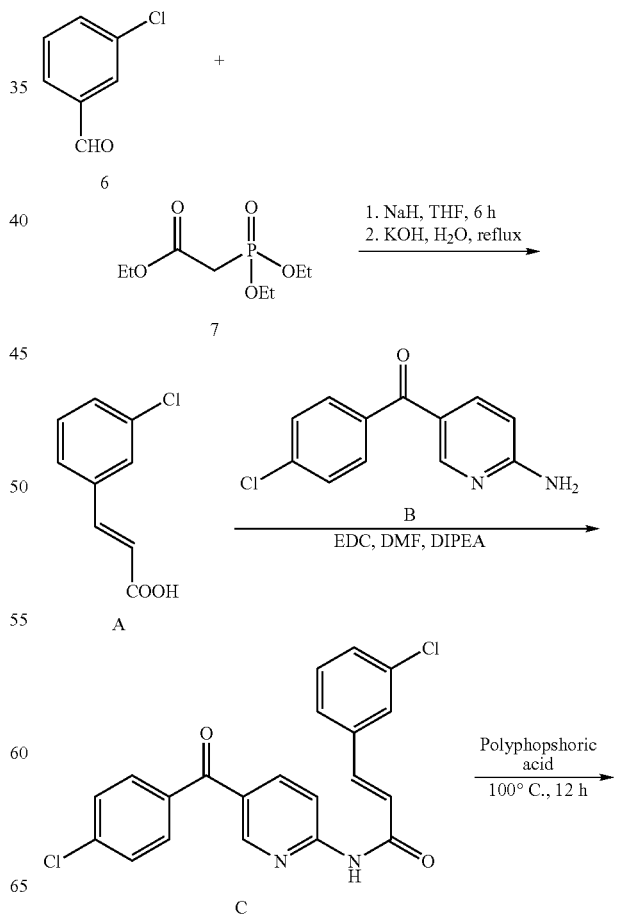

-continued

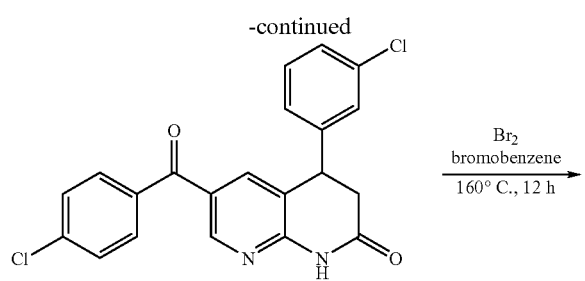
D

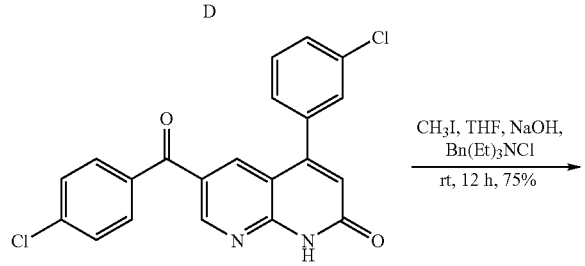
E

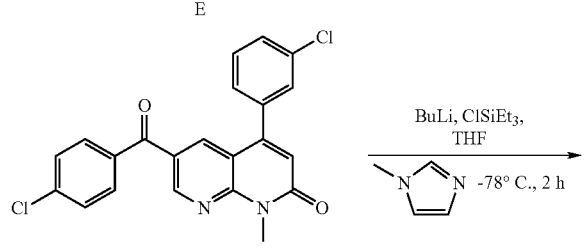
F

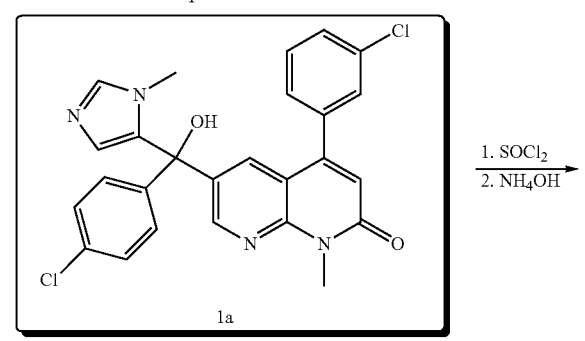
1a

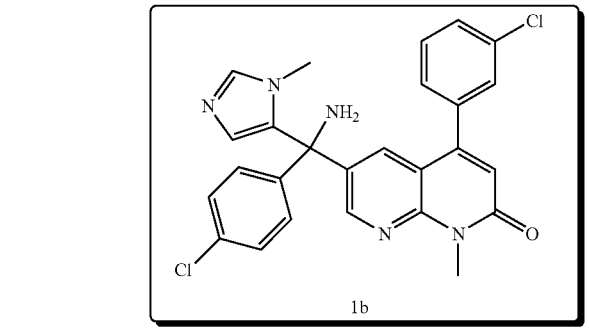
1b

Compounds 1a/1b (Scheme 5). Treatment of commercially available m-chlorobenzaldehyde 6 with diethylphosphonate 7 under basic conditions affords α,β-unsaturated acid A. Upon activation with EDC in DMF in the presence of DIPEA, the acid is coupled to amine B to furnish amide C. C can then undergo an acid-catalyzed intramolecular Michael addition to yield dihydroazaquinoline derivative D which, upon oxidation, affords azaquinolinone E. E is then N-methylated with methyl iodide under basic conditions to afford N-methyl-protected ketone F. Addition of lithiated N-methyl imidazole to F affords carbinol 1a. Treatment of carbinol 1a with thionyl chloride followed by treatment with ammonium hydroxide furnishes the product amine 1b. Chiral separation affords the desired enantiomers.

Scheme 6.

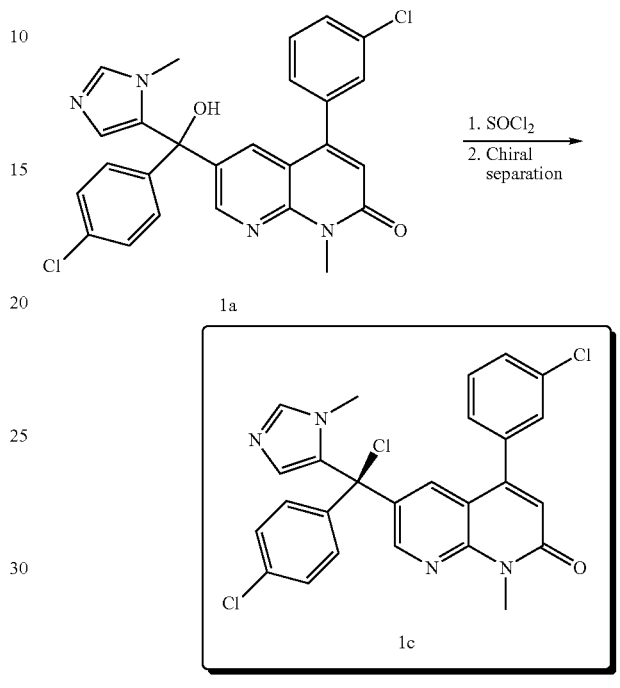

Compound 1c (Scheme 6). Carbinol 1a can alternatively be transformed into chloride 1c upon treatment with thionyl chloride. Chiral separation affords the desired enantiomers.

Scheme 7.

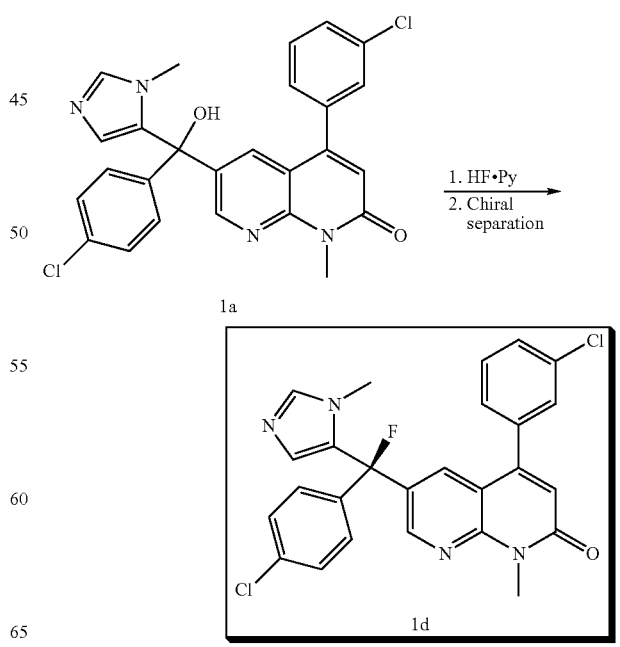

Compound 1d (Scheme 7). Carbinol 1a can alternatively be transformed into fluoride 1d upon treatment with HF-pyridine. Chiral separation affords the desired enantiomers.
Scheme 8.
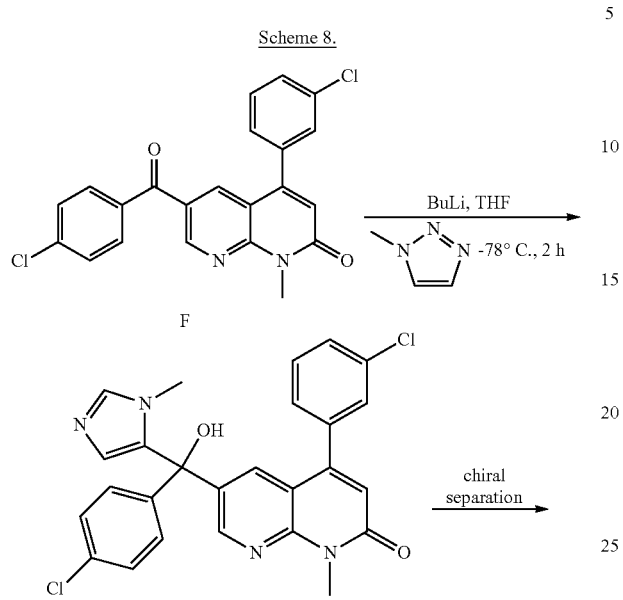
-continued
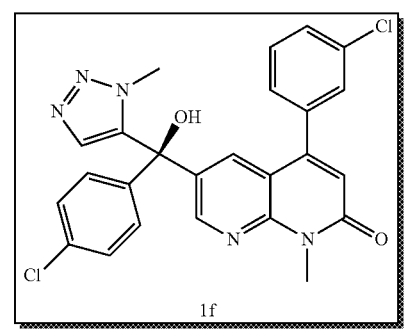
Compound 1f (Scheme 8). Compound 1f can be synthesized by exchanging N-methylimidazole for N-methyl triazole and proceeding in a fashion identical to that shown above.
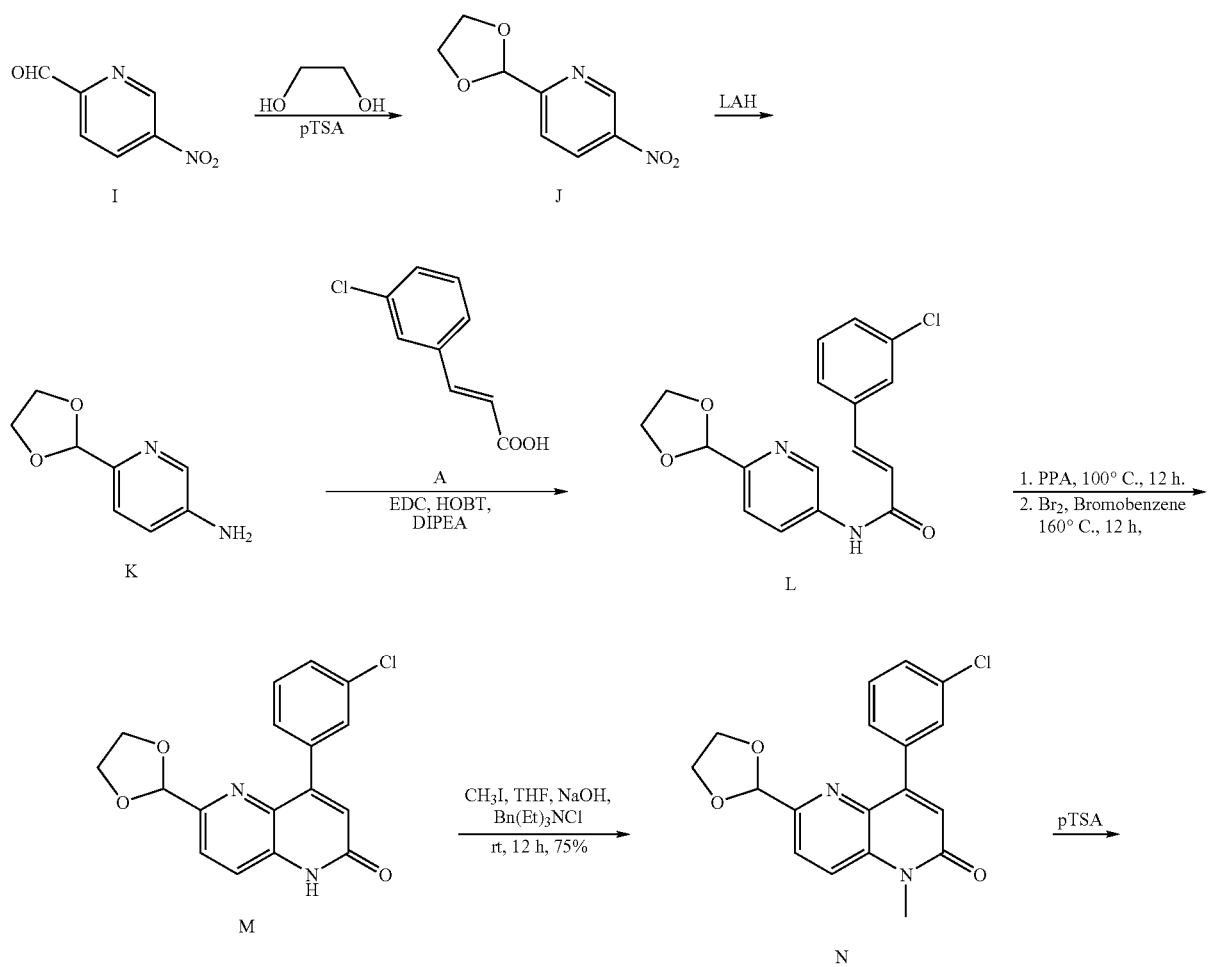

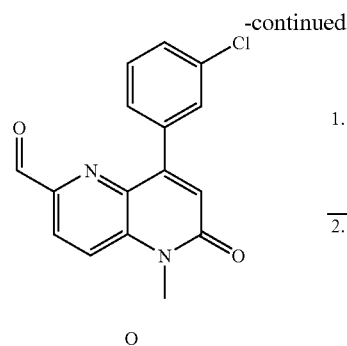
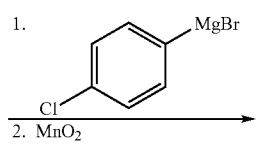

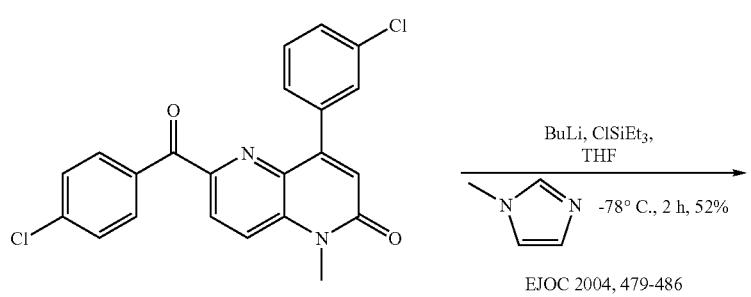

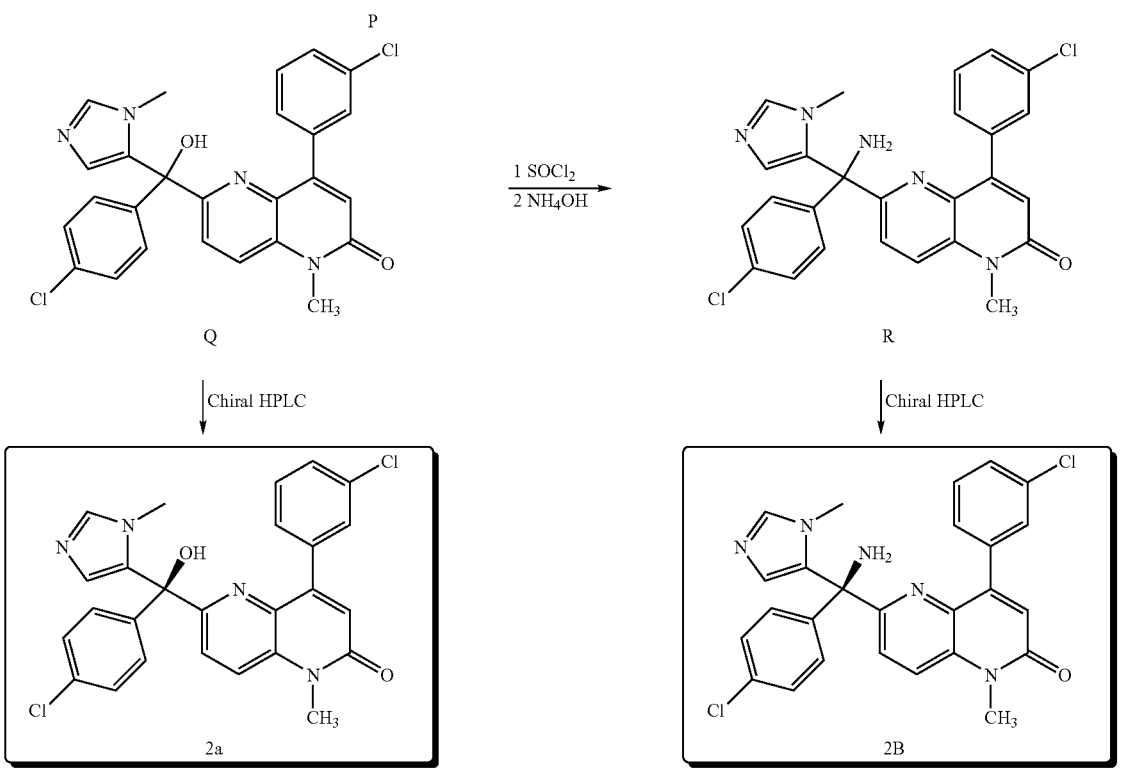

Compounds 2a/2b (Scheme 9). Protection of aldehyde I with ethylene glycol under acidic conditions affords acetal J. Reduction of the nitro substituent of J with lithium aluminum hydride yields amine K. Addition of K to acid A using EDC and HOBt under basic conditions affords amide L which, upon exposure to acid, undergoes an intramolecular Michael addition. Subsequent treatment with bromine affords azaisoquinoline M. N-methylation of M with methyl iodide affords acetal N, which is then deprotected using pTSA to afford aldehyde O. Grignard addition to O followed by oxidation of the resulting alcohol with MnO$_2$ furnishes P. Addition of lithiated N-methyl imidazole to P yields carbinol 2a. Treatment of carbinol 2a with thionyl chloride followed by treatment with ammonium hydroxide furnishes the product amine 2b. Chiral separation affords the desired enantiomers.

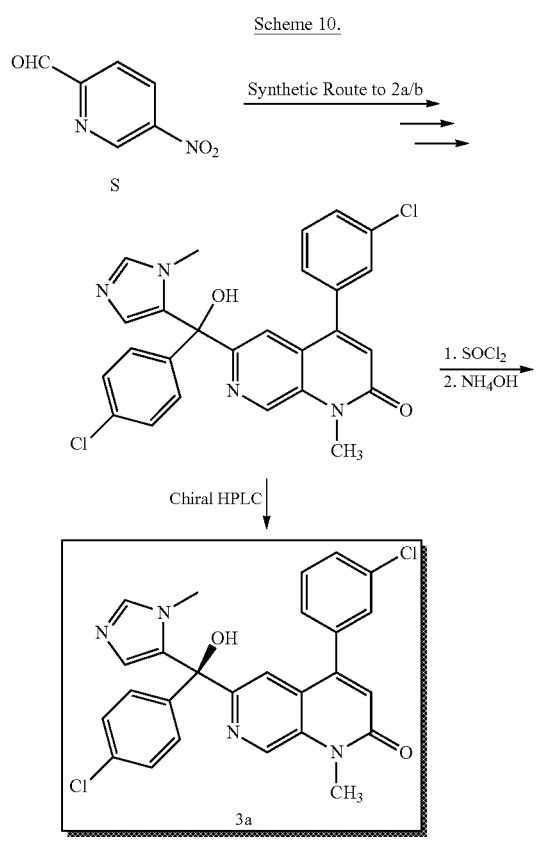
Compounds 3a/3b (Scheme 10). Compounds 3a and 3b can be accessed using the synthetic scheme shown above for compounds 2a and 2b.

-continued

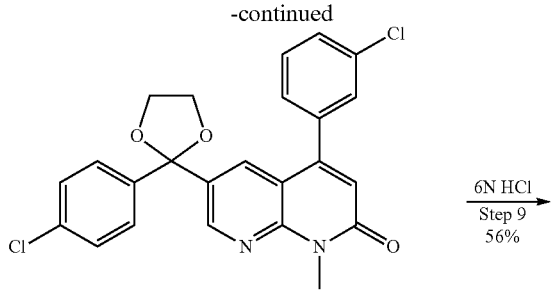

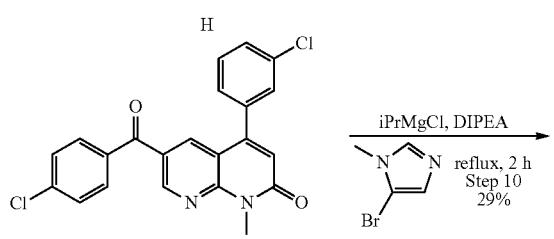

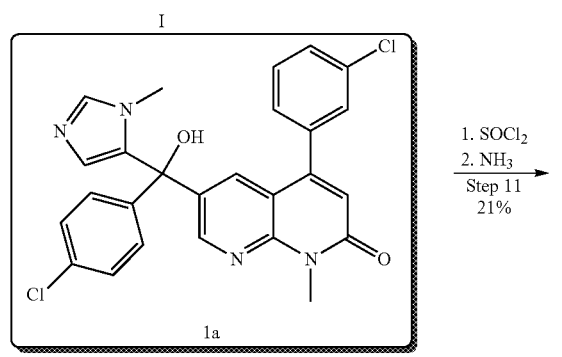

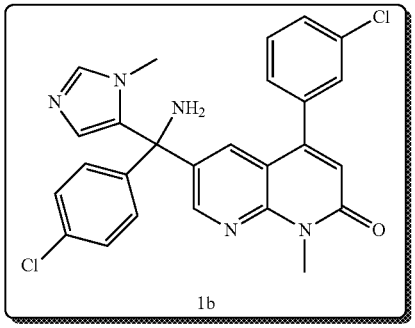

Experimental for Schemes 5-11:

Step-1: 6-Chloro-N-methoxy-N-methylnicotinamide (A)

To a solution of 6-chloronicotinic acid (20 g, 127 mmol) in acetonitrile (400 mL), methoxymethylamine hydrochloride (13.79 g, 141 mmol), EDC (27.1 g, 141 mmol), HOBT (5.2 g, 38.58 mmol) and TEA (53.3 mL, 386 mmol) were added at RT. The reaction mixture was stirred at 60° C. overnight. Solvent was removed under reduced pressure and the residue was dissolved in ethyl acetate (300 mL). The reaction mixture was washed with water and brine. The organic layer was dried, filtered and concentrated. Purification of the crude product provided 23.6 g (93%) of compound A as viscous colorless oil.

$^1$H NMR (400 MHz, CDCl$_3$): δ 3.38 (s, 3H), 3.57 (s, 3H), 7.39 (d, 1H), 8.04 (d, 1H), 8.77 (s, 1H); LCMS m/z: 201 (M+1).

Step-2: (4-chlorophenyl)(6-chloropyridin-3-yl) methanone (B)

To a solution of 4-chlorobromobenzene (33.88 g, 177 mmol) in THF (200 mL), a solution of BuLi (118 mL, 142 mmol, 1.2 M solution in hexane) was added at −78° C. The mixture was stirred for 1 h and a solution of compound A (23.6 g, 118 mmol) in THF (100 mL) was added to it dropwise. The mixture was stirred for additional 1 h, quenched with saturated NH$_4$Cl solution and extracted with ethyl acetate (300 mL). The organic layer was dried (Na$_2$SO$_4$), filtered and evaporated. The crude product was purified using column chromatography to obtain 23.4 g (79%) of compound B as light yellow solid.

$^1$H NMR (400 MHz, CDCl$_3$): δ 7.43-7.58 (m, 3H), 7.78 (d, 2H), 8.08 (d, 1H), 8.76 (s, 1H); LCMS m/z: 252 (M+1).

Step-3: (4-chlorophenyl)(6-(methylamino)pyridin-3-yl)methanone (C)

A mixture of compound B (23.4 g, 93.22 mmol), methylamine (88 mL, 932 mmol, 33% solution in ethanol) and Et$_3$N (37.51 mL, 280 mmol) in EtOH (100 mL) was heated in a sealed tube at 80° C. for 3 h. EtOH was removed under reduced pressure and the residue was dissolved in DCM (150 mL), washed with water and brine. The organic layer was dried (Na$_2$SO$_4$), filtered and evaporated. The crude product was purified by triturating with diethyl ether to obtain 12.5 g (55%) of compound C as off-white solid.

$^1$H NMR (400 MHz, CDCl$_3$): δ 3.06 (d, 3H), 5.02-5.17 (bs, 1H, NH), 6.44 (d, 1H), 7.43 (d, 2H), 7.71 (d, 2H), 7.96 (d, 1H), 8.55 (s, 1H); LCMS m/z: 247 (M+1).

Step-4: (5-bromo-6-(methylamino)pyridin-3-yl)(4-chlorophenyl)methanone (D)

A solution of bromine (2.29 mL, 14.31 mmol) in acetic acid (30 mL) was added to a solution of compound C (11.0 g, 44.7 mmol) in acetic acid (80 mL) at RT. The mixture was stirred for 1 h, neutralized by the addition of saturated NaHCO$_3$ solution and extracted with ethyl acetate (200 mL). The organic layer was washed with 10% sodium thiosulfate solution, water and brine. The organic layer was dried (Na$_2$SO$_4$), filtered and evaporated. The crude product was purified using column chromatography to obtain 9.0 g (62%) of compound D viscous light yellow colored oil.

$^1$H NMR (400 MHz, CDCl$_3$): δ 3.14 (d, 3H), 5.57-5.70 (bs, 1H, NH), 7.47 (d, 2H), 7.70 (d, 2H), 8.19 (s, 1H), 8.53 (s, 1H); LCMS m/z: 325 (M+1).

Step-5: 3-bromo-5-(2-(4-chlorophenyl)-1,3-dioxalan-2-yl)-N-methylpyridin-2-amine (E)

To a solution of compound D (6.0 g, 18.51 mmol) in toluene (120 mL), ethylene glycol (10.4 mL, 185 mmol) and PTSA (0.96 g, 5.55 mmol) was added. The mixture was refluxed overnight, quenched with water and extracted with ethyl acetate (150 mL). The organic layer was washed with water and brine, dried (Na$_2$SO$_4$), filtered and evaporated. The crude product was purified using column chromatography to obtain 5.0 g (74%) of compound E as off-white solid.

$^1$H NMR (400 MHz, CDCl$_3$): δ 3.02 (d, 3H), 3.93-4.17 (m, 4H), 7.33 (d, 2H), 5.01-5.16 (bs, 1H, NH), 7.42 (d, 2H), 7.71 (s, 1H), 8.09 (s, 1H); LCMS m/z: 369 (M+1).

Step-6: (3-chlorophenyl)(5-(2-(4-chlorophenyl)-1,3-dioxalan-2-yl)-2-(methylamino)pyridin-3-yl)methanol (F)

A solution of compound E (5.0 g, 13.6 mmol) in THF (100 mL) was cooled to −78° C. and n-butyllithium (13.6 mL, 13.6 mmol, 1 M solution in hexane) was added to it dropwise, while maintaining the temperature below −70° C. The mixture was stirred for 10 min, triethylsilyl chloride (2.28 mL, 13.6 mmol) was added dropwise at −70° C., and stirred for 30 min. n-BuLi (13.6 mL, 13.6 mmol, 1 M solution in hexane) was added dropwise, stirred for 10 min at −75° C., and a solution of 3-chlorobenzaldehyde (2.84 mL, 20.32 mmol) in THF was added, stirred for 1 h, quenched with saturated NH$_4$Cl and extracted with EtOAc (100 mL). The organic layer was dried over Na$_2$SO$_4$, filtered and concentrated under reduced pressure. The crude product was purified by column chromatography to obtain 4.0 g of compound F as viscous light yellow colored oil containing an inseparable impurity (81% pure by LCMS, actual yield=3.24 g, 56%). This material was used in the next step without further purification.

$^1$H NMR (400 MHz, CDCl$_3$): δ 2.92 (d, 3H), 3.93-4.17 (m, 4H), 5.23-5.34 (bs, 1H), 5.71 (s, 1H), 7.21-739 (m, 6H), 7.40-7.54 (m, 4H), 8.13 (d, 1H); LCMS m/z: 431 (M+1).

Step-7: (3-chlorophenyl)(5-(2-(4-chlorophenyl)-1,3-dioxalan-2-yl)-2-(methylamino)pyridin-3-yl)methanol (G)

PCC (3.99 g, 18.56 mmol) was added to a solution of compound F (4.0 g, 92.80 mmol) in DCM (80 mL). The mixture was stirred for 3 h, filtered through a pad of celite and the filtrate was evaporated. The crude product was dissolved in ether (50 mL) and filtered to remove the chromium impurities. The filtrate was evaporated and the crude product was purified by column chromatography to obtain 1.9 g (48%) of compound G viscous light yellow colored oil.

$^1$H NMR (400 MHz, CDCl$_3$): δ 3.13 (d, 3H), 3.93-4.11 (m, 4H), 7.28-7.32 (m, 2H), 7.33-7.42 (m, 3H), 7.43 (s, 1H), 7.52 (d, 1H), 7.68 (s, 1H), 8.45 (s, 1H), 8.83-8.92 (bs, 1H); LCMS m/z: 429 (M+1).

Step-8: 4-(3-chlorophenyl)-6-(2-(4-chlorophenyl)-1,3-dioxalan-2-yl)-1-methyl-1,8-napthyridin-2(1H)-one (H)

To a solution of diisopropylamine (4.98 mL, 35.51 mmol) in THF, a solution of BuLi (22.1 mL, 26.63 mmol, 1.2 M solution in hexane) was added at −20° C. and the resulting mixture was stirred for 30 min. To this solution of LDA was added tBuOAc (3.59 mL, 26.63 mmol) at −78° C. The mixture was stirred for 30 min and a solution compound G (1.9 g, 44.39 mmol) was added to it. The reaction mixture was allowed to warm to RT and stirred overnight. The reaction mixture was quenched with saturated ammonium chloride solution and extracted with EtOAc (50 mL). The organic layer was dried (Na$_2$SO$_4$), filtered and evaporated. The crude product was purified by column chromatography to obtain 1.1 g (55%) of compound H off-white solid.

$^1$H NMR (400 MHz, CDCl$_3$): δ 3.86 (s, 3H), 4.01-4.17 (m, 4H), 6.76 (s, 1H), 7.23-7.28 (m, 1H), 7.29-7.37 (m, 3H), 7.38-7.54 (m, 4H). 7.84 (d, 2H); LCMS m/z: 453 (M+1).

Step-9: 6-(4-chlorobenzoyl)-4-(3-chlorophenyl)-1-methyl-6,7-dihydro-1,8-naphthyridin-2(1H)-one (I)

To a solution compound H (0.6 g, 1.32 mmol) in dioxane (20 mL) was added conc. HCl (0.6 mL) at 0° C. The mixture was heated at 70° C. for 1.5 h and cooled to RT. Dioxane was removed under reduced pressure; the reaction mixture was neutralized with saturated NaHCO$_3$ solution and extracted with EtOAc (25 mL). The organic layer was dried over Na$_2$SO$_4$, filtered and concentrated under reduced pressure. The crude product was purified by column chromatography to obtain 0.3 g (56%) of compound I off-white solid.

$^1$H NMR (400 MHz, CDCl$_3$): δ 3.96 (s, 3H), 6.79 (s, 1H), 7.31 (d, 1H), 7.41-7.54 (m, 5H), 7.77 (d, 2H), 8.24 (d, 1H), 8.97 (d, 1H); LCMS m/z: 409 (M+1).

Step-10: 4-(3-chlorophenyl)-6-((4-chlorophenyl)(hydroxy)(1-methyl-1H-imidazol-5-yl)methyl)-1-methyl-1,8-napthyridin-2(1H)-one (1a)

To a solution of 5-bromo-1-methylimidazole (0.16 g, 1.0 mmol) in dry DCM (5 mL) DIPEA (0.35 mL, 2.06 mmol) and $^i$PrMgCl (0.66 mL, 1.32 mmol, 2.0 M solution in THF) was added at RT. The reaction mixture was stirred for 1.5 h and a solution of compound H (0.2 g, 0.49 mmol) was added to it. The mixture was refluxed for 5 h, quenched with saturated NH$_4$Cl solution and extracted with DCM (20 mL). The organic layer was dried, filtered and concentrated. The crude product was purified to obtain 70 mg (29%) of compound 1a as off-white solid. 0.1 g of compound H was also recovered.

$^1$H NMR (400 MHz, CDCl$_3$): δ 3.42 (s, 3H), 3.84 (s, 3H), 4.71-4.86 (bs, 1H, OH), 6.31 (s, 1H), 6.63 (s, 1H), 6.64 (s, 1H), 7.13 (d, 1H), 7.21-7.33 (m, 3H), 7.34-7.40 (m, 3H), 7.42-7.46 (m, 1H), 7.71 (s, 1H), 8.61 (s, 1H); LCMS m/z: 491 (M+1); HPLC purity: 98.7% (220 nm), 99.3% (254 nm).

Step-11: 6-(amino(4-chlorophenyl)(1-methyl-1H-imidazol-5-yl)methyl)-4-(3-chlorophenyl)-1-methyl-1,8-napthyridin-2(1H)-one (1a)

1a (70 mg, 0.125 mmol) was dissolved in SOCl$_2$ (1 mL) and the mixture was stirred at 40° C. overnight. Excess SOCl$_2$ was removed under reduced pressure; toluene (10 mL) was added to the residue and evaporated under reduced pressure. The process of addition and evaporation of toluene was repeated twice more to ensure the complete removal of SOCl$_2$. The crude chloro compound thus obtained was dissolved in THF (1 mL) and a solution of ammonia in methanol (3 mL, 33% W/W) was added to it. The mixture was stirred for 12 h, taken up in DCM (10 mL) and washed with water and brine. The organic layer was dried and evaporated. Purification of the crude product provided 15 mg (21%) of 1b as off white solid.

$^1$H NMR (400 MHz, CDCl$_3$): δ 3.43 (s, 3H), 3.92 (s, 3H), 6.37 (s, 1H), 6.77 (s, 1H), 7.11-7.19 (m, 3H), 7.28 (d, 2H), 7.36 (d, 2H), 7.38 (t, 1H), 7.48 (s, 1H), 7.57 (d, 1H), 8.59 (d, 1H); LCMS m/z: 490 (M+1); HPLC purity: 99.96% (220 nm), 99.91% (254 nm).

Example 2

Synthesis of 6-((4-chlorophenyl)(hydroxy)(1-methyl-1H-imidazol-5-yl)methyl)-4-(3-ethynylphenyl)-1-methyl-1,8-naphthyridin-2(1H)-one (4)

General Remarks

All solvents used for the reaction were LR grade solvents. Room temperature (RT) indicates temperature ranging from 27-32° C. All the reactions were monitored by TLC unless specified. Solutions were evaporated under reduced pressure using rotary evaporator. NMR was taken on Varian 400 MHz.

Scheme 12:
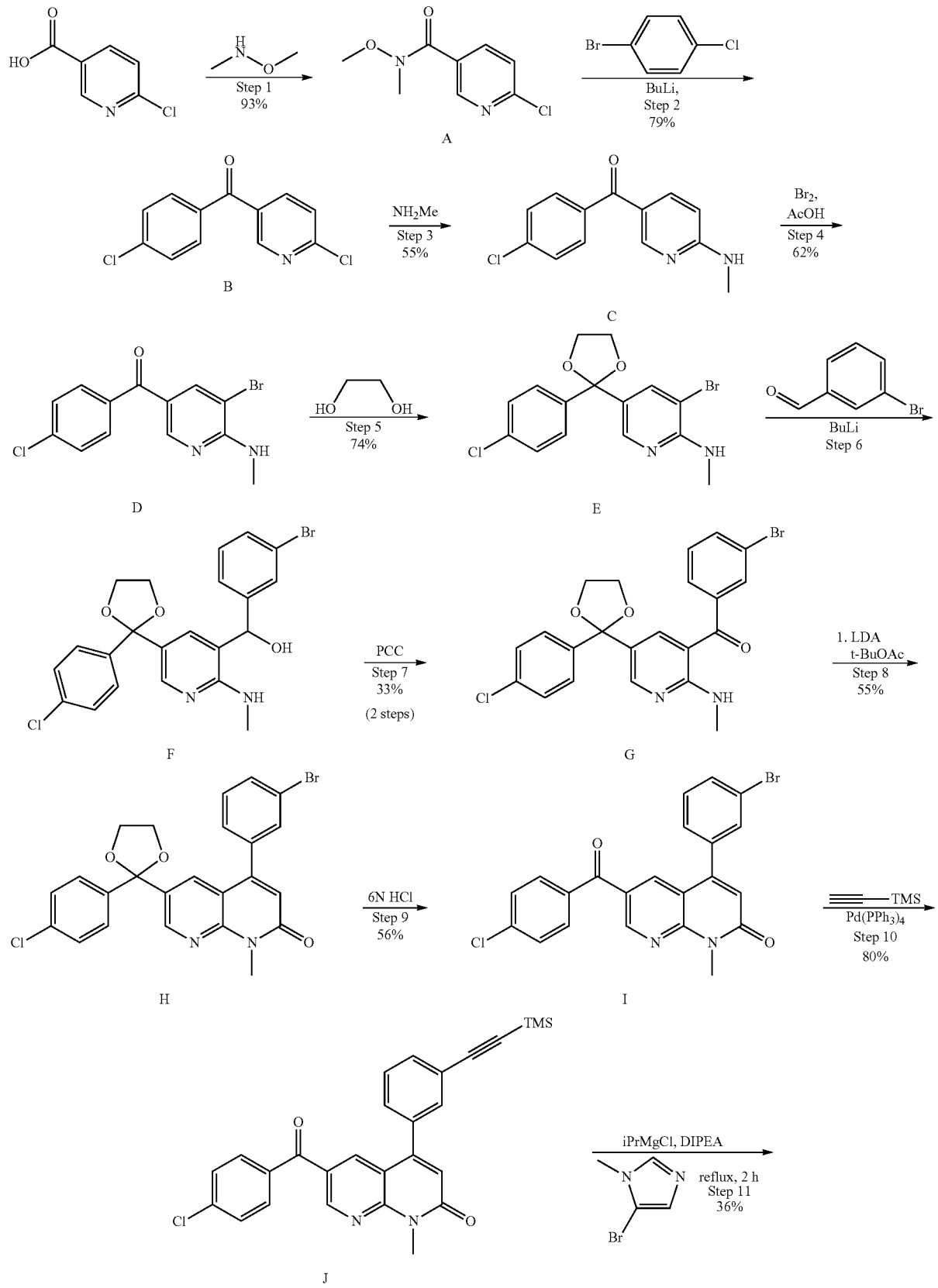

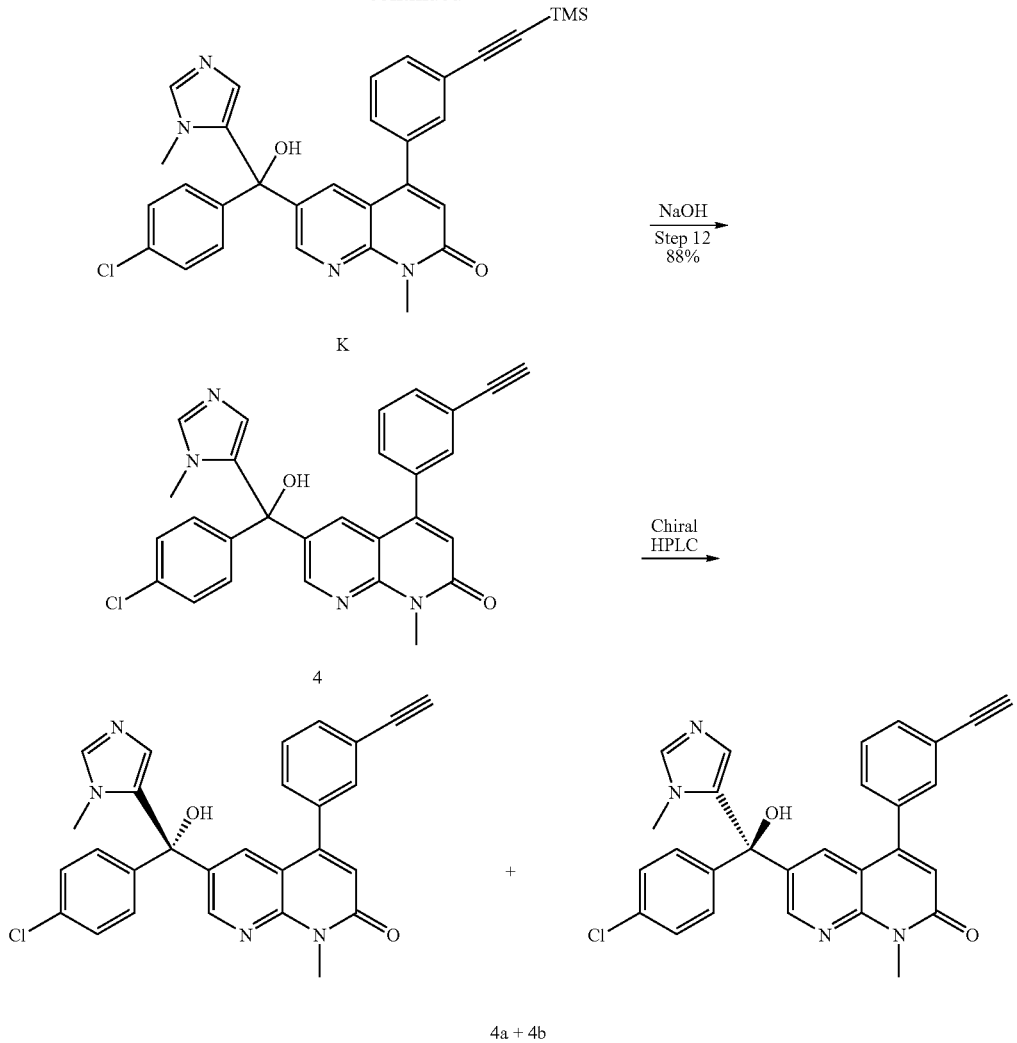

Experimental for Scheme 12.

Step-1: 6-Chloro-N-methoxy-N-methylnicotinamide (A)

To a solution of 6-chloronicotinic acid (20 g, 127 mmol) in acetonitrile (400 mL), methoxymethylamine hydrochloride (13.79 g, 141 mmol), EDC (27.1 g, 141 mmol), HOBT (5.2 g, 38.58 mmol) and TEA (53.3 mL, 386 mmol) were added at RT. The reaction mixture was stirred at RT overnight. Solvent was removed under reduced pressure and the residue was dissolved in ethyl acetate (300 mL). The reaction mixture was washed with water and brine. The organic layer was dried, filtered and concentrated. Purification of the crude product provided 23.6 g (93%) of compound A as viscous colorless oil.

$^1$H NMR (400 MHz, CDCl$_3$): δ 3.38 (s, 3H), 3.57 (s, 3H), 7.39 (d, 1H), 8.04 (d, 1H), 8.77 (s, 1H); LCMS m/z: 201 (M+1).

Step-2: (4-chlorophenyl)(6-chloropyridin-3-yl)methanone (B)

To a solution of 4-chlorobromobenzene (33.88 g, 177 mmol) in THF (200 mL), a solution of BuLi (118 mL, 142 mmol, 1.2 M solution in hexane) was added at −78° C. The mixture was stirred for 1 h and a solution of compound A (23.6 g, 118 mmol) in THF (100 mL) was added to it dropwise. The mixture was stirred for additional 1 h, quenched with saturated NH$_4$Cl solution and extracted with ethyl acetate (300 mL). The organic layer was dried (Na$_2$SO$_4$), filtered and evaporated. The crude product was purified using column chromatography to obtain 23.4 g (79%) of compound B as light yellow solid.

$^1$H NMR (400 MHz, CDCl$_3$): δ 7.43-7.58 (m, 3H), 7.78 (d, 2H), 8.08 (d, 1H), 8.76 (s, 1H); LCMS m/z: 252 (M+1).

Step-3: (4-chlorophenyl)(6-(methylamino)pyridin-3-yl)methanone (C)

A mixture of compound B (23.4 g, 93.22 mmol), methylamine (88 mL, 932 mmol, 33% solution in ethanol) and Et$_3$N (37.51 mL, 280 mmol) in EtOH (100 mL) was heated in a sealed tube at 80° C. for 3 h. EtOH was removed under reduced pressure and the residue was dissolved in DCM (150 mL), washed with water and brine. The organic layer was dried (Na$_2$SO$_4$), filtered and evaporated. The crude product was purified by triturating with diethyl ether to obtain 12.5 g (55%) of compound C as off-white solid.

¹H NMR (400 MHz, CDCl₃): δ 3.06 (d, 3H), 5.02-5.17 (bs, 1H, NH), 6.44 (d, 1H), 7.43 (d, 2H), 7.71 (d, 2H), 7.96 (d, 1H), 8.55 (s, 1H); LCMS m/z: 247 (M+1).

Step-4: (5-bromo-6-(methylamino)pyridin-3-yl)(4-chlorophenyl)methanone (D)

A solution of bromine (2.29 mL, 44.70 mmol) in acetic acid (30 mL) was added to a solution of compound C (11.0 g, 44.7 mmol) in acetic acid (80 mL) at RT. The mixture was stirred for 1 h, neutralized by the addition of saturated NaHCO₃ solution and extracted with ethyl acetate (200 mL). The organic layer was washed with 10% sodium thiosulfate solution, water and brine. The organic layer was dried (Na₂SO₄), filtered and evaporated. The crude product was purified using column chromatography to obtain 9.0 g (62%) of compound D as viscous light yellow colored oil.

¹H NMR (400 MHz, CDCl₃): δ 3.14 (d, 3H), 5.57-5.70 (bs, 1H, NH), 7.47 (d, 2H), 7.70 (d, 2H), 8.19 (s, 1H), 8.53 (s, 1H); LCMS m/z: 325 (M+1).

Step-5: 3-bromo-5-(2-(4-chlorophenyl)-1,3-dioxalan-2-yl)-N-methylpyridin-2-amine (E)

To a solution of compound D (6.0 g, 18.51 mmol) in toluene (120 mL), ethylene glycol (10.4 mL, 185 mmol) and PTSA (0.96 g, 5.55 mmol) was added. The mixture was refluxed overnight, quenched with water and extracted with ethyl acetate (150 mL). The organic layer was washed with water and brine, dried (Na₂SO₄), filtered and evaporated. The crude product was purified using column chromatography to obtain 5.0 g (74%) of compound E as off-white solid.

¹H NMR (400 MHz, CDCl₃): δ 3.02 (d, 3H), 3.93-4.17 (m, 4H), 7.33 (d, 2H), 5.01-5.16 (bs, 1H, NH), 7.42 (d, 2H), 7.71 (s, 1H), 8.09 (s, 1H); LCMS m/z: 369 (M+1).

Step-6: (3-bromophenyl)(5-(2-(4-chlorophenyl)-1,3-dioxolan-2-yl)-2-(methylamino)pyridin-3-yl)methanol (F)

A solution of compound E (20.0 g, 54.20 mmol) in THF (450 mL) was cooled to −78° C. and n-butyllithium (54.2 mL, 54.2 mmol, 1.0 M solution in hexane) was added to it dropwise, while maintaining the temperature below −70° C. The mixture was stirred for 10 min, triethylsilyl chloride (9.13 mL, 54.20 mmol) was added dropwise at −70° C., and stirred for 30 min. n-BuLi (54.2 mL, 54.2 mmol, 1.0 M solution in hexane) was added dropwise, stirred for 10 min at −75° C., and a solution of 3-bromobenzaldehyde (10.05 mL, 81.3 mmol) in THF (50 mL) was added, stirred for 1 h, quenched with saturated NH₄Cl solution and extracted with EtOAc (300 mL). The organic layer was dried over Na₂SO₄, filtered and concentrated under reduced pressure. The crude product was purified by column chromatography to obtain 20 g of compound F as viscous light yellow colored oil containing an inseparable impurity (59% pure by LCMS). This material was used in the next step without further purification.

¹H NMR (400 MHz, CDCl₃): δ 2.87 (d, J=5.2 Hz, 3H), 3.92-4.09 (m, 4H), 5.65 (s, 1H), 7.14-7.20 (m, 2H), 7.27-7.33 (m, 3H), 7.39 (d, J=9.2 Hz, 2H), 7.43 (s, 1H), 7.47-7.52 (m, 1H), 8.10 (d, J=2.0 Hz, 1H); LCMS m/z: 475 (M+1).

Step-7: (3-bromophenyl)(5-(2-(4-chlorophenyl)-1,3-dioxolan-2-yl)-2-(methylamino)pyridin-3-yl)methanone (G)

PCC (13.61 g, 63.28 mmol) was added to a solution of compound F (20 g, 42.19 mmol) in DCM (400 mL). The mixture was stirred at RT overnight and filtered through a pad of celite. The filtrate was concentrated and purified by column chromatography to obtain 8.5 g (33%, two steps) of compound G.

¹H NMR (400 MHz, CDCl₃): δ 3.11 (d, J=4.4 Hz, 3H), 3.95-4.12 (m, 4H), 7.28-7.34 (m, 3H), 7.38-7.45 (m, 2H), 7.61 (s, 1H), 7.66 (d, J=8.0 Hz, 1H), 7.69 (d, J=2.0 Hz, 1H), 8.44 (d, J=2.0 Hz, 1H), 8.70 (s, 1H); LCMS m/z: 473 (M+1).

Step-8: 4-(3-bromophenyl)-6-(2-(4-chlorophenyl)-1,3-dioxolan-2-yl)-1-methyl-1,8-naphthyridin-2(1H)-one (H)

To a solution of diisopropylamine (18.93 mL, 134.96 mmol) in THF, a solution of nBuLi (126 mL, 101.22 mmol, 0.8 M solution in hexane) was added at −20° C. and the resulting mixture was stirred for 30 min. To this solution of LDA was added tBuOAc (13.65 mL, 101.22 mmol) at −78° C. The mixture was stirred for 30 min and a solution compound G (8.0 g, 16.87 mmol) was added to it. The reaction mixture was allowed to warm to RT and stirred overnight. The reaction mixture was quenched with saturated ammonium chloride solution and extracted with EtOAc (250 mL). The organic layer was dried (Na₂SO₄), filtered and evaporated. The crude product was purified by column chromatography to obtain 4.2 g (50%) of compound H as off-white solid.

¹H NMR (400 MHz, CDCl₃): δ 3.86 (s, 3H), 4.04-4.15 (m, 4H), 6.72 (s, 1H), 7.27-7.36 (m, 3H), 7.37-7.45 (m, 3H), 7.50 (s, 1H), 7.64 (d, J=8.0 Hz, 1H), 7.87 (d, J=2.0 Hz, 1H), 8.72 (d, J=2.4 Hz, 1H); LCMS m/z: 497 (M+1).

Step-9: 4-(3-bromophenyl)-6-(4-chlorobenzoyl)-1-methyl-1,8-naphthyridin-2(1H)-one (I)

To a solution compound H (0.4 g, 0.81 mmol) in dioxane (5 mL) was added 6 N HCl (0.5 mL) at 0° C. The mixture was heated at 70° C. for 1.5 h and cooled to RT. Dioxane was removed under reduced pressure; the reaction mixture was neutralized with saturated NaHCO₃ solution and extracted with EtOAc (25 mL). The organic layer was dried over Na₂SO₄, filtered and concentrated under reduced pressure. The crude product was purified by column chromatography to obtain 0.32 g (88%) of compound I as off-white solid.

¹H NMR (400 MHz, CDCl₃): δ 3.92 (s, 3H), 6.79 (s, 1H), 7.36 (t, J=7.6 Hz, 1H), 7.40 (t, J=7.6 Hz, 1H), 7.51 (d, J=8.0 Hz, 2H), 7.58 (s, 1H), 7.64 (d, J=7.6 Hz, 1H), 7.74 (d, J=8.4 Hz, 2H), 8.26 (d, J=2.0 Hz, 1H), 9.00 (d, J=2.0 Hz, 1H); LCMS m/z: 453 (M+1).

Step-10: 6-(4-chlorobenzoyl)-1-methyl-4-(3-((trimethylsilyl)ethynyl)phenyl)-1,8-naphthyridin-2(1H)-one (J)

To a solution of compound I (1 g, 2.21 mmol) in THF (10.0 mL), TEA (4 mL) was added followed by (PPh₃)₄Pd (0.25 g, 0.22 mmol) and CuI (42 mg, 0.22 mmol). The mixture was degassed using N₂ for 30 min and TMS-acetylene (0.92 g, 6.64 mmol) was added. The mixture was heated in a microwave oven at 60° C. for 30 min. The reaction mixture was diluted with EtOAc (25 mL) and passed through a pad of celite. The filtrate was concentrated. Purification of the crude product provided 825 mg (80%) of compound J.

¹H NMR (400 MHz, CDCl₃): δ 0.27 (s, 9H), 3.93 (s, 3H), 6.79 (s, 1H), 7.34 (d, J=7.6 Hz, 1H), 7.46 (t, J=7.6 Hz, 1H), 7.49-7.54 (m, 3H), 7.59 (d, J=7.6 Hz, 1H), 7.74 (d, J=8.8 Hz, 2H), 8.24 (d, J=2.4 Hz, 1H), 9.01 (d, J=2.0 Hz, 1H); LCMS m/z: 471 (M+1).

Step-11: 6-((4-chlorophenyl)(hydroxy)(1-methyl-1H-imidazol-5-yl)methyl)-1-methyl-4-(3-((trimethylsilyl)ethynyl)phenyl)-1,8-naphthyridin-2(1H)-one (K)

To a solution of 5-bromo-1-methylimidazole (0.68 g, 4.26 mmol) in dry DCM (15 mL), DIPEA (0.77 mL, 4.47 mmol) and $^i$PrMgCl (2.13 mL, 4.26 mmol, 2.0 M solution in THF) was added at 10° C. The reaction mixture was stirred for 1.5 h and a solution of compound J (0.5 g, 1.06 mmol) in DCM was added to it. The reaction mixture was refluxed for 2 h and quenched with saturated NH$_4$Cl solution. The product was extracted with DCM (30 mL). The organic layer was dried, filtered and concentrated to give crude c. Purification of the crude product provided 210 mg (36%) of compound K.

$^1$H NMR (400 MHz, CDCl$_3$): δ 0.27 (s, 9H), 3.38 (s, 3H), 3.78 (s, 3H), 6.28 (s, 1H), 6.64 (s, 1H), 7.11 (d, J=7.6 Hz, 1H), 7.22 (s, 1H), 7.24 (s, 1H), 7.29 (s, 1H), 7.30-7.36 (m, 3H), 7.37 (s, 1H), 7.53 (d, J=7.6 Hz, 1H), 7.67 (d, J=2.0 Hz, 1H), 8.57 (d, J=5.0 Hz, 1H); LCMS m/z: 553 (M+1).

Step-12: 6-(4-chlorophenyl)(hydroxy)(1-methyl-1H-imidazol-5-yl)methyl)-4-(3-ethynylphenyl)-1-methyl-1,8-naphthyridin-2(1H)-one (4)

To a solution of compound K (210 mg, 0.38 mmol) in THF (5 mL) was added a 2 N NaOH solution (2.5 mL) and the mixture was stirred at RT for 4 h. The reaction mixture was neutralized using citric acid and then basified using NaHCO$_3$ solution. The product was extracted in DCM and washed with water and brine. The organic layer was dried, filtered and concentrated to afford compound 4 (0.16 g, 88%) in pure form. The racemic material was resolved using preparative chiral HPLC Chiralpak AD-H 250 mm×4.6 mm×5 um eluting with 80/20 hexanes/isopropanol to obtain 48 mg of 4a and 52 mg of 4b.

Data for 4a:
$^1$H NMR (400 MHz, CDCl$_3$): δ 3.16 (s, 1H), 3.39 (s, 3H), 3.82 (s, 3H), 4.03-4.09 (bs, 1H), 6.29 (s, 1H), 6.62 (s, 1H), 7.11 (d, J=7.6 Hz, 1H), 7.22-7.27 (m, 3H), 7.29-7.38 (m, 4H), 7.55 (d, J=7.6 Hz, 1H), 7.68 (d, J=2.0 Hz, 1H), 8.60 (d, J=2.4 Hz, 1H); LCMS m/z: 481 (M+1); HPLC purity: 98.21% (220 nm), 98.21% (254 nm); Chiral HPLC: 100% (220 nm); retention time 5-6 minutes.

Data for 4b:
$^1$H NMR (400 MHz, CDCl$_3$): δ 3.16 (s, 1H), 3.39 (s, 3H), 3.82 (s, 3H), 4.02-4.09 (bs, 1H), 6.32 (s, 1H), 6.64 (s, 1H), 7.14 (d, J=8.0 Hz, 1H), 7.22 (s, 1H), 7.23-7.29 (m, 2H), 7.32-7.40 (m, 4H), 7.56 (d, J=8.0 Hz, 1H), 7.69 (d, J=2.4 Hz, 1H), 8.59 (d, J=2.0 Hz, 1H); LCMS m/z: 481 (M+1); HPLC purity: 98.59% (220 nm), 98.56% (254 nm); Chiral HPLC: 100% (220 nm); retention time 7-8 minutes.

Example 3

Synthesis of 6-(amino(4-chlorophenyl)(1-methyl-1H-imidazol-5-yl)methyl)-4-(3-methoxyphenyl)-1-methyl-1,8-naphthyridin-2(1H)-one (5)

General Remarks

All solvents used for the reaction were LR grade solvents. Room temperature (RT) indicates temperature ranging from 27-32° C. All the reactions were monitored by TLC unless specified. Solutions were evaporated under reduced pressure using rotary evaporator. NMR was taken on Varian 400 MHz.

Scheme 13:

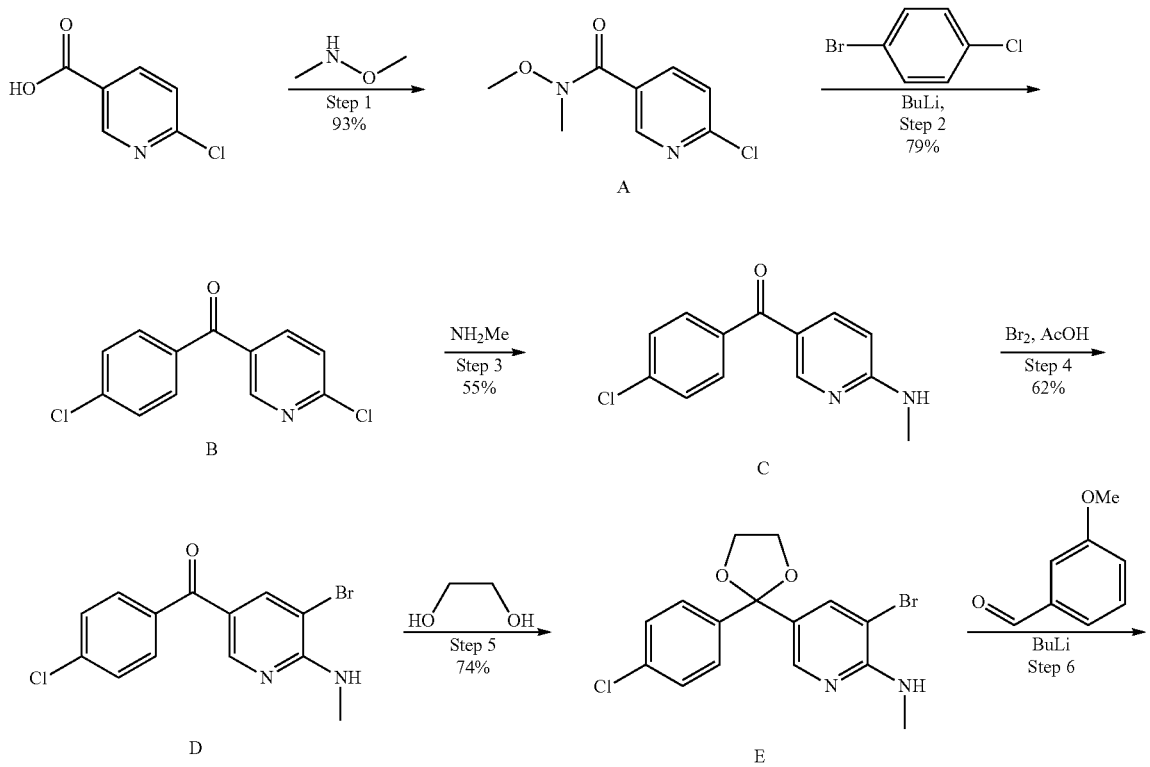

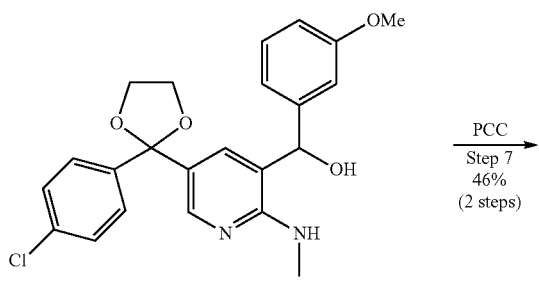
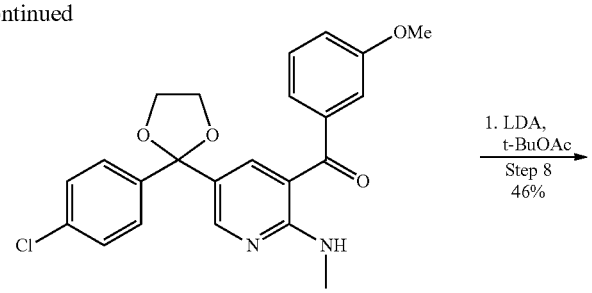
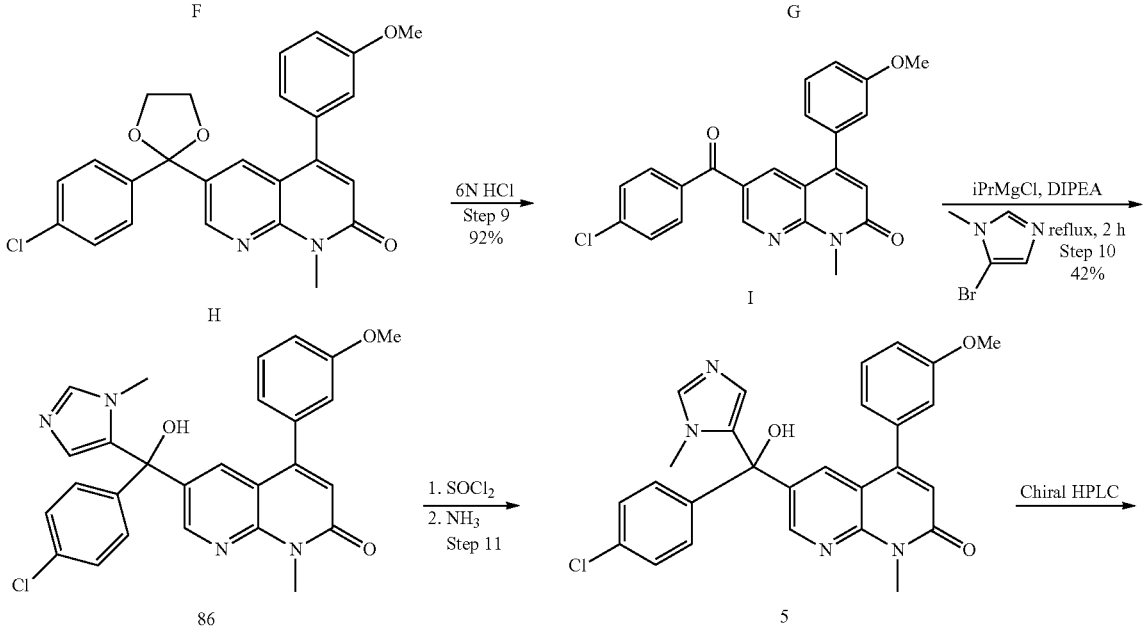
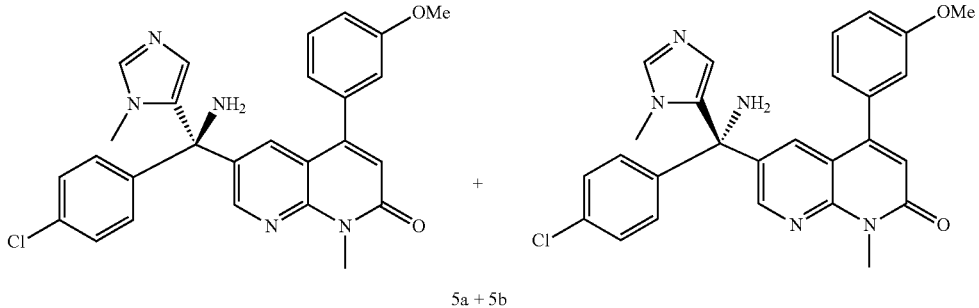

Experimental for Scheme 13:

Step-1: 6-Chloro-N-methoxy-N-methylnicotinamide (A)

To a solution of 6-chloronicotinic acid (20 g, 127 mmol) in acetonitrile (400 mL), methoxymethylamine hydrochloride (13.79 g, 141 mmol), EDC (27.1 g, 141 mmol), HOBT (5.2 g, 38.58 mmol) and TEA (53.3 mL, 386 mmol) were added at RT. The reaction mixture was stirred at RT overnight. Solvent was removed under reduced pressure and the residue was dissolved in ethyl acetate (300 mL). The reaction mixture was washed with water and brine. The organic layer was dried, filtered and concentrated. Purification of the crude product provided 23.6 g (93%) of compound A as viscous colorless oil.

$^1$H NMR (400 MHz, CDCl$_3$): δ 3.38 (s, 3H), 3.57 (s, 3H), 7.39 (d, 1H), 8.04 (d, 1H), 8.77 (s, 1H); LCMS m/z: 201 (M+1).

Step-2: (4-chlorophenyl)(6-chloropyridin-3-yl)methanone (B)

To a solution of 4-chlorobromobenzene (33.88 g, 177 mmol) in THF (200 mL), a solution of BuLi (118 mL, 142 mmol, 1.2 M solution in hexane) was added at −78° C. The mixture was stirred for 1 h and a solution of compound A (23.6 g, 118 mmol) in THF (100 mL) was added to it dropwise. The mixture was stirred for additional 1 h, quenched with saturated NH$_4$Cl solution and extracted with ethyl acetate (300 mL). The organic layer was dried (Na$_2$SO$_4$), filtered and evaporated. The crude product was purified using column chromatography to obtain 23.4 g (79%) of compound B as light yellow solid.

¹H NMR (400 MHz, CDCl₃): δ 7.43-7.58 (m, 3H), 7.78 (d, 2H), 8.08 (d, 1H), 8.76 (s, 1H); LCMS m/z: 252 (M+1).

Step-3: (4-chlorophenyl)(6-(methylamino)pyridin-3-yl)methanone (C)

A mixture of compound B (23.4 g, 93.22 mmol), methylamine (88 mL, 932 mmol, 33% solution in ethanol) and Et₃N (37.51 mL, 280 mmol) in EtOH (100 mL) was heated in a sealed tube at 80° C. for 3 h. EtOH was removed under reduced pressure and the residue was dissolved in DCM (150 mL), washed with water and brine. The organic layer was dried (Na₂SO₄), filtered and evaporated. The crude product was purified by triturating with diethyl ether to obtain 12.5 g (55%) of compound C as off-white solid.

¹H NMR (400 MHz, CDCl₃): δ 3.06 (d, 3H), 5.02-5.17 (bs, 1H, NH), 6.44 (d, 1H), 7.43 (d, 2H), 7.71 (d, 2H), 7.96 (d, 1H), 8.55 (s, 1H); LCMS m/z: 247 (M+1).

Step-4: (5-bromo-6-(methylamino)pyridin-3-yl)(4-chlorophenyl)methanone (D)

A solution of bromine (2.29 mL, 44.70 mmol) in acetic acid (30 mL) was added to a solution of compound C (11.0 g, 44.7 mmol) in acetic acid (80 mL) at RT. The mixture was stirred for 1 h, neutralized by the addition of saturated NaHCO₃ solution and extracted with ethyl acetate (200 mL). The organic layer was washed with 10% sodium thiosulfate solution, water and brine. The organic layer was dried (Na₂SO₄), filtered and evaporated. The crude product was purified using column chromatography to obtain 9.0 g (62%) of compound D as viscous light yellow colored oil.

¹H NMR (400 MHz, CDCl₃): δ 3.14 (d, 3H), 5.57-5.70 (bs, 1H, NH), 7.47 (d, 2H), 7.70 (d, 2H), 8.19 (s, 1H), 8.53 (s, 1H); LCMS m/z: 325 (M+1).

Step-5: 3-bromo-5-(2-(4-chlorophenyl)-1,3-dioxalan-2-yl)-N-methylpyridin-2-amine (E)

To a solution of compound D (6.0 g, 18.51 mmol) in toluene (120 mL), ethylene glycol (10.4 mL, 185 mmol) and PTSA (0.96 g, 5.55 mmol) was added. The mixture was refluxed overnight, quenched with water and extracted with ethyl acetate (150 mL). The organic layer was washed with water and brine, dried (Na₂SO₄), filtered and evaporated. The crude product was purified using column chromatography to obtain 5.0 g (74%) of compound E as off-white solid.

¹H NMR (400 MHz, CDCl₃): δ 3.02 (d, 3H), 3.93-4.17 (m, 4H), 7.33 (d, 2H), 5.01-5.16 (bs, 1H, NH), 7.42 (d, 2H), 7.71 (s, 1H), 8.09 (s, 1H); LCMS m/z: 369 (M+1).

Step-6 (5-(2-(4-chlorophenyl)-1,3-dioxolan-2-yl)-2-(methylamino)pyridin-3-yl)(3-methoxyphenyl)methanol (F)

A solution of compound E (30.0 g, 81.30 mmol) in THF (600 mL) was cooled to –78° C. and n-butyllithium (162.6 mL, 162.6 mmol, 1.0 M solution in hexane) was added to it dropwise, while maintaining the temperature below –70° C. The mixture was stirred for 10 min and triethylsilyl chloride (13.7 mL, 81.30 mmol) was added dropwise at –70° C. The reaction mixture was stirred for 30 min. n-BuLi (162.6 mL, 162.60 mmol, 1.0 M solution in hexane) was added dropwise and the reaction mixture was stirred for 10 min at –75° C. A solution of 3-methoxybenzaldehyde (15.07 mL, 121.95 mmol) in THF (50 mL) was added and stirred for 1 h. The reaction mixture was quenched with saturated NH₄Cl solution and extracted with EtOAc (100 mL). The organic layer was dried over Na₂SO₄, filtered and concentrated under reduced pressure. The crude product was purified by column chromatography to obtain 28 g of compound F as viscous light yellow colored oil containing an inseparable impurity (64% pure by LCMS). This material was used in the next step without further purification.

¹H NMR (400 MHz, CDCl₃): δ 2.86 (s, 1H, NH), 2.89 (d, J=3.6 Hz, 3H), 3.75 (s, 3H), 3.92-4.07 (m, 4H), 5.30-5.34 (bs, 1H, OH), 5.65 (s, 1H), 6.82 (s, 1H), 6.84 (s, 1H), 7.16-7.32 (m, 4H), 7.36-7.43 (m, 3H), 8.10 (s, 1H); LCMS m/z: 427 (M+1).

Step-7 (5-(2-(4-chlorophenyl)-1,3-dioxolan-2-yl)-2-(methylamino)pyridin-3-yl)(3-methoxyphenyl)methanone (G)

PCC (21.19 g, 98.58 mmol) was added to a solution of compound F (28 g, 65.72 mmol) in DCM (550 mL). The mixture was stirred at RT overnight and filtered through a pad of celite. The filtrate was concentrated and purified by column chromatography to obtain 16 g (46%, 2 steps) of compound G.

¹H NMR (400 MHz, CDCl₃): δ 3.11 (d, J=4.84 Hz, 3H), 3.80 (s, 3H), 3.96-4.08 (m, 4H), 6.96-7.09 (m, 3H), 7.30 (t, J=8.0 Hz, 2H), 7.39 (d, J=8.4 Hz, 2H), 7.77 (d, J=2.4 Hz, 1H), 8.42 (d, J=2.4 Hz, 1H), 8.71 (s, 1H); LCMS m/z: 425 (M+1).

Step-8: 6-(2-(4-chlorophenyl)-1,3-dioxolan-2-yl)-4-(3-methoxyphenyl)-1-methyl-1,8-naphthyridin-2(1H)-one (H)

To a solution of diisopropylamine (1.32 mL, 9.43 mmol) in THF, a solution of BuLi (7.86 mL, 7.08 mmol, 0.9 M solution in hexane) was added at –20° C. and the resulting mixture was stirred for 30 min. To this solution of LDA, tBuOAc (0.95 mL, 7.08 mmol) was added at –78° C. The mixture was stirred for 30 min and a solution compound G (500 mg, 1.18 mmol) was added to it. The reaction mixture was allowed to warm to RT and stirred overnight. The reaction mixture was quenched with saturated ammonium chloride solution and extracted with EtOAc (50 mL). The organic layer was dried (Na₂SO₄), filtered and evaporated. The crude product was purified by column chromatography to obtain 0.3 g (57%) of compound H off-white solid.

¹H NMR (400 MHz, CDCl₃): δ 3.82 (s, 3H), 3.86 (s, 2H), 4.01-4.14 (m, 4H), 6.75 (s, 1H), 6.87 (t, J=2 Hz, 1H), 6.93 (d, J=7.2 Hz, 1H), 7.03 (dd, J=8, 2 Hz, 1H), 7.30 (d, J=8.4 Hz, 2H), 7.39-7.47 (m, 4H), 7.98 (d, J=2.4 Hz, 1H), 8.71 (d, J=2.0 Hz, 1H); LCMS m/z: 449 (M+1).

Step-9: 6-(4-chlorobenzoyl)-4-(3-methoxyphenyl)-1-methyl-1,8-naphthyridin-2(1H)-one (I)

To a solution compound H (0.3 g, 0.67 mmol) in dioxane (5 mL) was added 6 N HCl (0.5 mL) at 0° C. The mixture was heated at 70° C. for 1.5 h and cooled to RT. Dioxane was removed under reduced pressure; the reaction mixture was neutralized with saturated NaHCO₃ solution and extracted with EtOAc (25 mL). The organic layer was dried over Na₂SO₄, filtered and concentrated under reduced pressure. The crude product was purified by column chromatography to obtain 0.25 g (92%) of compound I as off-white solid.

¹H NMR (400 MHz, CDCl₃): δ 3.86 (s, 3H), 3.92 (s, 3H), 6.82 (s, 1H), 6.94 (s, 1H), 6.99 (d, J=7.6 Hz, 1H), 7.03 (d, J=8.4 Hz, 1H), 7.42 (t, J=8.0 Hz, 1H), 7.49 (d, J=8.4 Hz, 2H), 7.74 (d, J=8.4 Hz, 2H), 8.37 (d, J=2.0 Hz, 1H), 8.97 (d, J=2.0 Hz, 1H); LCMS m/z: 405 (M+1).

Step-10: 6-(4-chlorophenyl)(hydroxy)(1-methyl-1H-imidazol-5-yl)methyl)-4-(3-methoxyphenyl)-1-methyl-1,8-naphthyridin-2(1H)-one (6)

To a solution of 5-bromo-1-methylimidazole (390 mg, 2.44 mmol) in dry DCM (5 mL), DIPEA (0.89 mL, 5.18 mmol) and $^i$PrMgCl (1.22 mL, 2.44 mmol, 2.0 M solution in THF) was added at RT. The reaction mixture was stirred for 1.5 h and a solution of compound I (0.25 g, 0.61 mmol) in DCM was added to it. The mixture was refluxed for 5 h. The reaction was quenched with saturated NH$_4$Cl solution and the product was extracted with DCM (50 mL). The organic layer was dried, filtered and concentrated. Purification of the crude product by column chromatography (DCM: NH$_3$ in MeOH 7N, 98:2) provided compound 6 (3.1 g, 42%) as brown solid. 350 mg of racemic compound 6 was resolved using chiral preparative HPLC to obtain 64 mg of 6a and 52 mg of 6b.
Data for 6a:
$^1$H NMR (400 MHz, CDCl$_3$): δ 3.39 (s, 3H), 3.78 (s, 3H), 3.79 (s, 3H), 4.44-4.53 (bs, 1H, OH), 6.31 (s, 1H), 6.63 (s, 1H), 6.74 (s, 1H), 6.77 (d, J=7.2 Hz, 1H), 6.97 (d, J=8.0 Hz, 1H), 7.18-7.27(m, 3H), 7.30-7.41 (m, 3H), 7.84 (s, 1H), 8.53 (s, 1H); LCMS m/z: 487 (M+1); HPLC purity: 99.5% (220 nm), 98.5% (254 nm); Chiral HPLC: 99.6% (220 nm).
Data for 6b:
$^1$H NMR (400 MHz, CDCl$_3$): δ 3.90 (s, 3H), 3.78 (s, 3H), 3.79 (s, 3H), 4.36-4.46 (bs, 1H, OH), 6.32 (s, 1H), 6.64 (s, 1H), 6.74 (s, 1H), 6.78 (d, J=7.2 Hz, 1H), 6.97 (d, J=6.8 Hz, 1H), 7.17-7.28 (m, 3H), 7.29-7.40 (m, 3H), 7.84 (s, 1H), 8.52 (s, 1H); LCMS m/z: (M+1); HPLC purity: 99.2% (220 nm), 98.7% (254 nm); Chiral HPLC: 96.8% (220 nm).

Step-11: 6(R)-(amino(4-chlorophenyl)(1-methyl-1H-imidazol-5-yl)methyl)-4-(3-methoxyphenyl)-1-methyl-1,8-naphthyridin-2(1H)-one and 6(S)-(amino(4-chlorophenyl)(1-methyl-1H-imidazol-5-yl)methyl)-4-(3-methoxyphenyl)-1-methyl-1,8-naphthyridin-2(1H)-one (5)

A solution of compound 6 (0.75 g, 1.54 mmol, racemic) in SOCl$_2$ (10 mL) was stirred at room temperature for 3 h. After complete conversion reaction mixture was concentrated and a solution of NH$_3$ (20 mL, 7 N in MeOH) was added. The reaction mixture was stirred for 16 h and concentrated under reduced pressure to afford crude product. DCM (50 mL) was added to the residue and washed with water (20 mL). The organic layer were dried and concentrated to afford crude product. Purification using column chromatography afforded 450 mg of impure compound 5. Further purification using preparative HPLC followed by resolution using Chiralpak AD-H column 250 mm×4.6 mm×5 um eluting with hexanes/ethanol to provide 100 mg of 5a and 50 mg of 5b.
Data for 5a:
$^1$H NMR (400 MHz, CDCl$_3$): δ 3.67 (s, 3H), 3.82 (s, 3H), 3.86 (s, 3H), 6.73 (s, 1H), 6.76 (s, 1H), 6.78-6.82 (m, 2H), 6.98 (dd, J=6.8, 2.4 Hz, 1H), 7.07 (d, J=8.4 Hz, 2H), 7.33 (d, J=7.6 Hz, 1H), 7.37 (d, J=8.8 Hz, 2H), 7.61 (d, J=2.4 Hz, 1H), 8.49 (d, J=2.4 Hz, 1H), 8.55 (s, 1H); LCMS m/z: 486 (M+1); HPLC purity: 93.9% (220 nm), 96.0% (254 nm); Chiral HPLC: 98.2% (220 nm); retention time 8-9 minutes.
Data for 5b:
$^1$H NMR (400 MHz, CDCl$_3$): δ 3.42 (s, 3H), 3.82 (s, 3H), 3.87 (s, 3H), 6.35 (s, 1H), 6.76 (s, 1H), 6.77-6.85 (m, 2H), 6.98 (d, J=8.4 Hz, 1H), 7.11 (d, J=8.4 Hz, 2H), 7.30 (d, J=8.4 Hz, 2H), 7.35 (d, J=8 Hz, 1H), 7.45 (s, 1H), 7.72 (d, J=2.4 Hz, 1H), 8.50 (d, J=2.4 Hz, 1H); LCMS m/z: 486 (M+1); HPLC purity: 98.3% (220 nm), 99.0% (254 nm); Chiral HPLC: 95.9% (220 nm); retention time 13-14 minutes.

Example 4

Synthesis of 6-((4-chlorophenyl)(hydroxy)(1-methyl-1H-imidazol-5-yl)methyl)-4-(3-methoxyphenyl)-1-methyl-1,8-naphthyridin-2(1H)-one (6)

General Remarks

All solvents used for the reaction were LR grade solvents. Room temperature (RT) indicates temperature ranging from 27-32° C. All the reactions were monitored by TLC unless specified. Solutions were evaporated under reduced pressure using rotary evaporator. NMR was taken on Varian 400 MHz.

Scheme 14:

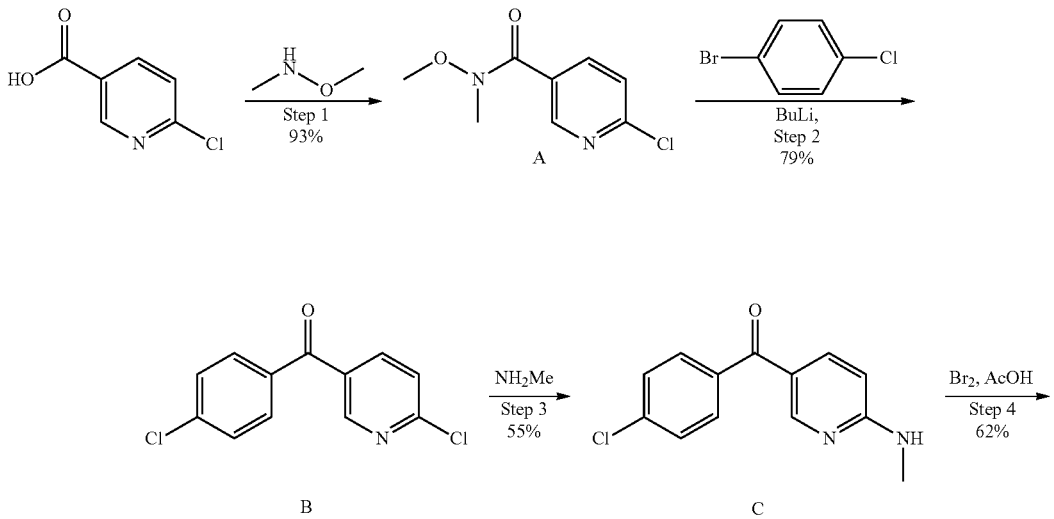

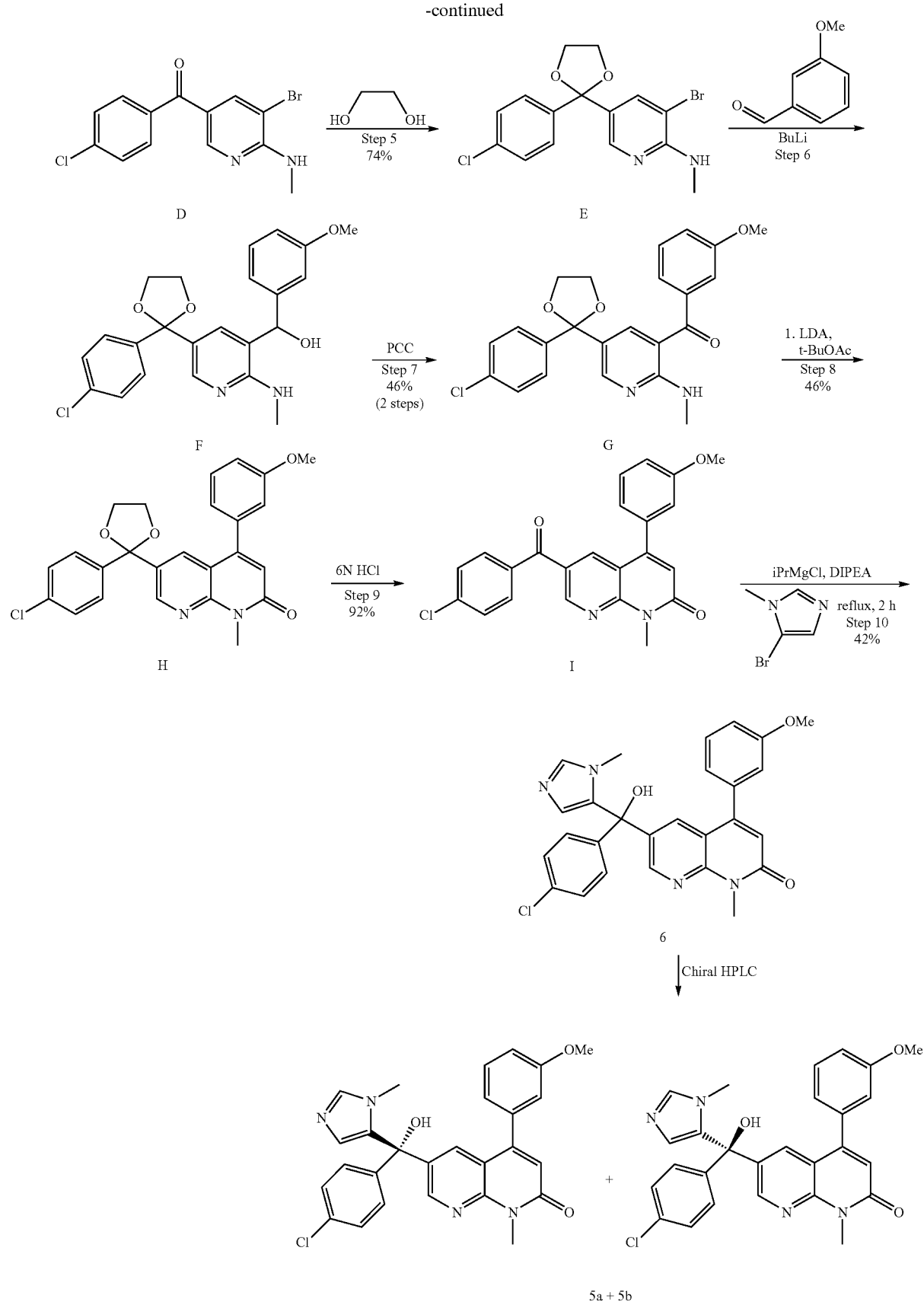

Experimental for Scheme 14:

Step-1: 6-Chloro-N-methoxy-N-methylnicotinamide (A)

To a solution of 6-chloronicotinic acid (20 g, 127 mmol) in acetonitrile (400 mL), methoxymethylamine hydrochloride (13.79 g, 141 mmol), EDC (27.1 g, 141 mmol), HOBT (5.2 g, 38.58 mmol) and TEA (53.3 mL, 386 mmol) were added at RT. The reaction mixture was stirred at RT overnight. Solvent was removed under reduced pressure and the residue was dissolved in ethyl acetate (300 mL). The reaction mixture was washed with water and brine. The organic layer was dried, filtered and concentrated. Purification of the crude product provided 23.6 g (93%) of compound A as viscous colorless oil.

$^1$H NMR (400 MHz, CDCl$_3$): δ 3.38 (s, 3H), 3.57 (s, 3H), 7.39 (d, 1H), 8.04 (d, 1H), 8.77 (s, 1H); LCMS m/z: 201 (M+1).

Step-2: (4-chlorophenyl)(6-chloropyridin-3-yl)methanone (B)

To a solution of 4-chlorobromobenzene (33.88 g, 177 mmol) in THF (200 mL), a solution of BuLi (118 mL, 142 mmol, 1.2 M solution in hexane) was added at −78° C. The mixture was stirred for 1 h and a solution of compound A (23.6 g, 118 mmol) in THF (100 mL) was added to it dropwise. The mixture was stirred for additional 1 h, quenched with saturated NH$_4$Cl solution and extracted with ethyl acetate (300 mL). The organic layer was dried (Na$_2$SO$_4$), filtered and evaporated. The crude product was purified using column chromatography to obtain 23.4 g (79%) of compound B as light yellow solid.

$^1$H NMR (400 MHz, CDCl$_3$): δ 7.43-7.58 (m, 3H), 7.78 (d, 2H), 8.08 (d, 1H), 8.76 (s, 1H); LCMS m/z: 252 (M+1).

Step-3: (4-chlorophenyl)(6-(methylamino)pyridin-3-yl)methanone (C)

A mixture of compound B (23.4 g, 93.22 mmol), methylamine (88 mL, 932 mmol, 33% solution in ethanol) and Et$_3$N (37.51 mL, 280 mmol) in EtOH (100 mL) was heated in a sealed tube at 80° C. for 3 h. EtOH was removed under reduced pressure and the residue was dissolved in DCM (150 mL), washed with water and brine. The organic layer was dried (Na$_2$SO$_4$), filtered and evaporated. The crude product was purified by triturating with diethyl ether to obtain 12.5 g (55%) of compound C as off-white solid.

$^1$H NMR (400 MHz, CDCl$_3$): δ 3.06 (d, 3H), 5.02-5.17 (bs, 1H, NH), 6.44 (d, 1H), 7.43 (d, 2H), 7.71 (d, 2H), 7.96 (d, 1H), 8.55 (s, 1H); LCMS m/z: 247 (M+1).

Step-4: (5-bromo-6-(methylamino)pyridin-3-yl)(4-chlorophenyl)methanone (D)

A solution of bromine (2.29 mL, 44.70 mmol) in acetic acid (30 mL) was added to a solution of compound C (11.0 g, 44.7 mmol) in acetic acid (80 mL) at RT. The mixture was stirred for 1 h, neutralized by the addition of saturated NaHCO$_3$ solution and extracted with ethyl acetate (200 mL). The organic layer was washed with 10% sodium thiosulfate solution, water and brine. The organic layer was dried (Na$_2$SO$_4$), filtered and evaporated. The crude product was purified using column chromatography to obtain 9.0 g (62%) of compound D as viscous light yellow colored oil.

$^1$H NMR (400 MHz, CDCl$_3$): δ 3.14 (d, 3H), 5.57-5.70 (bs, 1H, NH), 7.47 (d, 2H), 7.70 (d, 2H), 8.19 (s, 1H), 8.53 (s, 1H); LCMS m/z: 325 (M+1).

Step-5: 3-bromo-5-(2-(4-chlorophenyl)-1,3-dioxalan-2-yl)-N-methylpyridin-2-amine (E)

To a solution of compound D (6.0 g, 18.51 mmol) in toluene (120 mL), ethylene glycol (10.4 mL, 185 mmol) and PTSA (0.96 g, 5.55 mmol) was added. The mixture was refluxed overnight, quenched with water and extracted with ethyl acetate (150 mL). The organic layer was washed with water and brine. The organic layer was separated dried over Na$_2$SO$_4$, filtered and evaporated. The crude product was purified using column chromatography to obtain 5.0 g (74%) of compound E as off-white solid.

$^1$H NMR (400 MHz, CDCl$_3$): δ 3.02 (d, 3H), 3.93-4.17 (m, 4H), 7.33 (d, 2H), 5.01-5.16 (bs, 1H, NH), 7.42 (d, 2H), 7.71 (s, 1H), 8.09 (s, 1H); LCMS m/z: 369 (M+1).

Step-6: (5-(2-(4-chlorophenyl)-1,3-dioxolan-2-yl)-2-(methylamino)pyridin-3-yl)(3-methoxyphenyl)methanol (F)

A solution of compound E (30.0 g, 81.30 mmol) in THF (600 mL) was cooled to −78° C. and n-butyllithium (162.6 mL, 162.6 mmol, 1.0 M solution in hexane) was added to it dropwise, while maintaining the temperature below −70° C. The mixture was stirred for 10 min, triethylsilyl chloride (13.7 mL, 81.30 mmol) was added dropwise at −70° C., and stirred for 30 min. n-BuLi (162.6 mL, 162.60 mmol, 1.0 M solution in hexane) was added dropwise, stirred for 10 min at −75° C., and a solution of 3-methoxybenzaldehyde (15.07 mL, 121.95 mmol) in THF (50 mL) was added, stirred for 1 h, quenched with saturated NH$_4$Cl solution and extracted with EtOAc (100 mL). The organic layer was dried over Na$_2$SO$_4$, filtered and concentrated under reduced pressure. The crude product was purified by column chromatography to obtain 28 g of compound F as viscous light yellow colored oil containing an inseparable impurity (64% pure by LCMS). This material was used in the next step without further purification.

$^1$H NMR (400 MHz, CDCl$_3$): δ 2.86 (s, 1H, NH), 2.89 (d, J=3.6 Hz, 3H), 3.75 (s, 3H), 3.92-4.07 (m, 4H), 5.30-5.34 (bs, 1H, OH), 5.65 (s, 1H), 6.82 (s, 1H), 6.84 (s, 1H), 7.16-7.32 (m, 4H), 7.36-7.43 (m, 3H), 8.10 (s, 1H); LCMS m/z: 427 (M+1).

Step-7 (5-(2-(4-chlorophenyl)-1,3-dioxolan-2-yl)-2-(methylamino)pyridin-3-yl)(3-methoxyphenyl)methanone (G)

PCC (21.19 g, 98.58 mmol) was added to a solution of compound F (28 g, 65.72 mmol) in DCM (550 mL). The mixture was stirred at RT overnight and filtered through a pad of celite. The filtrate was concentrated and purified by column chromatography to obtain 16 g (46%, 2 steps) of compound G.

$^1$H NMR (400 MHz, CDCl$_3$): δ 3.11 (d, J=4.84 Hz, 3H), 3.80 (s, 3H), 3.96-4.08 (m, 4H), 6.96-7.09 (m, 3H), 7.30 (t, J=8.0 Hz, 2H), 7.39 (d, J=8.4 Hz, 2H), 7.77 (d, J=2.4 Hz, 1H), 8.42 (d, J=2.4 Hz, 1H), 8.71 (s, 1H); LCMS m/z: 425 (M+1).

Step-8: 6-(2-(4-chlorophenyl)-1,3-dioxolan-2-yl)-4-(3-methoxyphenyl)-1-methyl-1,8-naphthyridin-2(1H)-one (H)

To a solution of diisopropylamine (1.32 mL, 9.43 mmol) in THF, a solution of BuLi (7.86 mL, 7.08 mmol, 0.9 M solution in hexane) was added at −20° C. and the resulting mixture was stirred for 30 min. To this solution of LDA was added tBuOAc (0.95 mL, 7.08 mmol) at −78° C. The mixture was stirred for 30 min and a solution compound G (500 mg, 1.18 mmol) was added to it. The reaction mixture was allowed to warm to RT and stirred overnight. The reaction mixture was quenched with saturated ammonium chloride solution and extracted with EtOAc (50 mL). The organic layer was dried ($Na_2SO_4$), filtered and evaporated. The crude product was purified by column chromatography to obtain 0.3 g (57%) of compound H off-white solid.

$^1$H NMR (400 MHz, $CDCl_3$): δ 3.82 (s, 3H), 3.86 (s, 2H), 4.01-4.14 (m, 4H), 6.75 (s, 1H), 6.87 (t, J=2 Hz, 1H), 6.93 (d, J=7.2 Hz, 1H), 7.03 (dd, J=8, 2 Hz, 1H), 7.30 (d, J=8.4 Hz, 2H), 7.39-7.47 (m, 4H), 7.98 (d, J=2.4 Hz, 1H), 8.71 (d, J=2.0 Hz, 1H); LCMS m/z: 449 (M+1).

Step-9: 6-(4-chlorobenzoyl)-4-(3-methoxyphenyl)-1-methyl-1,8-naphthyridin-2(1H)-one (I)

To a solution compound H (0.3 g, 0.67 mmol) in dioxane (5 mL) was added 6 N HCl (0.5 mL) at 0° C. The mixture was heated at 70° C. for 1.5 h and cooled to RT. Dioxane was removed under reduced pressure; the reaction mixture was neutralized with saturated $NaHCO_3$ solution and extracted with EtOAc (25 mL). The organic layer was dried over $Na_2SO_4$, filtered and concentrated under reduced pressure. The crude product was purified by column chromatography to obtain 0.25 g (92%) of compound I as off-white solid.

$^1$H NMR (400 MHz, $CDCl_3$): δ 3.86 (s, 3H), 3.92 (s, 3H), 6.82 (s, 1H), 6.94 (s, 1H), 6.99 (d, J=7.6 Hz, 1H), 7.03 (d, J=8.4 Hz, 1H), 7.42 (t, J=8.0 Hz, 1H), 7.49 (d, J=8.4 Hz, 2H), 7.74 (d, J=8.4 Hz, 2H), 8.37 (d, J=2.0 Hz, 1H), 8.97 (d, J=2.0 Hz, 1H); LCMS m/z: 405 (M+1).

Step-10: 6-((4-chlorophenyl)(hydroxy)(1-methyl-1H-imidazol-5-yl)methyl)-4-(3-methoxyphenyl)-1-methyl-1,8-naphthyridin-2(1H)-one (6)

To a solution of 5-bromo-1-methylimidazole (390 mg, 2.44 mmol) in dry DCM (5 mL), DIPEA (0.89 mL, 5.18 mmol) and $^i$PrMgCl (1.22 mL, 2.44 mmol, 2.0 M solution in THF) was added at RT. The reaction mixture was stirred for 1.5 h and a solution of compound I (0.25 g, 0.61 mmol) in DCM was added to it. The mixture was refluxed for 5 h. The reaction was quenched with saturated $NH_4Cl$ solution and the product was extracted with DCM (50 mL). The organic layer was dried, filtered and concentrated. Purification of the crude product by column chromatography (DCM: $NH_3$ in MeOH 7N, 98:2) provided compound 6 (3.1 g, 42%) as brown solid. 350 mg of racemic compound 6 was resolved using an Chiralpak AD-H 250 mm×4.6 mm×5 um eluting with 90/10 hexanes/ethanol to obtain 64 mg of 6a and 52 mg of 6b.

Data for 6a:
$^1$H NMR (400 MHz, $CDCl_3$): δ 3.39 (s, 3H), 3.78 (s, 3H), 3.79 (s, 3H), 4.44-4.53 (bs, 1H, OH), 6.31 (s, 1H), 6.63 (s, 1H), 6.74 (s, 1H), 6.77 (d, J=7.2 Hz, 1H), 6.97 (d, J=8.0 Hz, 1H), 7.18-7.27(m, 3H), 7.30-7.41 (m, 3H), 7.84 (s, 1H), 8.53 (s, 1H); LCMS m/z: 487 (M+1); HPLC purity: 99.5% (220 nm), 98.5% (254 nm); Chiral HPLC: 99.6% (220 nm); retention time 21-22 minutes.

Data for 6b:
$^1$H NMR (400 MHz, $CDCl_3$): δ 3.90 (s, 3H), 3.78 (s, 3H), 3.79 (s, 3H), 4.36-4.46 (bs, 1H, OH), 6.32 (s, 1H), 6.64 (s, 1H), 6.74 (s, 1H), 6.78 (d, J=7.2 Hz, 1H), 6.97 (d, J=6.8 Hz, 1H), 7.17-7.28 (m, 3H), 7.29-7.40 (m, 3H), 7.84 (s, 1H), 8.52 (s, 1H); LCMS m/z: (M+1); HPLC purity: 99.2% (220 nm), 98.7% (254 nm); Chiral HPLC: 96.8% (220 nm); retention time 26-27 minutes.

Example 5

Reduction of α-Synuclein Levels in the Brain

Compounds of the invention are administered to mice of the α-synuclein transgenic line described in Masliah et al. (Masliah et al. "Dopaminergic loss and inclusion body formation in alpha-synuclein mice: implications for neurodegenerative disorders" *Science* 287(5456):1265-69, 2000; incorporated herein by reference). Animals from this line have α-synuclein neuronal inclusions in the cortex, hippocampus, and the olfactory bulb (Masliah et al. "Dopaminergic loss and inclusion body formation in alpha-synuclein mice: implications for neurodegenerative disorders" *Science* 287 (5456):1265-69, 2000; incorporated herein by reference). Transgenic mice are orally administered either a compound in 20% cyclodextrin solution or the same volume of vehicle alone twice a day for 30 or 90 days. In some cases, non-transgenic mice also receive a vehicle twice a day for 30 to 90 days. At the end of treatment, mice are sacrificed, and the brains are removed and hemisected. One hemisphere of each is fixed in 4% paraformaldehyde/PBS (pH 7.4), cryoperserved, then sectioned for histology. The other hemisphere is subdivided into four brain regions, including the cortex and hippocampus, that are homogenized and processed into cytoplasmic and membrane fractions.

Transgenic animals are treated with compound twice a day for 30 days. The number of inclusions was compared in treated animals verses transgenic animals administered vehicle alone. Formation of α-synuclein inclusions in the cortex and hippocampus are probed by immunostaining with an antibody for human α-synuclein. Cells positive for human α-synuclein are quantified. These regions are also analyzed for ubiquitin-immunoreactive inclusions and by the Campbell Switzer method of silver staining. Ubiquitin is known to be a constituent of Lewy bodies and in the α-synculein inclusions found in the transgenic mouse line used in the study (Masliah et al. "Dopaminergic loss and inclusion body formation in alpha-synuclein mice: implications for neurodegenerative disorders" *Science* 287(5456):1265-69, 2000; incorporated herein by reference). Campbell-Switzer staining is a general marker of Lewy Body type inclusions (Uchihara et al. "Silver stainings distinguish Lewy bodies and glial cytoplasmic inclusions: comparison between Gallyas-Braak and Campbell-Switzer methods" *Acta Neuropathol. (Berl.)* 110(3):255-60, 2005; incorporated herein by reference).

Levels of α-synuclein protein in the cortex and the amount of farnesylated UCH-L1 in the cortex of transgenic mice are analyzed. Total α-synuclein levels are analyzed by a sandwich ELISA assay similar to one previously described (El-Agnaf et al. "Detection of oligomeric forms of alpha-synuclein protein in human plasma as a potential biomarker for Parkinson's disease" *FASEB J.* 20(3):419-25, 2006; incorporated herein by reference). Farnesylated UCH-L1 in the cortex is contained in the membrane fraction. The amount of UCH-L1 is determined by quantitative Western Blot, then normalized to actin.

Example 6

In Vitro Farnesyl Transferase Assay

Compounds are analyzed for inhibition of farnesyl transferase (FTase) activity using an established fluorescent peptide-based assay (Pompliano et al 1992 *J. Am. Chem. Soc.* 114:7945; U.S. Pat. No. 5,525,479, issued Jun. 11, 1996; each of which is incorporated herein by reference). In summary, a dansyl-pentapeptide (dGCVLS) (SEQ ID NO: 22) is incubated at 4 µM with 5 µM farnesyl pyrophosphate (FPP) and 25-50 nM FTase in 50 mM Tris-HCl/12 mM $MgCl_2$/12 µM $ZnCl_2$/6 mM DTT/0.2% octyl-D-β-glucopyranoside/pH 7.0 at room temperature while the increase in fluorescence of the peptide at Ex=340 nm, Em=485 nm upon farnesyl addition is monitored continuously by a spectrofluorometer. The linear portion of the reaction progress curve thus created is measured to yield an initial rate (Vo); a plot of Vo versus inhibitor concentration is fit by non-linear regression analysis (Graph-Pad Prism software) to yield estimates of $K_i$. All reactions in the inhibitor experiments contain a final concentration of 1% DMSO.

Example 7

Cytosolic Ras Assay for Measurement of Farnesyl Transferase Activity

Ras is a small GTP binding protein whose farnesylation and consequent membrane association can be reduced by inhibition of farnesyl transferase (Appels et al., *Oncologist* 10:565-578, 2005; Basso et al., *J. Lipid Res.* 47:15-31, 2006; Tamanoi, *Trends Biochem. Sci.* 18:349-353, 1993; each of which is incorporated herein by reference). We have found that in untreated COS-7 (African green monkey kidney) cells, Ras exists predominantly in the membrane-bound state. Treatment with a compound of the invention reduces the farnesylation and membrane association of Ras, leading to accumulation of Ras in the cytosol of the cells. An assay was developed to monitor FTase activity, based on the amount of Ras present in the cytosolic fraction of COS-7 cells after FTI treatment. On day 0, COS-7 cells were passaged into 6-well plates at a density of $4 \times 10^5$ cells/well. Beginning on day 1, cells were treated with a compound of the invention in 0.2% DMSO for 24 hr. On day 2, cells were lysed by passage through a 25 gauge needle 10 times in 100 µl Buffer 1 (50 mM Tris, 140 mM NaCl, 2 mM EDTA, protease inhibitor cocktail, pH 7.4) and lysates were centrifuged at 16,000 g for 30 min to isolate the cytosolic fraction (supernatant). The cytosolic fraction was analyzed by Western blot using anti-Ras antibody and anti-actin antibody for loading control. Results were quantified based on densitometric analysis of Ras signal normalized to actin signal (Ras/actin ratio). Treatment with a compound of the invention increases the amount of Ras in the cytosolic fraction in a dose-dependent manner. Using this method, compounds of the invention were analyzed for their ability to inhibit FTase activity, in that an increase in the Ras/actin ratio indicates inhibition of FTase. Results of the is assay are shown below in Table 3.

TABLE 3

| Cmpd # | Structure | RAS Cell Assay (IC50 nM) |
|---|---|---|
| 4b | 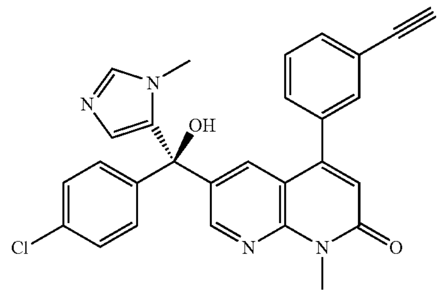 [SMILES: C#Cc1cccc(-c2cc(=O)n(C)c3ncc([C@](O)(c4ccc(Cl)cc4)c4cncn4C)cc23)c1] | 0.5700 0.5400 |
| 4a | 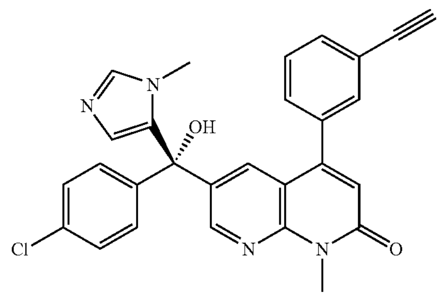 [SMILES: C#Cc1cccc(-c2cc(=O)n(C)c3ncc([C@@](O)(c4ccc(Cl)cc4)c4cncn4C)cc23)c1] | 300 |
| 5b | 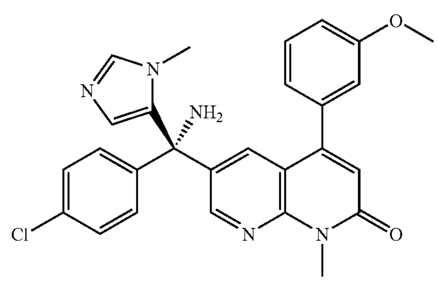 [SMILES: COc1cccc(-c2cc(=O)n(C)c3ncc([C@@](N)(c4ccc(Cl)cc4)c4cncn4C)cc23)c1] | 300 |
| 5a | 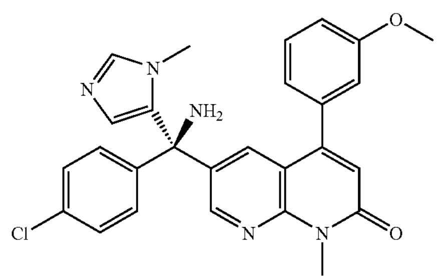 [SMILES: COc1cccc(-c2cc(=O)n(C)c3ncc([C@](N)(c4ccc(Cl)cc4)c4cncn4C)cc23)c1] | 3.9 2 |
| 6a | 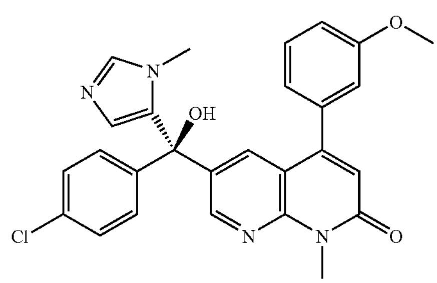 | 2.3 4.2 |

TABLE 3-continued

| Cmpd # | Structure | RAS Cell Assay (IC50 nM) |
|---|---|---|
| 6b | 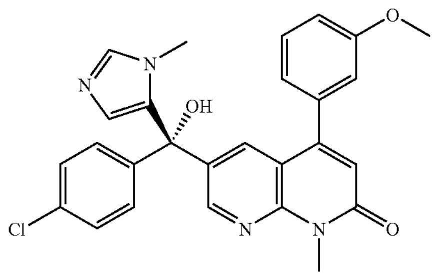 [SMILES: COc1cccc(-c2cc(=O)n(C)c3ncc([C@@](O)(c4ccc(Cl)cc4)c4cncn4C)cc23)c1] | 190 |

Example 8

Reduction of Phospho-Tau Accumulation in TAU Transgenic Mice

Like α-synuclein, tau is a highly expressed cytosolic protein and is an autophagy substrate (Hamano et al., *Eur. J. Neurosci.* 27(5):1119-30, March 2008). Cytosolic tau aggregates are characteristic of Alzheimer's disease (AD) (neurofibrillary tangles) and of frontotemporal dementia (FTD). Appearance of tau aggregates (detected by the presence of phosphorylated forms that correlate with disease) is induced by autophagy inhibition via a reduction of p62 expression (Ramesh et al., *J. Neurochem.* 106(1):107-120, July 2008). Autophagy stimulation by an inventive compound could be expected to have the opposite effect. We can study 5 month-old TAU transgenic (tg) mice with a CB6×C57HL/6 background which express TAU441 bearing the missense mutations V337M and R406W under the regulatory control of the murine Thy-1 promoter, where amygdala is the primary site of tau deposition and, therefore the primary behavioral abnormality is depression.

This study is designed to evaluate the effects of a treatment with an inventive compound on behavior, TAU and TAU-pT231 levels, and brain morphology of TAU441 Tg mice. Histological evaluations are performed to quantitatively evaluate TAU pathology. TAU depositions are determined using the monoclonal TAU-antibodies AT180 and HT7. AT180 recognizes phosphorylated TAU and tangle-like formations (the epitope of this antibody is the phosphorylated Thr231 residue), HT7 normal human TAU and phosphorylated TAU (the epitope of this antibody has been mapped to a region between residues 159 and 163 of human TAU). 5 µm thick coronal paraffin sections from each of the five different layers are stained with the above described monoclonal mouse anti-human TAU-antibodies (AT180 at 1:100; HT7 at 1:500) and visualized using an anti-mouse Cy3 secondary antibody (1:500, Jackson Laboratories). Tiled images are recorded using a PCO Pixel Fly camera mounted on a Nikon E800 with a StagePro software controlled table and an exposure time of 300 msec for AT180 and HT7 fluorescence at 200-fold magnification. Afterwards images are evaluated with ImageProPlus (version 6.2) image analysis software.

Example 9

Reversal of Tau-Dependent Depression in TAU Transgenic Mice

Tests relevant to depression-like behaviors in rodents are primarily stress-induced reductions in avoidance or escape, termed behavioral despair. One of the most widely used animal tests for depression is the Porsolt forced swim task (Porsolt et al., *Pharmacodyn. Ther.* 229(2):327-336, 1977; Porsolt et al., *Eur. J. Pharmacol.* 47(4):379-91, 1978). This study is designed to evaluate the effects of treatment with LNK-754 on behavior of TAU441 transgenic mice. At start of the treatment, the animals are 5 months old. Untreated non-transgenic animals of the same age are tested and sacrificed serving as the baseline group. Mice receive vehicle or test compound, daily, 7 days a week for 90 days. In the last week of the treatment period and before sacrifice, mice are evaluated using the Porsolt forced swim task (Porsolt et al., *Pharmacodyn. Ther.* 229(2):327-336, 1977; Porsolt et al., *Eur. J. Pharmacol.* 47(4):379-91, 1978.)

Example 10

Measurement of Autophagy Stimulation In Vitro

Cell culture media and reagents are purchased from Gibco. SH-SY5Y cells are grown in DMEM medium supplemented with 10% FBS and 1% pen/strep at 37° C. and 5% $CO_2$. Cells are plated in either 12 well plates for qPCR or 8 well chamber slides for immunohistochemistry, and allowed to grow until 70% confluent. Cells are then differentiated with 10 µM retinoic acid for 72 hr. Differentiated cells are then treated with the either rapamycin (100 nM or 1 µM) as a positive control or with a compound of the invention for 48-72 hr. For immuno-histochemistry, cells are then fixed with 4% paraformaldehyde/PBS or ice cold methanol. Cells are then stained for LC3 (Novus biological, NB 100-2331, dilution 1:800) followed by secondary Alexa-564 Anti-Rabbit (A-11011). Slides are then mounted using ProLong Gold antifade reagent with DAPI (Invitrogen).

For Western analysis of LC3-I and LC3-II ratio changes as a measurement of autophagy, SH-SY5Y cells are differentiated with 10 uM retinoic acid for 2-4 days prior to treatment with either DMSO or a test substance for 48-72 hr. For the last 18 hr, cells are treated with 5 nM bafilomycin A1. Cells are lysed in SDS-PAGE sample buffer and LC3-II levels are analyzed by Western blot, normalized to actin, and plotted relative to control cells treated with DMSO only (no bafilomycin). Antibodies used are anti-LC3B (Cell Signaling #2775) and anti-actin (Chemicon MAB1501R).

Autophagy gene expression profiles are done by qPCR on series of known autophagy genes. For cells used for qPCR, total RNA are extracted using Tri-reagent (Sigma) according to the manufacturer's specifications. The targeted genes and primers are listed below. The primers (18-22 mer) are designed using Primer3 (http://wwwgenome.wi.mit.edu/cgi-bin/primer/primer3_www.cgi). These primer sets are designed to amplify small amplicons for candidate mRNAs ranging from 100-300 bp in size. First-strand cDNA synthesis is carried out on total RNA extracted with Tri-reagent (Sigma), using iScript cDNA synthesis kit (Biorad) according to the manufacturer's specifications. qPCR analysis is carried out in a 96 well plate using an iCycler (BioRad, Hercules, Calif.), and iQ SYBR Green Supermix (Biorad) according to the manufacturer's specifications. A concentration curve with known concentrations of cDNA extracts from undifferentiated SH-SY5Y is used to calculate standard curves. The final concentration of each transcript is calculated using the myIQ2 software provided by Biorad followed by normalization to GAPDH (normalization to actin gave similar results).

| Primer sets | | Gene name |
|---|---|---|
| AACGGATTTGGTCGTATTGG | (SEQ ID NO. 1) | L-h-GAPDH |
| GCTCCTGGAAGATGGTGATG | (SEQ ID NO. 2) | R-h-GAPDH |
| AAGCCATCAAGGTGATGAGG | (SEQ ID NO. 3) | R-h-ATG1 |
| GGTCACACGCCACATAACAG | (SEQ ID NO. 4) | L-h-ATG1 |
| ATCACCTAGTCCACCACTGTCC | (SEQ ID NO. 5) | L-h-ATG3 |
| GTATCTACCATCCGCCATC | (SEQ ID NO. 6) | R-h-ATG3 |
| TTATGTCATGTCGGGTGTGG | (SEQ ID NO. 7) | L-h-ATG4 |
| ACAGGTGTAGGGCTCTGTG | (SEQ ID NO. 8) | R-h-ATG4 |
| GAGGAAAGCAGAGGTGATGC | (SEQ ID NO. 9) | R-h-ATG5 |
| GAGGCAACCTGACCAGAAAC | (SEQ ID NO. 10) | L-h-ATG5 |
| GGTTGAGAAAGGCGAGACAC | (SEQ ID NO. 11) | L-h-ATG6 (beclin 1) |
| TGAGGACACCCAAGCAAGAC | (SEQ ID NO. 12) | R-h-ATG6 |
| GAACATGGTGCTGGTTTCCT | (SEQ 10 NO. 13) | L-h-ATG7 |
| CATCCAGGGTACTGGGCTAA | (SEQ ID NO. 14) | R-h-ATG7 |
| AGGGACAACCCTAACACGAC | (SEQ ID NO. 15) | R-h-ATG8 (LC3) |
| AGCAGGAGAAAGACGAGGAC | (SEQ ID NO. 16) | L-h-ATG8 (LC3) |
| GAAGCTGCAACACAGACTGC | (SEQ ID NO. 17) | R-h-ATG12 |
| TTGAATGACTAGCCGGGAAC | (SEQ ID NO. 18) | L-hATG12 |
| GCATGGCCATCTTCTCTTTC | (SEQ ID NO. 19) | R-h-p62 |
| TGGATGGGACTCCATAGCTC | (SEQ ID NO. 20) | L-h-p62 |

Having now described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives. Acts, elements, and features discussed only in connection with one embodiment are not intended to be excluded from a similar role in other embodiments. Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

I claim:
1. A compound of formula I:

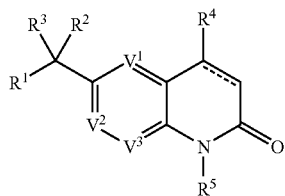

or a pharmaceutically acceptable salt thereof, wherein:
- ----- is a single or double bond;
- each of $V^1$ and $V^2$ is independently CH or N;
- $V^3$ is N;
- $R^1$ is phenyl, a 5-6 membered monocyclic heteroaryl ring having 1-4 heteroatoms independently selected from nitrogen, oxygen, or sulfur, or an 8-10 membered bicyclic ring having 0-4 heteroatoms independently selected from nitrogen, oxygen, or sulfur, and wherein $R^1$ is optionally substituted with —$(R^w)_j$, wherein j is 0-5;
- each $R^w$ is independently selected from —R, halogen, —OR, —CN, —$NO_2$, —SR, —S(O)R, —$SO_2R'$, —$SO_2N(R')_2$, —C(O)R, —$CO_2R$, —OC(O)R, —OC(O)N(R')$_2$, —C(O)N(R)$_2$, —NR'C(O)R, —NR'C(O)N(R')$_2$, —NR'$SO_2$R, —N(R')$_2$, —C(R)$_3$, or —Si(R)$_3$;
- each R is independently hydrogen, deuterium, or an optionally substituted group selected from $C_{1-12}$ aliphatic, phenyl, a 5-6 membered monocyclic heteroaryl ring having 1-4 heteroatoms independently selected from nitrogen, oxygen, or sulfur, or an 8-10 membered bicyclic aryl ring having 0-4 heteroatoms independently selected from nitrogen, oxygen, or sulfur, or wherein:
  - two R on the same nitrogen are taken together to form a 5-6 membered saturated, partially saturated, or aromatic ring having 1-3 heteroatoms independently selected from nitrogen, oxygen, and sulfur;
- each R' is independently selected from R, —C(O)R, —$CO_2R$—, —S(O)R, and —$SO_2R$;
- $R^2$ is —R, halogen, —OR, —CN, —$NO_2$, —SR, —S(O)R, —$SO_2R$, —$SO_2N(R')_2$, —C(O)R, —$CO_2R$, —C(R)$_2$CO$_2$R, —OC(O)R, —OC(O)N(R')$_2$, —C(O)N(R')$_2$, —NR'C(O)R, —NR'C(O)N(R')$_2$, —NR'$SO_2$R, —N(R')$_2$, —C(R)$_3$, —Si(R)$_3$, —$OPO_3H_2$, —$OCH_2OPO_3H_2$, or —$OCH_2OC(O)(CH_2)_kCH_3$, wherein k is 0-12;
- $R^3$ is phenyl, a 5-6 membered monocyclic heteroaryl ring having 1-4 heteroatoms independently selected from nitrogen, oxygen, or sulfur, or an 8-10 membered bicyclic ring having 0-4 heteroatoms independently selected from nitrogen, oxygen, or sulfur, wherein $R^3$ is optionally substituted with —$(R^x)_m$, wherein m is 0-5, or:
- $R^3$ is —$(CH_2)_p R^z$— wherein $R^z$ is selected from N-hydroxyurea, —$CO_2R$, —C(O)C(O)NHMe, —NHCHO, —NHC(O)CH$_2$SH, —NHC(O)NHNH$_2$, NHC(O)CH$_2$Br, —NHC(O)CH$_2$SAc, or —NHC(O)CH$_2$OH,

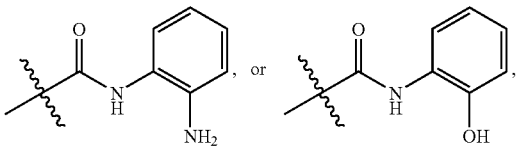 [SMILES: *C(=O)Nc1ccccc1N ; *C(=O)Nc1ccccc1O]

and wherein p is 0-5;
- each Rx is independently selected from —R, halogen, —OR, —CN, —$NO_2$, —SR, —S(O)R, —$SO_2R$, —$SO_2N(R')_2$, —C(O)R, —$CO_2R$, —OC(O)R, —OC(O)N(R')$_2$, —C(O)N(R)$_2$, —NR'C(O)R, —NR'C(O)N(R')$_2$, —NR'$SO_2$R, —N(R')$_2$, —C(R)$_3$, —Si(R)$_3$, or an optionally substituted benzyl group;
- $R^4$ is phenyl, a 5-6 membered monocyclic heteroaryl ring having 1-4 heteroatoms independently selected from nitrogen, oxygen, or sulfur, or an 8-10 membered bicyclic ring having 0-4 heteroatoms independently selected from nitrogen, oxygen, or sulfur, and wherein $R^4$ is optionally substituted with —$(R^y)_n$, wherein n is 0-4;
- each $R^y$ is independently selected from —R, halogen, —OR, —CN, —$NO_2$, —SR, —S(O)R, —$SO_2R$, —$SO_2N(R')_2$, —C(O)R, —$CO_2R$, —OC(O)R, —OC(O)N(R')$_2$, —C(O)N(R)$_2$, —NR'C(O)R, —NR'C(O)N(R')$_2$, —NR'$SO_2$R, —N(R')$_2$, —C(R)$_3$, or —Si(R)$_3$; and
- $R^5$ is R'.

2. The compound of claim 1 of formula I-a:

or a pharmaceutically acceptable salt thereof.

3. The compound of claim 1 or a pharmaceutically acceptable salt thereof, wherein ---- is a double bond.

4. The compound of claim 1 or a pharmaceutically acceptable salt thereof, wherein $R^1$ is phenyl, and wherein $R^1$ is optionally substituted with 0-5 —$R^w$.

5. The compound of claim 1 or a pharmaceutically acceptable salt thereof, wherein $R^3$ is a 5 membered monocyclic heteroaryl ring having 1-3 hetero atoms independently selected from nitrogen, oxygen, and sulfur, and optionally substituted with 1-2 $R^x$ groups.

6. The compound of claim 1 or a pharmaceutically acceptable salt thereof, wherein $R^4$ is phenyl substituted with 0-3 $R^y$ groups.

7. The compound of claim 1 of formula I-q:

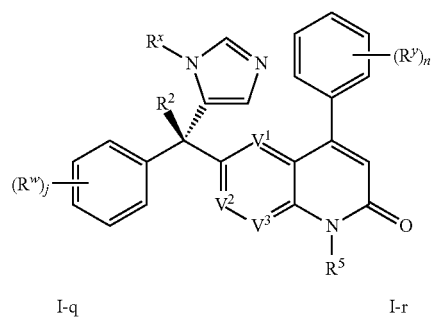

I-q            I-r or a pharmaceutically acceptable salt thereof.

8. The compound of claim 1 or a pharmaceutically acceptable salt thereof, wherein at least one Rw group is independently selected from the group consisting of R, halogen, —OR, —N(R')$_2$, and —C(R)$_3$.

9. The compound of claim 1 or a pharmaceutically acceptable salt thereof, wherein $R^2$ is selected from the group consisting of —OR, halogen, and —N(R')$_2$.

10. The compound of claim 1 or a pharmaceutically acceptable salt thereof, wherein $R^5$ is an acyclic $C_{1-12}$ aliphatic moiety.

11. The compound of claim 1 having any one of the following structures:

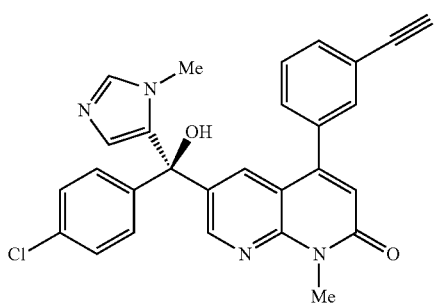 [SMILES: C#Cc1cccc(-c2cc(=O)n(C)c3ncc([C@](F)(c4ccc(Cl)cc4)c4cncn4C)cc23)n1]

-continued

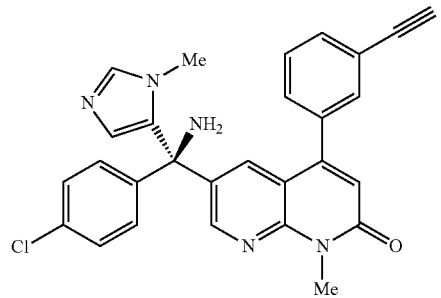

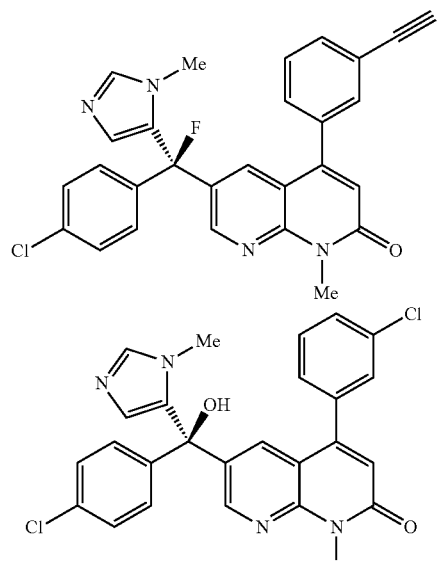

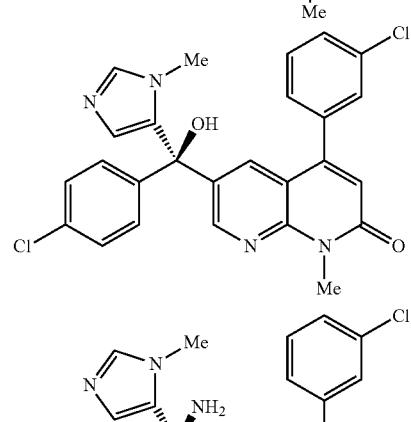

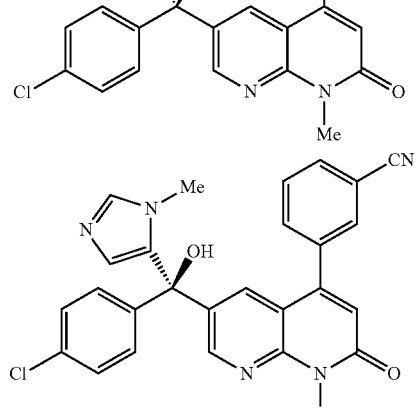

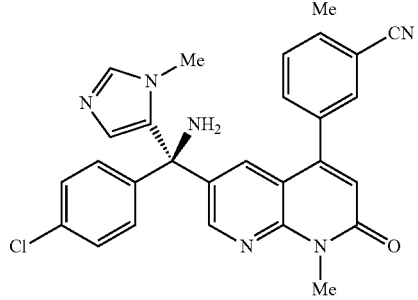

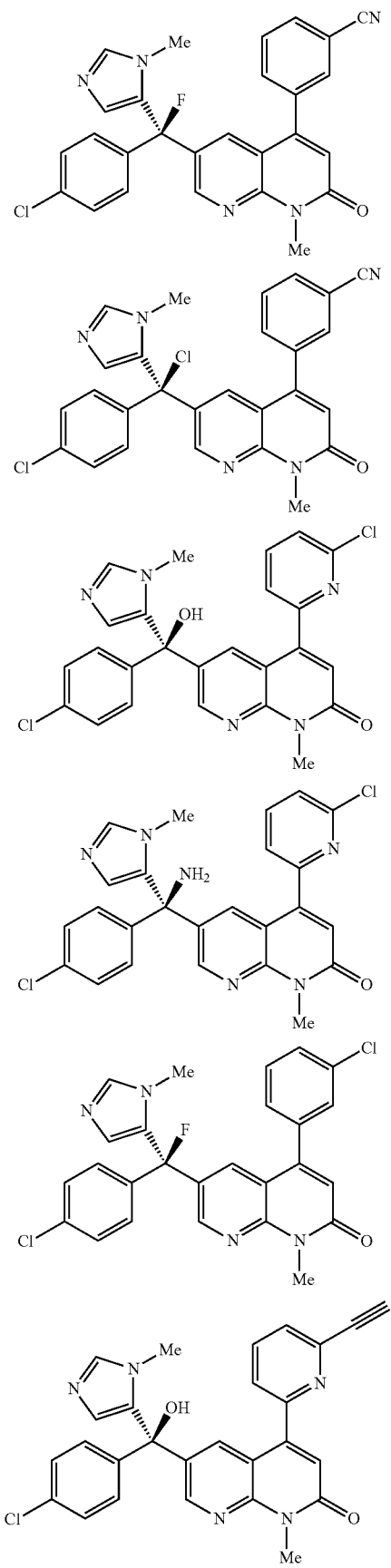
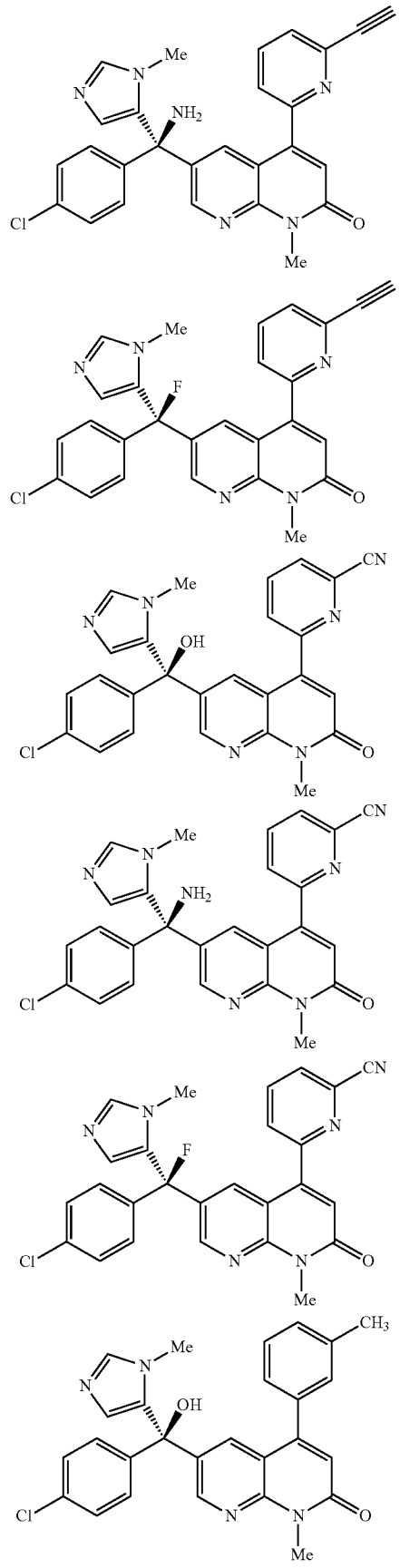

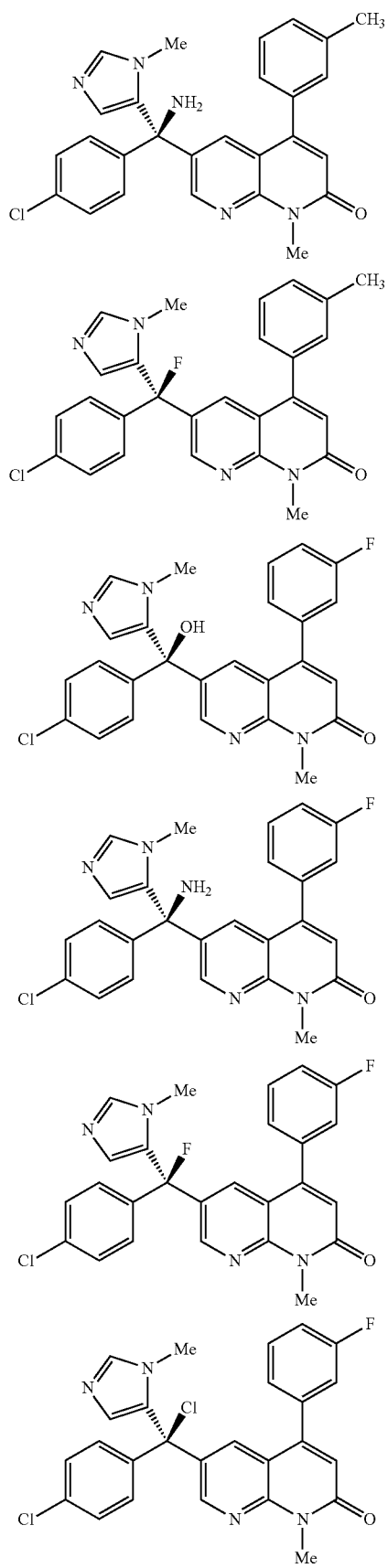
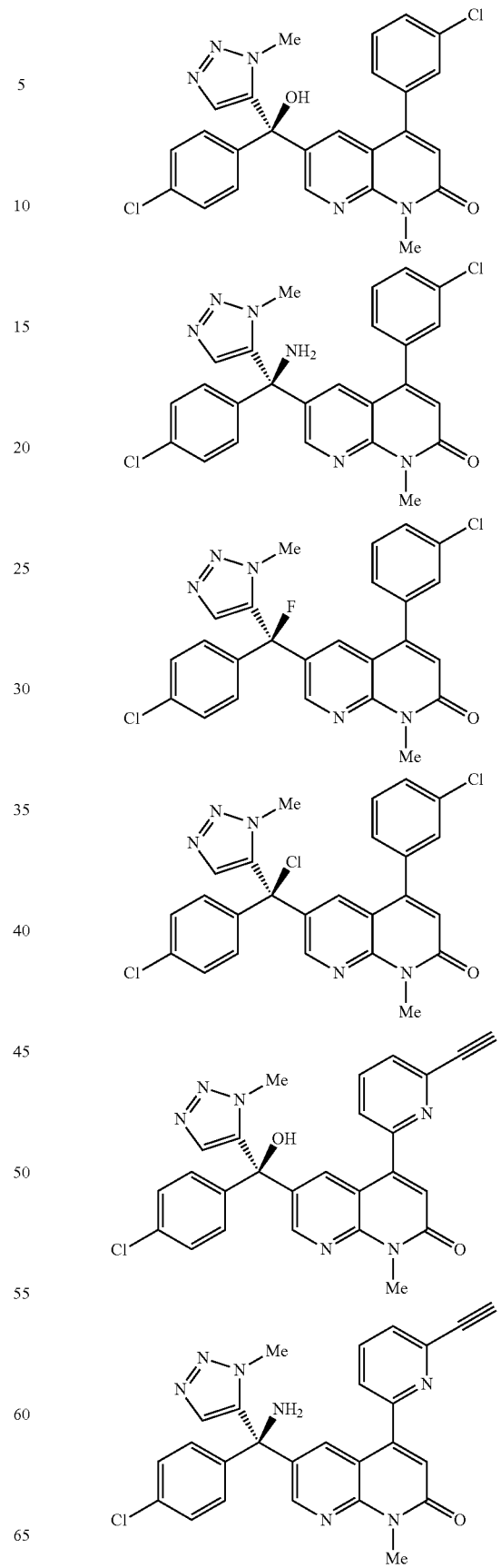

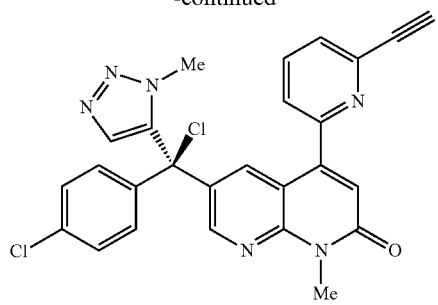
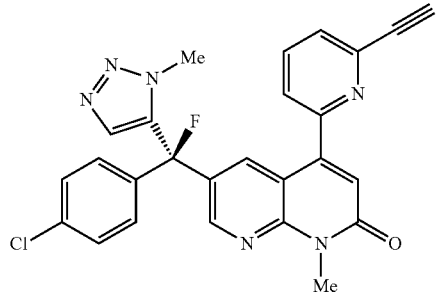 [SMILES: C#Cc1cccc(-c2cc(=O)n(C)c3ncc([C@](F)(c4ccc(Cl)cc4)c4cnnn4C)cc23)n1]
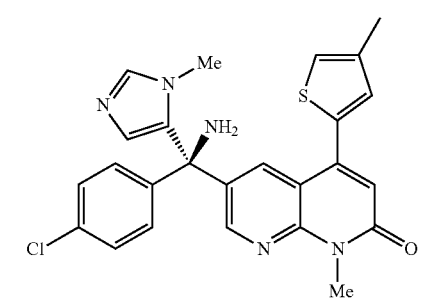 [SMILES: Cc1ccc(-c2cc(=O)n(C)c3ncc([C@](O)(c4ccc(Cl)cc4)c4cncn4C)cc23)s1]
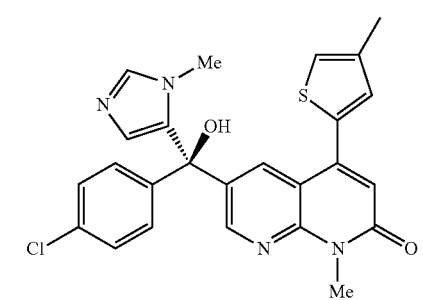
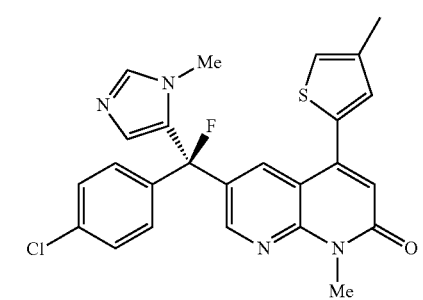
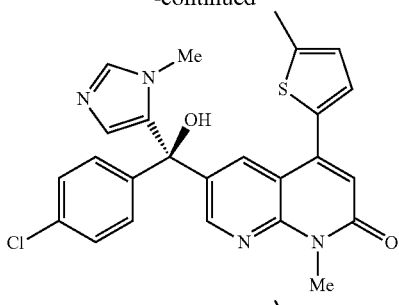
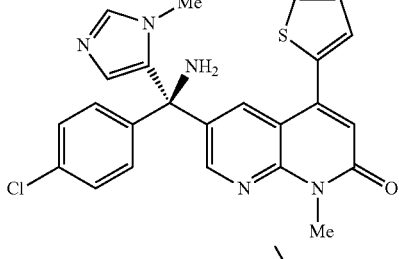
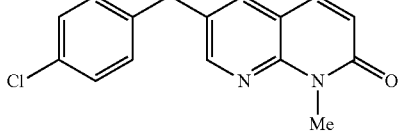
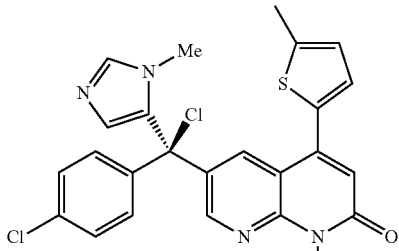
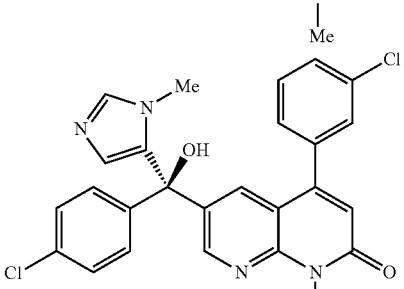
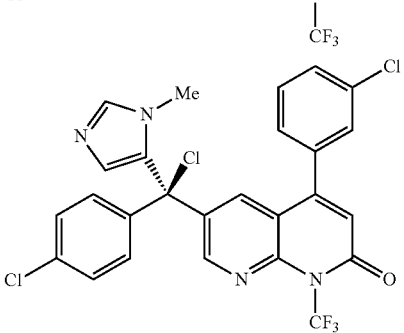

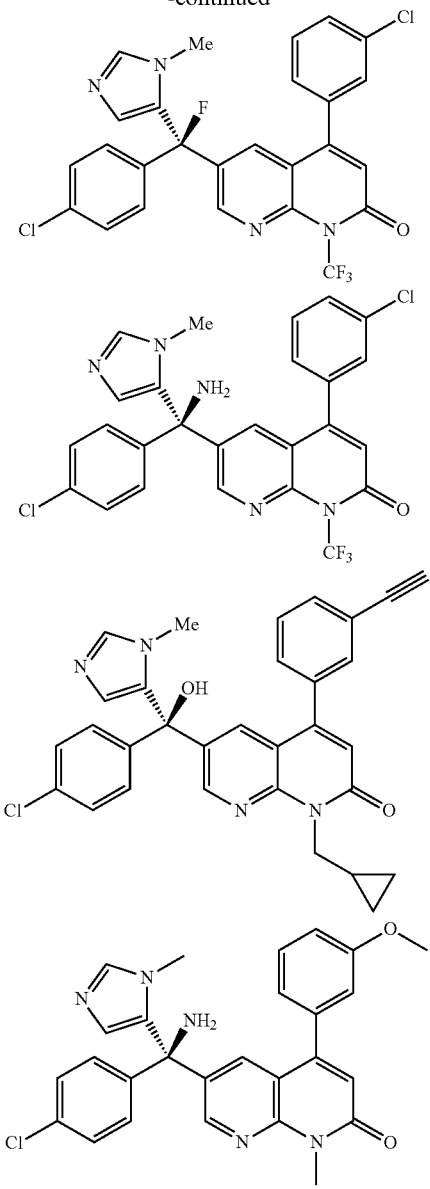
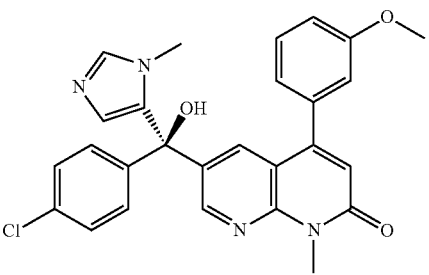
or a pharmaceutically acceptable salt thereof.
12. A pharmaceutical composition comprising a compound claim 1 or a pharmaceutically acceptable salt thereof, and a pharmaceutically acceptable excipient.
13. The compound
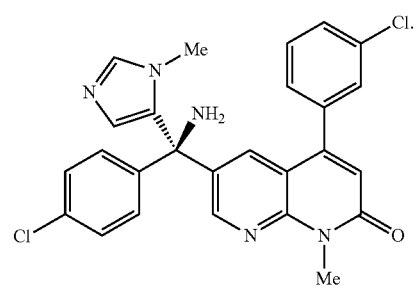 [SMILES: Cn1cncc1[C@@](N)(c1ccc(Cl)cc1)c1cnc2c(c1)c(-c1cccc(Cl)c1)cc(=O)n2C]
* * * * *